US006171856B1

(12) United States Patent
Thigpen et al.

(10) Patent No.: US 6,171,856 B1
(45) Date of Patent: Jan. 9, 2001

(54) METHODS AND COMPOSITIONS RELATING TO NO-MEDIATED CYTOTOXICITY

(75) Inventors: Anice Thigpen; Hans-Ewald Hohmeier; Christopher B. Newgard; Roger H. Unger, all of Dallas, TX (US); Michio Shimabukuro, Okinawa (JP); Guoxun Chen; Christopher J. Rhodes, both of Dallas, TX (US); Sigrun R. Hügl; Sharon Cousin, both of Irving, TX (US)

(73) Assignees: Board of Regents, The University of Texas System, Austin; Betagene, Inc, Dallas, both of TX (US)

( * ) Notice: Under 35 U.S.C. 154(b), the term of this patent shall be extended for 0 days.

(21) Appl. No.: 09/126,109

(22) Filed: Jul. 30, 1998

Related U.S. Application Data

(60) Provisional application No. 60/055,092, filed on Jul. 30, 1997, now abandoned, and provisional application No. 60/076,676, filed on Mar. 3, 1998, now abandoned.

(51) Int. Cl.⁷ .................................................. C12N 15/00
(52) U.S. Cl. ...................... 435/325; 435/440; 435/455; 435/183; 435/234; 435/235.1; 435/252.3; 435/253.35; 435/254.11; 435/372.3; 435/320.1; 435/317.1; 435/172.3; 435/69.1; 435/69.7; 435/240.21; 435/3; 435/14; 435/34; 435/176; 435/320; 435/375; 435/366; 435/69.4; 435/30; 424/94.4; 424/93.21; 424/93.3; 424/204.1; 424/196.11; 424/225; 514/9; 514/10; 514/14; 514/564; 514/31; 514/169; 514/806
(58) Field of Search ................................ 435/189, 172.3, 435/69.1, 325, 69.7, 35, 375, 7.1, 372.3, 30, 240.2, 320.1, 252, 20.3, 366, 33, 7.21, 91.33, 235.1, 69.4, 320, 240.1, 240.21, 3, 14, 34, 176; 424/94.4, 93.21, 93.3, 204.1, 196.11, 225, 229.1, 93.71; 514/9, 10, 14, 564, 31, 169, 565, 44, 806; 552/502; 536/23.4, 23.1, 23.5, 23.72; 530/350, 806; 935/41, 42, 43, 45, 60, 320.1, 69.4

(56) References Cited

U.S. PATENT DOCUMENTS

| | | | |
|---|---|---|---|
| 4,889,935 | 12/1989 | Musser | 546/176 |
| 5,108,930 | 4/1992 | Ulrich et al. | 436/111 |
| 5,126,252 * | 6/1992 | Oppenhein et al. | 435/69.4 |
| 5,246,847 * | 9/1993 | Hartman et al. | 435/189 |
| 5,472,691 * | 12/1995 | Marklund et al. | 424/94.4 |
| 5,534,404 * | 7/1996 | Laurance et al. | 435/3 |
| 5,539,132 | 7/1996 | Royer et al. | 549/545 |
| 5,585,402 * | 12/1996 | Moncada et al. | 514/564 |
| 5,614,551 | 3/1997 | Dick et al. | 514/454 |
| 5,700,820 | 12/1997 | Vyas et al. | 514/369 |
| 5,773,255 * | 6/1998 | Laurance et al. | 435/70.3 |
| 5,869,337 * | 2/1999 | Crabtree et al. | 435/372.3 |
| 5,928,913 * | 7/1999 | Efstathiou et al. | 435/172.3 |
| 5,994,313 * | 11/1999 | Crabtree et al. | 514/31 |
| 6,001,816 * | 12/1999 | Morsy et al. | 514/44 |

FOREIGN PATENT DOCUMENTS

| | | |
|---|---|---|
| WO 94/14950 | 7/1994 | (EP) . |
| 0676472 | 3/1996 | (EP) . |
| 60-051189 | 3/1985 | (JP) . |
| 08/228775 | 9/1996 | (JP) . |
| WO 87/01387 | 3/1987 | (WO) . |
| WO 91/18919 | 12/1991 | (WO) . |
| WO 93/19668 * | 10/1993 | (WO) ................................ 424/93.21 |
| WO 94/04680 | 3/1994 | (WO) . |
| WO 94/08606 | 4/1994 | (WO) . |
| WO 95/20402 | 8/1995 | (WO) . |
| WO 96/00790 | 1/1996 | (WO) . |

OTHER PUBLICATIONS

Newgard et al., Engineered cell lines for insulin replacement in diabetes:current status and future prospects, Diabetologia, 1997, 40; C69, pp. S42–S47.*
Clark et al., Novel Insulinoma cell lines produced by iterative engineering of GLUT2, glucokinase, and human insulin expression., Diabetes, vol. 46, Jun. 1997, pp. 958–967.*
Burkart et al., Protection of islet cells from inflammatory cell death in vitro., Clin. Exp. Immunol. 1993, vol. 93, C11, pp. 273–278.*
Hohmeier et al., Regulation of insulin secretion from novel engineered insulinoma cell lines., Diabetes, vol. 46, Jun. 1997, pp. 968–977.*
Kessler et al., Cytotoxicity of peritoneal murine macrophages against encapsulated pancreatic rat islets: in vivo and in vitro studies., Journal of Leukocyte Biology, vol. 60, c48, pp. 729–736, Dec. 1996.*
Sen et al., Antioxidant and redox regulation of gene transcription., FASEB J. 10, 709–720, 1996.*
Wong et al., Manganous superoxide dismutase is essential for cellular resistance to cytotoxicity of tumor necrosis factor., Cell, vol. 58, pp. 923–931, Sep. 8, 1989.*
Hohmeier et al., Stable expression of MNSOD in insulinoma cells prevents il–1beta–induced cytotoxicity and reduces nitric oxide production., J. Clin. Invest. vol. 1010, No. 9, May 1998, pp. 1811–1820.*

(List continued on next page.)

* cited by examiner

*Primary Examiner*—Christopher L. Chin
*Assistant Examiner*—Lisa V. Cook
(74) *Attorney, Agent, or Firm*—Fulbright & Jaworski LLP

(57) ABSTRACT

The present invention relates to methods and compositions for the treatment of diabetes involving free radicals. In particular, the present invention is directed to the treatment or prophylactic intervention of diabetes. The present invention demonstrates that MnSOD can play a protective role against cytokine killing, and provides strategies for engineering cell lines as islet surrogates for transplantation therapy of diabetes mellitus. Further, the present invention shows that β-cell destruction and dysfunction in adipogenic diabetes is mediated via fatty acids. Methods and compositions for ameliorating this disorder are provided herein.

4 Claims, 22 Drawing Sheets

OTHER PUBLICATIONS

Asayama et al., "Effect of vitamin E deficiency and selenium deficiency on insulin secretory reserve and free radical scavenging systems in islets: decrease of islet manganosuperoxide dismutase," *J. Lab. Clin. Med.*, 107(5):459–464, 1986.

Asfari et al., "Establishment of 2–mercaptoethanol–dependent differentiated insulin–secreting cell lines," *Endocrinology*, 130(1):167–178, 1992.

Bannister et al., "Aspects of the structure, function, and applications of superoxide dismutase," *CRC Crit. Rev. Biochem.*, 22(2):111–180, 1987.

Barbosa and Bach, "Cell–mediated autoimmunity in type I diabetes," *Diabetes Metab. Rev.*, 3(4):981–1004, 1987.

Bendtzen et al., "Cytotoxicity of human pI 7 interleukin–1 for pancreatic islets of Langerhans," *Science*, 232(4757):1545–1547, 1986.

Bendtzen, "Interleukin 1, interleukin 6 and tumor necrosis factor in infection, inflammation and immunity," *Immunol. Lett.*, 19(3):183–191, 1988.

Bhardwaj et al., "Evidence for the differential expression of the functional α–Melanocyte–stimulating hormone receptor MC–1 on human monocytes," *J. Immunol.*, 158:3378–3384, 1997.

Boitard et al., "Inhibition of insulin secretion of mouse pancreatic cells by T lymphocytes of insulin–dependent diabetics," *C R Acad. Sc.Paris, t. Série III*, 294(20):979–984, 1982 (English Abstract provided).

Burkart and Kolb, "Protection of islet cells from inflammatory cell death in vitro," *Clin. Exp. Immunol.*, 93(2):273–278, 1993.

Campbell et al., "Fat metabolism in human obesity," *Am. J. Physiol.*, 266(4 Pt 1):E600–E605, 1994.

Castaño and Eisenbarth, "Type–I diabetes: a chronic autoimmune disease of human, mouse, and rat," *Annu. Rev. Immunol.*, 8:647–679, 1990.

Charlton et al., "Administration of silica particles or anti–Lyt2 antibody prevents beta–cell destruction in NOD mice given cyclophosphamide," *Diabetes*, 37(7):930–935, 1988.

Chen et al., "Disappearance of body fat in normal rats induced by adenovirus–mediated leptin gene therapy," *Proc. Nat'l Acad. Sci. USA*, 93(25):14795–14799, 1996.

Akabane et al., "Nicotinamide inhibits IRF–1 mRNA induction and prevents IL–1 beta–induced nitric oxide synthase expression in pancreatic beta cells," *Biochem. Biophys. Res. Commun.*, 215(2):524–530, 1995.

Andersson et al., "Simultaneous production of interleukin 2, interleukin 4 and interferon–gamma by activated human blood lymphocytes, " *Eur. J. Immunol.*, 20(7):1591–1596, 1990.

Clark et al., "Novel insulinoma cell lines produced by iterative engineering of GLUT2 glucokinase, and human insulin expression," *Diabetes*, 46(6):958–967, 1997.

Clark and Chick, "Islet cell culture in defined serum–free medium," *Endocrinology*, 126(4):1895–1903, 1990.

Corbett and McDaniel, "Reversibility of interleukin–1β–induced islet destruction and dysfunction by the inibition of nitric oxide synthase," *J. Biochem.*, 299:719–724, 1994.

Corbett and McDaniel, "Intraislet release of interleukin 1inhibits beta cell function by inducing beta cell expression of inducible nitric oxide synthase," *J. Exp. Med*, 181(2):559–568, 1995.

Corbett and McDaniel, "Selective inhibition of inducible nitric oxide synthase by aminoguanidine," *Methods Enzymol*, 268:398–408, 1996.

Corbett et al., "Interleukin 1 beta induces the formation of nitric oxide by beta–cells purified form rodent islets of Langerhans. Evidence for the beta–cell as a source and site of action of nitric oxide," *J. Clin Invest.*, 90(6):2384–2391, 1992.

Corbett et al., "Nitric oxide production in islets from non-obese diabetic mice: aminoguanidine–sensitive and –resistant stages in the immunological diabetic process," *Proc. Nat'l. Acad. Sci. USA*, 90(19):8992–8995, 1993.

Cuvillier et al., "Suppression of ceramide–mediated programmed cell death by sphingosine–1–phosphate," *Nature*, 381:800–803, 1996.

DeFronzo, "Lilly lecture 1987. The triumvirate: beta–cell, muscle liver. A collusion responsible for NIDDM," *Diabetes*, 37(6):676–687, 1988.

Delaney et al., "Sensitivity of human pancreatic islets to peroxynitrite–induced cell dysfunction and death," *FEBS Lett.*, 394(3):300–306, 1996.

Eizirik et al., "Interleukin–1 beta depletes insulin messenger ribonucleic acid and increases the heat shock protein hsp70 in mouse pancreatic islets without impairing the glucose metabolism," *Endocrinology*, 127(5):2290–2297, 1990.

Eizirik et al., "An interleukin–1 receptor antagonist protein protects insulin–producing beta cells against suppressive effects of interleukin–1 beta," *Diabetologia*, 34(6):445–448, 1991.

Eizirik, "Interleukin–1 beta induces an early decrease in insulin release, (pro)insulin biosynthesis and insulin mRNA in mouse pancreatic islets by a mechanism dependent on gene transcription and protein synthesis," *Autoimmunity*, 10(2):107–113, 1991.

Eizirik et al., "Cytokines suppress human islet function irrespective of their effects on nitric oxide generation," *J. Clin. Invest.*, 93:1968–1974, 1994.

Eizirik et al., "Major species differences between humans and rodents in the susceptibility to pancreatic beta–cell injury," *Proc. Nat'l. Acad. Sci. USA.*, 91(20)9253–9256, 1994.

Eizirik et al., "The harmony of the spheres: inducible nitric oxide synthase and related genes in pancreatic beta cells," *Diabetologia*, 39:875–890, 1996.

Evers et al., "Establishment and characterization of a human carcinoid in nude mice and effect of various angents on tumor growth," *Gastroenterology*, 101:303–311, 1991.

Feldman, In: *Immunology*, 4th Ed., Roitt et al., eds., Times Mirron International Publishers Limited, Barcelona, Spain, 1996.

Fulgencio et al., "Troglitazone inhibits fatty acid oxidation and esterification, and gluconeogenesis in isolated hepatocytes from starved rats," *Diabetes*, 45(11):1556–1562, 1996.

Håkan Borg et al., "Interleukin–1β increases the activity of superoxide dismutase in rat pancreatic islets" *Endocrinology*, 130:2851–2857, 1992.

Halban et al., "Abnormal glucose metabolism accompanies failure of glucose to stimulate insulin release from a rat pancreatic cell line (RINm5F)," *Biochem. J.*, 212(2):439–443, 1983.

Hassan, "Biosynthesis and regulation of superoxide dismutases," *Free Radic. Biol. Med.*, 5(5–6):377–385, 1988.

Hirose et al., "Defective fatty acid–mediated beta–cell compensation in Zucker diabetic fatty rats. Pathogenic implications for obesity–dependent diabetes," *J. Biol. Chem*, 271(10):5633–5637. 1996.

Hügl et al., "Insulin–like growth factor I (IGF–I)–stimulated pancreatic β–cell growth is glucose–dependent. Synergistic activation of insulin receptor substrate–mediated signal transduction pathways by glucose and IGF–I in INS–1 cells,"*J. Biol. Chem.* 273(28):17771–17779, 1998.

Iida et al., "Substitution at codon 269 (glutamine→proline) of the leptin receptor (OB–R) cDNA is the only mutation found in the Zucker fatty (fa/fa) rat," *Biochem. Biophys. Res. Commun.*, 224(2):597–604, 1996.

Janjic and Asfarii, "Effects of cytokines on rat insulinoma INS–1 cells," *J. Endocrinol.*, 132(1):67–76, 1992.

Joshi et al., "Effect of aminoguanidine on in vivo expression of cytokines and inducible nitric oxide synthase in the lungs of endotoxemic rats," *Res. Commun. Mol. Pathol. Pharmacol.* 91(3):339–346, 1996.

Kaneto et al., "Apoptotic cell death triggered by nitric oxide in pancreatic beta–cells," *Diabetes*, 44(7):733–738, 1995.

Kessler et al., "Cytotoxicity of peritoneal murine macrophages against encapsulated pancreatic rat islets: in vivo and in vitro studies," *J. Leukocyte Biol.*, 60(6):729–736, 1996.

Kleemann et al., "Transcription and translation of inducible nitric oxide synthase in the pancreas of prediabetic BB rats," *FEBS Letters*, 328(1–2):9–12, 1993.

Kolb et al., "Suppression of low dose streptozotocin induced diabetes in mice by administration of a nitric oxide synthase inhibitor," *Life Sci.*, 49(25):PL213–217, 1991.

Kröet al., "Macrophage cytotoxicity towards isolated rat islet cells: neither lysis nor its protection by nicotinamide are beta–cell specific, et al.," *Diabetologia*, 34(4):232–238, 1991.

Kröet al., "Activated macrophages kill pancreatic syngeneic islet cells via arginine–dependent nitric oxide generation, Kroncke et al.," *Biochem. Biophys. Res. Commun.*, 175(3):752–758, 1991.

Lander, "An essential role for free radicals and derived species in signal transduction," *FASEB J.*, 11(2):118–124, 1997.

Lee et al., "Increased lipogenic capacity of the islets of obese rats: a role in the pathogenesis of NIDDM," *Diabetes*, 46(3):408–413, 1997.

Lee et al., "Beta–cell lipotoxicity in the pathogenesis of non–insulin–dependent diabetes mellitus of obese rats: impairment in adipocyte–beta–cell relationships," *Proc. Nat'l. Acad. Sci. USA.*, 91(23):10878–10882, 1994.

Lenzen et al., "Low antioxidant enzyme gene expression in pancreatic islets compared with various other mouse tissues," *Free Radic. Biol. Med.*, 20(3):463–466, 1996.

Lindsay et al., "N omega–nitro–L–arginine methyl ester reduces the incidence of IDDM in BB/E rats," *Diabetes*, 44(3):365–368, 1995.

Malaisse et al., "Determinants of the selective toxicity of alloxan to the pancreatic B cell," *Proc. Nat'l. Acad. Sci. U.S.A*, 79(3):927–930, 1982.

Mandrup–Poulsen et al., "Islet cytotoxicity of interleukin 1. Influence of culture conditions and islet donor characteristics," *Diabetes*, 36(5):641–647, 1987.

Mandrup–Poulsen, "The role of interleukin–1 in the pathogenesis of IDDM," *Diabetologia*, 39:1005–1029, 1996.

Martinez–Cayuela, "Oxygen free radicals and human disease," *Biochimie*, 77:147–161, 1995.

Massie et al., "Inducible overexpression of a toxic protein by an adenovirus vector with a tetracycline–regulatable expression cassette," *J. Virol.*, 72:3, 2289–2296, 1998.

Masuda et al., "Induction of mitochondrial manganese superoxide dismutase by interleukin 1," *FASEB J.*, 2:3087–3091, 1988.

McDaniel et al., "Cytokines and nitric oxide in islet inflammation and diabetes," *Proc. Soc. Exp. Biol. Med*, 211(1):24–32, 1996.

Meredith et al., "Dual functional effects of interleukin–1 beta on purine nucleotides and insulin secretion in rat islets and INS–1 cells," *Diabetes*, 45(12):1783–1791, 1996.

Milburn et al., "Pancreatic β–cells in obesity. Evidence for induction of functional, morphologic, and metabolic abnormalities by increased long chain fatty acids," *J. Biol. Chem.*, 270:1295–1299, 1995.

Moncada et al., "Nitric oxide: physiologoy, pathophysiology, and pharmacology," *Pharmacol. Rev.*, 43(2):109–142, 1991.

Mueller et al., "Pancreatic expression of interleukin–4 abrogates insulitis and autoimmune diabetes in nonobese diabetic (NOD) mice," *J. Exp. Med.*, 184:1093–1099, 1996.

Newgard et al., "Engineered cell lines for insulin replacement in diabetes: current status and future prospects," *Diabetologia*, 40(Suppl 2): S42–S47, 1997.

Ohneda et al., "Caloric restriction in obese pre–diabetic rats prevents beta–cell depletion, loss of beta–cell GLUT 2 and glucose incompetence," *Diabetologia*, 38(2):173–179, 1995.

Orci et al., "Evidence that down–regulation of beta–cell glucose transporters in non–insulin–dependent diabetes may be the cause of diabetic hyperglycemia," *Proc. Nat'l. Acad. Sci. USA*, 87(24):9953–9957, 1990.

Papaccio, "Prevention of low dose streptozotocin–induced diabetes by acetyl–homocysteine–thiolactone," *Diabetes Res. Clin. Pract.*, 13(1–2): 95–102, 1991.

Peterson et al., "Zucker diabetic fatty rat as a model for non–insulin–dependent diabetes mellitus" *ILAR News*, 32:16–19, 1990.

Phillips et al., "Leptin receptor missense mutation in the fatty Zucker rat," *Nat. Genet.*, 13(1):18–19, 1996.

Pozzilli et al., "Meta–analysis of nicotinamide treatment in patients with recent–onset IDDM. The Nicotinamide Trialists," *Diabetes Care*, 19(12):1357–1363, 1996.

Rabinovitch, "roles of cytokines in IDDM pathogenesis and islet β–cell destruction" *Diabetes Rev.*, 1:215–240, 1993.

Radons et al., "Nitric oxide toxicity in islet involves poly–(ADP–ribose) polymerase activation and concomitant NAD+ depletion," *Biochem. Biophys. Res. Commun.*, 199(3):1270–1277, 1994.

Ruddle, "Tumor necrosis factor and related cytotoxins" *Immunol. Today*, 8:129–130, 1987.

Schuppin et al., "A specific increased expression of insulin receptor substrate 2 in pancreatic β–cell lines is involved in mediating serum–stimulated β–cell growth," *Diabetes*, 47(7):1074–1085, 1998.

Sen and Packer, "Antioxidant and redox regulation of gene transcription" *FASEB J.*, 10:709–720, 1996.

Shimabukuro et al., "Role of nitric oxide in obesity–induced beta cell disease," *J. Cell. Invest.*, 100(2):290–295, 1997.

Shimabukuro et al., "Leptin– or troglitazone–induced lipopenia protects islets form interleukin 1 beta cytotoxicity," *J. Clin. Invest.*, 100(7):1750–1754, 1997.

Shimabukuro et al., "Fatty acid–induced β–cell apoptosis: a link bewtween obesity and diabetes," *Proc. Natl. Acad. Sci. USA*, 95(5):2498–2502, 1998.

Southern et al., "Inhibition of insulin secretion by interleukin–1β and tumour necrosis factor–α via an L–arginine–dependent nitric oxide generating mechanism," *FEBS*, 276(1, 2):42–44, 1990.

Sumoski et al., "Oxygen free radical scavengers protect rat islet from damage by cytokines," *Diabetologia*, 32:792–796, 1989.

Svensson et al., "Inhibition of nitric oxide synthase by NG–nitro–L–arginine causes a preferential decrease in pancreatic islet blood flow in normal rats and spontaneously diabetic GK rats," *Endocrinology*, 135(3):849–853, 1994.

Thorens, "Expression cloning of the pancreatic beta cell receptor for the gluco–incretin hormone glucagon–like peptide 1," *Proc. Nat'l. Acad. Sci. USA*, 89(18):8641–8645, 1992.

Touati, "Molecular genetics of superoxide dismutases," *Free Radic. Biol. Med.*, 5(5–6):393–402, 1988.

Unger, "Lipotoxicity in the pathogenesis of obesity–dependent NIDDM. Genetic and clinical implications," *Diabetes*, 44(8):863–870, 1995.

Wang et al., "Autoimmune diabetes in NOD mouse is L3T4 T–lymphocyte dependent," *Diabetes*, 36(4):535–538, 1987.

Welsh et al., "Interleukin–1 beta increases the biosynthesis of the heat shock protein hsp70 and selectivity decreases the biosynthesis of five proteins in rat pancreatic islets," *Autoimmunity*, 91(1):33–40, 1991.

Welsh and Sandler, "Interleukin–1 beta induces nitric oxide production and inhibits the activity of aconitase without decreasing glucose oxidation rates in isolated mouse pancreatic islets," *Biochem Biophys Res Commun.*, 182(1):333–340, 1992.

Wong and Goeddel, "Induction of manganous superoxide dismutase by tumor necrosis factor: possible protective mechanism," *Science*, 242(4880):941–944, 1988.

Yamada et al., "Effects of free radical scavengers on cytokine actions on islet cells," *Acta Endocrinol (Copenh)*, 128(4):379–384, 1993.

Yang et al., "Obesity increases sensitivity to endotoxin liver injury: implications for the pathogenesis of steatohepatitis," *Proc. Nat'l. Acad. Sci. USA.*, 94(6):2557–2562, 1997.

Yao et al., "Human IL–17: a novel cytokine derived from T cells," *J. Immunol.*, 155(12):5483–5486, 1995.

Kalden and Manger, "Biologic agents in the treatment of inflammatory rheumatic diseases," *Curr. Opin. Rheumatology*, 9:206–212, 1997.

Arreaza et al., "Interleukin–4: Potential Immunoregulatory Agent in Therapy of Insulin–Dependent Diabetes Mellitus," *Clin. Immunother.*, 6(4):251–260, Oct. 1996.

Hohmeier et al., "Stable Expression of Manganese Superoxide Dismutase (MnSOD) in Insulinoma Cells Prevents IL–1β–induced Cytotoxicity and Reduces Nitric Oxide Production," *J. Clin. Invest.*, 101(9):1811–1820, 1998.

Tokui et al., "Studies On the Prevention of Diabetes in NOD Mice by Intramuscular Administration of Plasmid Expressing GAD and IL–4," Abstract, *Diabetes Front.*, 7(4):420, 1996.

PCT Search Report dated Jan. 22, 1999.

Pathways involved in β-cell destruction and dysfunction

METHODS AND COMPOSITIONS RELATING TO NO-MEDIATED CYTOTOXICITY

BACKGROUND OF THE INVENTION

This application claims the benefit under 35 U.S.C. §119 (e) of provisional patent applications serial No. 60/055,092 filed Jul. 30, 1997, now abandoned and provisional patent application serial No. 60/076,676 filed Mar. 3, 1998, now abandoned. The entire text of these applications is incorporated herein by reference without prejudice or disclaimer.

1. Field of the Invention

The present invention relates generally to the fields of molecular biology. More particularly, it concerns the use of superoxide dismutase compositions to modulate cytokine mediated cytotoxicity. It also concerns techniques for the modulation of fatty acid-mediated lipotoxicity.

2. Description of Related Art

There is considerable evidence that classifies insulin-dependent diabetes mellitus (IDDM; type I diabetes) as a chronic autoimmune disease. IDDM occurs when insulin-producing islet β-cells are destroyed by autoimmune mechanisms (Castano and Eisenbarth, 1994; Rossini et al., 1991). This destruction leads to insulin deficiency, and acute metabolic abnormalities develop which will likely led to death in the absence of insulin therapy. Patients of type I diabetes are at constant risk from hypoglycemia from pharmacological intervention with insulin, with the majority of such individuals developing an alarming plethora of complications.

Significant evidence has accumulated in support of an important role for inflammatory cytokines, particularly IL-1β, as immunological effector molecules that induce dysfunction and destruction of the pancreatic β-cell (Mandrup-Poulsen, 1996; Rabinovitch, 1993). It has been proposed that cytokine-induced destruction of islet β-cells is mediated in part by generation of toxic oxygen radicals (Mandrup-Poulsen et al., 1987; Malaisse et al. 1982). Islet β-cells may be particularly susceptible to this mechanism of destruction due to unusually low levels of expression of enzymes involved in metabolism of reactive oxygen species, including superoxide dismutase, catalase, and various peroxidases (Malaisse et al. 1982; Asayama et al. 1986; Lenzen et al., 1995).

There are conflicting reports of the relative importance of oxygen radicals in islet cell destruction, making the field very unclear. One group reported that external application of chemical oxygen radical scavengers provided protection against cytokine killing (Sumoski, et al. 1989), while others using external application of superoxide dismutase or catalase reported no protective effect (Burkart and Kolb, 1993; Yamada et al. 1993).

The effects of a number of cytokines, including IL-1β, on islet β-cells also have been linked to induction of the inducible form of nitric oxide synthase (iNOS) and production of nitric oxide (NO) (Mandrup-Poulsen, 1996; Corbett and McDaniel, 1992; Eizirik et al., 1996). Indeed, inhibitors of iNOS effectively block both the short term metabolic and long-term cytotoxic effects of IL-1β on islet cells (Southern et al., 1990; Corbett and McDaniel, 1994).

An unresolved and important issue in this area is whether the induction of MnSOD in islets in response to cytokines represents a protective mechanism against free radical toxicity or is instead contributory to β-cell destruction. As pointed out by Eizirik and coworkers (Hakan Borg et al., 1992), induction of MnSOD could cause accumulation of NO by removal of the superoxide ion that would otherwise be free to react with NO to form peroxynitrite, a byproduct that has direct β-cell cytotoxic effects (Delaney et al., 1996). Thus, induction of MnSOD could either serve to lower the levels of toxic oxygen radicals and/or peroxynitrite (protective effect) or increase NO (potentially cytotoxic). These events are clearly important in IDDM.

NIDDM is another form of diabetes that occurs through β-cell destruction. The Zucker Diabetic Fatty (ZDF) rat provides a useful replica of the human phenotype of adipogenic NIDDM in which to study the islets (Peterson et al., 1990). Such studies implicate fat deposition in islets as the cause of the β-cell decompensation, so-called "lipotoxicity" (Lee et al., 1994; Unger, 1995).

β-cell decompensation in this form of diabetes may involve exaggerated induction by FFA of inducible nitric oxide synthase (iNOS) and excess nitric oxide (NO) generation (Shimabukuro et al., 1997a, 1997b). Because intracellular NO is an important mediator of programmed cell death (Moncada et al., 1991; Corbett et al., 1992; Kaneto et al., 1995), it seems possible that the loss of the β-cells observed late in the course of adipogenic NIDDM (Ohneda et al., 1995) might be the result of NO-induced apoptosis. Apoptosis has been reported in fat-laden hepatocytes (Yang et al., 1997).

Thus, it is clear that there is a need for information that provides a clue as to how β-cells are destroyed. In particular, it is necessary to pinpoint the involvement of NO cytotoxicity in β-cell dysfunction and destruction with a view to treatment and prophylaxis of diabetes.

SUMMARY OF THE INVENTION

In one embodiment, the present invention provides a method of protecting a mammalian cell against immunotoxicity comprising introducing into the mammalian cell an antioxidizing agent; wherein the antioxidizing agent protects the cell against immunotoxicity. In preferred embodiments, the immunotoxicity may be cytokine-mediated immunotoxicity. In particularly preferred embodiments, the immunotoxicity may be mediated by IL-1β, IL-1α, γIFN, TNF-α, TNF-β, an IL-8, an IL-12, IL-6, IL-2, IL-3, IL-5, IL-7, IL-9, IL-14, IL-17, granulocyte-macrophage colony stimulating factor or monocyte chemoattractant protein-1. In more particularly preferred embodiments, the cytokine is IL-1β.

In another embodiment, the present invention provides a method of protecting a mammalian cell against lipotoxicity comprising introducing into the mammalian cell an agent that protects the cell against lipotoxicity. In a particularly preferred embodiment, lipotoxicity may be mediated by free fatty acids or conjugated fatty acids. Conjugated fatty acids are well known to those of skill in the art, and include triglycerides, ceramides (and other sphingolipids), phospholipids and the like.

In certain aspects of the invention, the antioxidizing agent may be a protein. In other aspects, the antioxidizing agent may be a small molecule antioxidizing agent. In those embodiments in which the antioxidizing agent is a protein, the antioxidizing agent is introduced through an antioxidizing agent-encoding gene operatively linked to a first promoter. In particular embodiments, the antioxidizing agent may be selected from the group consisting of a superoxide dismutase, a catalase, glutathione peroxidase, Bcl-2, Mcl-1, α-melanocyte stimulating hormone, α-glycoprotein, a cytoprotective cytokine, DT-diaphorase, and epoxide hydrolase. In those embodiments in which the antioxidant is a small molecule, the antioxidizing agent may be selected from the group consisting of Vitamin C, Vitamin E, nicotinamide, troglitazone, aminoguanidine and uric acid.

In particular embodiments, the method may further comprise introducing into the cell, a therapeutic gene operatively linked to a second promoter. In more particular embodiments, the therapeutic gene may encodes insulin, growth hormone, prolactin, placental lactogen, luteinizing hormone, follicle-stimulating hormone, chorionic gonadotropin, thyroid-stimulating hormone, LCAT, adrenocorticotropin (ACTH), angiotensin I, angiotensin II, β-endorphin, β-melanocyte stimulating hormone (β-MSH), cholecystokinin, endothelin I, galanin, gastric inhibitory peptide (GIP), IGF-1, glucagon, amylin, lipotropins, neurophysins, GLP-1, leptin, leptin receptor, calcitonin and somatostatin.

In certain embodiments, the therapeutic gene and the antioxidizing agent-encoding gene are contained in the same vector. In other embodiments, therapeutic gene and the antioxidizing agent-encoding gene are contained in distinct vectors. In more particular embodiments, the first promoter may be inducible. In specific embodiments, the first promoter may be selected from the group consisting of CMV IE, SV40 IE, RSV LTR, RIP, modified RIP, POMC, βgal, lac operon, ecdysone-inducible expression system, tetracyline operon, glucocorticoid response element, heat shock promoter and growth hormone promoter. In other embodiments, the second promoter may selected from the group consisting of CMV IE, SV40 IE, RSV LTR, RIP, modified RIP, POMC and growth hormone promoter.

In those embodiments wherein the antioxidizing agent is superoxide dismutase, the superoxide dismutase may be Mn-dependent superoxide dismutase. In other embodiments, the superoxide dismutase may be Cu/Zn-dependent superoxide dismutase. In still further embodiments, the superoxide dismutase may be extracellular superoxide dismutase. In other embodiments, the superoxide dismutase gene may be a human superoxide dismutase gene. In those embodiments, in which the antioxidant is a cytoprotective cytokine, the cytoprotective cytokine may be interleukin-4, interleukin-10-or interleukin-13.

In specific embodiments, the mammalian cell may be a human cell or a non-human cell. The mammalian cell may be a secretory cell. The cell may be a neuroendocrine cell, a pancreatic beta cell, a pituitary cell, a lung cell or gastrointestinal cell. In specifically contemplated embodiments, the cell is an insulinoma cell. The cell also may be secretagogue-responsive, glucose-responsive or non-glucose-responsive. In preferred embodiments of the present invention the starting cell is derived from a BG 18/3E1 (cells for deposit shipped to ATCC Jul. 30, 1998), BG 204/45 (cells for deposit shipped to ATCC Jul. 30, 1998), BG 49/206 (cells for deposit shipped to ATCC Jul. 30, 1998), INS-1, HIT, NCI-696 (ATCC No. CCL-251); NCI-H810, (ATCC No. CRL-5596); NCI-H700, (ATCC No. CRL-5618); NCI-H2098; HCI-H508, (ATCC No. CCL-253); NCI-H345, (ATCC No. HTB-180), βHC, AtT20, PC12 or βG221/4 cell (cells for deposit shipped to ATCC Jul. 30, 1998). Of course these are merely exemplary of the cell that may be used herein, it is understood that additional cells that may be useful in the present invention will also be well known to those of skill in the art. Some additional cells are disclosed throughout the specification.

In certain embodiments, the antioxidizing agent-encoding gene may be linked to a selectable marker. In specific embodiments, the superoxide dismutase gene is linked to a selectable marker. In preferred embodiments, the selectable marker is selected from a group consisting of hygromycin resistance, neomycin resistance, puromycin resistance, zeocin resistance, mycophenolic acid resistance, methotrexate resistance, blastocydin resistance and histadinol resistance. In other embodiments, therapeutic gene is introduced into the mammalian cell along with a selectable marker gene.

Also provided by the present invention is a method of treating a subject for immunotoxicity comprising obtaining (a) a cell; (b) transfecting the cell with a vector comprising an antioxidizing agent-encoding gene operatively linked to a promoter; (c) selecting a cell from step b that exhibits increased antioxidizing activity when compared to the cell of step a; and (d) transplanting the selected cell into the individual; wherein the transplanted cell expresses antioxidizing activity and protects the subject against immunotoxicity and/or lipotoxicity.

In specific embodiments, the immunotoxicity is cytokine-mediated immunotoxicity. In other aspects of the present invention, the mammal may exhibit at least one pathologic condition selected from the group consisting of insulin-dependent diabetes mellitus (IDDM); insulin-independent diabetes mellitus (NIDDM); obesity; wasting syndromes; short stature; osteoporosis; inflammatory diseases; autoimmune diseases; neurodegenerative diseases. The pathological condition may result from hormone or peptide deficiency. In still other aspects, the method may further comprise, prior to the administering, (i) encapsulating the mammalian cell in a biocompatible coating or (ii) placing the cells into a selectively permeable membrane in a protective housing. In certain embodiments, the mammalian cell is administered intraperitoneally, subcutaneously or intraventricularly. In other preferred embodiments, the mammalian cell is contained within a selectively semi-permeable device, the device being operably connected to the vasculature of the mammal.

Specific embodiments of the present invention provide a method of generating a mammalian cell line that is resistant to immunotoxicity comprising (a) providing a mammalian cell; contacting the cell with a composition comprising an amount of cytokine sufficient to induce cytotoxicity; and selecting a cell from step (b) that survives exposure to the composition. In particular aspects of the present invention, the method may further comprise growing the cell from step (c) in a composition comprising an increase in cytokine concentration as compared to that used in step (b). In more particular embodiments, the mammalian cell is an INS-1 cell. In other particular embodiments, the cytokine may be selected form the group consisting of IL-1β, IL-1α, γIFN, TNF-α, TNF-β, an IL-8, an IL-12, interleukin-6, IL-2, IL-3, IL-5, IL-7, IL-9, IL-14, IL-17, granulocyte-macrophage colony stimulating factor or monocyte chemoattractant protein-1.

In yet another aspect, there is provided a method of generating a mammalian cell line that is resistant to immunotoxicity and/or lipotoxicity comprising (a) providing a mammalian cell; (b) introducing an antioxidizing agent-encoding gene operatively linked to a promoter into the mammalian cell; (c) selecting a cell from step b that exhibits an increased level of antioxidizing activity as compared to the mammalian cell of step a; and (d) propagating the selected cell into a cell line; wherein increased level of antioxidizing activity protects the cell line from immunotoxicity and/or lipotoxicity. The lipotoxicity may be fatty acid mediated lipotoxicity.

In another aspect of the present invention, there is provided a method of preventing diabetes mellitus in a subject comprising the steps of identifying a subject at risk of diabetes; and providing an antioxidizing agent to the subject; wherein the antioxidizing agent is provided by contacting the subject with an expression vector containing an antioxidizing agent-encoding gene operatively linked to a first promoter. The diabetes may be insulin-dependent (IDDM) or non-insulin independent diabetes (NIDDM). In particular aspects, the providing comprises introducing the antioxidizing agent to a cell of the subject in vivo. In other aspects, the providing comprises contacting with a secretory host cell ex vivo and administering the secretory host cell to the subject.

Also provided by the present invention is a method for inhibiting cytokine-mediated immunotoxicity and/or fatty acid mediated lipotoxicity of a target cell comprising blocking free radical production or accumulation in the cell. In particular embodiments, the free radical is selected from the group consisting of nitric oxide (NO), a superoxide, peroxynitrite, hydroxyl radical, perhydroxyl radical, peroxide ion, oxene ion, oxide ion, oxidized nucleic acid, oxidized carbohydrate, lipid free radical, oxidized protein, hydrogen peroxide; peroxidized lipid; or a reactive oxygen metabolite. In more particular embodiments, the free radical is NO.

In other aspects, blocking NO production is accomplished by inhibition of iNOS activity. Inhibition of iNOS activity refers to any method or agent that can be used to reduce, decrease, inhibit, abrogate or otherwise diminish iNOS activity and/or expression. In certain embodiments, the inhibition of the iNOS activity is accomplished by administering to the cell an amount of an iNOS inhibitor sufficient to block NO production and protect the cell from cytokine-mediated immunotoxicity. In other embodiments, the inhibition of the iNOS activity is by contacting the cell with an antisense iNOS operatively linked to a promoter. In still other embodiments, the inhibition of the iNOS activity is homologous recombination of iNOS gene.

In particular embodiments, the iNOS inhibitor is L-NMMA. In other embodiments, the iNOS inhibitor is a superoxide dismutase. In particular aspects the superoxide dismutase is administered as an expression vector comprising a superoxide dismutase-encoding gene operatively linked to a promoter.

In other embodiments, the iNOS inhibitor may be nicotinamide or alternatively the iNOS inhibitor may be aminoguanidine. In particular aspects the blocking of NO production comprises decreasing the triglyceride content of said target cell. Such a decrease in the triglyceride content may be accomplished by contacting said cell with troglitazone. In alternative embodiments, decreasing the triglyceride content is accomplished by contacting the cell with leptin or a leptin receptor. In more defined embodiments, the contacting comprises contacting said cell with an expression construct comprising a leptin encoding gene operatively linked to a promoter. In alternative embodiments, the cell expresses a leptin receptor. In these embodiments, contacting the cell with leptin may comprise contacting the cell with an expression construct comprising a gene encoding a leptin-receptor operatively linked to a promoter. In such an embodiment, the cell is engineered to be responsive to leptin that has either been added to the cells or to circulating endogenous leptin.

The present invention further provides a method of treating (and/or preventing) diabetes mellitus in a subject comprising blocking NO production in a pancreatic beta cell in the subject. The diabetes may be insulin-dependent or non-insulin independent diabetes. In particular embodiments the blocking NO production is accomplished by administering to the cell an amount of an iNOS inhibitor sufficient to protect the cell from cytokine-mediated immunotoxicity and/or lipid-mediated lipotoxicity. In specific embodiments, the cell is engineered to secrete insulin.

Particular aspects of the present invention specifically contemplate a method of inhibiting lipid-mediated cell death in a mammalian cell comprising contacting the cell with an agent that reduces levels of fatty acids in the cell as compared to an untreated cell. It is contemplated that the agent may inhibit fatty acid synthesis in the cell. In alternative and equally preferred embodiments, the agent may inhibit fatty acid uptake by the cell. In yet another alternative embodiment, the agent increases fatty acid degradation in the cell. In certain embodiments, the fatty acid is in the form of a triglyceride in the cell. In specific embodiments, the agent that reduces the level of fatty acids in the cell is triacsin C or troglitazone, or a derivative thereof.

In particular embodiments, it is contemplated that the cell may be further contacted with an agent that inhibits NO production in the cell. In particularly defined embodiments of the present invention the cell death is cytokine-mediated. In specific embodiments, the cytokine may be IL-1β, IL-1α, γIFN, TNF-α, TNF-β, an IL-8, an IL-12, interleukin-6, IL-2, IL-3, IL-5, IL-7, IL-9, IL-14, IL-17, granulocyte-macrophage colony stimulating factor or monocyte chemoattractant protein-1.

In certain aspects, the method of inhibiting lipid mediated cell death may further comprise introducing into the cell a gene operatively linked to a promoter. More particularly, the gene may encode an antioxidizing protein. In specific embodiment, it is contemplated that the antioxidizing protein may be selected from the group consisting of a superoxide dismutase, a catalase, glutathione peroxidase, Bcl-2, Mcl-1, α-melanocyte stimulating hormone, α-glycoprotein, a cytoprotective cytokine, DT-diaphorase, and epoxide hydrolase.

Also contemplated herein is a method of treating a subject for β-cell destruction comprising contacting the subject an agent that reduces levels of fatty acids in the cells of the subject as compared to the untreated level of fatty acids, wherein reduction in fatty acid level protects cells of the subject against lipotoxicity. In specific embodiments, the subject may exhibit at least one pathologic condition selected from the group consisting of insulin-dependent diabetes mellitus (IDDM); insulin-independent diabetes mellitus (NIDDM) and obesity.

Another embodiment contemplates a method of treating non-insulin dependent diabetes mellitus (NIDDM) in a subject comprising the steps of identifying a subject at risk of diabetes mellitus; and providing to the subject a composition comprising an agent that reduces levels of fatty acids in the cells of the subject as compared to the untreated level of fatty acids, wherein the reduction in fatty acid level protects cells of the subject against lipid-mediated cell death of β-cells. In particularly preferred embodiments, the NIDDM is NO-mediated NIDDM. In still further preferred embodiments, the NO-mediated NIDDM is cytokine-mediated.

The present invention also contemplates a method of treating non insulin dependent diabetes mellitus (NIDDM) in a subject comprising blocking free fatty acid production in a pancreatic beta cell in the subject. More particularly, the blocking of free fatty acid production may be accomplished by administering to the cell an amount of an inhibitory agent sufficient to protect the cell from NO-mediated lipotoxicity. In still further specific embodiments, the blocking of free fatty acid production results in a decrease in the triglyceride content of the target cell. In specific embodiments, decreasing the triglyceride content may be accomplished by contacting the cell with troglitazone. In other specific embodiments, decreasing the triglyceride content of the cell may be accomplished by contacting the cell with leptin. More particularly, the contacting may comprise contacting the cell with an expression construct comprising a leptin encoding gene operatively linked to a promoter. It is contemplated that the cell may be engineered to secrete insulin.

Another aspect of the present invention provides a method of identifying an inhibitor of FFA induced inhibition of glucose induced β-cell proliferation comprising the steps of (i) providing a glucose responsive β-cell (ii) contacting the cell with a candidate substance; and free fatty acid (FFA) in an amount sufficient to induce inhibition of glucose induced β-cell proliferation; and (iii) comparing the proliferation of the cell in step (ii) in the presence and absence of the candidate substance; wherein an increase in β-cell proliferation in the presence of the candidate substance indicates that the candidate substance is an inhibitor of FFA induced inhibition of glucose induced β-cell proliferation. In particularly preferred embodiments, the FFA may be selected from the group consisting of palmitic acid, oleic acid, linoleic acid, stearic acid, myristic acid, lauric acid, capric acid, lipoic acid, stearidonic acid and arachidonic acid. In specific embodiments, the cell is an INS-1 cell. In other particular embodiments, the cell is grown in defined media further supplemented with a growth factor specific for the cell. More specifically, the cell may be a human pancreatic β-cell and the growth factor may be HGF, IGF-1, PDGF, NGF or growth hormone.

The present invention provides an inhibitor of FFA induced inhibition of glucose induced β-cell proliferation identified according a method comprising the steps of (i) providing a glucose responsive β-cell; (ii) contacting the β-cell with a candidate substance; and free fatty acid (FFA) in an amount sufficient to induce inhibition of glucose induced β-cell proliferation; and (iii) comparing the proliferation of the cell in step (ii) in the presence and absence of the candidate substance; wherein an increase in β-cell proliferation in the presence of the candidate substance indicates that the candidate substance is an inhibitor of FFA induced inhibition of glucose induced β-cell proliferation.

Yet another embodiment of the present invention provides a method of identifying an inhibitor of FFA induced β-cell death comprising the steps of (i) providing a β-cell; (ii) contacting the β-cell with a candidate substance; and FFA in an amount sufficient to induce cell death; and (iii) comparing cell death in step (ii) in the presence and absence of the candidate substance; wherein an decrease in β-cell death in the presence of the candidate substance indicates that the candidate substance is an inhibitor of FFA induced cell death.

Yet another embodiment of the present invention provides an inhibitor of FFA induced β-cell death identified according a method comprising the steps of (i) providing a β-cell; (ii) contacting the β-cell with a candidate substance; and FFA in an amount sufficient to induce cell death; and (iii) comparing cell death in step (ii) in the presence and absence of the candidate substance; wherein an decrease in β-cell death in the presence of the candidate substance indicates that the candidate substance is an inhibitor of FFA induced cell death.

The invention further contemplates a method of identifying an inhibitor of FFA induced β-cell dysfunction comprising the steps of: (i) providing a β-cell; (ii) contacting the β-cell with a candidate substance; and FFA in an amount sufficient to induce β-cell dysfunction cell; and (iii) comparing dysfunction in step (ii) in the presence and absence of the candidate substance; wherein an decrease in β-cell dysfunction in the presence of the candidate substance indicates that the candidate substance is an inhibitor of FFA induced β-cell dysfunction. In particular embodiments, the β-cell dysfunction comprises FFA-mediated cell death. In still further embodiments, the β-cell dysfunction comprises an aberration in secretory function of the cell. In specific embodiments, the β-cell dysfunction may be monitored as impaired growth and/or proliferation of the β-cell. Additional specific embodiments contemplate that the β-cell proliferation is glucose induced β-cell proliferation.

The invention further provides an inhibitor of FPA induced β-cell dysfunction comprising the steps of (i) providing a β-cell; (ii) contacting the β-cell with a candidate substance; and FFA in an amount sufficient to induce β-cell dysfunction cell; and (iii) comparing dysfunction in step (ii) in the presence and absence of the candidate substance; wherein an decrease in β-cell dysfunction in the presence of the candidate substance indicates that the candidate substance is an inhibitor of FFA induced β-cell dysfunction.

Yet another aspect of the present invention provides a method of protecting a mammalian cell against NO-mediated cytotoxicity comprising introducing into the mammalian cell an antioxidizing agent; wherein the presence of the antioxidizing agent protects the cell against the cytotoxicity. In specific embodiments, the NO mediated cytotoxicity is lipid induced cytotoxicity. In alternative embodiments, the NO mediated cytotoxicity is cytokine-induced cytotoxicity. In preferred embodiments of this aspect of the present invention, the antioxidizing agent blocks NO production. More particularly, the agent that blocks NO production is an iNOS inhibitor delivered to the cell in an amount sufficient to protect the cell from NO-mediated cytotoxicity. Yet more particularly, the iNOS inhibitor may be a protein. In specific embodiments, the protein is provided by contacting the cell with a protein-encoding gene operatively linked to a first promoter active in the cell. In particularly preferred embodiments, the protein is superoxide dismutase. In certain embodiments, the lipid comprises a fatty acid. In specific embodiments, the fatty acid may be in the form of free fatty acid or in the form of triglyceride.

Also provided herein is a method of protecting a mammalian cell against lipotoxicity comprising contacting the cell with an agent that reduces levels of fatty acids in the cell as compared to an untreated cell.

Yet another embodiment contemplates a method of protecting a mammalian cell against lipotoxicity comprising contacting the cell with an agent that blocks NO production in the cell. A further embodiment contemplates a method of inhibiting lipotoxicity of a target cell comprising blocking free radical production or accumulation in the cell.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3A. Native INS-1 cells, INS-1 cells transfected with the pCB7/intron vector lacking the MnSOD insert (βG 221-1), and two of the clones stably transfected with pCB7/intron vector containing the MnSOD cDNA (βG 221-4, βG 221-11) were incubated with medium alone or with medium supplemented with 10 ng/ml IL-1β for 24 h. After this treatment, media were collected and assayed for nitrite, as a measure of NO production. Data represent the mean±standard deviation for 3 independent studies, each performed in triplicate. The symbol * indicates significantly reduced nitrite production in the MnSOD overexpressing clones relative to the control bG 221-v cells, at a level of significance of p<0.001. FIG. 3B. βG I/17 cells transfected with the empty pCB7/intron vector (clone βG 224-v) or with the pCB7/intron vector containing the MnSOD cDNA (βG 224-6, βG 224-10) were incubated with medium alone or with medium supplemented with 10 ng/ml IL-1β for 24 h. After this treatment, media were collected and assayed for nitrite, as a measure of NO production. Data represent the mean±standard deviation for 3 independent cell samples per condition. The symbol * indicates significantly reduced nitrite production in the MnSOD overexpressing clones relative to the control βG 224-v cells, at a level of significance of p<0.05.

FIG. 4A. PBMC were prepared from a normal human subject and treated with 10 ng/ml PMA+0.5 μM inomycin (PBMC+PMA) or 10 μg/ml LPS (PBMC+LPS) for 5 days. The conditioned media from these cells was then collected and added to the indicated cell lines for 48 h. Controls included application of medium alone (medium), medium supplemented with LPS (LPS), medium supplemented with PMA+ionomycin (PMA) or medium from unstimulated human PBMC (PBMC). The percentage of cells that were viable after these treatments was determined as described in the legends to FIG. 1 and FIG. 3 and expressed as a percentage of viable cells following treatment with medium alone. Data represent the mean±standard deviation for 2 independent studies, each done in triplicate. The symbol * indicates significantly increased viability of the MnSOD overexpressing line (βG 221-4) relative to the empty vector control cell line (βG 221-v), at a level of significance of p<0.001. FIG. 4B. PBMC were prepared from normal Wistar rats and treated as described for the human PBMC in FIG. 4A. An additional study included in FIG. 4B was antibody neutralization of γ-IFN. The anti-γ-IFN antibody was added to conditioned media obtained from rat PBMC treated with PMA+ionomycin (anti-g-IFN+PMA+PBMC), or as a control, the antibody was added to unconditioned medium supplemented with PMA+ionomycin (anti-γIFN+Med+PMA). Data represent the mean±standard deviation for 3 independent cell samples per condition. The symbol * indicates significantly increased viability of the MnSOD overexpressing line (βG 221-4) relative to the empty vector control cell line (βG 221-v), at a level of significance of p<0.01, while the symbol # indicates that anti-γ-IFN treatment of PBMC+PMA supernatants significantly increased viability relative to cells treated with PBMC+PMA supernatants not immunodepleted of γ-IFN, at p<0.02.

FIG. 5B: lean heterozygous littermates (fa/+); FIG. 5C: prediabetic obese ZDF rats (fa/fa)). Effects on iNOS/β-actin mRNA ratio semiquantified by reverse transcriptase-PCR™ (FIG. 5D: 6–7-wk-old Wistar rats; FIG. 5E: lean heterozygous littermates (fa/+); FIG. 5F: prediabetic obese ZDF rats (fa/fa)). Effects on insulin secretion (FIG. 5G: 6–7-wk-old Wistar rats; FIG. 5H: lean heterozygous littermates (fa/+); FIG. 5I: prediabetic obese ZDF rats (fa/fa)): Islets were perifused for 10 min with 3 (□) and 23 (■) mM glucose for 15 min. Bars represent the mean±SEM of the sum of all measurements in each study (n=3–5). Significant differences are indicated as follows: *P<0.05 vs. 0 mM FFA group, and †P<0.05 vs. 2 mM FFA group.

FIG. 12A Correlation between islet TG content and IL-1β-induced NO production in islets isolated from wild-type (+/+) and obese (fa/fa) ZDF rats and cultured for 24 h with 300 pg/ml IL-1β, with or without FFA and with or without troglitazone; in these studies variations in TG content were the result of in vitro manipulations during the 24-h culture period. FIG. 12B Values in islets isolated from AdCMV-leptin-infused rats, pair-fed controls, and AdCMV-β-Gal controls are shown in the inset; in these studies the differences in TG content were the result of in vivo manipulations carried out before islet isolation (compare with Table 10). Data are expressed as the mean±SEM of four or more studies.

SEQUENCE SUMMARY

Figure 1:
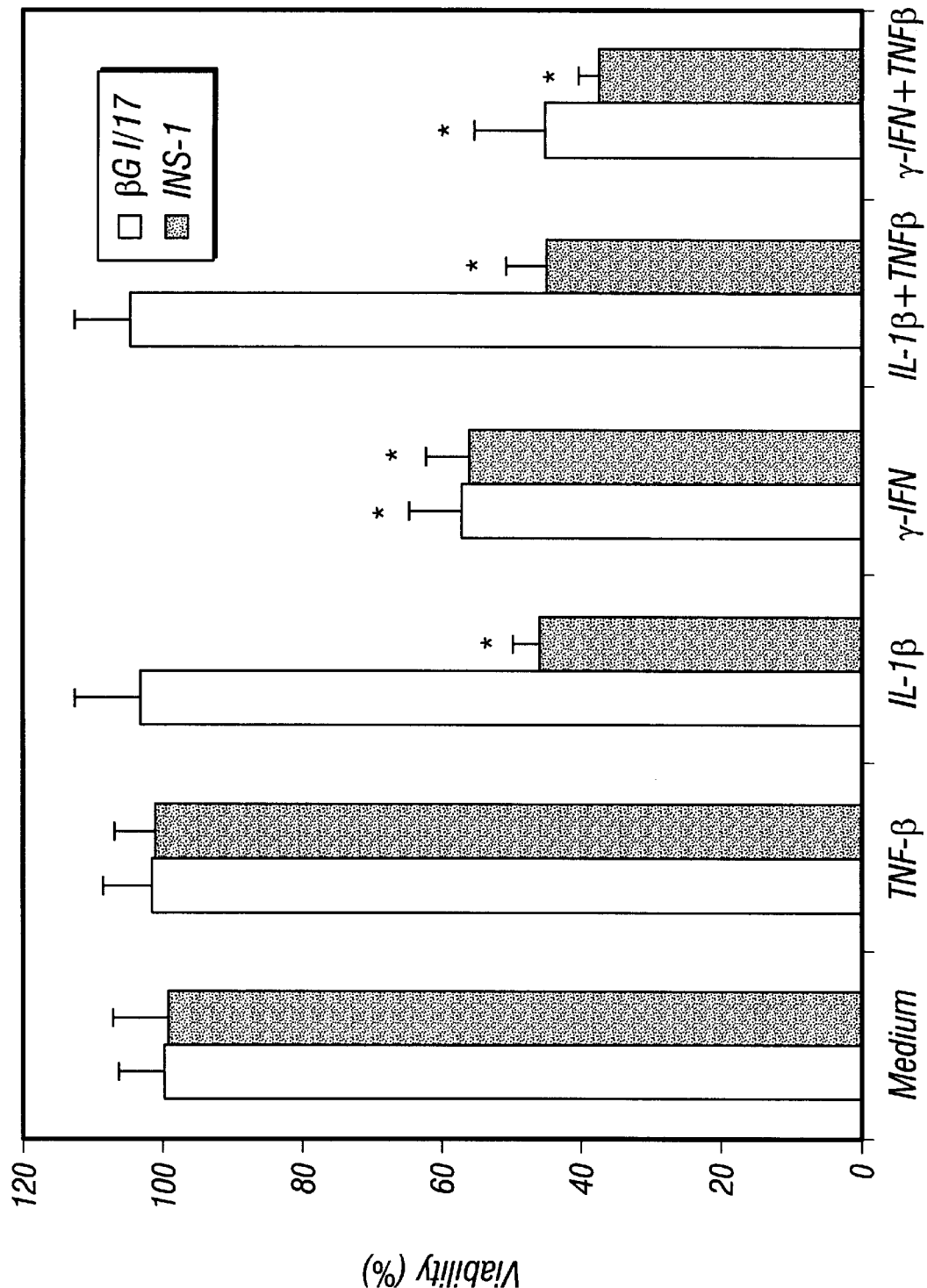
FIG. 1. Differential effects of cytokines on RIN-derived and INS-1 insulinoma cells. βG I/17 cells derived from RIN 1046-38 cells by stable overexpression of human insulin (Clark et al., 1997), and INS-1 cells (Wong and Goeddel, 1988), were incubated in the presence of the indicated cytokines for 48 h. The percentage of cells that were viable after these treatments was determined by the MTT colorimetric assay as described in Materials and Methods and expressed as a percentage of the viable cells present after treatment with medium lacking any cytokines (medium). The concentrations of cytokines used were: IL-1β, 10 ng/ml; g-IFN, 100 U/ml; TNF-β, 10 ng/ml. Data represent the mean±standard deviation for 3 independent studies, each performed in triplicate. The symbol * indicates significantly reduced viability relative to the appropriate medium-incubated control, at a level of significance of p<0.001.

Provided herein are sequences for exemplary antioxidizing agents for use in the present invention. SEQ ID NO:1 and SEQ ID NO:2: Human manganese-containing superoxide dismutase nucleic and amino acid sequences, respectively (Genbank Accession No. M36693); SEQ ID NO:3 and SEQ ID NO:4: Human mRNA for Cu/Zn superoxide dismutase (SOD) nucleic and amino acid sequences, respectively (Genbank Accession No. X02317 K00065); SEQ ID NO:5 and SEQ ID NO:6: Human B-cell leukemia/lymphoma 2 (bcl-2) proto-oncogene nucleic and amino acid sequences, respectively (Genbank Accession No. M13995); SEQ ID NO:7 and SEQ ID NO:8: Human mRNA for glutathione reductase nucleic and amino acid sequences, respectively (Genbank Accession No. X15722); SEQ ID NO:9 and SEQ ID NO:10: Human kidney mRNA for catalase nucleic and amino acid sequences, respectively (Genbank Accession No. X04076); SEQ ID NO:11 and SEQ ID NO:12: Human inducible nitric oxide synthase (NOS) nucleic and amino acid sequences, respectively (Genbank Accession No. U31511); SEQ ID NO:13 and SEQ ID NO:14 primers for amplification of type I interleukin 1 β receptor (IL-1βr); SEQ ID NO:15 and SEQ ID NO:16 primers for amplification of interferon gamma receptor(IFNγr); SEQ ID NO:17 and SEQ ID NO:18 primers for amplification of inducible nitric oxide synthase (iNOS); SEQ ID NO:19 and SEQ ID NO:20 primers for amplification to obtain the full-length cDNA encoding rat MnSOD.

DESCRIPTION OF ILLUSTRATIVE EMBODIMENTS

A. The Present Invention

The present invention relates to methods and compositions for the treatment of peptide or hormone deficiencies by cell based therapies. In particular, the present invention is directed to the treatment or prophylactic intervention of β-cell destruction seen in diabetes.

Diabetes is a multifactorial disease that occurs through the failure and/or destruction of the pancreatic β-cell. There is a large body of evidence in support of the idea that inflammatory cytokines have cytotoxic effects on islet β-cells (Mandrup-Poulsen, 1996; Rabinovitch, 1993; Corbett and McDaniel, 1992; Eizirik et al., 1996), and this cytotoxicity plays a part in β-cell destruction in IDDM.

Obesity-linked non-insulin-dependent diabetes mellitus (NIDDM) is preceded by years of insulin resistance, during which normal blood glucose levels are maintained through effective compensation by pancreatic β cells (DeFronzo, R. A. 1988). In approximately 20% of obese individuals, the compensation wanes, hyperglycemia appears, and overt NIDDM is diagnosed. The depressed β cell function is thought be due to excess free fatty acids released from adipocytes in obesity (Campbell et al., 1994) acting to initially stimulate, but ultimately impair, the function of β cells, and thus limit their compensatory capability. Thus, impaired β-cell function is a characteristic of both IDDM and NIDDM.

A phenomenon thought to play a role in β-cell dysfunction is the cytokine-mediated destruction of β-cells. It is thought that cytokine-induced destruction of islet β-cells is due to the generation of toxic oxygen radicals (Mandrup-Poulsen et al., 1987; Malaisse et al. 1982). Such a mechanism for cytokine-mediated islet cell injury is based on the observation that islet cells possess very low oxygen free radical scavenging enzyme activities and as such are extremely vulnerable to free radicals (Asayama et al., 1986; Malaisse et al., 1982). Indeed Sumoski et al., suggested that oxygen free radical scavengers may protect against cytokines IL-1, TNF and IFN-γ. However, it also has been demonstrated external application of free radical scavenging enzymes, such as superoxide dismutase or catalase, has no protective effect on cytokine toxicity (Burkart and Kolb, 1993; Yamada et al. 1993).

The present inventors have evaluated the cytotoxic effects of cytokines on two types of insulinoma cell lines demonstrated to have robust fuel-stimulated insulin secretion. The first of these, the INS-1 cell line, was derived by isolation of clonal cells with well-differentiated properties from a polyclonal population of RINm5F cells (Asfari et al., 1991). The second type of cell line, RIN1046-38 was derived from a radiation-induced insulinoma tumor in rats much like RINm5F, but is a sub-line which retains a higher insulin content and some glucose-stimulated insulin secretion at low passage numbers (Clark et al., 1990). RIN 1046-38 cells are of interest because recent findings have shown that stable introduction of combinations of the human insulin, GLUT-2, and/or glucokinase genes confers glucose-stimulated insulin secretion similar in magnitude and dynamics to that observed in normal islets (Clark et al., 1997; Hohmeier et al., 1997).

Surprisingly, RIN 1046-38 cells and their engineered derivatives βG I/17, βG 40/110 and βG 49/206 are completely resistant to IL-1β-induced cytotoxicity, even at very high doses of the cytokine. This finding was unexpected, given that the cytotoxic effects of IL-1β on primary rat islets and RINm5F cells are well established (Mandrup-Poulsen, 1996; Rabinovitch, 1993). This clear cytotoxic effect of IL-1β applied to INS-1 cells is consistent with previous reports of reduced insulin content and secretion in IL-β treated cells (Janjic and Asfari, 1992; Meredith et al., 1996).

The differential effect of IL-1β on INS-1 and RIN 1046-38 cells provided a unique opportunity to investigate operative mechanisms of IL-β-mediated cytotoxicity. The regulation of the inducible form of nitric oxide synthase (iNOS) was investigated given that there is extensive evidence implicating this enzyme in IL-1β-mediated β-cell destruction (Mandrup-Poulsen, 1996; Rabinovitch, 1993; Corbett and McDaniel, 1992; Eizirik et al., 1996). A second area of focus was expression of MnSOD, which like iNOS is an enzyme that is induced by IL-1β in rat islets (Hakan Borg et al., 1992). It was found that IL-1β was less effective at inducing expression of iNOS in RIN1046-38 cells and their derivatives than in INS-1 cells. Consistent with this, RIN 1046-38 cells treated with IL-1β produced approximately half as much NO (nitrite) as identically treated INS-1 cells. Conversely, IL-1β was much less effective at inducing expression of MnSOD in INS-1 cells than in RIN 1046-38 cells.

High levels of NO and various free radicals correlate with two levels of damage to β-cells and β-cell lines. In the first instance, the free radicals result in reduction in insulin secretion, that is they induce β-cell dysfunction. β-cell dysfunction also may include dysregulated growth, impaired growth, and/or impaired b-cell proliferation. In the second instance, these free radicals are cytotoxic and cause β-cell destruction. In either case, diabetes results due to aberrations in insulin production or secretion. Thus, the compositions of the present invention may be used to alleviate the deleterious effect of β-cell dysfunction and β-cell destruction caused by immunotoxicity. Of course, these aspects of dysfunction and destruction are equally applicable to other neuroendocrine cell in which free radicals may exert a deleterious effect.

As used herein, "immunotoxicity" refers to any event that results in cellular damage and can range from mild cellular dysfunction to cell death. Immunotoxicity can be associated with inflammation, acute rejection, and various immune responses including autoimmunity. Immunotoxicity may occur as a result of or be associated with the action of cytokines, free radicals, antibodies, immunoglobulins, T cell receptors, major histocompatibility complexes I and II, complement, and cell-cell contact.

Figure 18:
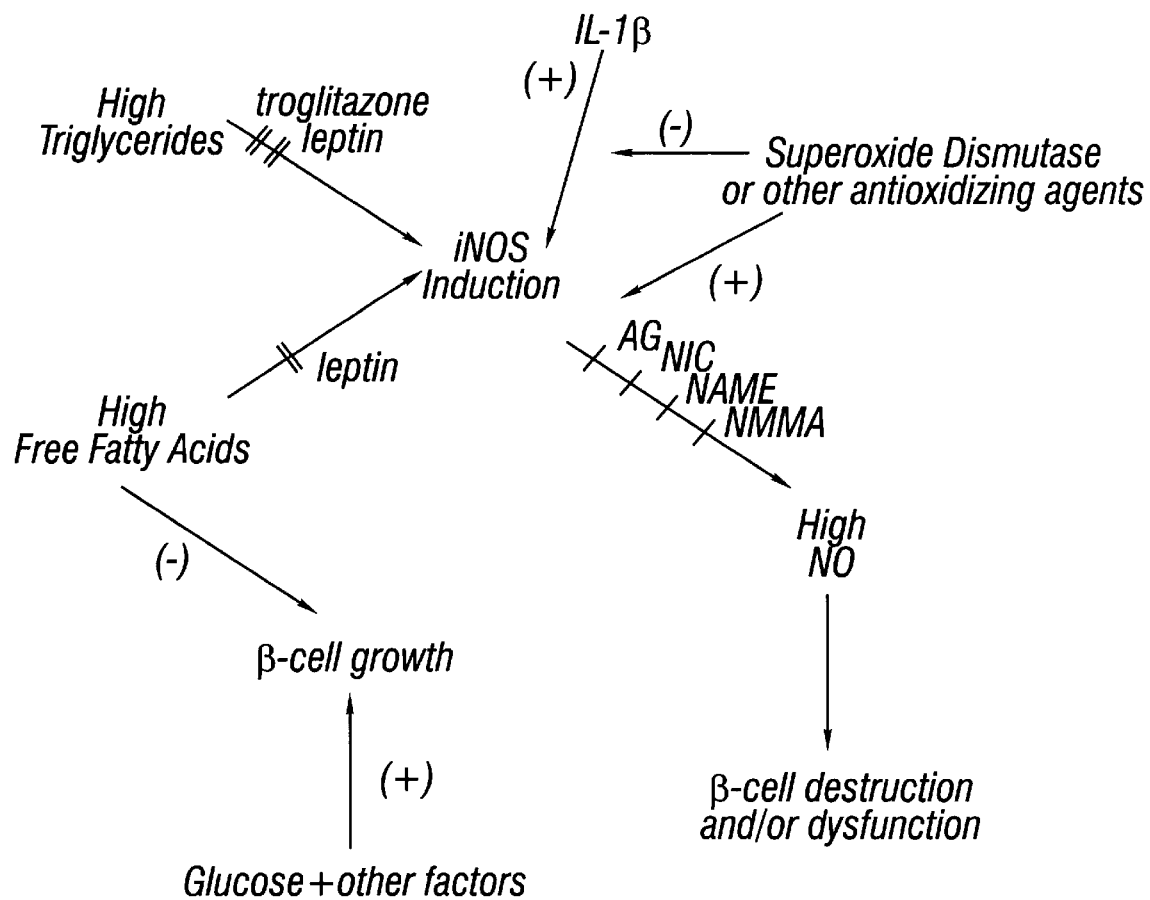
FIG. 18. The relationship between immunotoxicity and lipotoxicity in β-cell destruction and dysfunction. Increased lipids in the form of free fatty acids and/or triglyceride induce iNOS activity and/or expression. This leads to an increase in NO content which mediates β-cell destruction and/or dysfunction. Likewise IL-1β also increases iNOS induction and the increased NO similarly leads to β-cell destruction and/or dysfunction. Superoxide dismutase has been shown herein to interfere with the IL-1b induction of iNOS and will thus be preventative of β-cell destruction and/or dysfunction mediated through NO. The present invention further shows that FFA inhibit β-cell proliferation.

In a further aspect of the present invention, it is shown that iNOS activity is induced by lipids and in particular by free fatty acids (FFA) and triglycerides (TGs). The induction of iNOS produces an increase in NO production which mediates β-cell destruction and dysfunction as mentioned above. The phenomenon of fatty acid induced destruction is termed lipotoxicity. As used herein, "lipotoxicity" refers to any event that results in cellular damage and can range from mild cellular dysfunction to cell death. Lipotoxicity can be associated with obesity-linked disorders including diabetes, cardiovascular disease, stroke, muscoskeletal degeneration and hypertension. Lipotoxicity may occur as a result of or be associated with aberrant levels of intracellular and extracellular lipids, such as free fatty acids and conjugated fatty acids, and can exert cellular damage through increases in free radicals and cytokines. Lipotoxicity also may exert effects on cellular metabolism and contribute in this way to cellular damage and dysfunction. Thus, in certain embodiments, the compositions of the present invention may be used to alleviate the deleterious effects of β-cell destruction and dysfunction caused by lipotoxicity. FIG. 18 outlines the immunotoxic and lipotoxic pathways involved in β-cell destruction and dysfunction described in the present invention.

(i) MnSOD

Thus, the studies presented herein address whether induction of MnSOD represents a protective mechanism against cytokine destruction or is, instead, participatory in cell killing. Uncertainty in this area is introduced by prior studies showing that, while chemical free radical scavengers such as dimethylthiourea and citiolone effectively block cytokine-induced killing (Sumoski, et al. 1989), external addition of enzymes such as superoxide dismutase or catalase are without effect (Burkart and Kolb, 1993; Yamada et al. 1993).

The present invention establishes that an increase in the levels of intracellular MnSOD provides a protective mechanism. INS-1 cells were stably engineered for MnSOD overexpression. Such engineered lines were completely resistant to IL-1β cytotoxicity when this cytokine was added alone. These findings indicate that the resistance to IL-1β exhibited by the RIN 1046-38 lines is due to their natural capacity to maintain high levels of expression of MnSOD. That IL-1β-mediated killing of INS-1 cells also may be related to their enhanced propensity for induction of iNOS is indicated by the findings that MnSOD overexpressing lines have lower levels of iNOS mRNA and NO production when stimulated with the cytokine than control INS-1 cells. Further, iNOS inhibitors block the IL-1β effect in INS-1 cells, consistent with previous reports for rat islets and RINm5F cells (Southern et al., 1990; Corbett and McDaniel, 1994).

The present invention also demonstrates the clear cytotoxic effect of γ-IFN alone on both RIN 1046-38 and INS-1 cells. Previous studies with rat γ-IFN on isolated rat islets showed the absence of a cytotoxic effect of this cytokine alone, although it was able to potentiate the cytotoxic effect of a sub-optimal dose of IL-1β (Heitmeier et al., 1997). The inventors findings of a direct cytotoxic effect of purified rat γ-IFN on RIN 1046-38 or INS-1 cells is further supported by the observations that preincubation of stimulated rat PBMC supernatants with an anti-γ-IFN antibody reduces cell killing. The present invention also shows that unlike the case with IL-1β, the destructive effect of γ-IFN was not reversed by overexpression of MnSOD in INS-1 cells. Thus, it appears that RIN1046-38 cells and INS-1 cells are more sensitive to γ-IFN-mediated killing than rat islets, even though the RIN 1046-38 lines are naturally resistant to IL-1β-mediated destruction. In addition, the results presented herein suggest that γ-IFN killing in INS-1 and RIN 1046-38 cells occurs by a pathway distinct from that activated by IL-1β. Understanding of the pathway of γ-IFN killing in these cell lines will require further study.

These findings lead to the following conclusions about the potential utility of modified INS-1 or RIN 1046-38 cell lines for transplantation therapy of IDDM. First, IL-1β is the cytokine most directly linked to β-cell destruction in autoimmune diabetes (Mandrup-Poulsen, 1996; Rabinovitch, 1993). The fact that RIN 1046-38 cells and their derivatives are naturally resistant to IL-1β-mediated cytotoxicity provide further support for the idea that these lines are an appropriate vehicle for insulin replacement. Other advantages of cell lines derived from RIN 1046-38 have previously been enumerated, including their genotypic and phenotypic stability in vitro and in vivo, absence of expression of hormones other than insulin, and the ease with which multiple rounds of stable transfection can be accomplished (Clark et al., 1997; Hohmeier et al., 1997; Newgard et al., 1997). Further, INS-1 cells also can be rendered completely resistant to IL-1β killing by stable overexpression of MnSOD. Interestingly, RIN cell lines engineered to overexpress MnSOD also exhibit a lesser induction of NO production in response to IL-1β compared with unengineered control cells. Thus, while cells of the RIN 1046-38 cell lineage appear naturally resistant to IL-1β-mediated cell killing, the reduced production of NO in response to IL-1β in MnSOD expressing clones may provide additional protection during stimulation by complex mixtures of cytokines and other cytotoxic agents. Also, decreased NO response to IL-1β in RIN cell lines overexpressing MnSOD may provide for enhanced cellular function.

It was found that IL-1β is potently cytotoxic to the rat insulinoma cell line INS-1, while having minimal effects on the viability of a second insulinoma cell line RIN 1046-38 and its derivatives. The present invention also demonstrates that IL-1β is a more potent inducer of MnSOD expression in the RIN lines than in INS-1 cells. Finally, it is shown that stable, constitutive overexpression of MnSOD in INS-1 cells provides complete protection against IL-1β but not γ-IFN cytotoxicity, and that MnSOD expressing cells are protected against killing by activated human or rat peripheral blood lymphocytes. These results clearly demonstrate that MnSOD can play a protective role against cytokine killing, and suggest strategies for blocking or attenuating immunological destruction of engineered cell lines currently under development as islet surrogates for transplantation therapy of IDDM. The implication of such findings and methods and compositions for such therapy are discussed in further detail herein below.

In a particular embodiment, a preferred treatment for IDDM is an implantable, cell-based insulin delivery system that faithfully mimics the glucose-stimulated insulin secretion of the pancreatic β-cells. Though the treatment of diabetes mellitus through cellular medicine has been a therapeutic goal for over twenty years, it has not been applied in clinical settings. Several obstacles have hampered development of cell-based therapies for diabetes including immunological barriers in patients with IDDM, a shortage of implantable insulin-secreting cells, and a lack of manufacturing processes that can be validated to insure the safety and reproducibility of a cell based insulin delivery system. Development of immortalized cell lines that secrete insulin and of encapsulation devices that provide protection from immunological attack offers a potential solution to the obstacles that have hindered the developments and application of cell based insulin treatment for IDDM.

Despite the fact that encapsulation devices can afford protection from many aspects of immune-mediated destruction including those that are dependent on cell-cell contact between the host and the transplanted cells, host molecules with molecular weights of less than 100,000 daltons may cross a semi-permeable device. As most inflammatory cytokines have molecular masses of 30,000 to 50,000 daltons, these molecules will not be excluded by a semi-permeable device and could potentially have toxic effects on an encapsulated cellular implant (Kessler et al., 1996)

In a particular embodiment, the present invention relates to the production of superoxide dismutase species in a mammalian host cell system. A neuroendocrine cell-based system for either in vitro biologically active superoxide dismutase production, alone or in combination with insulin, or for in vivo cell-based delivery of biologically active superoxide dismutase alone or in combination with insulin, would provide an effective therapy in the treatment of diabetes, hypoglycemia and the restoration of β-cell function.

The present invention describes methods and compositions for generating superoxide dismutase from engineered eukaryotic cells. The methods and compositions described in this invention will be useful in the treatment and prophylaxis of pathogenic states resulting from the generation of free radicals in response to cytokines.

(ii) Other Factors Mediating iNOS Activity

As discussed above, damage to β-cells and β-cell lines has a correlation with high levels of NO. This is because NO reduces insulin secretion, thereby resulting in β-cell dysfunction; further, NO is cytotoxic and causes β-cell destruction.

In addition to the MnSOD studies discussed above, the inventors also have investigated the concept that the severe progressive functional and morphologic alterations of β cells at the onset of NIDDM in Zucker diabetic fatty (ZDF) rats (Lee et al., 1994; Unger, 1995) are entirely the consequence of interference by FFA (lipotoxicity) in the glucose metabolism of β cells. The possibility that some of the FFA-induced β cell changes, particularly the loss of β cell function that occurs late in the disease, are the result of excessive NO was examined.

NO has been shown to mediate IL-1β-induced impairment of β cell function (Corbett et al., 1992; Corbett and McDaniel, 1995; Eizirik et al., 1996; McDaniel et al., 1996), and ultimately cause β cell death (Kaneto et al., 1995). The present invention provides evidence that this mechanism is likely operative in the deterioration of β cells that occurs in obesity. Additionally, it provides in vitro and in vivo evidence that therapeutic strategies to reduce NO production in islets will be useful in preventing adipogenic NIDDM.

The present invention, for the first time, provides evidence that long-chain fatty acids influence pancreatic β-cells via the NO system. In other tissues, NO is thought to have a dual role, serving as a regulator under physiologic conditions (Moncada et al., 1991) and as a cytotoxin under pathophysiologic circumstances (Radons et al., 1994). As a physiologic regulator, NO mediates diverse functions in many organs (Moncada et al., 1991), including the cardiovascular, neuromuscular, neurological, genitourinary, gastrointestinal, and renal systems; in pancreatic islets, NO regulates islet blood flow (Svensson et al., 1994).

The constitutive forms of nitric oxide synthase, NOS I and III, have been identified in rat islets and in β-cell lines (Moncada et al., 1991), and iNOS (NOS II) has been induced in islets by IL-1β (Corbett et al., 1992; Corbett and McDaniel, 1995; Eizirik et al., 1996; McDaniel et al., 1996; Kaneto et al., 1995; Akabane, 1995). The induction of iNOS by IL-1β results in cytotoxicity (Corbett et al., 1992, Corbett and McDaniel, 1995; McDaniel et al., 1996; Kaneto et al., 1995). NO donors have been shown to cause both β-cell dysfunction and damage (Eizirik et al., 1996).

The present invention shows that the cytotoxic role of NO can be induced by FFA in islets of rats predisposed to NIDDM. FFA caused a reduction in both basal and glucose-stimulated insulin secretion in islets from lean fa/+ and obese prediabetic fa/fa ZDF rats in association with a greater than 20-fold FFA-induced increase in NO.

The addition of nicotinamide (NIC), an inhibitor of iNOS expression, prevents the induction of iNOS by FFA, reduces NO production, and prevents the FFA-induced decrease in insulin secretion in islets. Aminoguandine (AG), both a competitive inhibitor of iNOS and a suppressor of its expression (Corbett and McDaniel, 1996; Joshi et al., 1996), also prevents the decrease in insulin secretion in islets, as does NAME, a pure competitive inhibitor.

Thus, NO causes, or is required for, FFA-induced attenuation of insulin secretion in prediabetic rat islets. The relevance of the in vitro findings to clinical diabetes in vivo is supported by the fact that iNOS mRNA levels are 20 times higher in diabetic rats than in lean nondiabetic controls and that immunostainable iNOS could be detected in islets of diabetic obese ZDF rats but not in non-diabetic controls. The cellular source of iNOS and NO may well be the β-cells rather than macrophages. NO production by purified β-cells has been reported previously (Corbett et al., 1992) and iNOS expression in β-cells has been documented (Corbett and McDaniel, 1995). Moreover, there was no evidence of macrophages in pancreatic sections from ZDF rats, using two immunochemical stains specific for macrophages.

In these rats, plasma FFA are elevated and triacylglycerol (triglyceride) content of islets is increased. Further, there is evidence that intracellular FFA is high (Lee et al., 1994;

Unger, 1995). ZDF rats are leptin-resistant because of a Glu 269→Pro mutation in the leptin receptor (Phillips et al., 1996), and their islets have an increased capacity to esterify and a decreased capacity to oxidize FFA (Lee et al., 1997). This defect, which likely is related to the leptin resistance, somehow causes the greater induction of iNOS expression by FFA, perhaps by increasing intracellular levels of FFA. Although the mechanism by which FFA or high triacylglycerol increases iNOS expression and NO production in pancreatic islets is unknown, increased levels of diacylglycerol and/or ceramide are among the likely mediators of this mechanism.

NIC decreases plasma FFA levels and inhibits iNOS expression in obese prediabetic ZDF rats, while AG suppresses FFA-induced iNOS mRNA expression without lowering the high plasma FFA. This raises the possibility that clinical adipogenic NIDDM and its associated β-cell abnormalities (loss of glucose-stimulated insulin secretion, loss of GLUT-2, and a reduction in β-cell mass) might be prevented by treatment with agents that reduce the FFA levels and/or decrease FFA-mediated NO generation. Using the insights gained herein, the present invention provides approaches for preventing the β-cell changes and NIDDM associated with obesity.

Thus, like IL-1β, long-chain fatty acids (FFA) upregulate iNOS expression and enhance NO generation in rat islets, thereby suggesting a common pathway of β-cell failure. It is, therefore, likely that islet tissue lipopenia might protect β-cells against NO-mediated cytotoxicity. Indeed, as shown herein there is a striking relationship between islet triglyceride (TG) content and IL-1β-mediated NO production and cytotoxicity. Further, leptin and troglitazone, agents that lower islet TG content (Fulgencio et al., 1996; Shimabukuro et al., 1997a and 1997b), reduce IL-1β-induced NO production and cytotoxicity. The inventors therefore suggest that agents that decrease islet lipid content will likely be useful in the prevention of autoimmune diabetes. In further support of this aspect of the present invention, the inventors have shown (Example 15) that the increase of circulating FFA inhibits glucose induced β-cell proliferation suggesting that is this likely is a key factor in the reduction of the β-cell population during the evolution of type-II diabetes. Using the insights gained form the above observations, the present invention provides methods and compositions comprising agents that decrease islet content are disclosed. Also disclosed are methods and compositions for screening for additional agents that will decrease islet lipid content.

iNOS expression and nitrite production are upregulated in both immunogenic (IDDM) (Mandrup-Poulsen, 1996; McDaniel et al., 1996; Kröncke et al., 1991; Eizirik et al., 1996; Corbett and McDaniel 1992; Kleemann et al., 1993; Corbett et al., 1993; Lindsay et al., 1995) and adipogenic (NIDDM; Examples 8 through 11) diabetes. Agents that inhibit iNOS expression or nitrite production in vitro and in vivo, for example, nicotinamide and aminoguanidine, prevent β-cell abnormalities and hyperglycemia in both forms of diabetes (Corbett et al., 1993; Lindsay et al., 1995).

The inventors examined the possibility that islet TG content might influence the cytotoxic potency of IL-1β, a cytokine implicated in the pathogenesis of autoimmune diabetes (Mandrup-Poulsen, 1996; Bendtzen et al., 1986; McDaniel et al., 1996; Kröncke et al., 1991; Eizirik et al., 1996; Corbett and McDaniel 1992; Kleemann et al., 1993; Corbett et al., 1993; Lindsay et al., 1995; Shimabukuro et al., 1997a and 1997b). This premise is consistent with a recent report that obesity increases sensitivity to endotoxin-induced liver injury (Yang et al., 1997). The inventors suggest that lowering of lipid content to subnormal levels will confer a measure of protection against such damage.

The present invention demonstrates that the islets of obese ZDF rats are fat laden, while those of leptin-overexpressing rats are fat depleted. Normal rats pair-fed to the hyperleptinemic rats exhibit an islet TG content intermediate between the hyperleptinemic group and normal controls. A remarkable relationship between TG content of islets, NO generation, and cell viability was observed. NO production is minimal in islets of the hyperleptinemic rats and highest in those of the obese. Viability is maximal in the islets of hyperleptinemics and minimal in those of the obese rats.

These in vivo effects are also evident in vitro in cultured islets subjected to maneuvers that alter islet TG content. FFA increase islet TG content and NO production rises and viability declined. Troglitazone reduces TG content and NO production declines and viability improved. This was observed even in the islets of the obese ZDF rats, which are resistant to the lipopenic action of leptin because of the mutation in their leptin receptor (Phillips et al., 1996; Iida et al., 1996).

If an orally administered agent such as troglitazone lowers islet TG content in humans as it did in the rat islets herein, one could assess its co-administration with nicotinamide for the prevention of autoimmune diabetes without the use of immunosuppression. The striking reduction in nitrite production and improvement in cell viability associated with a decrease in islet TG content from normal to subnormal is consistent with the usefulness of this strategy. In addition, the leptin-like effects of troglitazone in lowering TG content provide a new mechanism for the treatment of adipogenic non-insulin-dependent diabetes.

The inventors postulate on the mechanism by which increased TG content induces iNOS expression. It is demonstrated herein that high levels of FFA induce iNOS, in addition, it has previously been speculated that intracellular FFA are required for formation of diacylglycerol and ceramide (Lee et al., 1997), both of which are believed to participate in the IL-1β signal cascade (Mandrup-Poulsen, 1996; McDaniel et al., 1996; Kleemann et al., 1993; Corbett et al., 1993). The inventors suggest that leptin-mediated depletion of TG in β-cells reduces diacylglycerol and ceramide formation and thus attenuates IL-1β-induced cytotoxicity.

B. Free Radical Generation in Islet β-Cells

A large body of evidence has accumulated in support of the idea that inflammatory cytokines have cytotoxic effects on islet β-cells (Mandrup-Poulsen, 1996; Rabinovitch, 1993; Corbett and McDaniel, 1992; Eizirik et al., 1996). In recent years, it also has become clear that susceptibility to cytokine effects varies among islets from different species, with rat islets being generally more prone to damage than mouse or human islets (Eizirik et al., 1994a; Eizirik et al. 1994b). Cytokines also have been reported to be cytotoxic to insulinoma cells, but almost all the work in this area has focused on the RINm5F cell line which lacks glucose-stimulated insulin secretion and has a very low insulin content (Halbanet et al., 1983).

It appears that pancreatic β-cell destruction in type 1 diabetes mellitus is the consequence of immune/inflammatory cell-mediated processes both in human subjects and in animal models (Barbosa and Bach, 1987; Boitard et al., 1982; Charlton et al. 1988; Wang et al., 1987). A variety of mononuclear cells such as T-lymphocytes, macrophages and natural killer cells have been implicated in β-cell destruction.

In particular, it was demonstrated by several groups that the cytokines interleukin-1β, tumor necrosis factor and interferon gamma acting either alone or in combination can impair insulin secretion and may be cytotoxic to islet cells in vitro. The cellular and molecular mechanisms responsible for mediating the effects of cytokines on β-cells however are unknown.

Among the various mechanisms proposed for the cell killing function of cytokines and other cytotoxic molecules, the generation of free radicals in the target cell has been implicated (Ruddle, 1987). Such a mechanism for cytokine mediated islet cell injury was first suggested by Mandrup-Poulsen et al. (1987). Cytotoxic cytokines relevant to the present invention are those that are directly proinflammatory and those that augment the immune response through stimulation of T cells, β-cells, macrophages, and natural killer cells. By way of example, such cytokines include but are not limited to, interleukin-1 beta (IL-1β), IL-1α, tumor necrosis factor alpha (TNF-α), tumor necrosis factor beta (TNF-β), gamma interferon (γ-IFN), interleukin-8 family (more than 30 members) interleukin-12, interleukin-6, IL-2, IL-3, IL-5, IL-7, IL-9, IL-13, IL-14, IL-17, granulocyte-macrophage colony stimulating factor or monocyte chemoattractant protein-1 (Nicolau, 1994; Dawson, 1991; Feldman, 1996; Yao et al., 1995)

In certain studies, it was shown that the deleterious effects of cytokines are related to the generation of the free radical nitric oxide (NO) (Southern et al., 1990; Welsh et al., 1991; Corbett et al., 1991). NO forms iron-nitrosyl complexes with enzymes containing FeS, like the Krebs cycle enzyme aconitase, leading to inhibition of the enzyme activity, decrease in glucose and amino acid metabolism and decrease in ATP generation. Further, it appears that in mouse islets IL-1β impairs insulin release parallel to NO generation (Eizirik et al., 1990; Eizirik, 1991; Welsh and Sandler 1992).

NO-mediated islet dysfunction and destruction induced by IL-1β appears to be reversible. Sequential studies in which islets were exposed to IL-1β for 18 h. and then treated with the NO synthase inhibitor $N^G$-monomethyl L-arginine (NMMA) showed that IL-1β induced inhibition of glucose stimulated insulin secretion is reversed in a time-dependent manner by NMMA (Corbett and McDaniel, 1994). Inhibition of NO synthase also restored IL-1β induced inhibition of mitochondrial aconitase activity in a time-dependent manner that mimics the recovery of glucose-stimulated insulin secretion in islet cells (Corbett and McDaniel, 1994). Other studies have shown that IL-1β impairment of insulin release in response to NO generation is not associated with impaired mitochondrial function or ATP generation (Eizirik et al., 1990; Eizirik, 1991; Welsh and Sandler 1992).

In studies designed to examine the biochemical events associated with cytokine mediated inhibition of growth, the effect of IL-1β on protein synthesis was examined by Masuda et al., (1988). IL-1β selectively and predominantly induced a 25 kDa polypeptide. Once purified it was determined that the amino acid sequence of this protein is identical to that of human manganese superoxide dismutase (MnSOD; SEQ ID NO: 2). It was suggested by Masuda et al., that the induction of MnSOD by IL-1 is a common biochemical event in IL-1-responsive cells.

The free radical generators, t-butylhydroperoxide (t-BHP) and alloxan, were shown to be highly cytotoxic to islet β-cells (Sumoski et al., 1989). This cytotoxicity can be significantly inhibited by the combination of free radical scavengers dimethylthiourea (DMTU) and citiolone, both of which are scavengers of •OH radicals. This free radical species is thought to be the most reactive and damaging of the oxygen-derived free radicals. In addition to scavenging •OH, citiolone has the ability to increase SOD activity in rat islet cells (Papaccio, 1991).

SOD catalyses the conversion of superoxide radicals ($O_2^{-•}$) to hydrogen peroxide ($H_2O_2$), thereby decreasing the amount of $O_2^{-•}$ available to form •OH. A few percent of the oxygen consumption in the body has been estimated to lead to the formation of these toxic reduction intermediates. The toxic effects of oxygen are mainly ascribable to the actions of these intermediates. Oxygen reacts slowly with most biochemical compounds. The toxic reactions are in general initiated by processes giving rise to oxygen radicals, which cause direct damage to biochemical compounds or start chain reactions involving oxygen.

Some compounds react spontaneously with oxygen, i.e. they autoxidize. Virtually all autoxidations result in the formation of toxic oxygen reduction intermediates. Autoxidation of adrenalin, pyrogallol and several other compounds leads to the formation of the superoxide radical. The superoxide radical is also released when methemoglobin is formed from oxyhemoglobin. Furthermore, some oxidases form superoxide. The most important of these enzymes is xanthine oxidase, which oxidizes hypoxanthine and xanthine to uric acid. A minor part of the oxygen reduction in mitochondria leads to the formation of superoxide and subsequently hydrogen peroxide. The microsomal cytochrome $P_{450}$ system also releases superoxide. When ionizing radiation passes through an aqueous solution containing oxygen, the superoxide radical is the radical formed in the highest concentration. Upon activation of phagocytosing leukocytes (polymorphonuclears, monocytes, macrophages, eosinophils) large amounts of superoxide are released. The toxic oxygen reduction products so formed are of fundamental importance for the killing ability of the cells, but might also lead to damage in the surrounding tissue.

Deleterious free radicals generated by cytokines include nitric oxide, peroxynitrite, superoxide, hydroxyl radicals and other reactive oxygen metabolite, hydrogen peroxide, peroxidized lipids, perhydroxyl radical, peroxide ion, oxene ion, oxide ion, oxidized nucleic acid, oxidized carbohydrate, lipid free radical, and oxidized protein. In adipogenic diabetes, the increase in lipids provides an increased source of oxidizable lipids for free radical generation. Organisms living in the presence of oxygen have been forced to develop a number of protective mechanisms against the toxic free radicals. The protective factors include superoxide dismutases (SOD) which dismutate the superoxide radical, and are found in relatively constant amounts in mammalian cells and tissue. The best known of these enzymes is CuZn SOD which is a dimer with a molecular weight of 33,000 Daltons containing two copper and two zinc atoms. CuZn SOD is found in the cytosol and in the intermembrane space of the mitochondria (Bannister et al. 1987; Hassan, 1988; Touati, 1988; Wong and Goeddel, 1988). Mn SOD is a tetramer with a molecular weight of 85,000 containing 4 Mn atoms, and is mainly located in the mitochondrial matrix. Expression of MnSOD is induced in a variety of cell types, including islet β-cells, in response to cytokines such as IL-1β and TNF-α (Wong and Goeddel, 1988; Masuda et al., 1988; Wong et al., 1989; Hakan Borg et al., 1992). Until recently, extracellular fluids were assumed to lack SOD-activity, however Marklund et al., have described the existence of an extracellular SOD that is a secreted protein and is different from CuZn SOD and MnSOD (U.S. Pat. No. 5,472,691).

Other protective factors include any antioxidizing agent whose presence will result in an increased antioxidizing activity that protects a selected cell against cytokine toxicity. "Antioxidizing agents" means any agent that either directly or indirectly reduces the amount of free radicals in the cell. Thus, apart from the superoxide dismutases listed above, a catalase, glutathione peroxidase, Bcl-2, Mcl-1 (Krajewski et al., 1995), α-melanocyte stimulating hormone, α-glycoprotein, a cytoprotective cytokine, DT-diaphorase, and epoxide hydrolase may prove effective. In a particular embodiment, interleukin-4 and interleukin-10 are contemplated to be useful as antioxidizing agents.

The inventors and others have actively been investigating the possibility that techniques of molecular engineering can be used to develop new insulinoma cell lines with well-differentiated properties, and that such cell lines could serve as surrogates for isolated islets in transplantation therapy of IDDM (reviewed in Bendtzen, 1988). An important component of such a strategy is to choose and develop cell lines that can be effectively protected from immune destruction when transplanted into individuals with IDDM. This may be so even when considering transplantation in the context of protective perm-selective membranes, since for some materials, graft rejection often occurs despite the fact that direct contact between cellular elements of the immune response and the transplanted tissue is prevented (Kessler et al., 1996).

In this regard, as discussed above, the inventors have demonstrated that IL-1β is potently cytotoxic to the rat insulinoma cell line INS-1, while having comparatively little effect on a second insulinoma cell line RIN 1046-38 and its derivatives. The inventors also demonstrated that IL-1β is a more potent inducer of MnSOD expression in the RIN lines than in INS-1 cells and that stable, constitutive overexpression of MnSOD in INS-1 cells provides complete protection against IL-1β but not γ-IFN cytotoxicity, and that MnSOD expressing cells are protected against killing by activated human or rat peripheral blood lymphocytes.

C. Compositions for Modulating Lipid Levels and iNOS Activity in Diabetes

In certain aspects of the present invention, it is suggested that formulations that decrease lipid content of cells will result in beneficial effects in that such modulation of lipid content will decreases iNOS expression and NO production in pancreatic islets. The present section describes various methods of achieving such a beneficial decrease in the cellular lipid content.

i) Leptin

In certain embodiments, it may be beneficial to contact cells or engineer cells to express and overexpress the adipocyte-associated protein known as leptin. Leptin is a peptide hormone that controls body composition through modulation of appetite and energy expenditure and is believed to do so, at least in part, via interaction with hypothalamic receptors that regulate food intake and body weight. The various isoforms of leptin receptor (Ob-R), including the long isoform (OB-Rb), are widely expressed in various tissues, suggesting that leptin may play an important role in actions on extraneural tissues as well.

Additional evidence that leptin has non-neural function comes from a report that extraordinary changes in body fat are seen in rats made chronically hyperleptinemic by treatment with an adenovirus vector expressing the leptin cDNA (Chen et al., 1996). In this report, rats lost all discernible body fat within 7 days of adenovirus infusion, while animals that were "pair-fed" at the same low rate of food intake as the hyperleptinemic animals retain more of their body fat. The magnitude and rapidity of the lipid depletion suggested the possibility of a direct "hormone-to-cell" action by leptin, in addition to effects cause through the sympathetic nervous system.

Chen et al. (1996) also examined the effects of leptin overexpression on plasma glucose, insulin, plasma triglycerides and free fatty acid levels. While glucose did not change, both plasma triglycerides and free fatty acids dropped by about 50% in adenoviral-leptin treated animals, when compared to controls (Ad-β-gal or saline). These studies now have been confirmed and extended with respect to phospholipids. No clear cut changes in phospholipid concentration was observed. However, using an in vitro system, it was established that reductions in triglyceride levels could be achieved in the absence of sympathetic nervous system effects. Studies performed to determine what pathways are involved in the triglyceride depletion indicated that leptin-induced triglyceride depletion involves a novel mechanisms by which triglyceride disappears through enhanced intracellular triglyceride metabolism, rather than through more traditional free fatty acid export pathways.

Insulin levels in adenovirus-leptin infected rats dropped even more dramatically than the fatty acids, being only about ⅓ of the amount seen in controls. As stated above, the glucose levels of these animals was normal, however. These findings are consistent with enhanced insulin sensitivity in treated animals. Pancreata were isolated from hyperleptinemic rats and examined for β-cell function and morphology. The most striking finding was the complete absence of insulin secretion in response to either glucose or arginine. The morphology appeared normal, and it was determined that insulin secretion could be reestablished following perfusion of pancreatic tissue in the presence of free fatty acids, thereby establishing an important role for these molecules in β-cell function. These studies also indicate that leptin-mediated reduction of elevated tissue lipid levels will improve β-cell function, reduce insulin resistance and help restore abnormal glucose homeostasis in obese individuals.

A further connection between diabetes and leptin comes from studies with genetically obese ZDF rats, which contain mutant OB-R genes. The islets of these animals become overloaded with fat at the time that hyperglycemia begins. Because maneuvers that reduce islet fat content prevent diabetes in ZDF rats, it has been proposed that the accumulation of triglycerides in islets plays a causal role in β-cell dysfunction. Thus, the predisposition to diabetes in homozygous ZDF rats may reflect the fact that their tissue have been completely "unleptinized" throughout their life and therefore have accumulated high levels of TG. In normal rats, this accumulation is prevented by the action of leptin. It is expected that any therapy that reduces triglycerides in islets and in the target tissues of insulin will improve β-cell function and reduce insulin resistance.

In hyperleptinemic rats, every tissue that was examined was lipopenic. Thus, it is speculated that normal non-adipocytes carry a minute quantity of triglyceride, perhaps to serve as a reserve source of fuel in adipocytes that are depleted of fat by starvation and become unable to meet the fuel needs of certain tissues. It is suspected that this triglyceride storage function is closely regulated by leptin. In the obese ZDF rats, this regulatory control is absent, and these putative intracellular triglycerides reserves soar to levels of over 1000-times that of hyperleptinemic rats.

In light of these observations, the present application therefore encompasses various engineered cells which express leptin in amounts in excess of normal. The methods by which leptin genes may be manipulated and introduced are much the same as for other genes included herein, such as amylin. A preferred embodiment would involve the use of a viral vector to deliver a leptin-encoding gene, for example, an adenoviral vector. This approach may be exploited in at least two ways. First, in the engineering of cells to produce certain polypeptides in vitro, it may be desirable to express high levels of leptin in order to downregulate various cellular functions, including synthesis of certain proteins. Similarly, leptin overexpression may synergize with cellular functions, resulting in the increased expression of an endogenous or exogenous polypeptide of interest.

Second, it may be desirable to use a leptin-overexpressing cell, or a leptin expression construct, such as a leptin-expressing adenovirus, in an in vivo context. This includes various "combination" approaches to the treatment of disease states such as obesity, hyperlipidemia and diabetes. For example, leptin expressing cell lines may provide for prolonged expression of leptin in vivo and for high level expression. Preliminary results indicate that injection of recombinantly produced leptin is less efficacious at achieving weight loss and reduction of lipids. Induction of hyperleptinemia using cells lines or expression constructs also may find use in reducing fat content in livestock just prior to slaughter. Moreover, because leptin-induced weight loss may act through different mechanisms than those currently employed, it may be possible to avoid related side effects such as diet-induced ketosis, heart attack and other diet-related symptoms. These regimens may involve combinations of other engineered cells, cells engineered with leptin and at least one other gene or genetic construct (knock-out, antisense, ribozyme, etc.), combination gene therapy or combination with a drug. The methods of delivering such pharmaceutical preparations are described elsewhere in this document As shown in the results presented herein, leptin reduced IL-1β-induced NO production and cytotoxicity. The inventors therefore suggest that the use of leptin and other agents that decrease islet lipid content will likely be useful in the treatment and/or prevention of both type 1 and type 2 diabetes.

ii) Troglitazone

Out of the many drugs available for the treatment of diabetic ailments, the thiazolidinedione derivatives are very prominent and are considered effective constituents working through a different mechanism than the other class of commonly used anti-diabetic agents, the sulfonylureas. Troglitazone (5-[[4-[3(3,4-dihydro-6-hydroxy-2,5,7,8-tetramethyl-2H-1-benzopyran-2-yl)methoxy]phenyl]methyl]2,4-thiazolidinedione), is one such thiazolidinedione, which exhibits euglycemic effect, was reported first in 1983 by Sankyo Co. Ltd., Japan (Japanese Patent No. 60-051189/Australian Patent No. 570067) and has created interest in the field ever since.

Pharmaceutical troglitazone is known as Rezulin™ and is sold as an oral antihyperglycemic agent which acts primarily by decreasing insulin resistance, and is used in the management of type II diabetes (NIDDM). It improves sensitivity to insulin in muscle and adipose tissue and inhibits hepatic gluconeogenesis. Troglitazone is not chemically or functionally related to either the sulfonylureas, the biguanides, or the α-glucosidase inhibitors.

Troglitazone is a white to yellowish crystalline compound; it may have a faint, characteristic odor. Troglitazone has a molecular formula of $C_{24}H_{27}NO_5S$ and a molecular weight of 441.55 daltons. It is soluble in N,N-dimethylformamide or acetone; sparingly soluble in ethyl acetate; slightly soluble in acetonitrile, anhydrous ethanol, or ether; and practically insoluble in water.

Troglitazone is available as 200 and 400 mg tablets for oral administration formulated with the following excipients: croscarmellose sodium, hydroxypropyl methylcellulose, magnesium stearate, microcrystalline cellulose, polyethylene glycol 400, polysorbate 80, povidone, purified water, silicon dioxide, titanium dioxide, and synthetic iron oxides.

Troglitazone is a thiazolidinedione antidiabetic agent that lowers blood glucose by improving target cell response to insulin. It has a unique mechanism of action that is dependent on the presence of insulin for activity. Troglitazone decreases hepatic glucose output and increases insulin-dependent glucose disposal in skeletal muscle. Its mechanisms of action is thought to involve binding to nuclear receptors (peroxisome proliferator-activated receptor, PPAR) that regulate the transcription of a number of insulin responsive genes critical for the control of glucose and lipid metabolism. Unlike sulfonylureas, troglitazone is not an insulin secretagogue.

In animal models of diabetes, troglitazone reduces the hyperglycemia, hyperinsulinemia, and hypertriglyceridemia characteristic of insulin-resistant states such as type II diabetes. Plasma lactate and ketone body formation are also decreased. The metabolic changes produced by troglitazone result from the increased responsiveness of insulin-dependent tissues and are observed in numerous animal models of insulin resistance. Treatment with troglitazone did not affect pancreatic weight, islet number or glucagon content, but did increase regranulation of the pancreatic beta cells in rodent models of insulin resistance.

Since troglitazone enhances the effects of circulating insulin (by decreasing insulin resistance), it does not lower blood glucose in animal models that lack endogenous insulin.

Maximum plasma concentration (Cmax) and the area under plasma concentration-time curve (AUC) of troglitazone increase proportionally with increasing doses over the dose range of 200 to 600 mg/day. Following daily drug administration, steady-state plasma concentrations of troglitazone are reached within 3 to 5 days. Thus, the present invention contemplates the use of troglitazone doses including but not limited to 100 mg/day, 150 mg/day, 200 mg/day, 300 mg/day, 400 mg/day, 500 mg/day, 600 mg/day, 700 mg/day.

Clinical studies demonstrate that troglitazone improves insulin sensitivity in insulin-resistant patients. Troglitazone increases insulin-dependent glucose disposal, reduces hepatic gluconeogenesis, and enhances cellular responsiveness to insulin and thus, improves dysfunctional glucose homeostasis. In patients with type II diabetes, the decreased insulin resistance produced by Troglitazone causes decreases in serum glucose, plasma insulin, and hemoglobin $A_{1C}$. These effects are independent of weight loss and persist with troglitazone treatment.

Following troglitazone treatment, LDL, HDL, and total cholesterol (total-C) increase, although total-C/HDL and LDL/HDL ratios do not change. The increase in total cholesterol is due to the increase in HDL and LDL cholesterol. Despite the observed increase in total and LDL cholesterol, ApoB fraction levels are not increased. Patients treated with troglitazone and concomitant insulin exhibit an initial reduction in triglyceride levels. With the reduction in insulin doses that may occur following Troglitazone therapy, some attenuation of the triglyceride reduction may occur.

Troglitazone has only been shown to exert its antihyperglycemic effect in the presence of insulin. Because troglitazone does not stimulate insulin secretion, hypoglycemia in patients treated with troglitazone alone is not to be expected.

Thus, troglitazone is considered one of the most effective antidiabetic drugs available today. It has a multipurpose activity not only acting on diabetes itself but also on the reduction of the triglycerides and also on the accompanying complications, such as, cataract, neuropathy, retinopathy etc. (which are usually the chronic ailments accompanied by diabetes). Indeed, troglitazone is emerging as the first drug candidate of englycemic class of antidiabetic agents. The present invention contemplates the use of troglitazone in order to reduce the triglyceride content of cells and to ameliorate diabetic ailments. Other troglitazone derivatives, for example those disclosed in U.S. Pat. No. 5,700,820, have been shown to have enhanced anti-diabetic effects as compared to the native troglitazone structure. In as much as these compounds will also be useful in the present invention, U.S. Pat. No. 5,700,820, is specifically incorporated herein by reference.

iii) Nitric Oxide Synthase Inhibitors

Aminoguanidine is a known inhibitor of NO formation. The skilled artisan is referred to U.S. Pat. No. 5,108,930 (specifically incorporated herein by reference) for discussions regarding the nitric oxide formation inhibiting capacity of aminoguanidine and its use in a warm blooded mammals. Aminoguanidine analogues as described in U.S. Pat. No. 4,889,935 (specifically incorporated herein by reference) also may prove useful as NO production inhibitory agents.

U.S. Pat. No. 5,585,402 (specifically incorporated herein by reference) discusses a method for inhibiting tissue damage in mammals caused by pathological NO production, by administering a NO synthase inhibitor, preferably L-NMMA. U.S. Pat. No. 5,585,402 describes doses and routes of administration for L-NMMA.

iv) Inhibition of Fatty Acid Synthesis

FFA also have been shown herein to mediate the iNOS related destruction of β-cells. Thus, the inventors suggest that decreasing the level of FFA in the islet cells will be beneficial in the prevention or treatment of obesity and NIDDM. Decreasing the level of fatty acids in the islet cells may be achieved by an inhibition of fatty acid synthesis, inhibiting FFA uptake by the islet cells and/or increasing fatty acid degradation.

Triacsin A and triacsin C are naturally occurring potent inhibitors of fatty acyl CoA synthase (Tomada et al., 1987). These and other inhibitors of fatty acid synthesis (FAS) are described and discussed in U.S. Pat. No. 5,614,551 (specifically incorporates herein by reference). The compositions and formulations described therein are used as therapeutics, as such the entire document is incorporated herein to provide description of the use of such compositions and formulations as therapeutic in obesity and NIDDM.

U.S. Pat. No. 5,539,132 describes another group of compounds known as cerulenins which are commonly used as inhibitors of fatty acid synthesis. These compounds are also contemplated to be useful in the present invention. While these are just exemplary inhibitor of FAS it is contemplated that any agent that inhibits the synthesis, uptake or accumulation of free fatty acids in cells will be useful herein. Likewise any agent that increases the degradation of free fatty acids will also be useful.

D. Cells

Secretory cells, especially neuroendocrine cells, have several endogenous functions that make them uniquely suited for production of a wide range of proteins, including secreted peptide hormones. These specialized functions include the regulated secretory pathway. The regulated secretory pathway embodies the secretory granules of neuroendocrine cells which serve as the site of maturation and storage of a large class of peptide hormones with profound biological functions. Proper biological function of the peptides is due both to their secretion in a regulated and titratable manner, as well as a complex set of post-translational modifications resulting in the final biologically active product. As a result, these cells can be used in vitro to produce large amounts of proteins, in vivo to supply therapeutic proteins, or in vivo to immunize hosts, for example, in the production of monoclonal antibodies.

The present invention is designed to take advantage of cell based production of proteins for the purpose of producing superoxide dismutase to combat the cytotoxicity of cytokines. A variety of different modifications may be made to increase the efficiency of the cell, one example is the blocking of production of an endogenous protein in the host cell. This will, in essence, "make room" for the heterologous protein and, hence, avoid competition between the endogenous and heterologous proteins during synthesis. The components for such a system, and methods of producing proteins therewith, are set forth in detail below.

Engineering of cells to synthesize proteins for either in vitro large scale production, or for in vivo cell-based delivery, will advantageously make use of many attributes of these cells. Regulated secretory cells present a natural bioreactor containing specialized enzymes involved in the processing and maturation of secreted proteins. These processing enzymes include endoproteases (Steiner et al., 1992) and carboxypeptidases (Fricker, 1988) for the cleavage of pro-hormones to hormones and PAM, an enzyme catalyzing the amidation of a number of peptide hormones (Eipper et al., 1992a). Similarly, maturation and folding of peptide hormones is performed in a controlled, stepwise manner with defined parameters including pH, calcium and redox states.

Complete processing requires sufficient levels of the processing enzymes as well as sufficient retention of the maturing peptides. In this way, physiological signals leading to the release of the contents of the secretory granules ensures release of fully processed, active proteins. This is important for both maximum production for in vitro purposes and for the possible use of cells for in vivo purposes.

All cells secrete proteins through a constitutive, non-regulated secretory pathway. A subset of cells are able to secrete proteins through a specialized regulated secretory pathway. Proteins destined for secretion by either mechanism are targeted to the endoplasmic reticulum and pass through the Golgi apparatus. Constitutively secreted proteins pass directly from the Golgi to the plasma membrane in vesicles, fusing and releasing the contents constitutively without the need for external stimuli. In cells with a regulated pathway, proteins leave the Golgi and concentrate in storage vesicles or secretory granules. Release of the proteins from secretory granules is regulated, requiring an external stimuli. This external stimuli, defined as a secretagogue, can vary depending on cell type, optimal concentration of secretagogue, and dynamics of secretion. Proteins can be stored in secretory granules in their final processed form for long periods of time. In this way a large intracellular pool of mature secretory product exists which can be released quickly upon secretogogue stimulation.

A cell specialized for secreting proteins via a regulated pathway can also secrete proteins via the constitutive secretory pathway. Many cell types secrete proteins by the constitutive pathway with little or no secretion through a regulated pathway. As used herein, "secretory cell" defines cells specialized for regulated secretion, and excludes cells that are not specialized for regulated secretion. The regulated secretory pathway is found in secretory cell types such as endocrine, exocrine, neuronal, some gastrointestinal tract cells and other cells of the diffuse endocrine system.

(i) Glucose Responsive Cells.

For delivery of some peptide hormones or factors, it may be desirable to cause the polypeptide to be released from cells in response to changes in the circulating glucose concentration. The most obvious example of a secretory cell type that is regulated in this fashion is the β-cell of the pancreatic islets of Langerhans, which releases insulin in response to changes in the blood glucose concentration.

Engineering of primary β-cells for production of products other than insulin is not practical. Instead, a preferred vehicle may be one of the several cell lines derived from islet β-cells that have emerged over the past two decades. While early lines were derived from radiation- or virus-induced tumors (Gazdar et al., 1980, Santerre et al., 1981), more recent work has centered on the application of transgenic technology (Efrat et al., 1988, Miyazaki et al., 1990). A general approach taken with the latter technique is to express an oncogene, most often SV40 T-antigen, under control of the insulin promoter in transgenic animals, thereby generating β-cell tumors that can be used for propagating insulinoma cell lines (Efrat et al., 1988, Miyazaki et al., 1990).

While insulinoma lines provide an advantage in that they can be grown in essentially unlimited quantity at relatively low cost, most exhibit differences in their glucose-stimulated insulin secretory response relative to normal islets. These differences can be quite profound, such as in the case of RINm5F cells, which were derived from a radiation-induced insulinoma and which in their current form are completely lacking in any acute glucose-stimulated insulin secretion response (Halban et al., 1983). RIN 1046-38 cells are also derived from a radiation-induced insulinoma but can be shown to be glucose responsive when studied at low passage numbers (Clark et al., 1990). This response is maximal at subphysiological glucose concentrations and is lost entirely when these cells are cultured for more than 40 passages (Clark et al., 1990). GLUT-2 and glucokinase are expressed in low passage RIN 1046-38 cells but are gradually diminished with time in culture in synchrony with the loss of glucose-stimulated insulin release (Ferber et al., 1994). Restoration of GLUT-2 and glucokinase expression in RIN 1046-38 cells by stable transfection restores glucose-stimulated insulin secretion (Ferber et al., 1994), and the use of these genes as a general tool for engineering of glucose sensing has been described in a previously issued patent (Newgard, U.S. Pat. No. 5,427,940). RIN 1046-38 cells transfected with the GLUT-2 gene alone are maximally glucose responsive at low concentrations of the sugar (approximately 50 µM), but the threshold for response can be shifted by preincubating the cells with 2-deoxyglucose, which when converted to 2-deoxyglucose-6-phosphate inside the cell serves as an inhibitor of low $K_m$ hexokinase, but not glucose activity (Ferber et al., 1994).

Recently, Asafari et al. have reported on the isolation of a new insulinoma cell line called INS-1 that retains many of the characteristics of the differentiated β-cell, most notably a relatively high insulin content and a glucose-stimulated insulin secretion response that occurs over the physiological range (Asafari et al., 1992). This line was isolated by propagating cells freshly dispersed from an X-ray induced insulinoma tumor in media containing 2-mercaptoethanol. Consistent with the finding of physiological glucose responsiveness, a recent report indicates that INS-1 cells express GLUT-2 and glucokinase as their predominant glucose transporter and glucose phosphorylating enzyme, respectively (Marie et al., 1993). INS-1 cells grow very slowly and require 2-mercaptoethanol. It remains to be determined whether glucose responsiveness and expression of GLUT-2 and glucokinase are retained with prolonged culturing of these cells.

Cell lines derived by transgenic expression of T-antigen in β-cells (generally termed βTC cells) also exhibit variable phenotypes (Efrat et al., 1988, Miyazaki et al., 1990, Whitesell et al., 1991 and Efrat et al., 1993). Some lines have little glucose-stimulated insulin release or exhibit maximal responses at subphysiological glucose concentrations (Efrat et al., 1988, Miyazaki et al., 1990, Whitesell et al., 1991), while others respond to glucose concentrations over the physiological range (Miyazaki et al., 1990 and Efrat et al., 1993). It appears that the near-normal responsiveness of the latter cell lines is not permanent, since further time in culture results in a shift in glucose dose response such that the cells secrete insulin at subphysiological glucose concentrations (Efrat et al., 1993). In some cases, these changes have been correlated with changes in the expression of glucose transporters and glucose-phosphorylating enzymes.

Miyazaki et al. isolated two classes of clones from transgenic animals expressing an insulin promoter/T-antigen construct. Glucose-unresponsive lines such as MIN-7 were found to express GLUT-1 rather than GLUT-2 as their major glucose transporter isoform, while MIN-6 cells were found to express GLUT-2 and to exhibit normal glucose-stimulated insulin secretion (Miyazaki et al., 1990). More recently, Efrat and coworkers demonstrated that their cell line βTC-6, which exhibits a glucose-stimulated insulin secretion response that resembles that of the islet in magnitude and concentration dependence, expressed GLUT-2 and contained a glucokinase:hexokinase activity ratio similar to that of the normal islet (Efrat et al., 1993). With time in culture, glucose-stimulated insulin release became maximal at low, subphysiological glucose concentrations. GLUT-2 expression did not change with time in culture, and glucokinase activity actually increased slightly, but the major change was a large (approximately 6-fold) increase in hexokinase expression (Efrat et al., 1993). Furthermore, overexpression of hexokinase I, but not GLUT-1, in well-differentiated MIN-6 cells results in both increased glucose metabolism and insulin release at subphysiological glucose concentrations. Similar results have been obtained upon overexpression of hexokinase I in normal rat islets (Becker et al., 1994). These results are all consistent with the observations of Ferber, et al. described above in showing that a high hexokinase:glucokinase ratio will cause insulin-secreting cells to respond to glucose concentrations less than those required to stimulate the normal β-cell.

(ii) Non-glucose Responsive Cells

An alternative to insulinoma cell lines are non-islet cell lines of neuroendocrine origin that are engineered for insulin expression. The foremost example of this is the AtT-20 cell, which is derived from ACTH secreting cells of the anterior pituitary. A decade ago, Moore et al. demonstrated that stable transfection of AtT-20 cells with a construct in which a viral promoter is used to direct expression of the human proinsulin cDNA resulted in cell lines that secreted the correctly processed and mature insulin polypeptide (Moore et al., 1983). Insulin secretion from such lines (generally termed AtT-20ins) can be stimulated by agents such as forskolin or dibutyryl cAMP, with the major secreted product in the form of mature insulin. This suggests that these cells contain a regulated secretory pathway that is similar to that operative in the islet β-cell (Moore et al., 1983, Gross et al., 1989). More recently, it has become clear that the endopeptidases that process proinsulin to insulin in the islet β-cell, termed PC2 and PC3, are also expressed in AtT-20ins cells (Smeekens and Steiner., 1990, Hakes et al., 1991). AtT-20ins cells do not respond to glucose as a secretagogue (Hughes et al., 1991). Interestingly, AtT-20 cells express the glucokinase gene (Hughes et al., 1991, Liang et al., 1991) and at least in some lines, low levels of glucokinase activity (Hughes et al., 1991 and 1992, Quaade et al., 1991), but are completely lacking in GLUT-2 expression (Hughes et al., 1991 and 1992). Stable transfection of these cells with GLUT-2, but not the related transporter GLUT-1, confers glucose-stimulated insulin secretion, albeit with maximal responsiveness at subphysiological glucose levels, probably because of a non-optimal hexokinase:glucokinase ratio (Hughes et al., 1992, 1993).

The studies with AtT-20ins cells are important because they demonstrate that neuroendocrine cell lines that normally lack glucose-stimulated peptide release may be engineered for this function. Other cell lines that are characterized as neuroendocrine, but lacking in endogenous glucose response include PC12, a neuronal cell line (ATCC CRL 1721) and GH3, an anterior pituitary cell line that secretes growth hormone (ATCC CCL82.1). It is not possible to determine whether such cell lines will gain glucose responsiveness by engineering similar to that described for the AtT-20ins cell system without performing the studies. However, these lines do exhibit other properties important for this invention such as a regulated secretory pathway, expression of endopeptidases required for processing of prohormones to their mature hormone products, and post-translational modification enzymes. In sum, all neuroendocrine cell lines are useful for the essential aspect of this invention, which is the production of heterologous products in a cell line for use in treating cytokine-mediated cell distress. In particular embodiments, the cell used herein may be a cell that is cytokine-resistant. Such a cytokine-resistant cell may be one which possesses high levels and/or activities of antioxidizing proteins. Some or all of these lines will also be useful for glucose-regulated product delivery, using the methods described in U.S. Pat. No. 5,427,940 to generate such responsiveness.

(iii) Stable Human Secretory Cells

In particular embodiments, the present invention uses stable human secretory cells by transforming a secretory cell such that it is immortalized and retains its phenotype through numerous cell culture passages. The final attributes of such cell lines of the present invention are functionally defined as having maintained a regulated secretory pathway, being stable to in vitro culture and, preferably, as being amenable to further engineering. The present section describes the cells that may be used in the present invention.

The human secretory or neuroendocrine cell will be "culturable," i.e. it will be capable of growing in vitro and producing the desired endogenous secretory polypeptide with a demonstrated regulated secretory pathway. A "stable, transformed" human regulated secretory cell in the context of the present invention will be a cell that exhibits in vitro growth for at least twenty population doublings. The resultant human regulated secretory cell also will maintain the required differentiated phenotype after transformation, i.e. it will exhibit the phenotypic properties of a demonstrable regulated secretory pathway, secretory storage granules, the capacity for peptide processing, and will produce the selected endogenous secretory polypeptide.

In particular embodiments, the stable human secretory cell is a β-cell. The human β-cells of the present invention will exhibit the capacity to grow in vitro, with a minimum of at least about 20 population doublings, or preferably, of about 30, about 40, about 50, about 60, about 70, or about 80 population doublings. Even more preferably, the resultant human β-cells of the invention will have even further increments of population doublings up to and including a completely transformed state wherein the cells grow in perpetuity.

The human β-cells of the present invention will also exhibit the capacity to produce biologically active human insulin. The insulin produced may be comprised entirely of mature insulin; or entirely of the biological precursor of mature insulin, termed proinsulin; or of all possible mixtures of proinsulin, insulin, and processing intermediates that are produced in the course of conversion of proinsulin to insulin. While the preferred embodiment of the present invention are cells that produce primarily or exclusively mature insulin, cells that produce proinsulin will also be useful in various embodiments. Such cells are useful per se, particularly as any form of insulin can be obtained in vitro, purified and converted to mature insulin. Furthermore, insulin is an exemplary secretory protein, the stable human neuroendocrine cell line may be engineered to express a variety of secretory proteins for the purposes of identifying specific modulators of secretory function.

Cells that produce primarily or exclusively immature insulin are also useful in that the capacity to produce mature insulin can be re-engineered into the cells themselves, in which instances the stable cells can then be used in vivo. By way of example only, proteases known as PC2 and PC3 that are responsible for the conversion of proinsulin to insulin can be introduced into the stable human β cells by genetic engineering methods, thereby enhancing the efficiency of conversion of proinsulin to insulin.

The stable human β cells of the present invention will generally exhibit a minimal insulin content of about 5 ng/million cells, but may contain as much as, or even more insulin than, normal isolated human islets, which have approximately 1–10 μg/million cells. It will be understood that the cells of the present invention may contain any amount of insulin within the above-specified ranges, such as about 10 ng insulin/million cells, about 50 ng, about 100 ng, about 200 ng, about 500 ng, about 1000 ng (1 μg), about 2 μg, about 5 μg, about 10 μg, about 20 μg, about 50 μg, about 75 μg, up to and including about 100 μg insulin/million cells. It will be understood that any and all integers within these ranges will define an insulin content that may be present within the stable human β cells of the invention.

In further preferred embodiments, the human β cells of the present invention may be defined as cells having an insulin content of between about 10%, about 20%, about 30%, about 40%, about 50%, about 60%, about 70%, about 80%, about 90%, up to and including about 100% of normal human islet content, which is about 1–10 μg/million cells.

The human β cells of the present invention will preferably exhibit enhanced insulin secretion when exposed to one or more secretagogues selected from IBMX, carbachol, amino acids, and glucose, or when exposed to a secretory "cocktail" of such compounds. The human β cells will more preferably exhibit enhanced insulin secretion when exposed to glucose, and will most preferably exhibit enhanced insulin secretion when exposed to 10 mM glucose.

The increase in insulin secretion in response to a non-glucose secretagogue or cocktail thereof should be at least about 1.1 times or about 1.5 times that observed in cells incubated in the absence of the secretagogue or secretory cocktail. However, in preferred embodiments, the increase in insulin secretion in response to a non-glucose secretagogue or cocktail thereof should be at least about double that observed in cells incubated in the absence of the secretagogue or secretory cocktail. In more preferred embodiments, a higher increase will be observed, up to and including a 3-fold, 5-fold, 10-fold, 20-fold, 50-fold, 100-fold, 200-fold, 300-fold, 500-fold, 750-fold or even about a 1000-fold enhancement.

The human β-cells of the present invention will preferably exhibit a glucose-stimulated insulin secretion (GSIS) response. This increase in secretion should be at least about 1.1 times or about 1.5 times that observed in cells incubated in the absence of glucose. More preferred are increases in secretion of at least about double that observed in cells incubated in the absence of glucose, with even more preferred increases being higher, up to and including a 3-fold, 5-fold, 10-fold, 20-fold, 50-fold, 100-fold, 200-fold, 300-fold, 500-fold, 750-fold or even about a 1000-fold enhancement, including all increments therebetween.

In preferred embodiments, glucose responsive insulin secretion will be observed in the range of 1.0 to 20 mM glucose. GSIS response will more preferably occur with a threshold for response of 3–5 mM glucose, with maximal secretion stimulated by 10–20 mM glucose, as occurs in normal human islets. Cell lines with glucose dose responses occurring over a higher or lower range will also have significant utility, given that any regulated insulin production will be useful.

Many secretory cells have a GSIS response not originally in the range observed for normal human islets will still be useful as such cells will be amenable to genetic engineering methods, as embodied in U.S. Pat. No. 5,427,940, and as further disclosed herein, in order to alter the glucose dose response. These methods are contemplated for use in applications with stable human cells to achieve the desired glucose concentration dependence. Furthermore, as stated, human β cells that are completely lacking glucose responsiveness are also included within the invention, since the known genetic engineering methods (U.S. Pat. No. 5,427,940) can be used to confer glucose sensing in neuroendocrine cell lines previously lacking a glucose response.

a. Starting Cells

Primary human neuroendocrine secretory cells are immortalized as described in further detail elsewhere in the specification. The present section is directed to describing the starting cells that may be further engineered for the purposes of the present invention.

Fetal Cells. Human fetal pancreases at 18 to 24 gestational wk can be obtained through nonprofit organ procurement centers, with patient consent for tissue donation being obtained. Dissection of specific organs from the fetuses is often done at the procurement centers. Isolation of fetal pancreases and islets is performed by established techniques (Otonkoski et al., 1993; incorporated herein by reference).

Cells from Primary Human Tissues. Human organs can be obtained from autopsies through nonprofit organ procurement centers. High quality human islets are available, for example, from Dr. Camillo Ricordi of the University of Miami Medical Center, an islet transplant surgeon who supplies human islets to scientists throughout the United States. Automated methods for isolation of human pancreatic islets have been established (Ricordi et al., 1988; incorporated herein by reference).

Cells from Resected Neuroendocrine Tumors. Explanted tumor samples from surgically resected tumors are another preferred starting material. More preferred are insulinomas and pituitary tumors. Two exemplary insulinomas have been reported (Gueli et al., 1987; Cavallo et al., 1992). Although none of the described human "insulinomas" actually have the properties required to be properly described as stable human β cells, the techniques of the present invention are still suitable for use with such cell populations as starting materials in order to procure a pure population of stable, human insulin-producing cells from the mixture of cells currently available.

Human Neuroendocrine Cell Lines. It will be understood that tumor cell lines and insulinomas arising from explants of resected neuroendocrine tumors are not necessarily, by definition, stable cells; some such cells maintain a differentiated phenotype for two, four or about six months at the maximum. However, such cells are intended for use as starting materials in the present invention.

Other Neuroendocrine Cell Types. Table 1 shown below (Pearse and Takor, 1979; Nylen and Becker, 1995), while not a complete list, is exemplary of the types of cells contemplated for use in the present invention. β cells, α-cells and pituitary cells are preferred for use in the present invention, with β cells being more preferred. Additional cell types useful in the present invention will be readily known to those of skill in the art.

TABLE 1

Neuroendocrine Cell Types

| Neuroendocrine cell | Endogenous hormone | Tissue specific promoter | Context specific promoter | Associated Tumors |
| --- | --- | --- | --- | --- |
| Hypothalamic/pituitary cells | | | | |
| Coticotropes | ACTH,LPH | | POMC (V01510, K02406) | Corticotrope adenoma |
| Somatotropes | Growth Hormone | Growth Hormone (J03071, K00470) | | GH producing adenoma |
| Melanotropes | alpha-MSH, endorphins | | POMC (V01510, K02406) | |
| Lactotropes | Prolactin | Prolactin (X00368, L33865) | | Prolactin adenomas |
| Thyrotropes | Thyroid-stimulating hormone | TSH (M23669, S70587) | | Thyrotrope adenomas |
| Gonadotropes | Follicle Stimulating hormone Luteinizing hormone | FSH (M16646), LH (X00264) | | Gonadotrope adenoma |

TABLE 1-continued

Neuroendocrine Cell Types

| Neuroendocrine cell | Endogenous hormone | Tissue specific promoter | Context specific promoter | Associated Tumors |
|---|---|---|---|---|
| Adrenal medulla | enkephalins, dynorphin NPY, bombesin | NPY (M14296) | | |
| Thyroid C Cell | Calcitonin, CGRP, Somatostatin, Bombesin | | Calcitonin (X15943), Somatostatin (J00306) | Thyroid carcinomas |
| Parathyroid Chief Cells | Parathyroid hormone | Parathyroid hormone (J00301) | | parathyroid adenomas |
| Pulmonary neuroendocrine cells/ K cells | Calcitonin, Bombesin, CGRP, cholecystokinin, endothelin | | Calcitonin (X15943) | Small Cell Lung Carcinoma |
| Gastric G cells | Gastrin, enkephalin | | Gastrin (X00183) | Gastrinoma |
| Gastric D cells | Somatostatin | | Somatostatin (J00306) | Somatostatinoma |
| Enteroneuroendocrine cell types | | | | |
| L cells | Glucagon Family peptides Peptide YY | Peptide YY (L25648, D13897) | Glucagon (X03991) | Glucagonoma |
| D cells | Somatostatin | | Somatostatin (J00306) | Somatostatinoma |
| S cells | Secretin | Secretin | | |
| G cells | Gastrin | | Gastrin (X00183) | Gastrinoma |
| K cells | GIP | GIP (M31674) | | |
| I cells | CCK | CCK (L29399, M15843, N00050) | | Enteroneurocrinomas |
| N cells | Neurotensin | Neurotensin (S47339) | | Neurotensinoma |
| H cells | VIP | | VIP (M33027, M37460) | VIPomas |
| Enterochromafin cells | Motilin, Substance P, Substance K | Motilin (X15392, Y07505, M30277) | Substance P (M68906) | Carcinoid tumors |
| Pancreatic Cells | | | | |
| β cells | Insulin, amylin | Insulin (V00565), amylin (L08226) | | Insulinoma |
| α cells | Glucagon, Corticotropin releasing hormone | Glucagon (X03991), Corticotropin releasing hormone (X55962) | Glucagon (X03991), | Glucagonoma |
| PP cells | Pancreatic polypeptide | Pancreatic polypeptide (M11726) | | PPoma |
| δ cells | Somatostatin | | Somatostatin (J00306) | Somatostatinoma |
| G cells | Gastrin | | Gastrin (X00183) | Gastrinoma |
| Carotid I cell | Substance P, enkephalin | | Substance P (M68906) | Carcinoid tumors |
| Urigenital tract Merkel cells | Calcitonin, bombesin, VIP | VIP (M33027, M37460) | VIP (M33027, M37460) | VIPomas |
| syncytiotrophoblast cell | chorionic-gonadotropin | chorionic-gonadotropin (M13504) | | Trophoblast tumors |
| Neurons | | | | |
| Supraoptic and paraventricular nuclei | Vasopressin, oxytocin | Vasopressin (X62890), oxytocin (M11186) | | |
| Sympathetic ganglion | VIP, enkephalin | | VIP (M33027, M37460) | VIPomas |
| Paraganglia | enkephalin | | | |

In addition to β cells, pituitary cells are preferred for use with this invention. In general, pituitary cells may allow for higher efficiency of transformation as culture conditions have been reported for promoting the proliferation of rodent pituitary cells in vitro (Nicol et al., 1990). The inventors contemplate establishing similar conditions for human pituitary cells which will allow for retroviral infection and provide a means for efficiently introducing transforming genes.

Cells from the intermediate lobe may have an advantage for use in cell-based therapies of IDDM as there is a suggestion that this cell type can survive and sustain secretory function in autoimmune disease. These cells would therefore be useful in providing an indication of the effects of the modulators in vivo, as these cells would be less prone to attack from the host. The POMC promoter was used to drive expression of insulin in the cells of the intermediate lobe of transgenic nonobese diabetic (NOD) mice. Such cells were resistant to autoimmune-dependent destruction even when implanted next to islets in which β cells were destroyed during the course of the disease (Lipes et al., 1996).

TABLE 2

Evaluation and Engineering of Human Cell Lines

| βG ID | NCI/ATCC | Origin | NEprofile PEP+/− | SELEC AB^{S/R} | TG+/− | NuTum Grow+/− | AlgBeads vitro | AlgBeads vivo |
|---|---|---|---|---|---|---|---|---|
| H01 | H716/CCL-251 | Colon | PAM+, SYN+, PC1/PC3+, PC2−, VIM+ | G^S, H^S, O^S | − | − | − | NT |
| H02 | NA/CRL-1803 | Thyroid | PAM+, SYN+, PC1/PC3+, PC2+, VIM− | G^R, H^R, O^R | | | NT | NT |
| H03 | H810/CRL-5816 | Lung | PAM+, SYN+, PC1/PC3+, PC2+, VIM− | G^S, H^S, O^S, P^S, B^S, Hd^S, Mca^S, Z^S | NP+, I+, G+, GH+, L^{IP} | + | + | + |
| H04 | H1299/CRL-5803 | Lung | PAM+, SYN−, PC1/PC3+, PC2−, VIM+ | G^S, H^S, O^S | I+ | | NT | NT |
| H05 | H378/CRL-5808 | Lung | PAM+, SYN+ PC1/PC3(+), PC2+, VIM− | G^R, H^R, O^R | | | NT | NT |
| H06 | H727/CRL-5815 | Lung | PAM+, SYN+ PC1/PC3+, PC2− VIM− | G^R, H^R, O^S | | | NT | NT |
| H07 | H187/CRL-5804 | Lung | PAM+, SYN+, PC1/PC3+, PC2−, VIM− | G^S, H^S, O^S | | | NT | NT |
| H08 | H1385/CRL-5867 | Lung | PAM+, SYN−, PC1/PC3(+), PC2+, VIM+ | G^S, H^R, O^R | | | NT | NT |
| H09 | H720/CRL-5838 | Lung | PAM+, SYN+, PC1/PC3+, PC2+, VIM− | G^S, H^S, O^S | | −/+ | + | NT |
| H10 | NA(A-549)/CCL-185 | Lung, ES | PAM+, SYN, PC1/PC3(+), PC2−, VIM+ | G^S, O^{NT}, H^{NT} | | | NT | NT |
| H11 | NA/HTB-9 | Bladder | PAM+, SYN−, PC1/PC3−, PC2−, VIM+ | G^S, H^S, O^S | | | NT | NT |
| H12 | NA/(CM from Pozilli) | Insulinoma | PAM+, SYN+, PC1/PC3−, PC2−, VIM+ | G^S, H^S, O^S, P^S | | | NT | NT |
| H13 | NA/CRL-2139 | Neuro-ectodermal | PAM+, SYN−, PC1/PC3(+), PC2−, VIM+ | G^S, H^S, O^S | | | NT | NT |
| H14 | H548/CCL-249 | Colon | PAM-NT, SYN-NT, PC1/PC3-NT, PC2-NT, VIM-NT | NT | | | NT | NT |
| H15 | H508/CCL-253 | Cecum | PAM+, SYN+, PC1/PC3−, PC2−, VIM | G^S, H^S, O^S | NP+ | | + | NT |
| H16 | H1770/CRL-5893 | Lung | PAM+, SYN, PC1/PC3 (+), PC2+, VIM− | G^S, H^S, O^S | | | NT | NT |
| H17 | NA/CRL-5974 | Gastric | PAM+, SYN+, PC1/PC3−, PC2−, VIM− | G^S, H^S, O^S | NP+ | | + | NT |
| H18 | H345/HTB-10 | Lung | PAM+, SYN+, PC1/PC3+, PC2+, VIM− | G^S, H^S, O^S | NP+ | | + | NT |
| H19 | H510A/HTB-184 | Lung | PAM+, SYN+, PC1/PC3+, PC2+, VIM− | G^S, H^S, O^S | NP− | | − | NT |
| H20 | H460/HTB-177 | Lung | PAM+, SYN−, PC1/PC3−, PC2−, VIM+ | G^R, H^R, O^R | | | NT | NT |
| H21 | NA/CRL-2195 | Lung | PAM-NT, SYN-NT, PC1/PC3-NT, PC2-NT, VIM-NT | NT | | | NT | NT |
| H22 | H2098/Gazdar insulinoma | Insulinoma | PAM+, SYN+, PC1/PC3+, PC2+, VIM− | G^S, H^S, O^S | | | NT | NT |
| H23 | NA/NA (BON) | Pancreatic Carcinoma | PAM+, SYN+, PC1/PC3+, PC2−, VIM+ | G^S, H^S, O^S | NP+, I−, G− | | + | NT |
| H25 | NA (HepG)/HB-8065 | Hepatocytes | PAM+, SYN−, PC1/PC3−, PC2−, VIM− | G^S, N^{NT}, O^{NT} | L+, N+ | | NT | NT |
| 293 | | Kidney | PAM+, SYN−, | G^S, H^S, O^S | NP+, I+, G+, | | + | + |

TABLE 2-continued

Evaluation and Engineering of Human Cell Lines

| βG ID | NCI/ATCC | Origin | NEprofile PEP+/− | SELEC AB^S/R | TG+/− | NuTum Grow+/− | AlgBeads vitro | vivo |
|---|---|---|---|---|---|---|---|---|
| | | | PC1/PC3−, PC2−, VIM+ | | L+, GH+ | | | |

KEY:
NCI, National Cancer Institute; ATCC, American Type Culture Collection; NE, neuroendocrine; PAM, peptidylglycine alpha-amidating monooxygenase; SYN, synaptophysin; PC, proconvertase; VIM, vimentin; AB, antibiotic; S/R, sensitive/resistant; G, G418; H, hygromycin; O, ouabain; P, puromycin; B, blasticidin; Hd, histidinol; Mca, mycophenolic acid; Z, Zeocin; TG, transgene
expression +/−; NP, neomycin phosphotransferase; I, insulin; G, glucagon/glycentin; GH, growth hormone; L leptin, NT, not tested Table 2 describes the properties of certain cell lines that are exemplary starting cells for use in the instant application. βG H03 cells are derived from a human non-small cell lung carcinoma (ATCC Number: CRL-5816). These cells have a neuroendocrine phenotype, and can be grown in a monolayer. This line was derived by Gazdar and associates from a lung tissue obtained from a patient prior to therapy. H03 cells as obtained from the ATCC are not able to synthesize the peptide neuromedin B (NMB) or the gastrin releasing peptide (GRP).

Other lung carcinoma cells include cells designated herein as βG H04, βG H05, βG H07, βG H09, βG H19, βG H20 and βG H21. These, as well as additional cells lines derived from other sources, are described in further detail herein below. These cell lines are only exemplary starting cells for use in the present application, given the teachings provided herein, one of ordinary skill in the art will be able to identify additional cells with characteristics that would make them appealing as cells to be engineered for use in the present invention.

H01 cells (ATCC Number: CCL-251) also may be used in the present invention. These cells are human colorectal carcinoma cells having an epithelial morphology. These cells grow in floating aggregates of round cells. A characteristic that makes these cells useful in the context of the present invention is that they contain cytoplasmic dense core granules characteristic of endocrine secretion.

βG H02 cells are obtained from the ATCC (CRL-1803) are derived from a thyroid medullary carcinoma. Their morphology is epithelial and are known to produce high levels of calcitonin and carcinoembryonic antigen (CEA). Chromosomal analysis of the cell line and tumors induced in nude mice reveal an aneuploid human karyotype with several marker chromosomes.

βG H04 cells are obtained from the ATCC (CRL-5803) are lung carcinoma cells and have a neuroendocrine phenotype. The cells have a homozygous partial deletion of the p53 protein, and lack expression of p53 protein. The cells are able to synthesize the peptide NMB at 0.1 pmol/mg protein, but not the gastrin releasing peptide (GRP).

Another lung carcinoma cell that may prove a useful host cell in the context of the resent invention is designated βG H05 (ATCC Number: CRL-5808). This is a classic small cell lung cancer cell line with an epithelial morphology. This line was derived from cells recovered from pleural effusion taken from a patient after chemotherapy. NCI-H378 expresses elevated levels of the 4 biochemical markers of SCLC: neuron specific enolase, the brain isoenzyme of creatine kinase, L-dopa carboxylase and bombesin-like immunoreactivity. The cells express the c-kit gene as well as the L-myc gene, and L-myc is amplified. The cells express easily detectable levels of p53 mRNA compared to levels found in normal lung Also useful is βG H06, (ATCC Number: CRL-5815), having an epithelial morphology, these cells produce neuromedin B (NMB). This line was derived from tissue taken prior to therapy. This is the best differentiated of the available bronchial carcinoid lines. The cells express easily detectable levels of p53 mRNA compared to levels found in normal lung. The cells are able to synthesize the peptide NMB (at 0.1 pmol/mg protein), but not the gastrin releasing peptide (GRP). The cell line secretes a parathyroid hormone-like protein which is calcium stimulated through a protein kinase C pathway. Further, growth of NCI-H727 cells is inhibited by epidermal growth factor (EGF) receptor monoclonal antibodies.

Another classic small cell lung cancer cell line is βG H07 (ATCC Number: CRL-5804). This line was derived from cells recovered from pleural effusion obtained from a patient prior to therapy, and expresses elevated levels of the 4 biochemical markers of SCLC: neuron-specific enolase, the brain isoenzyme of creatine kinase, L-dopa carboxylase and bombesin-ike immunoreactivity. Only trace amounts of the retinoblastoma susceptibility gene (RB) mRNA, were detected. RB protein was not detected. The cells express the c-kit gene as well as the N-myc gene. N-myc is not amplified. The cells are not able to synthesize the peptide neuromedin B (NMB) or the gastrin-releasing peptide (GRP). They express easily detectable levels of p53 mRNA compared to levels found in normal lung. These cells are useful for transfection studies.

βG H08 are carcinoma cells isolated from a stage 3A squamous cell lymph node carcinoma (ATCC Number: CRL-5867). βG H09 are derived from an atypical lung carcinoid and are available form the ATCC (CRL-5838). βG H10 cell line is a commercially available cell line derive from lung carcinoma (ATCC Number CCL-185) Another similar cell line is ATCC number CCL-185.1 derived from CCL-185 which was initiated through explant culture of lung carcinomatous tissue. CCL-185.1 are adapted to growth in serum-free medium.

βG H11 cells may be obtained form ATCC (number HTB-9) and are derived from a bladder carcinoma. βG H13 (ATCC Number: CRL-2139) are from a primitive neuroectodermal brain tumor. The cells express CCK specific mRNA and synthesize considerable quantities of variably processed CCK prohormone.

ATCC Number: CCL-249 are designated herein as βG H14 and are derived from a colon adenocarcinoma. This is one of 14 colorectal carcinoma cell lines derived from a well differentiated sigmoid tumor from a patient prior to therapy. The line was initially grown in medium with fetal bovine serum, but was later adapted to growth in the chemically defined medium ACL-4. Floating aggregates produce tubuloglandular structures lined by columnar epithelia.

βG H15 are from a colorectal carcinoma (ATCC Number: CCL-253) and have an epithelial phenotype. This line was derived from a metastasis to the abdominal wall obtained from a patient after treatment with 5-fluorouracil.

βG H16 are the same as the commercially available cell line of ATCC Number: CRL-5974. These are gastric carcinoma cells that express the surface glycoproteins carcinoembryonic antigen (CEA) and TAG 72 and the muscarinic cholinergic and vasoactive intestinal peptide (VIP) receptors but lack gastrin receptors ATCC Number: HTB-10 are the cells referred to herein as βG H18, these cells are derived from a neuroblastoma cell line and is one of two cell lines (see also ATCC HTB-11) of neurogenic origin.

βG H19 or ATCC Number: HTB-184 are small cell lung carcinoma cells of an extrapulmonary origin and are from an adrenal metastasis in an adult. The cells produce easily detectable p53 mRNA at levels comparable to those in normal lung tissue.

βG H20 (ATCC Number: HTB-177) are a large cell carcinoma cell line derived from the pleural fluid of a patient with large cell cancer of the lung. The cells stain positively for keratin and vimentin but are negative for neurofilament triplet protein. The line expresses some properties of neuroendocrine cells, is relatively chemosensitive and can be cloned in soft agar (with or without serum).

βG H21 (ATCC Number: CRL-2195) is yet another small cell lung carcinoma cell that may be useful as a starting cell in the present invention. It can grow as suspension and loosely adherent culture and is a biochemically stable continuously cultured cell line which has retained important features of SCLC. The line was derived from a non-encapsulated primary lung tumor from the apical portion of the upper lobe of the left lung. This cell line is an unusual undifferentiated large cell variant of small cell lung carcinoma. It has the morphology of a variant, but the biochemical properties of a classic SCLC. Electron microscopy revealed the presence of gland formation and intracytoplasmic lamellar bodies. The cells have neuroendocrine markers L-dopa decarboxylase and dense core secretory granules.

βG H23 is a long-term tissue culture cell line derived from a metastatic human carcinoid tumor of the pancreas (Evers el al., 1991; Parekh et al., 1994). This cell line is also known as BON (Evers et al., 1991), tumors derived from this cell line are histologically identical to the original tumor. The cells have significant amounts of neurotensin, pancreastatin, and serotonin (5-HT) are demonstrated in the cells by radioimmunoassay (RIA) and the presence of chromogranin A, bombesin, and 5-HT is confirmed by immunocytochemistry. Further, the cells possess neurosecretory granules and functional receptors for acetylcholine, 5-HT, isoproterenol, and somatostatin. BON cells possess a specific transport system for uptake of 5-HT from the medium; this uptake system may be a route for regulation of autocrine effects of 5-HT on carcinoid cells (Parekh et al., 1994). This unique human carcinoid tumor cell line should provides an exemplary starting material for the bioengineering described herein and will be useful in that they possess intracellular mechanisms ideally adapted for secretagogue action in the release of amines and peptides.

Yet another starting cell that may be useful in the present invention is designated βG H25 (ATCC Number: HB-8065) derived from a hepatoblastoma. This cell line produces alpha-fetoprotein (α fetoprotein); albumin; alpha2 macroglobulin (α-2-macroglobulin); alpha1 antitrypsin (α-1-antitrypsin); transfenin; alpha1 antichymotrypsin; (α-1-antichymotrypsin); haptoglobin; ceruloplasmin; plasminogen and demonstrates decreased expression of apoA-I mRNA and increased expression of catalase mRNA in response to gramoxone (oxidative stress) complement (C4); C3 activator; fibrinogen; alpha1 acid glycoprotein (α-1 acid glycoprotein); alpha2 HS glycoprotein (α-2-HS-glycoprotein); beta lipoprotein (β-lipoprotein); retinol binding protein.

E. Altered Protein Production

The present invention also may engineer cells in order to increase or decrease the production of peptides from the secretory cells listed above. The present section is directed toward method of augmenting/increasing protein production and other methods of blocking endogenous protein production.

(i) Methods for Increasing Production of Recombinant Peptides from Secretory Cells The present invention contemplates augmenting or increasing the capabilities of cells to produce biologically active superoxide dismutase. Expression of proteins involved in maintaining the specialized phenotype of host cells, especially their secretory capacity, is important. Engineering the overexpression of a cell type-specific transcription factor such as the Insulin Promoter Factor 1 (IPF1) found in pancreatic β-cells (Ohlsson et al., 1993) could increase or stabilize the capabilities of engineered neuroendocrine cells. Insulin promoter factor 1 (IPF-1; also referred to as STF-1, IDX-1, PDX-1 and bTF-1) is a homeodomain-containing transcription factor proposed to play an important role in both pancreatic development and insulin gene expression in mature b-cells (Ohlsson et al., 1993, Leonard et al., 1993, Miller et al., 1994, Kruse et al., 1993). In embryos, IPF-1 is expressed prior to islet cell hormone gene expression and is restricted to positions within the primitive foregut where pancreas will later form. Indeed, mice in which the IPF-1 gene is disrupted by targeted knockout do not form a pancreas (Jonsson et al., 1994). Later in pancreatic development, as the different cell types of the pancreas start to emerge, IPF-1 expression becomes restricted predominantly to b-cells. IPF-1 binds to TAAT consensus motifs contained within the FLAT E and P1 elements of the insulin enhancer/promoter, whereupon, it interacts with other transcription factors to activate insulin gene transcription (Peers et al., 1994).

Stable overexpression of IPF-1 in neuroendocrine β-cell lines will serve two purposes. First, it will increase transgene expression under the control of the insulin enhancer/promoter. Second, because IPF-1 appears to be critically involved in β-cell maturation, stable overexpression of IPF-1 in β-cell lines should cause these mostly dedifferentiated β-cells to regain the more differentiated function of a normal animal β-cell. If so, then these redifferentiated β-cell lines could potentially function as a more effective neuroendocrine cell type for cell-based delivery of fully processed, bioactive peptide hormones.

Also, further engineering of cells to generate a more physiologically-relevant regulated secretory response is contemplated. Examples would include engineering the ratios of glucokinase to hexokinase in rat insulinoma cells that also overexpress the Type II glucose transporter (GLUT-2) such that a physiologically-relevant glucose-stimulated secretion of peptide hormones is achieved. Other examples include engineering overexpression of other signaling proteins known to play a role in the regulated secretory response of neuroendocrine cells.

These include cell surface proteins such as the alpha-2 adrenergic receptor (ATTC number 59303, HPalpha2GEN Genbank accession numbers M18415, M23533, incorporated herein by reference), glucagon-like peptide I receptor (Genbank accession numbers: L23503, U10037, U01156, U01104: each incorporated herein by reference), somatostatin receptor V (mouse Genbank accession number AF004740; human Genbank accession numbers: L14865, L14856, M81830, M96738, M81829, L07833 each incorporated herein by reference), SUR channel (Genbank accession numbers L78207, U63455, L78243, incorporated herein by reference), KIR channel, pancreatic polypeptide receptor (Genbank accession numbers: Z66526, U42387, U42389 each incorporated herein by reference), muscarinic receptor (Genbank accession numbers: X52068, X15264, X15265, X15266, AF026263 each incorporated herein by reference); glucocorticoid receptor (Genbank accession numbers: M10901, M11050 each incorporated herein by reference), human (glucose-dependent insulinotropic peptide) GIP receptor (Genbank accession number X81832, incorporated herein by reference) human PACAP/VIP receptor (Genbank accession numbers L36566, D17516, U18810, each incorporated herein by reference) human β-cell type Ca2+ channel (Genbank accession number M83566 incorporated herein by reference) and leptin receptor (Genbank accession numbers: U43168, U52912, U52913, U52914 each incorporated herein by reference).

Other cell surface signaling receptors which help potentiate the glucose-stimulated degranulation of β-cells including the glucagon-like peptide I receptor (Thorens, 1992) and the glucose-dependent insulinotropic polypeptide receptor (also known as gastric inhibitory peptide receptor) (Usdin, 1993) can be engineered into neuroendocrine cells. These β-cell-specific signaling receptors, as well as GLUT-2 and glucokinase, are involved in secretory granule release in response to glucose. In this way, glucose stimulated release of superoxide dismutase can be engineered.

(ii) Methods for Blocking Endogenous Protein Production

Blocking expression of an endogenous gene product may be an important modification of cells according to the present invention. For example, in certain aspects of the present invention it may prove useful to inhibit endogenous iNOS activity of cells. Blocking expression of this endogenous gene product, while engineering high level expression of genes of anti-oxidizing capabilities will be useful in the context of the present invention.

Cells generated by this two-step process express heterologous proteins, including a variety of natural or engineered proteins (fusions, chimeras, protein fragments, etc.). Cell lines developed in this way are uniquely suited for in vivo cell-based delivery.

Five basic approaches are contemplated for blocking of expression of an endogenous gene in host cells. First, constructs are designed to homologously recombine into particular endogenous gene loci, rendering the endogenous gene nonfunctional. Second, constructs are designed to randomly integrate throughout the genome, resulting in loss of expression of the endogenous gene. Third, constructs are designed to introduce nucleic acids complementary to a target endogenous gene. Expression of RNAs corresponding to these complementary nucleic acids will interfere with the transcription and/or translation of the target sequences. Fourth, constructs are designed to introduce nucleic acids encoding ribozymes—RNA-cleaving enzymes—that will specifically cleave a target mRNA corresponding to the endogenous gene. Fifth, endogenous gene can be rendered dysfunctional by genomic site directed mutagenesis Antisense. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

Ribozymes. Although proteins traditionally have been used for catalysis of nucleic acids, another class of macromolecules has emerged as useful in this endeavor.

Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Homologous Recombination. Another approach for blocking of endogenous protein production involves the use of homologous recombination. Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, a target gene is selected within the host cell. Sequences homologous to the target gene are then included in a genetic construct, along with some mutation that will render the target gene inactive (stop codon, interruption, etc.). The homologous sequences flanking the inactivating mutation are said to "flank" the mutation. Flanking, in this context, simply means that target homologous sequences are located both upstream (5') and downstream (3') of the mutation. These sequences should correspond to some sequences upstream and downstream of the target gene. The construct is then introduced into the cell, thus permitting recombination between the cellular sequences and the construct.

As a practical matter, the genetic construct will normally act as far more than a vehicle to interrupt the gene. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, a heterologous gene that is to be expressed in the cell also may advantageously be included within the construct. The arrangement might be as follows:

. . . vector•5'-flanking sequence•heterologous gene•selectable marker gene•flanking sequence-3'•vector . . .

Thus, using this kind of construct, it is possible, in a single recombinatorial event, to (i) "knock out" an endogenous gene, (ii) provide a selectable marker for identifying such an event and (iii) introduce a heterologous gene for expression.

Another refinement of the homologous recombination approach involves the use of a "negative" selectable marker. This marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired "knock out" phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

In a particular aspect of this embodiment, the negative selectable maker is GLUT-2. It is also contemplated that GLUT-5 would function in a similar manner to GLUT-2. Therefore, the selection protocols described are intended to refer to the use of both GLUT-2 and GLUT-5.

In a first embodiment, a target gene within a host cell is selected as the location into which a selected gene is to be transferred. Sequences homologous to the target gene are included in the expression vector, and the selected gene is inserted into the vector such that target gene homologous sequences are interrupted by the selected gene or, put another way, such the target gene homologous sequences "flank" the selected gene. In preferred embodiments, a drug selectable marker gene also is inserted into the target gene homologous sequences. Given this possibility, it should be apparent that the term "flank" is used broadly herein, namely, as describing target homologous sequences that are both upstream (5') and downstream (3') of the selected gene and/or the drug selectable marker gene. In effect, the flanking sequences need not directly abut the genes they "flank."

The construct for use in this embodiment is further characterized as having a functional GLUT-2 gene attached thereto. Thus, one possible arrangement of sequences would be:

5'-GLUT-2•flanking target sequences•selected gene•drug-selectable marker gene•flanking target sequences-3' . . .

Of course, the GLUT-2 could come at the 3'-end of the construct and the selected gene and drug-selectable marker genes could exchange positions.

Application of a drug to such cells will permit isolation of recombinants, but further application of Streptozotocin (glucopyranose, 2-deoxy-2-[3-methyl-e-nitrosourido-D]; STZ) to such cells will result in killing of non-homologous recombinants because the incorporated GLUT-2 gene will produce GLUT-2 transporter, rendering the cells susceptible to STZ treatment (the original cell was GLUT-2⁻).

On the other hand, site-specific recombination, relying on the homology between the vector and the target gene, will result in incorporation of the selected gene and the drug selectable marker gene only; GLUT-2 sequences will not be introduced in the homologous recombination event because they lie outside the flanking sequences. These cells will be drug resistant and but not acquire the GLUT-2 sequences and, thus, remain insensitive to STZ. This double-selection procedure (drug$^{res}$/STZ$^{res}$) should yield recombinants that lack the target gene and express the selected gene. Further screens for these phenotypes, either functional or immunologic, may be applied.

A modification of this procedure is one where no selected gene is included, i.e. only the selectable marker is inserted into the target gene homologous sequences. Use of this kind of construct will result in the "knock-out" of the target gene only. Again, proper recombinants are screened by drug resistance and STZ resistance (the original cell was GLUT-2$^-$).

Genomic Site-Directed Mutagenesis with Oligonucleotides. Through analysis of radiation-sensitive mutants of *Ustilago maydis*, genes have been characterized that participate in DNA repair (Tsukuda et al., 1989; Bauchwitz and Holloman, 1990). One such gene, REC2, encodes a protein that catalyzes homologous pairing between complementary nucleic acids and is required for a functional recombinational repair pathway (Kmiec et al., 1994; Rubin et al., 1994). In vitro characterization of the REC2 protein showed that homologous pairing was more efficient between RNA-DNA hybrids than the corresponding DNA duplexes (Kmiec et al, 1994; PCT, WO 96/22364). However, efficiency in pairing between DNA:DNA duplexes could be enhanced by increasing the length of the DNA oligonucleotides (Kmiec et al., 1994). These observations led investigators to test the use of chimeric RNA-DNA oligonucleotides (RDOs) in the targeted modification of genes in mammalian cell lines (Yoon et al., 1996; Cole-Strauss et al., 1996; PCT WO95/15972). The RNA-DNA oligonucleotides that were used to test this application contained self-annealing sequences such that double-hairpin capped ends are formed. This feature is thought to increase the in vivo half-life of the RDO by decreasing degradation by helicases and exonucleases. Further, the RDOs contained a single base pair that differs from the target sequence and otherwise aligns in perfect register. It is believed that the single mismatch will be recognized the DNA repair enzymes. And the RDOs contained RNA residues modified by 2'-O-methylation of the ribose sugar. Such modification makes the RDO resistant to degradation by ribonuclease activity (Monia et al., 1993).

Two separate experimental systems have been used to test the use of RDOs for targeted gene disruption in mammalian cell lines. In one system RDOs were used to target and correct an alkaline phosphatase cDNA in that was maintained in the episomal DNA of Chinese hamster ovary cells. An inactive form of alkaline phosphatase was converted to a wild-type form with an efficiency of about 30% (Yoon et al., 1996). In a second system, a genetic mutation within chromosomal DNA was targeted and corrected. A lymphoid blast cell line was derived from a patient with sickle cell disease who was homozygous for a point mutation in the β-globin gene. Here again the overall frequency of gene conversion from the mutant to the wild-type form was very high and was found to be dose-dependent on the concentration of the RDOs (Cole-Strauss et al., 1996).

If the use of RDOs or DNA oligonucleotides for the purposes of targeted gene conversion is broadly applicable to various mammalian cell lines, then it offers several advantages to current technologies that have been used to accomplish gene disruption such as homologous recombination. First, if gene conversion by RDO or DNA oligonucleotides occurs in various cell lines at an efficiency of 30% then this will represent a much higher rate than has been reported for targeted gene disruption via homologous recombination. Secondly, only short sequences are required for gene disruption by RDOs or DNA oligonucleotides (typically 60-mers to 70-mers); whereas homologous recombination requires very long stretches of complementary sequences. Homologous sequences from 9 to 15 kilobases are typically recommended in the construction of targeting vectors. As a result, construction of DNA vectors for homologous recombination usually involves extensive gene mapping studies and time consuming efforts in the isolation of genomic DNA sequences. Such efforts are unnecessary if RDOs are used for targeted gene conversions. Thirdly, assays for gene conversion by RDOs can be performed 4 to 6 h following introduction of the RDOs or DNA oligonucleotides into the cell. In contrast, gene conversion by homologous recombination requires a relatively long period of time (days to weeks) between the time of introducing the targeting vector DNA and assaying for recombinants.

Random Integration. Though lacking the specificity of homologous recombination, there may be situations where random integration will be used as a method of knocking out a particular endogenous gene. Unlike homologous recombination, the recombinatorial event here is completely random, i.e. not reliant upon base-pairing of complementary nucleic acid sequences. Random integration is like homologous recombination, however, in that a gene construct, often containing a heterologous gene and a selectable marker, integrates into the target cell genomic DNA via strand breakage and reformation.

Because of the lack of sequence specificity, the chances of any given recombinant integrating into the target gene are greatly reduced. Also possible is integration into a second loci, resulting in the loss of expression of the gene of interest. This second locus could encode a transcription factor needed for expression of the first gene, a locus control region needed for the expression of the first gene, etc. As a result, it may be necessary to "brute force" the selection process. In other words, it may be necessary to screen hundreds of thousands of drug-resistant recombinants before a desired mutant is found. Screening can be facilitated, for example, by examining recombinants for expression of the target gene using immunologic or even functional tests; expression of the target gene indicate recombination elsewhere and, thus, lack of suitability.

(iii) Methods for Re-engineering Engineered Cells

In many situations, multiple rounds of iterative engineering will be undertaken in generating the final cell lines. The events that may be conducted as separate construction events include blocking expression of endogenous gene products by molecular methods (including targeting of both copies of the endogenous gene), introducing a heterologous gene, and further modification of the host cell to achieve high level expression. The particular difficulty in performing multiple steps like this is the need for distinct selectable markers. This is a limitation in that only a few selectable markers are available for use in mammalian cells and not all of these work sufficiently well for the purposes of this invention.

The present invention therefore contemplates the use of the Cre/Lox site-specific recombination system (Sauer, 1993, available through Gibco/BRL, Inc., Gaithersburg, Md.) to rescue specific genes out of a genome, most notably drug selection markers. It is contemplated as a way of increasing the number of rounds of engineering. Briefly, the system involves the use of a bacterial nucleotide sequence knows as a LoxP site, which is recognized by the bacterial Cre protein. The Cre protein catalyzes a site-specific recombination event. This event is bidirectional i.e. Cre will catalyze the insertion of sequences at a LoxP site or excise sequences that lie between two LoxP sites. Thus, if a construct containing a selectable marker also has LoxP sites flanking the selectable marker, introduction of the Cre protein, or a polynucleotide encoding the Cre protein, into the cell will catalyze the removal of the selectable marker. If successfully accomplished, this will make the selectable marker again available for use in further genetic engineering of the cell. This technology is explained in detail in U.S. Pat. No. 4,959,317, which is hereby incorporated by reference in its entirety.

It also is contemplated that a series of different markers may be employed in some situations. These markers are discussed in greater detail, below.

F. Proteins

The present invention contemplates providing superoxide dismutase protein in order to abrogate cytokine mediated cytotoxicity in a diabetic state. Furthermore, a variety of other proteins can also be expressed in combination with superoxide dismutase according to the present invention. Proteins can be grouped generally into two categories—non-secreted and secreted—discussions of each are detailed below. There are some general properties of proteins that are worthy of discussion at this juncture.

First, it is contemplated that many proteins will not have a single sequence but, rather, will exists in many forms. These forms may represent allelic variation or, rather, mutant forms of a given protein. Second, it is contemplated that various proteins may be expressed advantageously as "fusion" proteins. Fusions are generated by linking together the coding regions for two proteins, or parts of two proteins. This generates a new, single coding region that gives rise to the fusion protein. Fusions may be useful in producing secreted forms of proteins that are not normally secreted or producing molecules that are immunologically tagged. Tagged proteins may be more easily purified or monitored using antibodies to the tag. A third variation contemplated by the present invention involves the expression of protein fragments. It may not be necessary to express an entire protein and, in some cases, it may be desirable to express a particular functional domain, for example, where the protein fragment remains functional but is more stable, or less antigenic, or both.

(i) Superoxide Dismutase And Other Non-Secreted Proteins

Expression of non-secreted proteins can be engineered into neuroendocrine cells. Superoxide dismutase is such a protein. Two general classes of such proteins can be defined. The first are proteins that, once expressed in cells, stay associated with the cells in a variety of destinations. These destinations include the cytoplasm, nucleus, mitochondria, endoplasmic reticulum, Golgi, membrane of secretory granules and plasma membrane. Non-secreted proteins are both soluble and membrane associated. The second class of proteins are ones that are normally associated with the cell, but have been modified such that they are now secreted by the cell. Modifications would include site-directed mutagenesis or expression of truncations of engineered proteins resulting in their secretion as well as creating novel fusion proteins that result in secretion of a normally non-secreted protein.

Cells engineered to produce such proteins could be used for either in vitro production of the protein or for in vivo, cell-based therapies. In vitro production would entail purification of the expressed protein from either the cell pellet for proteins remaining associated with the cell or from the conditioned media from cells secreting the engineered protein. In vivo, cell-based therapies would either be based on secretion of the engineered protein or beneficial effects of the cells expressing a non-secreted protein.

Superoxide dismutase is a protein contemplated for such purposes. The cDNA encoding human SOD is available. Mutated, truncated or fusion proteins comprising SOD may be engineered into neuroendocrine cells. Examples of each type of engineering resulting in secretion of a protein are given (Ferber et al., 1991). Reviews on the use of such proteins for studying the regulated secretion pathway are also cited (Burgess et al., 1987; Chavez et al., 1994).

The role of cytokines in the destruction of β-cells has been identified by the present inventors. The cytokines act by generating free radical species which are then responsible for the destruction and dysfunction of the β-cell. β-cells are renowned for their poor antioxidant capacity. Thus superoxide dismutase, a free radical scavenger and antioxidant, if expressed in β-cells may be effective in alleviating symptoms of and treating IDDM.

The production of superoxide dismutase from mammalian cell lines, in particular those that are derived from pancreatic β-cells, will allow for the large scale production of superoxide dismutase species that faithfully mimic the chemical identity of naturally occurring superoxide dismutase.

Due to the correlation between a potential role for superoxide dismutase in the intervention of cytokine mediated cytotoxicity in diabetes, it is clear that there is a need to express SOD from a mammalian system which may then be used for therapeutic intervention IDDM. The availability of such SOD will allow for the treatment and prophylaxis of IDDM resulting from the β-cell destruction due to cytokines. Further a neuroendocrine cell-based system for either in vitro, biologically active superoxide dismutase production, alone or in combination with insulin/and/or other proteins described herein or for in vivo, cell-based delivery of biologically active SOD alone or in combination with insulin would provide an effective SOD therapy in the treatment of diabetes, hypoglycemia and the restoration of β-cell function.

In the context of the present invention, the term "SOD" is intended to refer to a peptide or peptides having biological and/or immunological identity of the superoxide dismutase, or other peptides derived from the SOD cDNA for example, as exemplified by naturally occurring SODs such as those found in human, rat, or other mammalian species.

The sequence for MnSOD is given in SEQ ID NO: 2. Cu/Zn superoxide dismutase is depicted in SEQ ID NO:4. Any variation in the sequence of SOD depicted in SEQ ID NO:2 or SEQ ID NO:4 that allows for the biological and/or immunological integrity of the SOD peptide to be maintained is incorporated as part of the present invention. Recombinant SODs are well known to those of skill in the art and will be useful in the present invention. The skilled artisan is referred to U.S. Pat. Nos. 5,540,911; 5,589,371; 5,246,847 and 5,472,691 (specifically incorporated herein by reference) for further detail pertaining to SOD compositions.

Co-expression of insulin and SOD at, conceivably, any ratio, and at therapeutically efficient levels, has several benefits in the context of cell based co-administration. Also novel is the use of a novel expression plasmid leading to the efficient co-expression of insulin and SOD.

Co-administration of SOD and SOD-related species with insulin to animals results in novel physiologic effects, including enhanced blood glucose lowering effects.

Co-administration can be by in vivo cell-based delivery of SOD and SOD-related species with insulin. Alternatively, co-administration can be achieved by injection of purified recombinant SOD and SOD related species formulated with or in conjunction with insulin.

The present invention allows for the production of mammalian cell-produced recombinant SOD and SOD-related species. In her embodiments, these SOD species are used as a reagents for in vitro and in vivo drug testing, biological screens and a reagent for identification and isolation of novel SOD related peptides. The drugs and SOD produced by the present invention may be used in the treatment and/or prevention of insulin-dependent diabetes mellitus (IDDM); insulin-independent diabetes mellitus (NIDDM); obesity; wasting syndromes; short stature; osteoporosis; inflammatory diseases; autoimmune diseases; neurodegenerative diseases, various diseases of peptide or hormone deficiency or any other disorder involving free radical generation. The methods of treatment of such disorders can be found in U.S. Pat. Nos. 5,527,771; 5,508,260; 5,405,831; 5,376,638; 5,367,052; 5,364,841; 5,321,008; 5,281,581; 5,280,014; 5,266,561 the entire text of each patent being specifically incorporated herein by reference.

The present invention further provides methods for the co-expression of insulin and SOD at conceivably any ratio and at therapeutically efficient levels. In light of the earlier discussion regarding the role of SOD in diabetes these methods undoubtedly have several benefits and possibly novel functions in the context of cell based co-administration. The present invention further provides for the use of a novel expression plasmid leading to the efficient co-expression of insulin and SOD.

In still further embodiments, of the present invention, the engineered cells may express and/or overexpress certain enzymes of therapeutic value. Such enzymes include by are not limited to adenosine deaminase (e.g., Genbank Accession Nos. P55265; U18121; U73107; Z97053; P00813; U75503; DUHUA), galactosidase (e.g., Genbank Accession Nos P54803; P51569; P23780; D00039), glucosidase (e.g., Genbank Accession Nos P29064 (α-glucosidase), P26208 (β-glucosidase), lecithin:cholesterol acyltransferase (LCAT, e.g., Genbank Accession Nos. 729921 (baboon), P04180 (human), XXHUN human LCAT precursor), X04981), factor IX (e.g., Genbank Accession Nos. P00740 (human) K02402 (human) P00741 (bovine) and A22493), sphingolipase, lysosomal acid lipase (e.g., Genbank Accession Nos P38571; S41408), lipoprotein lipase (e.g., Genbank Accession No. P06858), hepatic lipase (e.g., Genbank Accession Nos. AF037404; P11150; P07098), pancreatic lipase related protein (e.g., Genbank Accession Nos. P54315; P54317) pancreatic lipase (P16233) and uronidase.

(ii) Secreted Proteins

As stated earlier, the present invention provides for the expression of SOD alone or in combination with a plethora of other proteins. For this purpose, it is contemplated that neuroendocrine and other cells can be engineered for the co-expression of SOD with several proteins that are normally secreted. The cDNA's encoding a number of useful human proteins are available. Examples would include soluble CD-4, Factor VIII, Factor IX, von Willebrand Factor, TPA, urokinase, hirudin, certain interferons and interleukins, hematopoietic growth factors, antibodies, albumin, leptin, transferin and nerve growth factors.

Peptide Hormones. Peptide hormones claimed herein for engineering in neuroendocrine cells are grouped into three classes with specific examples given for each. These classes are defined by the complexity of their post-translational processing. Class I is represented by Growth Hormone, Prolactin and Parathyroid hormone. A more extensive list of human peptides that are included in Class I is given in Table 3. These require relatively limited proteolytic processing followed by storage and stimulated release from secretory granules. Class II is represented by Insulin and Glucagon. A more extensive list of human peptide hormones that are included in Class II are given in Table 4. Further proteolytic processing is required, with both endoproteases and carboxypeptidases processing of larger precursor molecules occurring in the secretory granules. Class III is represented by Amylin, Glucagon-like Peptide I and Calcitonin. Again, a more extensive list of Class III human peptide hormones is given in Table 5. In addition to the proteolytic processing found in the Class II peptides, amidation of the C-terminus is required for proper biological function. Examples of engineering expression of all three of these classes of peptide hormones in a neuroendocrine cell are found in this patent.

TABLE 3

Class I Human Peptide Hormones

Growth Hormone
Prolactin
Placental Lactogen
Luteinizing Hormone
Follicle-stimulating Hormone
Chorionic Gonadotropin
Thyroid-stimulating Hormone
Leptin

TABLE 4

Human Peptide Hormones Processed by
Endoproteases from Larger Precursors

Adrenocorticotropin (ACTH)
Angiotensin I and II
β-endorphin
β-Melanocyte Stimulating Hormone (β-MSH)
Cholecystokinin
Endothelin I
Galanin
Gastric Inhibitory Peptide (GIP)
Glucagon
Insulin
Lipotropins
Neurophysins
Somatostatin

TABLE 5

Amidated Human Peptide Hormones

Calcium Metabolism Peptides:

Calcitonin
Calcitonin Gene related Peptide (CGRP)
β-Calcitonin Gene Related Peptide
Hypercalcemia of Malignancy Factor (1–40) (PTH-rP)
Parathyroid Hormone-related protein (107–139)(PTH-rP)
Parathyroid Hormone-related protein (107–111)(PTH-rP)
Gastrointestinal Peptides:

Cholecystokinin (27–33)(CCK)
Galanin Message Associated Peptide,
Preprogalanin (65–105)
Gastrin I
Gastrin Releasing Peptide

TABLE 5-continued

Amidated Human Peptide Hormones

Glucagon-like Peptide (GLP-1)
Pancreastatin
Pancreatic Peptide
Peptide YY
PHM
Secretin
Vasoactive Intestinal Peptide (VIP)
Pituitary Peptides:

Oxytocin
Vasopressin (AVP)
Vasotocin
Enkephalins:

Enkephalinamide
Metorphinamide (Adrenorphin)

Alpha Melanocyte Stimulating Hormone (alpha-MSH)
Atrial Natriuretic Factor (5-28) (ANF)
Amylin
Amyloid P Component (SAP-1)
Corticotropin Releasing Hormone (CRH)
Growth Hormone Releasing Factor (GHRH)
Luteinizing Hormone-Releasing Hormone (LHRH)
Neuropeptide Y
Substance K (Neurokinin A)
Substance P
Thyrotropin Releasing Hormone (TRH)

G. Expression of Polypeptides

The SOD gene can be inserted into an appropriate expression system. The gene can be expressed in any number of different recombinant DNA expression systems to generate large amounts of the polypeptide product, which can then be purified and used to vaccinate animals to generate antisera with which further studies may be conducted.

In one embodiment, amino acid sequence variants of a polypeptide can be prepared. These may, for instance, be minor sequence variants of a polypeptide that arise due to natural variation within the population or they may be homologues found in other species. They also may be sequences that do not occur naturally but that are sufficiently similar that they function similarly and/or elicit an immune response that cross-reacts with natural forms of the polypeptide. Sequence variants can be prepared by standard methods of site-directed mutagenesis such as those described below in the following section.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are smaller insertions than the fusion proteins described above and are introduced, for example, into a protease cleavage site.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR™ can be used to prepare a range of cDNAs encoding peptides lacking successively longer fragments of the C-terminus of the protein. The immunoprotective activity of each of these peptides then identifies those fragments or domains of the polypeptide that are essential for this activity. Further studies in which only a small number of amino acids are removed at each iteration then allows the location of the antigenic determinants of the polypeptide.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in *BIOTECHNOLOGY AND PHARMACY*, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within an polypeptide can be predicted by computer-based algorithms as discussed above. Once the component amino acids of the turn are determined, peptide mimetics can be constructed to achieve a similar spatial orientation of the essential elements of the amino acid side chains.

Modification and changes may be made in the structure of a gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by change the codons of the DNA sequence, according to the following data.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982).

TABLE 6

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGCAGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

H. Site-Specific Mutagenesis

It may be desirable to engineer proteins that are functional or structural equivalents of the proteins listed herein but have a sequence that is different than that of the wild-type protein or peptide. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

I. Genetic Constructs and Their Delivery to Cells (i) Formation of Genetic Constructs Also claimed in this patent are examples of DNA expression plasmids designed to optimize production of the heterologous proteins such as SOD. These include a number of enhancers/promoters from both viral and mammalian sources that drive expression of the genes of interest in neuroendocrine cells. Elements designed to optimize messenger RNA stability and translatability in neuroendocrine cells are defined. The conditions for the use of a number of dominant drug selection markers for establishing permanent, stable neuroendocrine cell clones expressing the peptide hormones are also provided, as is an element that links expression of the drug selection markers to expression of the heterologous polypeptide.

(a) Vector Backbone

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding a particular gene is not believed to be important, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter (CMV IE), the SV40 early promoter, the Rous sarcoma virus long terminal repeat, rat insulin promoter and glyceraldehyde-3-phosphate dehydrogenase can be used to obtain high-level expression of the gene of interest. In particular embodiments, the CMV promoter may be one which has been engineered to enhance production of recombinant proteins. Massie et al., (1998) describe one such recombinant promoter that has a CMV IE gene and the major late promoter from adenovirus that acts as an enhancer of the CMV-IE promoter. The use of other viral or mammalian cellular or bacterial phage promoters which are well-known in the art to achieve expression of a gene of interest is contemplated as well, provided that the levels of expression are sufficient for a given purpose.

By employing a promoter with well-known properties, the level and pattern of expression of the gene product following transfection can be optimized. Further, selection of a promoter that is regulated in response to specific physiologic signals can permit inducible expression of the gene product. Tables 7 and 8 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 7 and Table 8). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 7

ENHANCER

Immunoglobulin Heavy Chain
Immunoglobulin Light Chain
T-Cell Receptor
HLA DQ α and DQ β
β-Interferon
Interleukin-2
Interleukin-2 Receptor
MHC Class II 5
MHC Class II HLA-DRα
β-Actin
Muscle Creatine Kinase
Prealbumin (Transthyretin)
Elastase 1
Metallothionein
Collagenase
Albumin Gene
α-Fetoprotein
τ-Globin
β-Globin
e-fos
c-HA-ras
Insulin
Neural Cell Adhesion Molecule (NCAM)
α1-Antitrypsin
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 8

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X |
| | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

In preferred embodiments of the invention, the expression construct comprises a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

(b) Other Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. The inventors have employed the human Growth Hormone and SV40 polyadenylation signals in that they were convenient and known to function well in the target cells employed. Also contemplated as an element of the expression cassette is a terminator. These elements can serve to enhance message levels and to minimize read through from the cassette into other sequences.

(c) Selectable Markers

In certain embodiments of the invention, the delivery of a nucleic acid in a cell may be identified in vitro or in vivo by including a marker in the expression construct. The marker would result in an identifiable change to the transfected cell permitting easy identification of expression. Usually the inclusion of a drug selection marker aids in cloning and in the selection of transformants, for example hygromycin resistance, neomycin resistance, puromycin resistance, zeocin resistance, mycophenolic acid resistance, methotrexate resistance, blastocydin resistance and histadinol resistance. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(d) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(ii) In Vivo Delivery and Treatment Protocols

It is proposed that engineered cells of the present invention may be introduced into animals with certain needs, such as animals with insulin-dependent diabetes. In the diabetic treatment aspects, ideally cells are engineered to achieve glucose dose responsiveness closely resembling that of islets. However, other cells will also achieve advantages in accordance with the invention. It should be pointed out that the studies of Madsen and coworkers have shown that implantation of poorly differentiated rat insulinoma cells into animals results in a return to a more differentiated state, marked by enhanced insulin secretion in response to metabolic fuels (Madsen et al., 1988). These studies suggest that exposure of engineered cell lines to the in vivo milieu may have some effects on their response(s) to secretagogues.

The preferred methods of administration involve the encapsulation of the engineered cells in a biocompatible coating. In this approach, the cells are entrapped in a capsular coating that protects the contents from immunological responses. One preferred encapsulation technique involves encapsulation with alginate-polylysine-alginate. Capsules made employing this technique generally have a diameter of approximately 1 mm and should contain several hundred cells.

Cells may thus be implanted using the alginate-polylysine encapsulation technique of O'Shea and Sun (1986), with modifications, as later described by Fritschy et al., (1991; both references incorporated herein by reference). The engineered cells are suspended in 1.3% sodium alginate and encapsulated by extrusion of drops of the cell/alginate suspension through a syringe into $CaCl_2$. After several washing steps, the droplets are suspended in polylysine and rewashed. The alginate within the capsules is then reliquified by suspension in 1 mM EGTA and then rewashed with Krebs balanced salt buffer.

An alternative approach is to seed Amicon fibers with stable cells of the present invention. The cells become enmeshed in the fibers, which are semipermeable, and are thus protected in a manner similar to the micro encapsulates (Altman et al., 1986; incorporated herein by reference). After successful encapsulation or fiber seeding, the cells may be implanted intraperitoneally, usually by injection into the peritoneal cavity through a large gauge needle (23 gauge).

A variety of other encapsulation technologies have been developed that are applicable to the practice of the present invention (see, e.g., Lacy et al., 1991; Sullivan et al., 1991; WO 91/10470; WO 91/10425; WO 90/15637; WO 90/02580; U.S. Pat. No. 5,011,472; U.S. Pat. No. 4,892,538; U.S. Pat. No. 5,002,661, U.S. Pat. No. 5,569,462, U.S. Pat. No. 5,593,440, U.S. Pat. No. 5,549,675, U.S. Pat. No. 5,545,223, U.S. Pat. No. 5,314,471, U.S. Pat. No. 5,626,561 and WO 89/01967; each of the foregoing being incorporated by reference). To the extent that these references describe encapsulation techniques that will be useful in combination with the present invention, some of these references are described in further detail herein below.

Lacy et. al. (1991) encapsulated rat islets in hollow acrylic fibers and immobilized these in alginate hydrogel. Following intraperitoneal transplantation of the encapsulated islets into diabetic mice, normoglycemia was reportedly restored. Similar results were also obtained using subcutaneous implants that had an appropriately constructed outer surface on the fibers. It is therefore contemplated that engineered cells of the present invention also may be straightforwardly "transplanted" into a mammal by similar subcutaneous injection.

Sullivan et. al. (1991) reported the development of a biohybrid perfused "artificial pancreas," which encapsulates islet tissue in a selectively permeable membrane. In these studies, a tubular semi-permeable membrane was coiled inside a protective housing to provide a compartment for the islet cells. Each end of the membrane was then connected to an arterial polytetrafluoroethylene (PTFE) graft that extended beyond the housing and joined the device to the vascular system as an arteriovenous shunt. The implantation of such a device containing islet allografts into pancreatectomized dogs was reported to result in the control of fasting glucose levels in 6/10 animals. Grafts of this type encapsulating engineered cells could also be used in accordance with the present invention.

U.S. Pat. No. 5,626,561, specifically incorporated herein by reference, describes an implantable containment apparatus for a therapeutic device and method for loading and reloading the device. The implantable containment apparatus is made of selectively permeable material and can be used to contain a therapeutic device, such as a drug delivery device, a cell encapsulation device, or a gene therapy device. A therapeutic device can be easily placed and replaced in the apparatus without damaging tissues associated with the selectively permeable material of the apparatus.

U.S. Pat. No. 4,402,694, also is incorporated herein by reference and describes a body cavity access device containing a hormone source. In this patent, the device supplies a hormone to a patient. The device is made of an implantable housing which is placed in the body and has an impermeable extracorporeal segment and a semipermeable subcutaneous segment. A hormone source such as live, hormone-producing cells, e.g., pancreatic islet cells or the engineered human cells of the present invention are then removably positioned in the housing to provide a hormone/ and/or other peptide supply to the patient. Such a device also can contain a sensor located within the subcutaneous segment and operably associated with a dispenser to release medication into the housing and to the patient.

Hydrophilic polymeric chambers for encapsulating biologically active tissue and methods for their preparation are described in U.S. Pat. No. 4,298,002. In the technology described therein the tissue refers to those essential cellular components of a particular organ that is capable of receiving, modifying or secreting hormones. A device comprising such chamber and such tissue is fabricated and implanted in a living body so that said tissue is permitted normal function without being rejected by the host's immunological system. The viability of the tissue in the device is maintained by a correlation of factors including pore size and membrane thickness of the hydrophilic chamber. To maintain the viability of the tissue, the implanted device allows the inflow of essential nutrients and gases, and outflow of metabolites and products while simultaneously excluding the ingress of cellular components of the host's immunological system. To the extent that the device described therein can be used to implant the engineered cells of the present invention, U.S. Pat. No. 4,298,002 is incorporated by reference herein.

U.S. Pat. No. 5,011,472 describes devices and methods to provide hybrid, modular systems for the constitutive delivery of appropriate dosages of active factor to a subject and, in some instances, to specific anatomical regions of the subject. This patent is incorporated herein by reference in that it contains devices and methods that may be useful in conjunction with the present invention. This system includes a cell reservoir containing living cells capable of secreting an active agent, which is preferably adapted for implantation within the body of the subject and further includes at least one semipermeable membrane, whereby the transplanted cells can be nourished by nutrients transported across the membrane while at the same time protected from immunological, bacterial, and viral assault. The systems further include a pumping means, which can be implantable or extracorporeal, for drawing a body fluid from the subject into the cell reservoir and for actively transporting the secreted biological factors from the cell reservoir to a selected region of the subject.

Similarly, U.S. Pat. No. 4,892,538 describes methods and compositions for the in vivo delivery of neurotransmitters by implanted, encapsulated cells and the technology described therein may be useful in combination with the present invention.

U.S. Pat. No. 5,002,661 describes an artificial pancreatic perfusion device in which a hollow fiber having an inner diameter of about 5 mm is surrounded by islets of Langerhans enclosed in a housing. The islets are suspended in a semi-solid matrix which ensures desired distribution of the cells about the hollow fiber. The hollow fiber and suspended islets are enclosed in a housing which further aids the desired distribution of islets about the hollow fiber. The hollow fiber has a porosity which selectively allows passage of substances having a molecular weight of less than about 100,000 Daltons. The semi-solid matrix in which the islets are embedded and suspended is formed of an appropriate supporting material such as alginate or agar. This device may be used with the present invention in that the engineered cells of the present invention may substitute for the islet cells.

U.S. Pat. No. 5,549,675, incorporated herein by reference, describes additional methods for implanting tissue in a host. The method comprises creating an implant assembly for holding cells including a wall for forming a porous boundary between the host tissue and the implanted cells in the device and implanting the device and then adding the cells. The pore size of the boundary is such that it is sufficient to isolate the implanted cells from the immune response. U.S. Pat. No. 5,545,223, describes methods of making and using ported tissue implant systems and is therefore incorporated herein by reference.

In certain instances it may be necessary to enhance vascularization of implant devices, methods for achieving such an aim are disclosed in U.S. Pat. No. 5,569,462. The methods involve placing a population of therapeutic substance-producing cells into the cell receiving chamber of an immunoisolation apparatus, implanting the apparatus into a patient, and administering an immunomodulatory agent to the patient. The immunomodulatory agent increases the number of close vascular structures in the vicinity of the implanted device, which increases the long term survival of the cell population housed therein.

In other instances, it may be necessary to supply the cells of the present invention in a relatively high density. Brauker, et. al. (U.S. Pat. No. 5,593,440, and U.S. Pat. No. 5,314,471 each incorporated herein by reference) describe tissue implant systems and methods for sustaining viable high cell densities within a host.

Implantation employing such encapsulation techniques are preferred for a variety of reasons. For example, transplantation of islets into animal models of diabetes by this method has been shown to significantly increase the period of normal glycemic control, by prolonging xenograft survival compared to unencapsulated islets (O'Shea and Sun, 1986; Fritschy et al., 1991). Also, encapsulation will prevent uncontrolled proliferation of clonal cells. Capsules containing cells are implanted (approximately 1,000–10,000/animal) intraperitoneally and blood samples taken daily for monitoring of blood glucose and insulin.

An alternate approach to encapsulation is to simply inject glucose-sensing cells into the scapular region or peritoneal cavity of diabetic mice or rats, where these cells are reported to form tumors (Sato et al., 1962). Implantation by this approach may circumvent problems with viability or function, at least for the short term, that may be encountered with the encapsulation strategy. This approach will allow testing of the function of the cells in experimental animals, which is a viable use of the present invention, but certainly is not applicable as an ultimate strategy for treating human diabetes. Nonetheless, as a pre-clinical test, this will be understood to have significant utility.

Engineering of primary cells isolated from patients is also contemplated as described by Dr. Richard Mulligan and colleagues using retroviral vectors for the purposes of introducing foreign genes into bone marrow cells (see, e.g., Cone et al., 1984; Danos et al., 1988). The cells of the bone marrow are derived from a common progenitor, known as pluripotent stem cells, which give rise to a variety of blood borne cells including erythrocytes, platelets, lymphocytes, macrophages, and granulocytes. Interestingly, some of these cells, particularly the macrophages, are capable of secreting peptides such as tumor necrosis factor and interleukin 1 in response to specific stimuli. There is also evidence that these cells contain granules similar in structure to the secretory granules of $\beta$-cells, although there is no clear evidence that such granules are collected and stored inside macrophages as they are in $\beta$-cells (Stossel, 1987).

It may ultimately be possible to use the present invention in combination with that previously described by the one of the present inventors (U.S. Pat. No. 5,427,940, incorporated herein by reference) in a manner described for clonal cells to engineer primary cells that perform glucose-stimulated insulin secretion. This approach would completely circumvent the need for encapsulation of cells, since the patient's own bone marrow cells would be used for the engineering and then re-implanted. These cells would then develop into their differentiated form (i.e. the macrophage) and circulate in the blood where they would be able to sense changes in circulating glucose by secreting insulin.

In summary, biohybrid artificial organs encompass all devices which substitute for an organ or tissue function and incorporate both synthetic materials and living cells. Implantable immunoisolation devices will preferably be used in forms in which the tissue is protected from immune rejection by enclosure within a semipermeable membrane. Those of skill in the art will understand device design and performance, as it relates to maintenance of cell viability and function. Attention is to be focused on oxygen supply, tissue density and the development of materials that induce neovasclarization at the host tissue-membrane interface; and also on protection from immune rejection. Membrane properties may even be further adapted to prevent immune rejection, thus creating clinically useful implantable immunoisolation devices.

An effective amount of the stable cells is determined based on the intended goal. The term "unit dose" refers to a physically discrete unit suitable for use in a subject, each unit containing a predetermined quantity of the therapeutic composition calculated to produce the desired response in association with its administration, i.e. the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

Alternatively, it may be desirable to introduce genetic constructs to cells in vivo. There are a number of way in which nucleic acids may introduced into cells. Several methods are outlined below.

(a) Adenovirus

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization or adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al., (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest also may be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

(b) Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

(c) Adeno-associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector of the present invention can be obtained by restriction endonuclease digestion of AAV or a plasmid such as psub201, which contains a modified AAV genome (Samulski et al. (1987)), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e. stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicle for gene delivery in vitro, and these vectors are now being developed and tested in pre-clinical and clinical stages for a wide range of applications in potential gene therapy, both ex vivo and in vivo. However, wide variations in AAV transduction efficiency in different cells and tissues in vitro as well as in vivo has been repeatedly observed (Ponnazhagan et al., 1997b; 1997c; 1997d; 1997d) and others (Carter and Flotte, 1996 ; Chatterjee et al., 1995; Ferrari et al., 1996; Fisher et al., 1996; Flotte et al., 1993; Goodman et al., 1994; Kaplitt et al., 1994; 1996, Kessler et al., 1996; Koeberl et al., 1997; Mizukami et al., 1996; Xiao et al., 1996).

AAV-mediated efficient gene transfer and expression in the lung has led to clinical trials for the treatment of cystic fibrosis (Carter and Flotte, 1996; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

(d) Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) and herpes viruses may be employed. They offer several attractive features for various mammalian cells (Friedmann, 1989; Ridgeway, 1988; Baichwal and Sugden, 1986; Coupar et al., 1988; Horwich et al., 1990).

Lentiviruses can also be used as vectors in the present application. In addition to the long-term expression of the transgene provided by all retroviral vectors, lentiviruses present the opportunity to transduce nondividing cells and potentially achieve regulated expression. The development of lentiviral vectors requires the design of transfer vectors to ferry the transgene with efficient encapsidation of the transgene RNA and with full expression capability, and of a packaging vector to provide packaging machinery in trans but without helper virus production. For both vectors, a knowledge of packaging signal is required-the signal to be included in the transfer vector but excluded from the packaging vector. Exemplary human lentiviruses are human immunodeficiency virus type 1 and type 2 (HIV-1 and HIV-2). HIV-2 is likely better suited for gene transfer than HIV-1 as it is less pathogenic and thus safer during design and production; its desirable nuclear import and undesirable cell-cycle arrest functions are segregated on two separate genes (Arya et al., 1998; Blomer et al., 1997).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

(e) Non-viral vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, the preferred mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al., (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest also may be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

J. Bioreactors and Large Scale Cultures

In particular embodiments, it will be possible to employ the novel cell lines of the present invention to produce SOD and other protein compositions of the present invention. The ability to produce biologically active polypeptides is increasingly important to the pharmaceutical industry. Over the last decade, advances in biotechnology have led to the production of important proteins and factors from bacteria, yeast, insect cells and from mammalian cell culture. Mammalian cultures have advantages over cultures derived from the less advanced lifeforms in their ability to post-translationally process complex protein structures such as disulfide-dependent folding and glycosylation. Neuroendocrine cell types have added unique capacities of endoproteolytic cleaving, C-terminal amidation and regulated secretion. Indeed, mammalian cell culture is now the preferred source of a number of important proteins for use in human and animal medicine, especially those which are relatively large, complex or glycosylated.

Development of mammalian cell culture for production of pharmaceuticals has been greatly aided by the development in molecular biology of techniques for design and construction of vector systems highly efficient in mammalian cell cultures, a battery of useful selection markers, gene amplification schemes and a more comprehensive understanding of the biochemical and cellular mechanisms involved in procuring the final biologically-active molecule from the introduced vector.

However, the traditional selection of cell types for expressing heterologous proteins has generally been limited to the more "common" cell types such as CHO cells, BHK cells, C127 cells and myeloma cells. In many cases, these cell types were selected because there was a great deal of preexisting literature on the cell type (e.g., "cookbook" methods for transfection of the cells) or the cell was simply being carried in the laboratory at the time the effort was made to express a peptide product. Frequently, factors which affect the downstream (in this case, beyond the T-75 flask) side of manufacturing scale-up were not considered before selecting the cell line as the host for the expression system. Also, development of bioreactor systems capable of sustaining very high density cultures for prolonged periods of time have not lived up to the increasing demand for increased production at lower costs.

The present invention will take advantage of the biochemical and cellular capacities of secretory cells as well as of recently available bioreactor technology. Growing cells according to the present invention in a bioreactor allows for large scale production and secretion of complex, fully biologically-active polypeptides into the growth media. By designing a defined media with low contents of complex proteins and using a scheme of timed-stimulation of the secretion into the media for increased titer, the purification strategy can be greatly simplified, thus lowering production cost.

(i) Anchorage-dependent versus non-anchorage-dependent cultures.

Animal and human cells can be propagated in vitro in two modes: as non-anchorage dependent cells growing freely in suspension throughout the bulk of the culture; or as anchorage-dependent cells requiring attachment to a solid substrate for their propagation (i.e. a monolayer type of cell growth).

Non-anchorage dependent or suspension cultures from continuous established cell lines are the most widely used means of large scale production of cells and cell products. Large scale suspension culture based on microbial (bacterial and yeast) fermentation technology has clear advantages for the manufacturing of mammalian cell products. The processes are relatively simple to operate and straightforward to scale up. Homogeneous conditions can be provided in the reactor which allows for precise monitoring and control of temperature, dissolved oxygen, and pH, and ensure that representative samples of the culture can be taken.

However, suspension cultured cells cannot always be used in the production of biologicals. Suspension cultures are still considered to have tumorigenic potential and thus their use as substrates for production put limits on the use of the resulting products in human and veterinary applications (Petricciani, 1985; Larsson and Litwin, 1987). Viruses propagated in suspension cultures as opposed to anchorage-dependent cultures can sometimes cause rapid changes in viral markers, leading to reduced immunogenicity (Bahnemann, 1980). Finally, sometimes even recombinant cell lines can secrete considerably higher amounts of products when propagated as anchorage-dependent cultures as compared with the same cell line in suspension (Nilsson and Mosbach, 1987). For these reasons, different types of anchorage-dependent cells are used extensively in the production of different biological products.

The current invention includes cells which are anchorage-dependent of nature. RIN cells, e.g., are strictly anchorage-dependent, and when grown in suspension, the cells will attach to each other and grow in clumps, eventually suffocating cells in the inner core of each clump as they reach a size that leaves the core cells unsustainable by the culture conditions. Therefore, an efficient means of large-scale culture of anchorage-dependent cells is needed in order to effectively take advantage of these cells' capacity to secrete heterologous proteins.

(ii) Reactors and processes for suspension.

Large scale suspension culture of mammalian cultures in stirred tanks was undertaken. The instrumentation and controls for bioreactors adapted, along with the design of the fermentors, from related microbial applications. However, acknowledging the increased demand for contamination control in the slower growing mammalian cultures, improved aseptic designs were quickly implemented, improving dependability of these reactors. Instrumentation and controls are basically the same as found in other fermentors and include agitation, temperature, dissolved oxygen, and pH controls. More advanced probes and autoanalyzers for on-line and off-line measurements of turbidity (a function of particles present), capacitance (a function of viable cells present), glucose/lactate, carbonate/bicarbonate and carbon dioxide are available. Maximum cell densities obtainable in suspension cultures are relatively low at about $2-4 \times 10^6$ cells/ml of medium (which is less than 1 mg dry cell weight per ml), well below the numbers achieved in microbial fermentation.

Two suspension culture reactor designs are most widely used in the industry due to their simplicity and robustness of operation—the stirred reactor and the airlift reactor. The stirred reactor design has successfully been used on a scale of 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easy, has good mass transfer of gasses and generates relatively low shear forces.

Most large-scale suspension cultures are operated as batch or fed-batch processes because they are the most straightforward to operate and scale up. However, continuous processes based on chemostat or perfusion principles are available.

A batch process is a closed system in which a typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a fed-batch process is still a closed system because cells, products and waste products are not removed.

In what is still a closed system, perfusion of fresh medium through the culture can be achieved by retaining the cells with a fine mesh spin filter and spinning to prevent clogging. Spin filter cultures can produce cell densities of approximately $5 \times 10^7$ cells/ml. A true open system and the simplest perfusion process is the chemostat in which there is an inflow of medium and an outflow of cells and products. Culture medium is fed to the reactor at a predetermined and constant rate which maintains the dilution rate of the culture at a value less than the maximum specific growth rate of the cells (to prevent washout of the cells mass from the reactor). Culture fluid containing cells and cell products and byproducts is removed at the same rate. These perfused systems are not in commercial use for production from mammalian cell culture.

(iii) Non-perfused attachment systems.

Traditionally, anchorage-dependent cell cultures are propagated on the bottom of small glass or plastic vessels. The restricted surface-to-volume ratio offered by classical and traditional techniques, suitable for the laboratory scale, has created a bottleneck in the production of cells and cell products on a large scale. In an attempt to provide systems that offer large accessible surfaces for cell growth in small culture volume, a number of techniques have been proposed: the roller bottle system, the stack plates propagator, the spiral film bottles, the hollow fiber system, the packed bed, the plate exchanger system, and the membrane tubing reel. Since these systems are non-homogeneous in their nature, and are sometimes based on multiple processes, they suffer from the following shortcomings—limited potential for scale-up, difficulties in taking cell samples, limited potential for measuring and controlling the system and difficulty in maintaining homogeneous environmental conditions throughout the culture.

Despite these drawbacks, a commonly used process of these systems is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling. With frequent media changes, roller bottle cultures can achieve cell densities of close to $0.5 \times 10^6$ cells/cm$^2$ (corresponding to $10^9$ cells/bottle or $10^7$ cells/ml of culture media).

(iv) Cultures on microcarriers

In an effort to overcome the shortcomings of the traditional anchorage-dependent culture processes, van Wezel (1967) developed the concept of the microcarrier culturing systems. In this system, cells are propagated on the surface of small solid particles suspended in the growth medium by slow agitation. Cells attach to the microcarriers and grow gradually to confluency of the microcarrier surface. In fact, this large scale culture system upgrades the attachment dependent culture from a single disc process to a unit process in which both monolayer and suspension culture have been brought together. Thus, combining the necessary surface for a the cells grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products.

Cell yields are up to $1-2 \times 10^7$ cells/ml when cultures are propagated in a perfused reactor mode. Second, cells can be propagated in one unit process vessels instead of using many small low-productivity vessels (i.e. flasks or dishes). This results in far better utilization and a considerable saving of culture medium. Moreover, propagation in a single reactor leads to reduction in need for facility space and in the number of handling steps required per cell, thus reducing labor cost and risk of contamination. Third, the well-mixed and homogeneous microcarrier suspension culture makes it possible to monitor and control environmental conditions (e.g., pH, $pO_2$, and concentration of medium components), thus leading to more reproducible cell propagation and product recovery. Fourth, it is possible to take a representative sample for microscopic observation, chemical testing, or enumeration. Fifth, since microcarriers settle out of suspension easily, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension.

(v) Microencapsulation of mammalian cells

One method which has shown to be particularly useful for culturing mammalian cells is microencapsulation. The mammalian cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. Lim (1982) describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquefied by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150–1500 $\mu$m in diameter, are easily retained in a perfused reactor using a fine-meshed screen. The ratio of capsule volume to total media volume can kept from as dense as 1:2 to 1:10. With intracapsular cell densities of up to $10^8$, the effective cell density in the culture is $1-5 \times 10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for implantation.

(vi) Perfused attachment systems

Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential. The current use of perfused culture is in response to the challenge of growing cells at high densities (i.e. $0.1-5\times10^8$ cells/ml). In order to increase densities beyond $2-4\times10^6$ cells/ml (or $2\times10^5$ cells/cm$^2$), the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

Microcarrier and microencapsulated cultures are readily adapted to perfused reactors but, as noted above, these culture methods lack the capacity to meet the demand for cell densities above $10^8$ cells/ml. Such densities will provide for the advantage of high product titer in the medium (facilitating downstream processing), a smaller culture system (lowering facility needs), and a better medium utilization (yielding savings in serum and other expensive additives). Supporting cells at high density requires extremely efficient perfusion techniques to prevent the development of non-homogeneity. This means the use of highly sophisticated procedures and apparati and has, until recently, been confined to a relatively small scale.

(vii) CelliGen™ bioreactor system

The development of a perfused packed-bed reactor using a bed matrix of a non-woven fabric has provided a means for maintaining a perfusion culture at densities exceeding $10^8$ cells/ml of the bed volume (CelliGen™, New Brunswick Scientific, Edison, N.J.; Wang et al., 1992; Wang et al., 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 $\mu$m to 100 $\mu$m, providing for a high internal volume with pore volumes corresponding to 1 to 20 times the volumes of individual cells.

In comparison to other culturing systems, this approach offers several significant advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and produced in low-protein medium which facilitates subsequent purification steps. Also, the unique design of this reactor system offers an easier way to scale up the reactor. Currently, sizes up to 30 liter are available. One hundred liter and 300 liter versions are in development and theoretical calculations support up to a 1000 liter reactor. This technology is explained in detail in WO 94/17178 (Aug. 4, 1994, Freedman et al.), which is hereby incorporated by reference in its entirety.

A number of culturing parameters, used in conjunction the CelliGen™ system, have been demonstrated to play a role in increased production. For example, the CelliGen™ Plus reactor system, including the use of non-woven polyester fiber matrix (preferably, Fibra-Cel™) and centrifugal lift impeller (preferably, Fibra-Cel™) are system components that give improved yields. Also, several media formulations have been employed with improved performance. For example, use of serum free medium is preferred, as is the use of cholesterol rich lipid extract (0.01% to 0.10%, volume to volume), ascorbic acid (from between about 0.001 to 0.100 mM), glutamate (rather than 2 mM glutamine) at 2 to 20 mM, preferably 4 mM, alpha ketoglutarate (rather than 2 mM glutamine) at 2 to 20 mM, preferably 4 mM, and the absence of growth promoting factors.

(viii) CellCube™ bioreactor system

The Cellcube™ (Corning-Costar) module provides a large styrenic surface area for the immobilization and growth of substrate attached cells. It is an integrally encapsulated sterile single-use device that has a series of parallel culture plates joined to create thin, sealed laminar flow spaces between adjacent plates. The Cellcube™ module has inlet and outlet ports that are diagonally opposite each other and help distribute the flow of media to the parallel plates. The medium is constantly recirculated from the module through an oxygenator and back to the cube. The external oxygenator provides a bubble free stream of oxygenated medium and allows for the additional control of the pH of the medium. With concurrent addition of fresh medium, medium with secreted product and wastes can be harvested continuously, retaining the cell population in the cube.

During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Cells within the system reach a higher density of solution (cells/ml) than in traditional culture systems. Many typically used basal media are designed to support $1-2\times10^6$ cells/ml/day. A typical CellCube™ run with an 21 000 cm$^2$ surface, contains approximately 1.2 liters of media within the module. The final cell density can exceeds $2.5\times10^6$ cell/cm$^2$ or $5\times10^7$ cells/ml in the culture vessel. At confluence, depending on the cell line used, media required can vary anywhere form 4–16 module volumes per day.

The advantage of the CellCube™ system is that it to a large extent replicates the conditions the cells experience in T flask culture. This allows for very linear scale up of any culture that is successfully grown in flask culture without severe loss in per-cell performance.

K. Purification of Proteins

Once the cell lines have produced the proteins in culture, as outlined above, it will be necessary to purify such proteins from the cultures. Protein purification techniques are well known to those of skill in the art. These techniques tend to involve the fractionation of the cellular milieu to separated the SOD form other components of the mixture. Having separated SOD from the other plasma components the SOD sample may be purified using chromatographic and electrophoretic techniques to achieve complete purification. Analytical methods particularly suited to the preparation of a pure peptide are ion-exchange chromatography, exclusion chromatography; polyacrylamide gel electrophoresis; isolectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e. in this case, relative to its purity within a hepatocyte or β-cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater -fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of min, or a most an h. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

L. Immunodetection Assays

In certain aspects it will be useful to employ immunodetection methods in the detecting of conditions associated with SOD expression. Such immunodetection will employ monoclonal and polyclonal antibodies against SOD for detection of the protein in diseased state. Monoclonal antibodies against SOD and methods of generating such antibodies are well known to those of skill in the art. Diseased states that are monitored by such methods may include, for example, insulin-dependent diabetes mellitus (IDDM), insulin-independent diabetes mellitus (NIDDM), obesity, wasting syndromes, short stature, osteoporosis, inflammatory diseases, autoimmune diseases and neurodegenerative diseases.

In some instances, it may be necessary to determine whether SOD expression in a tissue is increased as a result of transplantation of engineered cells that provide SOD expressing capabilities. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like.

Those of skill in the art are very familiar with differentiating between significant expression of a protein, which represents a positive identification, and low level or background expression of such a protein. Indeed, background expression levels are often used to form a "cut-off" above which increased staining will be scored as significant or positive. Significant expression may be represented by high levels of antigens in tissues or within body fluids, or alternatively, by a high proportion of cells from within a tissue that each give a positive signal.

(i) Immunodetection Methods

In still further embodiments, the present invention concerns immunodetection methods for binding, purifying, removing, quantifying or otherwise generally detecting biological components. The encoded proteins or peptides of the present invention may be employed to detect antibodies having reactivity therewith, or, alternatively, antibodies prepared in accordance with the present invention, may be employed to detect the encoded proteins or peptides. The steps of various useful immunodetection methods have been described in the scientific literature and are well known to those of skill in the art.

In general, the immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods include methods for detecting or quantifying the amount of a reactive component in a sample, which methods require the detection or quantitation of any immune complexes formed during the binding process. Here, one would obtain a sample suspected of containing an SOD, an SOD-related peptide or a corresponding antibody, and contact the sample with an antibody or encoded protein or peptide, as the case may be, and then detect or quantify the amount of immune complexes formed under the specific conditions.

In terms of antigen detection, the biological sample analyzed may be any sample that is suspected of containing an SOD antigen, such as a pancreatic β-cell, a homogenized tissue extract, an isolated cell, a cell membrane preparation, separated or purified forms of any of the above protein-containing compositions, or even any biological fluid that comes into contact with diabetic tissue, including blood.

Contacting the chosen biological sample with the protein, peptide or antibody under conditions effective and for a period of time sufficient to allow the formation of immune complexes (primary immune complexes) is generally a matter of simply adding the composition to the sample and incubating the mixture for a period of time long enough for the antibodies to form immune complexes with, i.e. to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. Pat. Nos. concerning the use of such labels include 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

The encoded protein, peptide or corresponding antibody employed in the detection may itself be linked to a detectable label, wherein one would then simply detect this label, thereby allowing the amount of the primary immune complexes in the composition to be determined.

Alternatively, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

(ii) Immunohistochemistry

The antibodies of the present invention also may be used in conjunction with both fresh-frozen and formalin-fixed, paraffin-embedded tissue blocks prepared for study by immunohistochemistry (IHC). For example, each tissue block consists of 50 mg of residual "pulverized" diabetic tissue. The method of preparing tissue blocks from these particulate specimens has been successfully used in previous IHC studies of various prognostic factors, and is well known to those of skill in the art.

Briefly, frozen-sections may be prepared by rehydrating 50 ng of frozen "pulverized" diabetic tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections.

Permanent-sections may be prepared by a similar method involving rehydration of the 50 mg sample in a plastic microfuge tube; pelleting; resuspending in 10% formalin for 4 h fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

(iii) ELISA

As noted, it is contemplated that the encoded proteins or peptides of the invention will find utility as immunogens, e.g., in connection with vaccine development, in immunohistochemistry and in ELISA assays. One evident utility of the encoded antigens and corresponding antibodies is in immunoassays for the detection of SOD and SOD-related peptides, as needed in diagnosis and prognostic monitoring of various diseased states.

Immunoassays, in their most simple and direct sense, are binding assays. Certain preferred immunoassays are the various types of enzyme linked immunosorbent assays (ELISA) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like also may be used.

In one exemplary ELISA, antibodies binding to the encoded proteins of the invention are immobilized onto a selected surface exhibiting protein affinity, such as a well in a polystyrene microtiter plate. Then, a test composition suspected of containing the SOD, such as a clinical sample, is added to the wells. After binding and washing to remove non-specifically bound immune complexes, the bound antibody may be detected. Detection is generally achieved by the addition of a second antibody specific for the target protein, that is linked to a detectable label. This type of ELISA is a simple "sandwich ELISA". Detection also may be achieved by the addition of a second antibody, followed by the addition of a third antibody that has binding affinity for the second antibody, with the third antibody being linked to a detectable label.

In another exemplary ELISA, the samples suspected of containing the SOD antigen are immobilized onto the well surface and then contacted with the antibodies of the invention. After binding and washing to remove non-specifically bound immune complexes, the bound antigen is detected. Where the initial antibodies are linked to a detectable label, the immune complexes may be detected directly. Again, the immune complexes may be detected using a second antibody that has binding affinity for the first antibody, with the second antibody being linked to a detectable label.

Another ELISA in which the proteins or peptides are immobilized, involves the use of antibody competition in the detection. In this ELISA, labeled antibodies are added to the wells, allowed to bind to the SOD protein, and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immune complexes. These are described as follows:

In coating a plate with either antigen or antibody, one will generally incubate the wells of the plate with a solution of the antigen or antibody, either overnight or for a specified period of h. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating of nonspecific adsorption sites on the immobilizing surface reduces the background caused by nonspecific binding of antisera to the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the control and/or clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween™. These added agents also tend to assist in the reduction of nonspecific background.

The "suitable" conditions also mean that the incubation is at a temperature and for a period of time sufficient to allow effective binding. Incubation steps are typically from about 1 to 2 to 4 h, at temperatures preferably on the order of 25° to 27° C., or may be overnight at about 4° C. or so.

Following all incubation steps in an ELISA, the contacted surface is washed so as to remove non-complexed material.

A preferred washing procedure includes washing with a solution such as PBS/Tween™, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this label will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 h at room temperature in a PBS-containing solution such as PBS-Tween™).

After incubation with the labeled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation, e.g., using a visible spectra spectrophotometer.

(iv) Use of Antibodies for Radioimaging

The antibodies of this invention will be used to quantify and localize the expression of antigens such as SOD. The antibody, for example, will be labeled by any one of a variety of methods and used to visualize the localized concentration of the cells producing the encoded protein. Such an assay also will reveal the subcellular localization of the protein, which can have diagnostic and therapeutic applications.

In accordance with this invention, a monoclonal antibody or fragment thereof may be labeled by any of several techniques known to the art. The methods of the present invention also may use paramagnetic isotopes for purposes of in vivo detection. Elements particularly useful in Magnetic Resonance Imaging ("MRI") include $^{157}Gd$, $^{55}Mn$, $^{162}Dy$, $^{52}Cr$, and $^{56}Fe$.

Administration of the labeled antibody may be local or systemic and accomplished intravenously, intraarterially, via the spinal fluid or the like. Administration also may be intradermal or intracavitary, depending upon the body site under examination. After a sufficient time has lapsed for the monoclonal antibody or fragment thereof to bind with the diseased tissue, for example 30 min to 48 h, the area of the subject under investigation is examined by routine imaging techniques such as MRI, SPECT, planar scintillation imaging or newly emerging imaging techniques. The exact protocol will necessarily vary depending upon factors specific to the patient, as noted above, and depending upon the body site under examination, method of administration and type of label used; the determination of specific procedures would be routine to the skilled artisan. The distribution of the bound radioactive isotope and its increase or decrease with time is then monitored and recorded. By comparing the results with data obtained from studies of clinically normal individuals, the presence and extent of the diseased tissue can be determined.

It will be apparent to those of skill in the art that a similar approach may be used to radio-image the production of the encoded SOD or SOD-related proteins in human patients. The present invention provides methods for the in vivo detection of SOD or SOD-related peptide with a view to correlating such detection to diagnosis diabetes in a patient. Such methods generally comprise administering to a patient an effective amount of an SOD antibody, to which antibody is conjugated a marker, such as a radioactive isotope or a spin-labeled molecule, that is detectable by non-invasive methods. The antibody-marker conjugate is allowed sufficient time to come into contact with reactive antigens that are present within the tissues of the patient, and the patient is then exposed to a detection device to identify the detectable marker.

M. Screening For Inhibitors of FFA Mediated Effects

The present invention contemplates the use of screening assays for identifying novel agents to prevent, reduce, decrease, diminish or otherwise abrogate FFA induced inhibition of glucose-induced β-cell proliferation and/or β-cell death. Therefore, within certain embodiments of the invention, methods are provided for identifying inhibitors of FFA induced inhibition of glucose induced β-cell proliferation. Further methods are provided for identifying inhibitors of FFA induced β-cell death.

Screening methods may use any of the cells mentioned herein as adherent cells on a culture dish, in 96-well assay plates, as part of an alginate biomatrix in suspension culture or in any other form that permits the cell proliferation or cell death to be monitored. These cells are used as reagents to screen small molecule and peptide libraries to identify inhibitors and other modulators of FFA induced inhibition of glucose-induced β-cell proliferation and/or FFA induced β-cell death.

The present invention provides methods of screening for substances that will inhibit the deleterious effects of FFA on β-cells. Such substances may act on β-cells to increase resistance to the FFA mediated resistance or act on cellular pathways that prevent the FFA uptake by the cells, increase FFA degradation or inhibit FFA synthesis. Screening methods will monitoring the β-cell proliferation and/or cell death. These parameters may be monitored in the presence of effectors such as glucose and glucose dependent IGF-1. Alternatively, other parameters such as secretory function also may be measured.

It is contemplated that this screening technique will prove useful in the general identification of a compound that will serve the purpose of inhibiting, decreasing, preventing, diminishing or otherwise abrogating FFA induced inhibition of β-cell proliferation and/or FFA mediated β-cell death. It is contemplated that such compounds will be useful in the treatment of diabetes.

In these embodiments, the present invention is directed to a method for determining the ability of a candidate substance to inhibit FFA induced β-cell destruction, dysfunction, or proliferation inhibition. The method including generally the steps of:

(i) providing a glucose responsive β-cell
(ii) contacting said cell with
  a) a candidate substance; and
  b) free fatty acid (FFA) in an amount sufficient to induce inhibition of glucose induced β-cell proliferation;
(iii) comparing the proliferation of said cell in step (ii) in the presence and absence of said candidate substance;

To identify a candidate substance as being capable of inhibiting glucose induced β-cell proliferation in the assay above, one would measure or determine the β-cell proliferation in the absence of the candidate substance. One would then add the candidate substance to the cell and determine the β-cell proliferation in the presence of the candidate substance. A candidate substance which increases the β-cell proliferation relative to the β-cell proliferation in its absence is indicative of a candidate substance being an inhibitor of FFA induced inhibition of glucose induced β-cell proliferation. A similar assay may be set up to identify an inhibitor of FFA mediated β-cell death. Of course agents that produce the opposite effect i.e. stimulate FFA induced β-cell proliferation and/or β-cell death may prove to be useful in certain scenarios and may be identified by the present invention.

β-cell proliferation may be determined by measuring cell growth using any of a number of techniques well known to those of skill in the art. In particular embodiments, the present invention employs [$^3$H]thymidine incorporation to determine the rate of β-cell proliferation. This assay is well known to those of skill in the art and is described in e.g., Hugl et al., (1998). Alternatively, β-cell function may be used as a parameter to quantify cell viability. In other preferred embodiments, cell viability may be measured by well known assays for apoptosis. DNA fragmentation can therefore be used as a measure of cell death. DNA fragmentation may be assayed by the method of Duke and Sellins (1989), alternatively a modified assay has been described herein in Example 1. Cell viability further may be measured by a calorimetric assay as described by Mosmann, 1983 and Schnedl. et al., 1994 and in Example 1, herein below.

As used herein, the term "candidate substance" refers to any molecule that is capable of inhibiting FFA induced inhibition of glucose induced β-cell proliferation. The candidate substance may be a protein or fragment thereof, a small molecule inhibitor, or even a nucleic acid molecule. It may prove to be the case that the most useful pharmacological compounds for identification through application of the screening assay will be compounds that are structurally related to other known inhibitors of FFA function and/or action (e.g., troglitazone, triacsin C, and derivatives thereof). The active compounds may include fragments or parts of naturally-occurring compounds or may be only found as active combinations of known compounds which are otherwise inactive. However, prior to testing of such compounds in humans or animal models, it will possibly be necessary to test a variety of candidates to determine which have potential.

Accordingly, the active compounds may include fragments or parts of naturally-occurring compounds or may be only found as active combinations of known compounds which are otherwise inactive. Accordingly, the present invention provides screening assays to identify agents which inhibit FFA uptake and/or synthesis or stimulate FFA degradation or otherwise inhibit the action of FFA on β-cells, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be polypeptide, polynucleotide, small molecule inhibitors or any other compounds that may be designed through rational drug design starting from known inhibitors of FFA such as triacsin C and troglitazone.

The candidate screening assays are simple to set up and perform. Thus, in assaying for a candidate compound, after obtaining a β-cell, preferably a glucose responsive β-cell, one will admix a candidate substance with the cell, under conditions which would allow measurable proliferation and/ or cell death. In this fashion, one can measure the ability of the candidate substance to inhibit the FFA mediated effects of the cell in the presence of the candidate substance.

"Effective amounts" in certain circumstances are those amounts effective to reproducibly inhibit FFA induced inhibition of cell proliferation in comparison to the FFA induced inhibition in the absence of the candidate substance. Compounds that achieve significant appropriate changes in activity will be used.

Significant changes in cell proliferation, e.g., as thymidine incorporation, DNA fragmentation, colorimetric assays and the like are represented by an increase in cell proliferation or decrease in cell death of at least about 30%–40%, and most preferably, by increases/decreases of at least about 50%, with higher values of course being possible.

It will, of course, be understood that all the screening methods of the present invention are useful in themselves notwithstanding the fact that effective candidates may not be found. The invention provides methods for screening for such candidates, not solely methods of finding them.

N. Pharmaceutical Compositions

Where clinical applications are contemplated, it will be necessary to prepare pharmaceutical compositions—either gene delivery vectors or engineered cells—in a form appropriate for the intended application. Generally, this will entail preparing compositions that are essentially free of pyrogens, as well as other impurities that could be harmful to humans or animals. In other embodiments, the pharmaceutical compositions of the present invention will have an effective amount of an agent that is capable of decreasing the lipid content (e.g., fatty acid, ceramide triglyceride) of a cell. Also, the present invention contemplates the use of agents to inhibit NO production in a cell. In certain embodiments, the pharmaceutical composition may further comprise delivery vectors and/or recombinant cells for the production of leptin and other lipid-lowering peptides to ameliorate the deleterious effects of β-cell destruction caused by excess lipids.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors and cells of the present invention are advantageously administered in the form of injectable compositions either as liquid solutions or suspensions; solid forms suitable for solution in, or suspension in, liquid prior to injection also may be prepared. These preparations also may be emulsified. A typical composition for such purposes comprises a 50 mg or up to about 100 mg of human serum albumin per milliliter of phosphate-buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well-known parameters.

Orally administrable formulations may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier. In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active agent, optionally with one or more accessory ingredients such as an immune adjuvant.

The pharmaceutical compositions also may be formulated for parenteral systemic administration to the host. The compositions for parenteral administration, may be subcutaneously, intramuscularly, or intravenously administered. Thus, the present invention provides compositions for administration to a host, where the compositions comprise a pharmaceutically acceptable solution of the identified compound in an acceptable carrier, as described above. Typically, injectibles are prepared either as liquid solutions or suspensions; solid forms suitable for using to prepare solutions or suspensions upon the addition of a liquid prior to injection can also be prepared; and the preparations can also be emulsified.

The pharmaceutical compositions suitable for injectable use may include sterile aqueous solutions or dispersions; formulations including sesame oil, peanut oil or aqueous propylene glycol; and sterile powders for the extemporaneous preparation of sterile injectible solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Sterile injectible solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectible solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for local injection also is contemplated. In this regard, the use of DMSO as solvent is preferred as this will result in extremely rapid penetration, delivering high concentrations of the active agents to a small area.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e. the appropriate route and treatment regimen. The quantity to be administered, both according to number of treatments and unit dose, depends on the subject to be treated, the state of the subject, and the protection desired. Precise amounts of the therapeutic composition also depend on the judgment of the practitioner and are peculiar to each individual.

In certain embodiments, the present invention contemplates the use of varying doses of nicotinamide, aminoguanidine, troglitazone and inhibitors of iNOS, in the therapeutic intervention of diabetes. Troglitazone may be administered in doses ranging from about 100 to about 1000 mg per day. Thus it is contemplated that 100 mg/day, 200 mg/day, 300 mg/day, 400 mg/day, 500 mg/day, 600 mg/day, 700 mg/day, 800 mg/day, 900 mg/day or 1000 mg/day dosages may be administered to an individual. This troglitazone may be administered as one, two, three, four or more doses per day.

Similarly, doses of aminoguanidine or an analog thereof may be administered to an individual. Analogs of aminoguanidine include but are not limited to N,N'-diaminoguanidine, 1,1-dimethylguanidine and methylguanidine. Compositions of aminoguanidine comprising a daily dose of 5 mg/kg body weight, 10 mg/kg body weight, 20 mg/kg body weight, 30 mg/kg body weight, 40 mg/kg body weight, 50 mg/kg body weight, 60 mg/kg body weight, 70 mg/kg body weight, 80 mg/kg body weight, or 100 mg/kg body weight, are contemplated. Such compositions may comprise formulations containing 50 mg, 60 mg, 70 mg, 80 mg, 100 mg, 200 mg, 300 mg, 400 mg, 500 mg, 600 mg, 700 mg, 1000 mg, or 2000 mg may be administered as a daily dose. These doses may be administered one, two, three, four or more times a day as deemed necessary by the clinician.

Nicotinamide compositions have been described in U.S. Pat. No. 5,382,574, which describes the use of molar concentration of nicotinamide in therapeutic compositions. Such concentrations include 0.1M, 0.2M, 0.3M, 0.4M and 0.5M nicotinamide formulation. In other embodiments, it is contemplated that the compositions of nicotinamide comprising a daily dose of 5 mg/kg body weight, 10 mg/kg body weight, 20 mg/kg body weight, 30 mg/kg body weight, 40 mg/kg body weight, 50 mg/kg body weight, 60 mg/kg body weight, 70 mg/kg body weight, 80 mg/kg body weight, or 100 mg/kg body weight, will be useful. Such compositions may comprise formulations containing 50 mg, 60 mg, 70 mg, 80 mg, 100 mg, 200 mg, 300 mg, 400 mg, 500 mg, 600 mg, 700 mg, 1000 mg, or 2000 mg may be administered as a daily dose. These doses may be administered one, two, three, four or more times a day as deemed necessary by the clinician.

In those embodiments in which an NO synthase inhibitor is administered orally or via injection, the dose may be from about 1 mg to 100 mg/kg body weight per day. When the NO synthase inhibitors are given by injection, this will normally be in the form of an intravenous bolus or by infusion, preferably the latter. The dose range for adult humans is generally from 70 mg to 2.5 g/day and preferably 150 mg to 2 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. Thus, it is contemplated that doses of 5 mg/day, 10 mg/day, 20 mg/day, 40 mg/day, 60 mg/day, 80 mg/day, 100 mg/day, 200 mg/day, 400 mg/day, 600 mg/day, 800 mg/day and 1000 mg/day will be useful.

L-NMMA is preferably administered by injection, conveniently in the form of an infusion so that between 5 and 250 mg/Kg of L-NMMA is administered per day. L-NMMA also may be administered by intravenous bolus in which case the maximum dose per bolus is 20 mg/Kg body weight and preferably 10 mg/Kg body weight, the total amount of L-NMMA administered by this method in a day will be between 5 mg/Kg body weight and 250 mg/Kg body weight.

Of course it is understood that the formulations and compositions described herein above are only exemplary in each category and that these compositions may be varied by the clinician on an individual basis according to the physical and physiological characteristics of the individual being treated.

The compositions of the present invention may be advantageously packaged into a kit comprising the active reagent(s) a suitable container means and even instructions for use of said kit. The reagent(s) of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

The container means will generally include at least one vial, test tube, flask, bottle, syringe or other container means, into which the reagents may be placed, and preferably suitably aliquoted. Where a second reagent is provided, the kit will also generally contain a second vial or other container into which this additional reagent may be placed. The kits of the present invention will also typically include a means for containing the reagent containers in close confinement for commercial sale. Such containers may include injection or blow-molded plastic containers into which the desired vials are retained.

O. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Cell lines and reagents. Studies were conducted with RIN1046-38 cells (Clark et al., 1990) and several cell lines derived from these cells by stable transfection of the human insulin gene (βG I/17), the human insulin gene and the glucokinase gene (βG 40/110) or the human insulin gene, the GLUT-2 gene, and the glucokinase gene (βG 49/206), as previously described (Clark et al., 1997; Hohmeier et al., 1997). RIN cell lines were cultured in Medium 199 supplemented with 5% fetal calf serum, 100 U/ml penicillin, and 100 µg/ml streptomycin. The rat insulinoma cell line INS-1 (Asfari et al., 1991) was obtained from Drs. Claes Wollheim and Philippe Halban, University of Geneva, and cultured in RPMI-1640 medium supplemented with 10% fetal calf serum, 10 mM Hepes, 2 mM L-glutamine, 1 mM Na-pyruvate and 50 µM β-mercaptoethanol (Noel et al., 1997). All cells were gown in 10 cm tissue culture dishes at 37° C. and 5% $CO_2$ in a humidified atmosphere and passaged every 4 days by light trypsinization. Recombinant human IL-1 1β and recombinant human TNF-α were obtained from Endogen (Cambridge, Mass.). Recombinant rat γ-IFN was obtained from Gibco BRL.

MTT viability assay. Cell viability was measured by a previously described colorimetric assay, with some modifications (Mosmann, 1983; Schnedl. et al., 1994). Cells were seeded at 50,000 cells/well in flat bottom 96-well tissue culture dishes (Coming). After 24 h the medium was discarded and 150 µl of the appropriate medium (INS-1 or RIN medium) containing the cytokines was added to the wells. The test medium was left on the cells for the indicated time. Medium was discarded and replaced with 0.75 mg/ml C,N diphenyl-N'-[4,5-dimethylthiazol-2-yl]-2,5-diphenyltetrazolium bromide (MTT) dissolved in 115 µl INS-1 or RIN cell growth medium. Plates were incubated at 37° C. for 2 h. The resulting formazan crystals were solubilized in 115 µl 0.04 N HCl in isopropanol. The optical density was read at 575 nm and 690 nm using a SpectraMax 340 (Molecular Devices, Sunnyvale, Calif.) plate reader. The reduction in optical density induced by cytokine treatment was used as a measure of viability, normalized to cells incubated in the absence of cytokines, which were considered 100% viable.

DNA Fragmentation Assay. DNA fragmentation was assayed by a modification of the method of Duke and Sellins (1989). Groups of freshly isolated or cultured islets were washed twice with ice-cold PBS and suspended in 100 µl of lysis buffer (10 mM Tris-HCl/10 mM EDTA/0.5% Triton X-100, pH 8.0), vortex-mixed, sonicated, and incubated on ice for 20 min. After centrifugation for 20 min at 4° C. (14,000×g), the supernatant containing fragmented (soluble)

DNA was transferred to another tube. Lysis buffer (100 µl) was added to the pellet containing insoluble DNA. Both samples were treated with RNase A (0.5 mg/ml) for 1 h at 37° C. and then with proteinase K (Sigma, 0.4 mg/ml) for 1 h at 37° C. After adding 20 µl of 5 M NaCl and 120 µl of isopropanol, the samples were incubated overnight at −20° C., and the DNA concentrations were measured by the method of Hopcroft et al. (1985). Fragmented DNA was calculated as 100% xsoluble DNA/(soluble+insoluble DNA). The soluble fraction of DNA was determined by electrophoresis on 1.5% agarose gel and has a ladder-like appearance.

RNA Isolation and Analysis. Total RNA was isolated from cells and reverse transcribed (RT) according to the manufacturer's protocol using the Microscreen™ RNA and First Strand cDNA Synthesis Kit (5'→3', Inc.). Specific sequences were amplified from the cDNAs by the polymerase chain reaction (PCR™). 50 ml amplification reactions were performed in a PTC-100 Programmable Thermal Controller (MJ Research, Inc.) using Taq DNA polymerase (Gibco BRL) and the following cycles: 40 rounds of 92° C., 40 sec/ 57° C., 40 sec/ 75° C., 1 min 30 sec followed by 75° C. for 5 min. The oligonucleotides used for amplification are as follows: type I interleukin 1 β receptor (IL-1βr), 5'-AAGCTGACCCAGGATCCACG-3' (SEQ ID NO:13) and 5'-TCTGCTCTTCAGATGACTGG (SEQ ID NO:14) (Hart et al., 1993); interferon gamma receptor(IFNgr), 5'-AGAGTTAAAGCTAAGGTTGG' (SEQ ID NO:15) and 5'-ACAGAGAGCAAGGACTTAGG (SEQ ID NO:16) (Gray et al., 1989); inducible nitric oxide synthase (iNOS) 5'-CCATCATTGCGTGTGCCTGC-3' (SEQ ID NO:17) and 5'-AGCTTCTTCAAAGTGGTAGC-3' (SEQ ID NO:18) (Karlsen et al., 1995). Following subcloning into the pNO-TAT7 plasmid (5'→3', Inc.), recombinant plasmids were sequenced to confirm the identity of the insert. Inserts from each of the plasmids were isolated by gel purification using the Prep-A-Gene DNA Purification Kit (Bio-Rad). DNA fragments were radiolabeled with 32P-dCTP by random priming with the redi-prime labeling kit (Amersham Life Science) and used as hybrization probes. For Northern blot analysis, 5 µg of total RNA was resolved on methyl mercury/ 1.5% argarose gels as described (Bailey and Davidson, 1976). Samples were transferred to nylon membrane and hybridized with $^{32}$P-labeled cDNA probes using Rapid-Hyb Buffer (Amersham Life Science) in a Hybaid Micro 4 Hybridization Oven (National Labnet Company). Following hybridization, nylon membranes were exposed to film to create autoradiographs.

Stable expression of MnSOD in INS-1 cells. To obtain the full-length cDNA encoding rat MnSOD, oligonucleotides that flanked the start and stop codons the corresponding mRNA were used in RT-PCR™ reactions, using RIN 1046-38 cell total RNA as template. The oligonucleotide sequences employed for this amplification were 5'-CGCCTCAGCAATGTTGTGTCG-3' (SEQ ID NO:19) and 5'-AGGGCTTCACTTCTTGCAAAC-3' (SEQ ID NO:20) (Ho and Crapo, 1987). The resultant cDNAs were subcloned into pNOTAT7 and sequenced to confirm insert identities and the fidelity of DNA replication. Following digestion with BamHI, SOD inserts were subcloned into the pCB7/intron vector (Clark el al, 1997). In this plasmid, hygromycin resistance is conferred by expression of hygromycin phosphotransferase from the SV40 early promoter. bG I/17 and INS-1 cell lines were stably transfected with SOD expression vectors, using previously described protocols (Clark et al., 1997). Briefly, 1×107 cells were transfected by electroporation (170 volts, 510 uF, 129 ohms in a 2 mm cuvette), and maintained in 300 mg/ml hygromycin (Boerhinger Mannheim) for about 2 wk. Single colonies were isolated and screened for the expression of transgenes by the pyrogallol autoxidation MnSOD enzymatic assay, as previously described (Marklund, 1985).

MnSOD immunoblot analysis. The level of MnSOD protein in RIN and INS-1 cell lines was measured by immunoblot analysis with a rat anti-human MnSOD antiserum obtained from Dr. L. Oberley, University of Iowa (Oberley et al., 1990). Cells were lysed in PBS containing 0.1% Triton X-100. Supernatants were prepared by centrifuigation at 14,000×g in a refrigerated microcentrifuge. Protein concentration in the supernatant fractions was determined by the method of Bradford (Bradford, 1976), using the BioRad kit. Protein was suspended in an equal volume of 2×sample buffer (100 mM Tris, 4% SDS, 0.2% bromophenol blue, 20% glycerol, 10% β-mercaptoethanol, pH 6.8), heated for 5 min and electrophoresed using 10% precast Tris-glycine gels (Bio-Rad). Protein was transferred to PVDF membranes (Millipore) and blocked with 4% dry milk in TBST (10 mM Tris, 150 mM NaCl, 0.1% Tween 20 pH 8.0). The blot was incubated with antiserum diluted 1:1000 in TBST+2% BSA for 1 h at room temperature and bands were visualized with horseradish peroxidase conjugated goat anti-rat (Amersham) and ECL luminescence (Amersham).

Measurement of nitric oxide (nitrite) formation. Nitrite formation in cell supernatants as an indication of NO production was determined as previously described (Green et al., 1982). The cells were plated in 24-well plates at 0.5×10$^6$ cells/well two days prior to experimental manipulation. The appropriate tissue culture media was replaced with supplemented RPMI medium with or without cytokines for 24 h. Supplemented RPMI medium was used for both INS-1 and RIN cells in this study in order to have identical arginine concentrations. After the 2 h incubation, media were collected, centrifuged for 5 min at 14,000×g, and 100 µl of supernatant was incubated with 100 µl of Griess reagent for 2 h. The optical density was read at 540 nm using a SpectraMax340 (Molecular Devices, Sunnyvale, Calif.) plate reader. Nitrite concentration was calculated using a sodium-nitrite standard curve prepared in RPMI medium.

Preparation of activated supernatants from human and rat peripheral blood mononuclear cells (PBMC). Heparinized blood was collected from a normal human volunteer or Wistar rats, and PBMC were isolated over Histopaque 1077 (Sigma) using standard methods (Coligunet et al., 1992). 2×10$^6$ cells/ml were incubated in RPMI medium supplemented with 10% fetal calf serum, penicillin and streptomycin. Cells were stimulated for 48 h with either 10 µg/ml LPS (*E. coli* 0127:B8, obtained from Sigma) or a combination of 10 ng/ml PMA (Sigma) plus 50 nM ionomycin (Sigma). Control supernatants were incubated in complete RPMI medium. Medium controls containing LPS and PMA+ionomycin but lacking PBMC were also incubated for 48 h at 37° C. After harvesting, conditioned media samples were centrifuged at 2,000×g for 15 min to remove cellular components. For MTT assay, supernatants were diluted 1:2 with complete RPMI medium. Prior to adding diluted supernatants to INS-1 cell lines and clones 2% of a 50×INS-1 supplement (0.5M Hepes, 200 mM L-glutamine, 100 mM Na-pyruvate, 14.2 mM β-mercaptoethanol, pH 7.4) was added.

EXAMPLE 2

Susceptibility of INS-1 and RIN17 cells to cytokines

The inventor's group has worked with modified RIN 1046-38 cells as a potential vehicle for cell-based insulin replacement in IDDM (Clark et al., 1997; Hohmeier et al., 1997; Ferber et al., 1994; Newgard et al., 1997). The inventors used a clonal line called βG I/17 derived from RIN 1046-38 cells by stable overexpression of the human pro-insulin cDNA (Clark et al., 1997; Hohmeier et al., 1997). For comparison, the inventors also studied the effects of cytokines on the well-established INS-1 insulinoma line (Asfari et al., 1991). As shown in FIG. 1, addition of 10 ng/ml TNFβ had no effect on the viability of either cell line, while 1000 U/ml γIFN was equally cytotoxic to both lines (approximately 42% of cells killed). A clear differential effect was noted, however, with 10 ng/ml IL-1β, which killed more than 50% of INS-1 cells but was without effect on βG I/17 cells.

The inventors also studied the effect of mixing of cytokines, and observed that the combination of TNFβ+γ-IFN killed either cell line with similar efficiency (55% βG I/17 and 62% INS-1 cells killed), the mixture of cytokines being slightly more effective than γ-IFN alone. In contrast, the combination of TNF+IL-1β only had a cytotoxic effect on INS-1 cells, with a similar percentage of cells killed as with IL-1β alone. Although data are presented only for 48 h of incubation with 10 ng/ml IL-1β, the effects of this cytokine on INS-1 cells were observed at concentrations as low as 0.5 ng/ml and within the first 24 h of incubation, whereas in βG I/17 cells no significant cytotoxic effect was observed even at the highest dose of IL-1β administered for 72 h. It is notable that the effects observed with TNFβ also were reproducible with TNFα.

Finally, the resistance to IL-1β, cytotoxicity exhibited by the βG I/17 line was not a peculiar feature of this transfected clone, since the parental RIN 1046-38 cells from which βGI/17 cells were derived and other clonal lines expressing combinations of the GLUT-2, glucokinase, and human insulin genes (βG 49/206 and βG 40/110 (Clark et al., 1990; Clark et al., 1997) were also completely refractory to the effects of IL-1β in the MTT-based viability assay.

EXAMPLE 3

Northern blot analysis of gene induction by cytokines

The inventors measured the induction of RNAs encoding inducible nitric oxide synthase (iNOS) and manganese superoxide dismutase (MnSOD) following stimulation with cytokines for 4, 8, or 12 h. Increases in the levels of RNA encoding these enzymes have been described in response to IL-1β stimulation of islet β-cells (Mandrup-Poulsen, 1996; Rabinovitch, 1993; Hakan Borg et al., 1992). IL-1β caused a pronounced increase in MnSOD mRNA levels in βG I/17 cells at both 8 and 12 h of incubation, while a similar increase was observed in INS-1 cells only after 12 h of cytokine treatment. γ-IFN and TNF-β caused induction of MnSOD expression at the 4 h time point in βG I/17 cells, but unlike the case with IL-1β, these effects waned at the later time points. MnSOD mRNA levels in INS-1 cells were largely insensitive to TNFβ or γ-IFN alone, expect for a modest induction at 12 h in response to γ-IFN. Combinations of cytokines (TNFβ+IL1β or TNFβ 4- γIFN) effectively increased MnSOD mRNA levels in both βG I/17 and INS-1 cells, but with a generally more rapid time course and larger magnitude of effect in the former cells. A general observation was that MnSOD mRNA levels were more effectively increased by cytokine treatment in RIN βG I/17) cells than in INS-1 cells. This difference was not due to differences in levels of expression of the relevant cytokine receptors, as IL-1β and γ-IFN receptor mRNA levels were equivalent in RIN and INS-1 cells.

Reprobing of the same blot used for evaluation of MnSOD expression with radiolabeled iNOS cDNA revealed different patterns of cytokine regulation. In βG I/17 cells, the individual cytokines were either completely ineffective or weak and transient inducers of iNOS mRNA levels, and only the combination of TNFβ+γ-IFN caused a large increase in iNOS mRNA that remained at the 8 and 12 h time points. In contrast, IL-1β alone or IL-1β+TNFβ caused a large and sustained induction of iNOS expression in INS-1 cells.

EXAMPLE 4

Stable Expression of Manganese Superoxide Dismutase in INS-I cells

The foregoing data suggested that the enhanced cytotoxicity of IL-1β on INS-1 cells relative to the RIN-derived lines could be explained either by increased IL-1β-mediated induction of iNOS expression or a lesser induction of MnSOD, or some combination of these two. To further evaluate the potential role of MnSOD expression, the inventors measured MnSOD protein levels in βG I/17 and INS-1 cells. βG I/17 or INS-1 cells were left untreated, treated with 10 ng/ml IL-1β, or treated with 10 ng/ml IL-1β+10 ng/ml TNF-β for 24 h. After this treatment, cell extracts were prepared and 25 µg total protein per sample was resolved by SDS PAGE and immunoblotted with an anti-MnSOD antibody as Example 1.

INS-1 cells incubated in the absence of any cytokines contained very low levels of MnSOD protein relative to the basal content in RIN cells. Exposure of either cell line to IL-1β caused a substantial increase in immunodetectable MnSOD, but the level attained in IL-1β-stimulated INS-1 cells remained lower than that in unstimulated βG I/17 cells. Finally, the combination of IL-1β+TNFβ caused a large increase in MnSOD protein in both cell lines, consistent with the effect of these cytokines on MnSOD mRNA levels. These data are consistent with the idea that INS-1 cells contain levels of MnSOD that are insufficient to protect against damage by IL-1β.

Next, the inventors stably transfected INS-1 cells with a vector in which MnSOD expression is under the control of the CMV promoter (pCB7/MnSOD). Following electroporation of INS-1 cells with this plasmid, hygromycin resistant clones that expressed the transgene were initially identified by measurement of superoxide dismutase activity. This resulted in the identification of three clones with high levels of MnSOD activity (βG 221-4, βG 221-11 and βG 221-14).

Immunoblot analysis of MnSOD protein levels was performed in native INS-1 cells, INS-1 cells transfected with the pCB7/intron vector lacking the MnSOD insert (βG 221-v), and the three clones stably transfected with pCB7/intron containing the MnSOD cDNA. The level of MnSOD protein in INS-1 cells stably transfected with the vector pCB-7/intron lacking the MnSOD cDNA insert ("empty vector") is similar to that in control INS-1 cells not exposed to cytokines. In contrast, the three stably transfected clones contain approximately 10 times as much MnSOD protein as found in empty-vector-treated (βG221-v) control INS-1 cells. These results provide proof of efficient overexpression of MnSOD in INS-1 cells.

The inventors also transfected (βG I/17 cells by the same methods and obtained 2.5-3-fold increase in expression of the enzyme in two independent clones (βG 224-6, βG 224-10) relative to a clone transfected with the empty vector. The fold-increase in MnSOD expression may be lower in the RIN versus the INS-1-derived clones due to the higher basal MnSOD expression in the former cell type.

EXAMPLE 5

Cytokine cytotoxicity of cell lines expressing MnSOD

Figure 2:
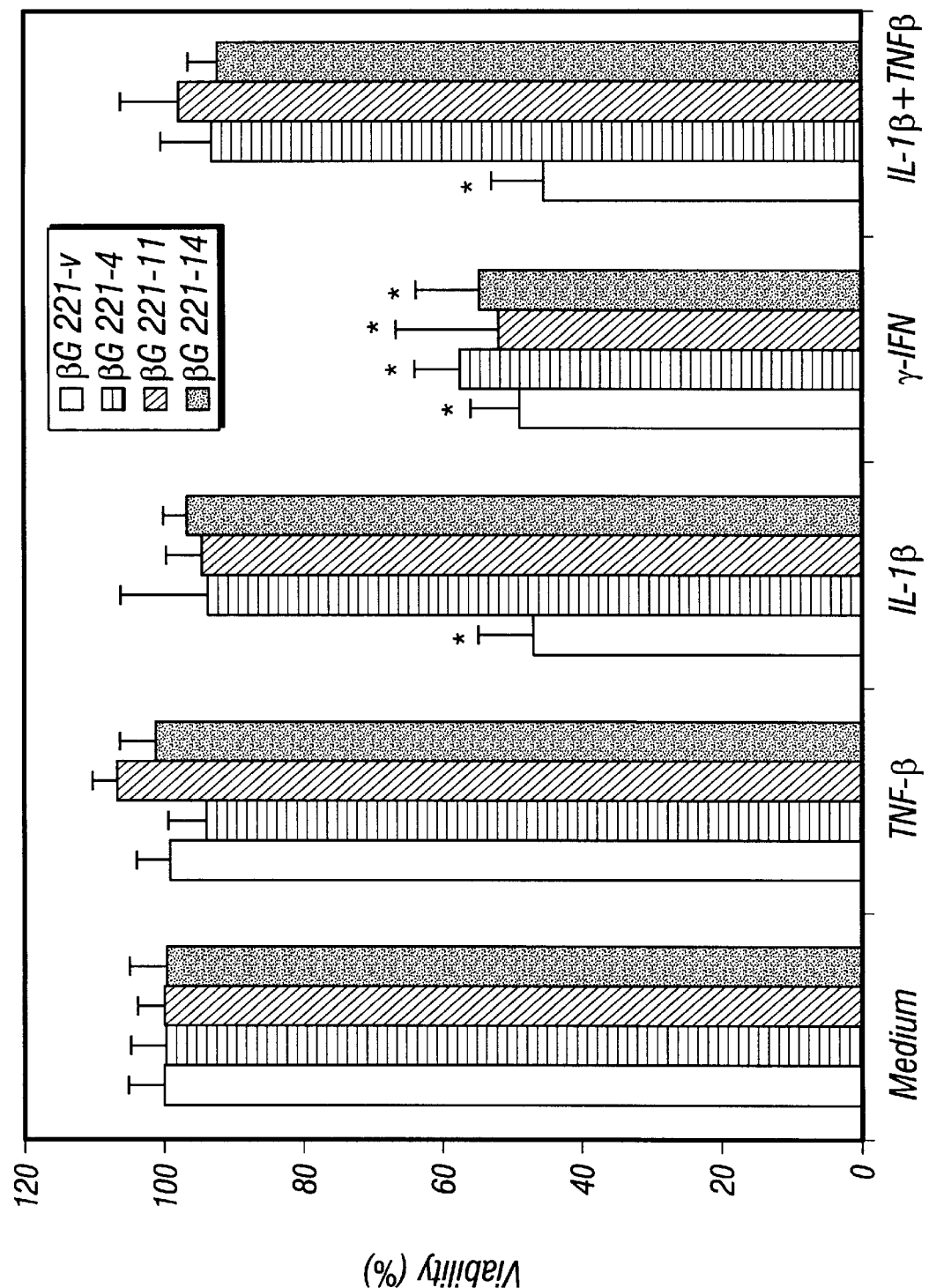
FIG. 2. Protection against IL-1β cytotoxicity in INS-1 cells conferred by MnSOD overexpression. INS-1 cells transfected with the pCB7/intron vector lacking the MnSOD insert (βG 221-1) and three clones stably transfected with pCB7/intron containing the MnSOD cDNA (βG 221-4, βG 221-11, βG 221-14) were incubated with the indicated cytokines for 48 h. The cytokine concentrations and methods used were the same as defined in the legend to FIG. 1. Data represent the mean±standard deviation for 3 independent studies, each performed in triplicate. The symbol * indicates significantly reduced viability relative to the medium-incubated βG 221-1 cell line, at a level of significance of p<0.001. Note the absence of IL-1β or IL-1β+TNFβ-mediated cell killing in the three MnSOD overexpressing lines.

The three representative INS-1 cell lines engineered for stable overexpression of MnSOD described above were tested for cytokine-induced cytotoxicity using the MTT assay and compared with the INS-1 clone that was transfected with the empty vector. As shown in FIG. 2, all three clones engineered for MnSOD expression exhibited complete resistance to killing by IL-1β alone or the combination of IL-1β+TNFα, while only about 50% of the (G221-v control cells remained viable after these treatments. In contrast, MnSOD expression did not provide any protection against γ-IFN-mediated INS-1 cell destruction at either of the two concentrations of the cytokine tested (0.2 μl/ml or 1 μl/ml). In addition, βG I/17 cells engineered for a similar degree of MnSOD overexpression as achieved in INS-1 cells remained resistant to IL-1β-mediated cytotoxicity but gained no protection against γ-IFN-induced killing.

EXAMPLE 6

NO Production During Cytokine Treatment of RIN and INS-1 cell Lines.

Figure 3A:
FIG. 3A and FIG. 3B. NO production (nitrite) from cytokine stimulated INS-1 and RIN-derived cell lines.
Figure 3B:
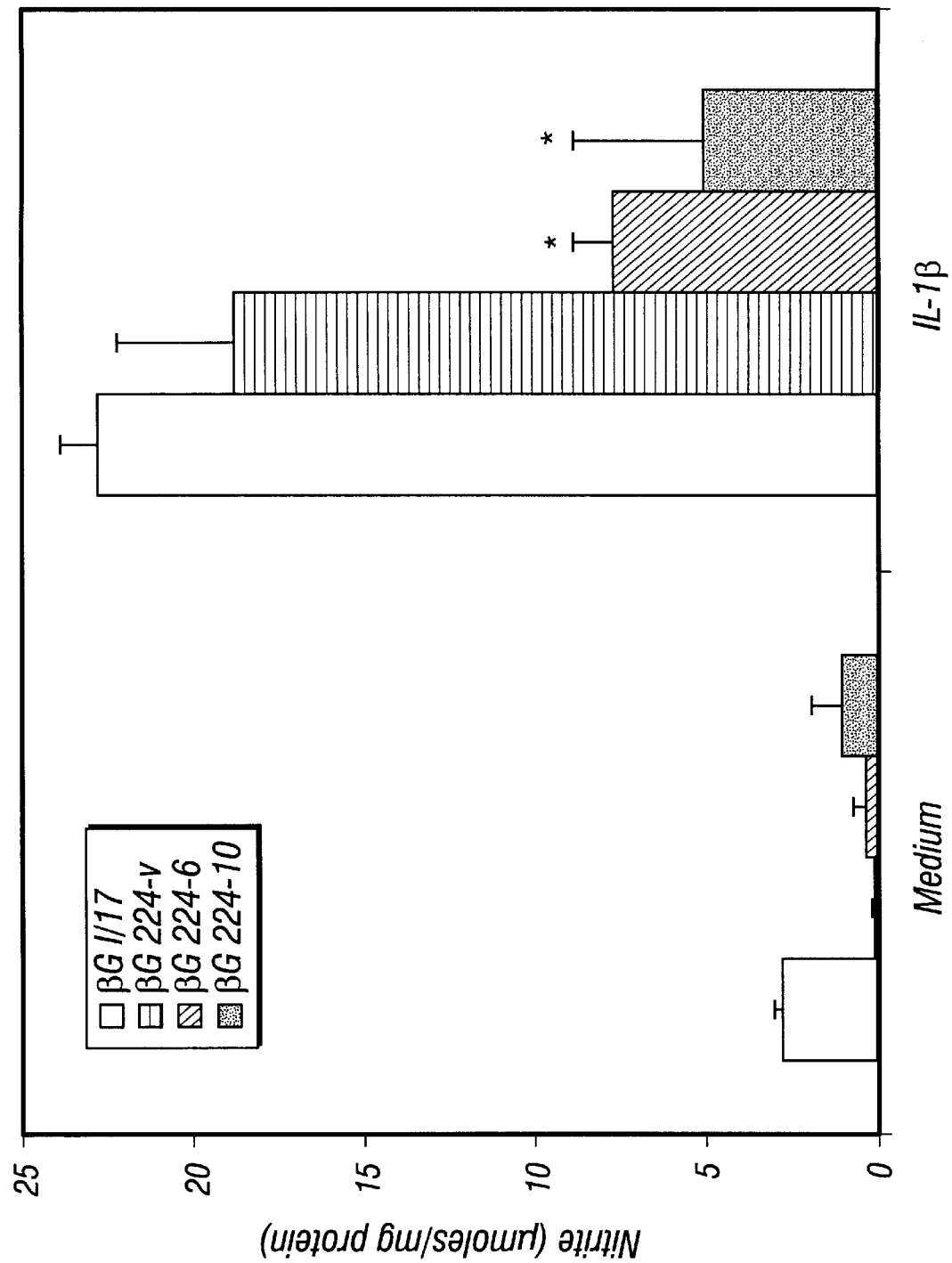

To begin to investigate the mechanism of protection against IL-1 1β cytotoxicity conferred by MnSOD expression in INS-1 cells, the inventors measured NO production (in the form of nitrile) in control and MnSOD-transfected lines. As shown in FIG. 3A, the ability of MnSOD overexpression to protect against IL-1 1β-mediated cytotoxicity was correlated with its ability to block NO production. Thus, NO production in response to IL-1β treatment was reduced by 80% in two independent MnSOD overexpressing clones relative to βG221-v control cells. Interestingly, a similar degree of suppression of NO production in response to IL-1β was observed in MnSOD overexpressing βG I/17 cells relative to controls transfected with empty, vector (FIG. 3B). These results suggest that IL-1β induces INS-1 cell killing by activating iNOS expression and production of NO, and that MnSOD expression in INS-1 cells somehow blocks NO production, thus preventing IL-1β-mediated cytotoxicity. Consistent with the idea that iNOS induction and NO production are critical to the IL-1β-mediated destruction of unengineered INS-1 cells, addition of the iNOS inhibitor L-NMMA during IL-1β treatment of these cells completely blocked NO production and cell killing.

To investigate whether the block in IL-1β-mediated NO production occurs at the level of iNOS expression, the inventors measured iNOS mRNA levels in IL-1β-treated control and MnSOD overexpressing INS-1 cells. INS-1 cells transfected with the pCB7/intron vector lacking the MnSOD insert (βG221-v), and two of the clones stably transfected with pCB7/intron vector containing the MnSOD cDNA (βG 221-4, βG 221-11) were incubated with medium alone or with medium supplemented with 10 ng/ml IL-1b for 8 h. Total RNA was prepared and 5 μg per lane was resolved and probed with a radiolabeled iNOS cDNA as described in Example 1.

IL-1β treatment for 8 h increased iNOS mRNA levels in both groups but the levels achieved in the MnSOD transfected clones were reduced by 65% (clone βG 221-4) and 66% (clone βG 221-11) of the levels in the control βG 221-v cells (n=3, p<0.001 for comparison of either MnSOD overexpressing clone with control). Similarly, all the clones exhibited induction of iNOS protein in response to 8 h f IL-1β treatment but levels achieved in MnSOD transfected clones were reduced by 90% (clone βG 221-4) and 70% (clone βG 221-11) relative to control βG 221-v cells (n=3, p<0.001 for comparison of either MnSOD overexpressing clone with control). These finding strongly suggest that reduced NO production in response to cytokines in MnSOD overexpressing insulinoma cells is linked to a reduced capacity to increase iNOS gene expression.

Clearly, MnSOD has a cytoprotective effect in against IL-1β-mediated cytotoxicity. The relationship between the protective effect of MnSOD expression and its capacity to suppress iNOS and NO production may now be explored. One indication that NO accumulation may be directly involved in IL-1β mediated killing of INS-1 cells is that iNOS inhibition by completely blocks NO production and largely prevents cell killing consistent with other reports for rat islets and RINm5F cells (Southern et al., 1990; Corbett and McDaniel, 1994).

There is a large body of evidence that suggests that reactive oxygen species are potent regulators of signal transduction and transcription in mammalian cells, in some cases via a direct chemical modification of relevant transcription factors or signal transduction elements (Sen and Packer, 1996; Lander, 1997). Regulation of the iNOS gene appears to be highly complex, with some 30 different consensus sequences for transcription factor binding contained in the proximal 1500 base pairs of iNOS gene promoter/enhancer region. Further, the 3' untranslated region of the iNOS mRNA contains a UA rich sequence that is conserved among iNOS transcripts of different species and that is similar to a sequence in the TNF transcript that has been implicated in the control of mRNA stability (Eizirik et al., 1996). iNOS and MnSOD are part of a group of "late response genes" that also includes cyclooxygenase II and heat shock protein 70 that are activated by a variety of stressors including cytokines. These genes are in turn regulated by factors that are induced early in the stress response such as c-fos and c-jun and by translocation of the NF-kB transcription factor from the cytosol to the nucleus (Eizirik et al., 1996; Kwon et al., 1995). Interestingly, both fos/jun activation and binding to the AP-1 cis acting sequences and activation of the NF-KB have been shown to be regulated by oxygen radicals. It would be of interest to determine whether MnSOD overexpression somehow interrupts the expression or activation of these transacting factors or influences the stability of iNOS mRNA or both.

EXAMPLE 7

MnSOD Expression in INS-I Cells Confers Protection Against

Cytotoxicity Induced by Supernatants from Activated Peripheral Blood

Lymphocytes or Macrophages

The failure of MnSOD expression to block γ-IFN-mediated cytotoxicity raises the issue of whether this approach will be relevant to protection of transplanted cells in an immunologically hostile environment. To address this issue in an in vitro model, the inventors isolated peripheral blood lymphocytes or macrophages from normal humans or rats, stimulated these cells with LPS or PMA, collected the supernatants from the stimulated cells, and incubated control and MnSOD-expressing INS-1 clones with the supernatants.

Figure 4A:
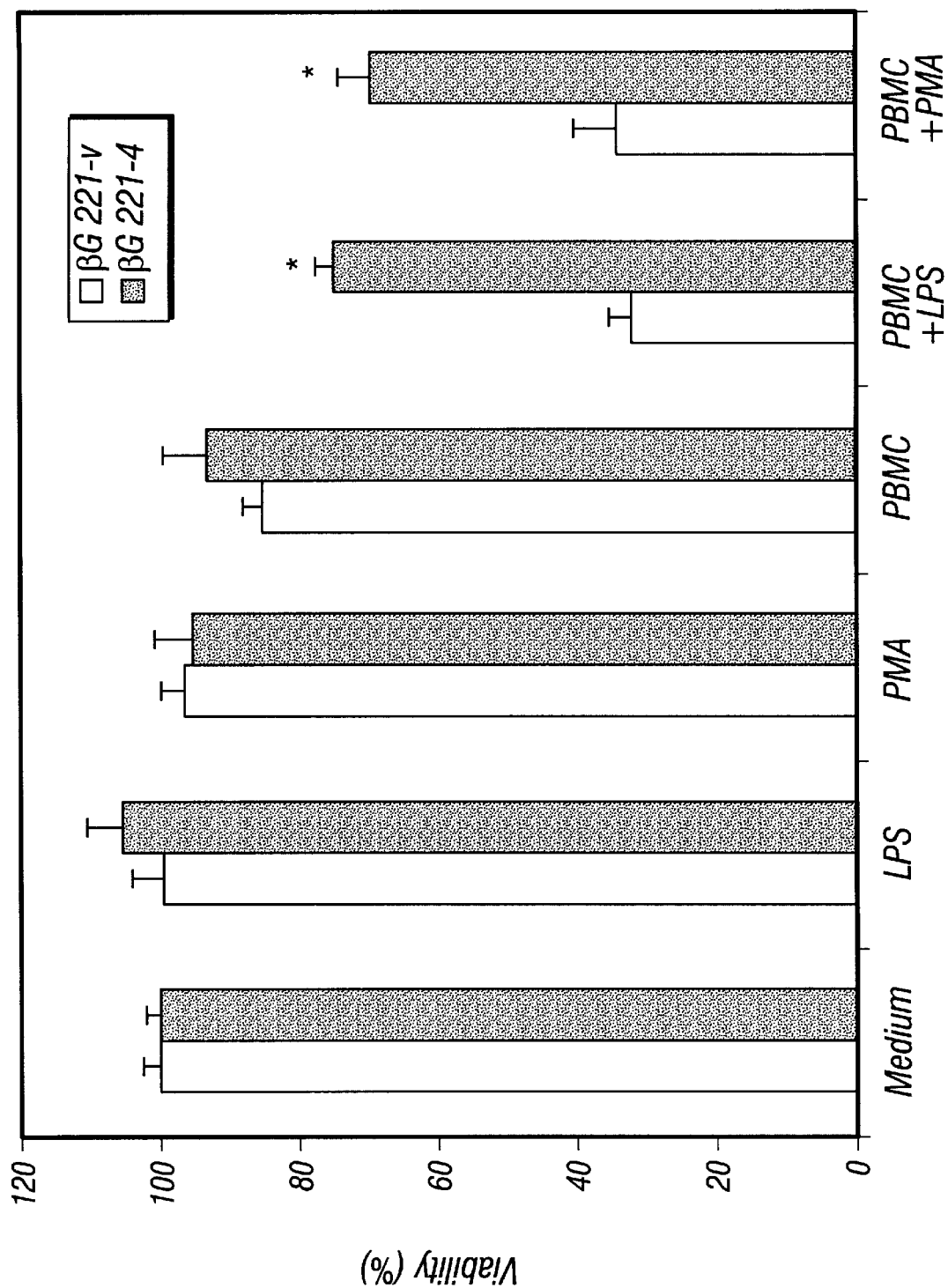
FIG. 4A and FIG. 4B. MnSOD overexpression provides protection against killing by activated human and rat peripheral blood mononuclear cells (PBMC).
Figure 4B:
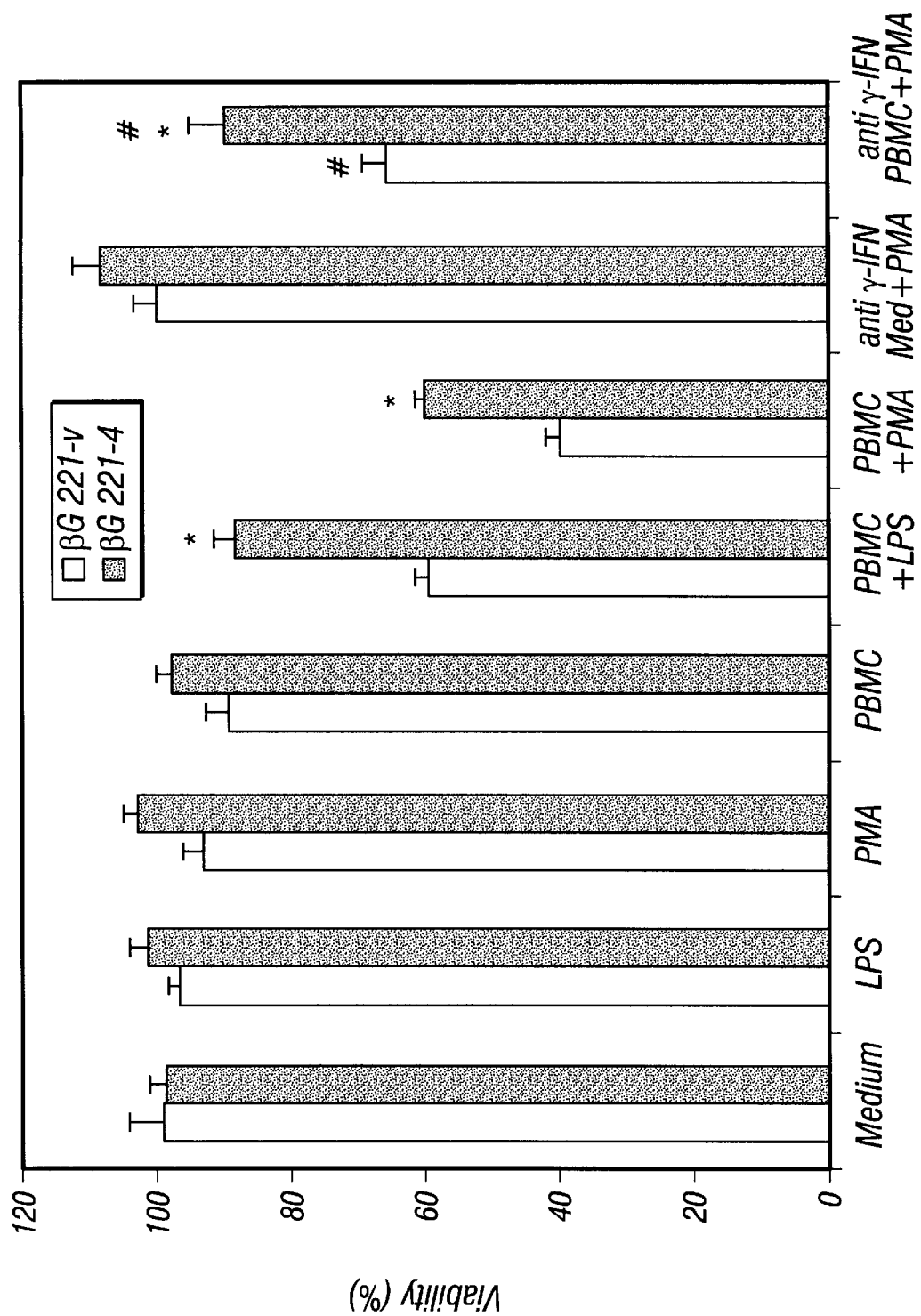

As shown in FIG. 4A, incubation of βG221-v clones with stimulated human PBMC or macrophage supernatants killed approximately 70% of the cells in 48 h, while supernatants from unstimulated PBMC or macrophages had no effect. The activated supernatants were much less cytotoxic when applied to either the βG 221-4 or βG221-11 MnSOD-expressing INS-1 clones, such that LPS-activated PBMC or macrophage supernatants killed 25–30% of the cells, while supernatants PMA-stimulated PBMC killed approximately 35%. Similar findings were obtained with rat PBMC and macrophage supernatants (FIG. 4B). Cell killing was reduced from 40% of control cells incubated with LPS-activated rat PBMC supernatant to 10–15% when the PG 221-4 or βG221-11 clones were tested. Protection was less apparent when PMA-or CONA-stimulated rat PBMC supernatants were tested, with an improvement from 60% of control cells killed to 40% of MnSOD-expressing cells. This could be explained by the fact that PMA and CONA are known to stimulate γ-IFN production from peripheral cells, while LPS primarily stimulates IL-1β production (Bendtzen, 1988; Andersson et al. 1990). Consistent with this model, antibody neutralization of γ-IFN in supernatants prepared from PMA-treated rat PBMC reduced killing of MnSOD expressing INS-1 cells from 40 to 20% (FIG. 4B). Further, the enhanced capacity of MnSOD expression to confer protection against activated supernatants from human cells relative to rat cells is consistent with the absence of any cytotoxic effect of human γ-IFN on either INS-1 or RIN cells.

EXAMPLE 8

Free Fatty Acids and NO Production

Figures 5A, 5B, 5C:
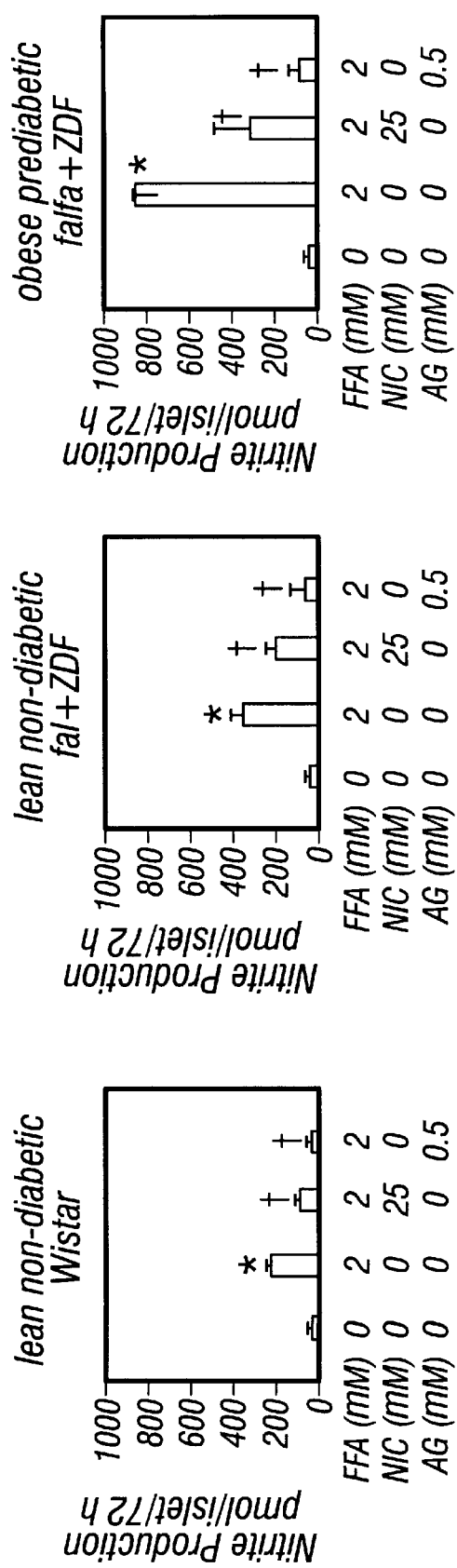
FIG. 5A, FIG. 5B, FIG. 5C, FIG. 5D, FIG. 5E, FIG. 5F, FIG. 5G, FIG. 5H and FIG. 5I. Effects of long-chain FFA with and without nicotinamide (NIC) or aminoguanidine (AG) on islets isolated from 6–7-wk-old Wistar rats, prediabetic obese ZDF rats (fa/fa), and lean heterozygous littermates (fa/+). Islets were cultured for 72 h in medium containing either 0 or 2 mM FFA plus either 0 or 25 mM NIC, or 0 or 0.5 mM AG. Effects on NO formation determined spectrophotometrically as nitrite (FIG. 5A: 6–7-wk-old Wistar rats.

Effects of FFA on NO production by islets. To test the possibility that NO mediates FFA-induced β cell impairment, normal and prediabetic islets were cultured in 0 or 2 mM FFA in 2% BSA for 3 d (FIG. 5A, FIG. 5B and FIG. 5C). The nitrite method of Green (1982) was used to quantify NO in islets from lean Wistar, lean fa/+ ZDF, or obese prediabetic fa/fa ZDF rats. In the absence of FFA, NO in islets of Wistar rats reached a plateau of 40 pmol/islet at 72 h; in the presence of 2 mM FFA, NO rose to 200 pmol/islet. In the presence of FFA, NO rose to 400 pmol/islet in islets of lean fa/+ rats, and 900 pmol/islet in islets from prediabetic obese fa/fa ZDF rats. The presence in the culture medium of 25 mM nicotinamide (NIC), which prevents induction of iNOS by IL-1β in islets (Akabane, 1995), reduced the FFA-induced increase in NO in islets from all groups (FIG. 5A, FIG. 5B and FIG. 5C). Similarly, 0.5 mM aminoguanidine (AG), which is also a competitive inhibitor for iNOS (Corbett and McDaniel, 1996) but lowers iNOS expression as well (Joshi et al., 1996), reduced islet NO release (FIG. 5A, FIG. 5B and FIG. 5C).

Figures 5D, 5E, 5F:
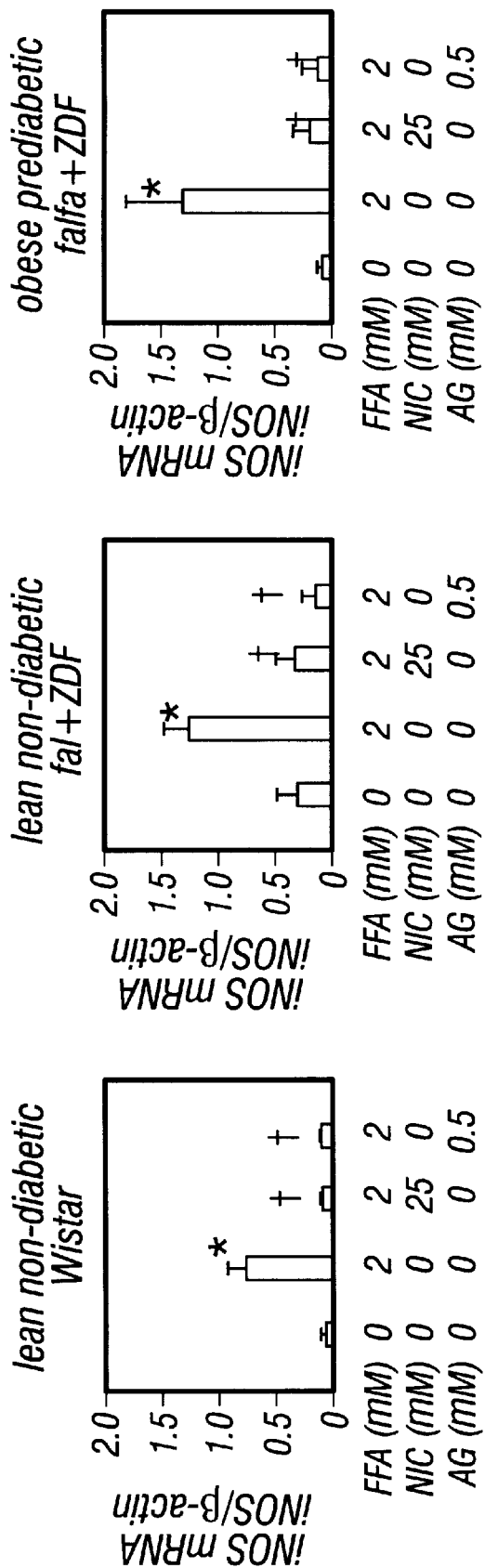

Effects of FFA on inducible NO synthase expression. To determine the relationship between FFA-induced NO observed in these groups and iNOS expression, the mRNA for the enzyme was semiquantified by reverse transcriptase-PCR™ (FIG. 5D, FIG. 5E and FIG. 5F). FFA dramatically increased iNOS mRNA in islets from all groups; the induction was somewhat greater in the islets of heterozygous and homozygous ZDF rats than in islets of Wistar rats (P<0.05). The addition of 25 mM NIC to the culture medium lowered iNOS mRNA in all groups, indicating that this may contribute to the lowering of FFA-induced NO levels by NIC in vitro. AG also lowered iNOS.

EXAMPLE 9

NO and β Cell Function

Figure 5I:
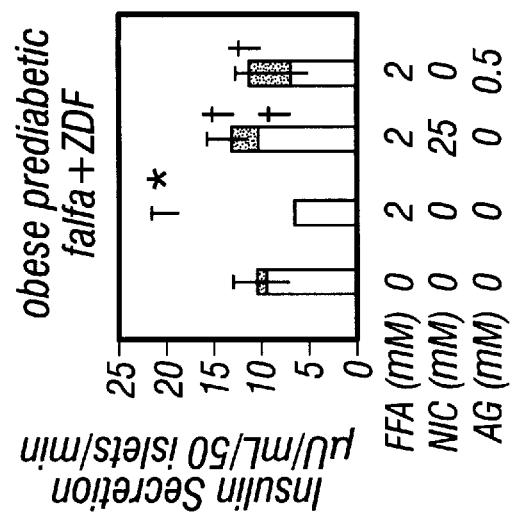
Figure 5H:
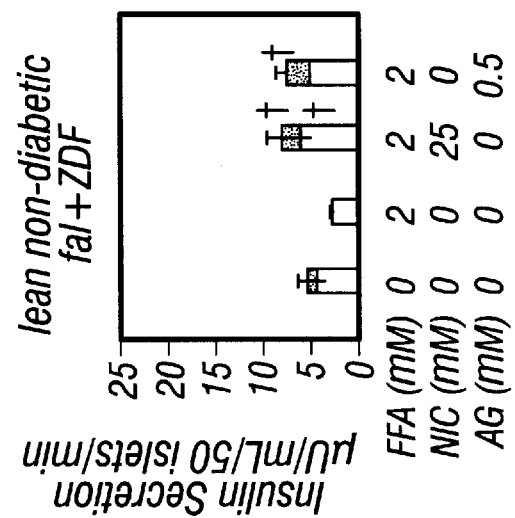
Figure 5G:
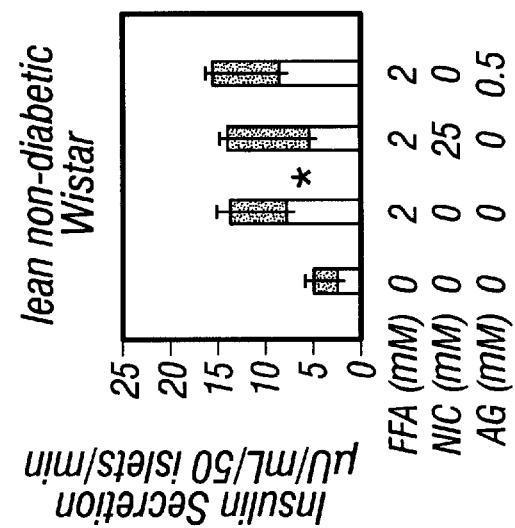

To evaluate the relationship of the foregoing changes in NO and iNOS to β cell function, the effects of 2 mM FFA on insulin secretion were compared by perifusing islets from various rat groups with 3 or 23 mM glucose (FIG. 5G, FIG. 5H and FIG. 5I). In confirmation of earlier reports (Milburn et al., 1995; Hirose et al., 1996), in islets from Wistar rats basal and glucose-stimulated insulin secretion were both enhanced by 2 mM FFA; by contrast, in islets from lean fa/+ and obese fa/fa ZDF rats, the presence of 2 mM FFA paradoxically reduced basal insulin secretion and glucose-stimulated insulin responses to below control levels (Hirose et al., 1996). In normal islets, the addition of 25 mM NIC to the culture medium attenuated the stimulatory effect of FFA on basal insulin secretion but did not alter glucose-stimulated secretion; 0.5 mM AG did not cause a statistically significant change in either.

By contrast, the effects of NIC and AG on islets of ZDF rats were dramatic. 25 mM NIC or 0.5 mM AG in the culture medium reduced the inhibitory effects of FFA on insulin production by islets of the heterozygous lean and homozygous obese ZDF rats (FIG. 5A, FIG. 5B, FIG. 5C and FIG. 5G, FIG. 5H, FIG. 5I). These results suggest that NO plays a role in FFA-induced suppression of insulin secretion observed in islets of rats with a mutant fa allele. For this reason, the effect of 1 mM NG-arginine methylester (NAME), a competitive inhibitor of iNOS, was studied on insulin secretion. NAME, like NIC and AG, caused a marked improvement in glucose-stimulated insulin secretion in the presence of 2 mM FFA (6.3±0.16 vs. 11.2±0.7 U/ml per 50 islets/min).

EXAMPLE 10

Effect of Anti-NO Therapy on Development of NIDDM in Prediabetic ZDF Rats

Figure 6A:
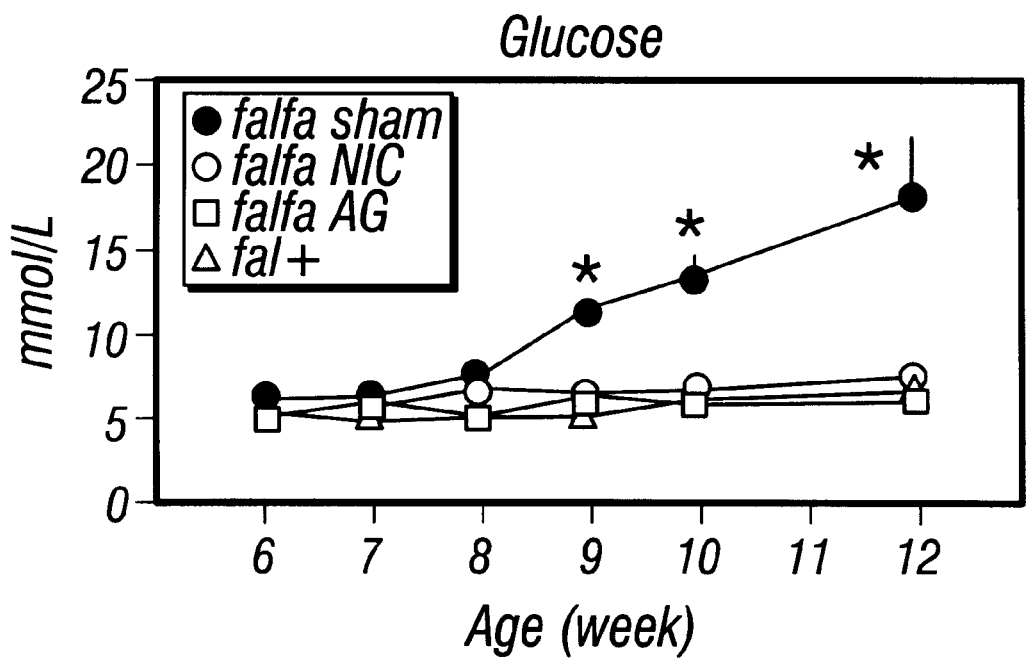
FIG. 6A and FIG. 6B. Effects of a 6-wk course of NIC and AG treatment on blood glucose (FIG. 6A) and FFA levels (FIG. 6B) of obese prediabetic fa/fa ZDF rats (levels in untreated lean fa/+ controls are also shown). Values represent the mean±SEM of three to six animals. Significant differences are marked as follows: *P<0.05 vs. untreated lean fa/+ ZDF group, and †P<0.05 vs. sham-treated obese fa/fa ZDF group.
Figure 6B:
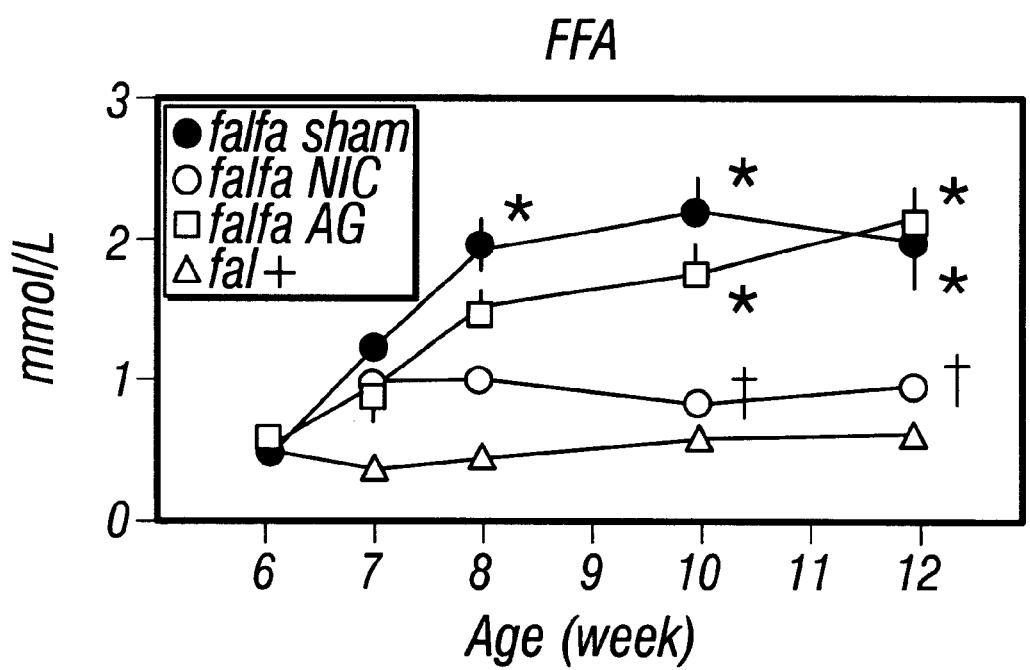
Figure 7:
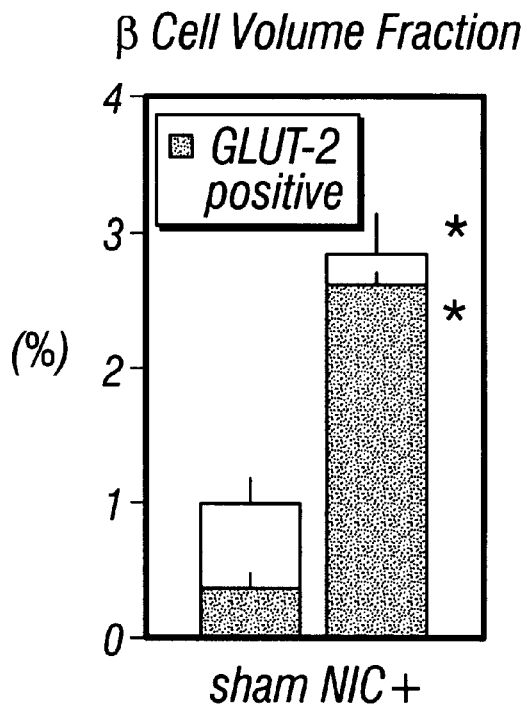
FIG. 7 Effects of a 6-wk course of NIC treatment on morphometrically determined β cell volume fraction and GLUT-2 positivity in obese fa/fa ZDF rats. From 6 to 12 wk of age, obese prediabetic fa/fa ZDF rats received daily intraperitoneal injections of 0.5 g/kg-1 NIC (NIC+), 0.4 g/kg-1 AG (AG+), or 0.9% saline (sham). Values shown are the mean±SEM of three studies. Significant differences are marked as follows: *p<0.05 vs. untreated obese fa/fa ZDF group.

NIC has been shown to prevent the deleterious effects of IL-1β-induced NO on β cells (Akabane, 1995), and is currently being evaluated in autoimmune insulin-dependent diabetes (Pozzilli et al., 1996). To determine if NIC and AG prevent obesity-related NIDDM in vivo, prediabetic obese ZDF rats (fa/fa) were treated for 6 wk with daily intraperitoneal injections of 0.5 g NIC or 0.4 g AG/kg body wt beginning at the age of 6 wk. None of the animals treated with NIC or AG became diabetic; their blood glucose levels averaged 7.5±0.1 and 6.7±0.2 mmol/ liter, respectively, at the end of the treatment period, compared with 18.0±0.4 mmol/liter in untreated controls (FIG. 6A). Plasma FFA levels of NIC-treated rats were lower than in the sham-treated controls, although they exceeded the values in lean rats (FIG. 6B). In AG-treated rats, FFA levels were no different than in untreated controls. Glucose tolerance was normal in NIC- and AG-treated prediabetic ZDF rats, with blood glucose returning to the fasting level at 2 h after an intraperitoneal injection of glucose (2 g/kg). The profound reduction in the number of β cells was prevented by both NIC and AG therapy, as was the β cell GLUT-2 loss (FIG. 7). GLUT-2 loss is a morphological marker of NIDDM (Orci et al., 1990), and is now recognized to be secondary to metabolic changes (Thorens et al., 1992). Perfusion of pancreata from NIC-treated rats showed marked improvement in β cell function; instead of the negative insulin response to glucose observed in untreated diabetic controls, there was a positive response in the low normal range (Table 9) that was nine times that of sham-treated animals. AG caused a sevenfold improvement over sham-treated controls. Thus, two agents that lower NO production by different mechanisms prevented the development of the NIDDM phenotype in β cells. By contrast, 6 wk of daily treatment with 0.05 g/kg 3-aminobenzamide, which, like NIC, inhibits poly-ADP-ribose synthetase (Radons et al., 1994) but has no other known action in common with NIC, failed to prevent diabetes.

TABLE 9

Insulin Secretion by Pancreata Isolated from
fa/+ and fa/fa ZDF Rats Treated with NIC, or
AG (Microunit per milliliter per Minute, Mean ± SEM)

| | Lean fa/+ ZDF | Obese prediabetic fa/fa ZCF | | |
|---|---|---|---|---|
| | sham-rx n = 3 | sham-rx n = 6 | NIC-rx n = 3 | AG-rx n=3 |
| 5.6 mM glucose | 10.2 ± 1.4 | 43.3 ± 7.7 | 36.3 ± 10.9 | 45.2 ± 8.6 |
| 20 mM glucose* | 83.6 ± 6.6 | 2.8 ± 2.0‡ | 26.9 ± 12.2§ | 22.2 ± 11.1† |

*Insulin values represent increments above the levels at 5.6 mM glucose;
‡P < 0.05 vs. lean fa/+; §P < 0.05 vs. sham-treated obese fa/fa.

EXAMPLE 11

In vivo iNOS Expression in Diabetic ZDF Rats

Figure 8:
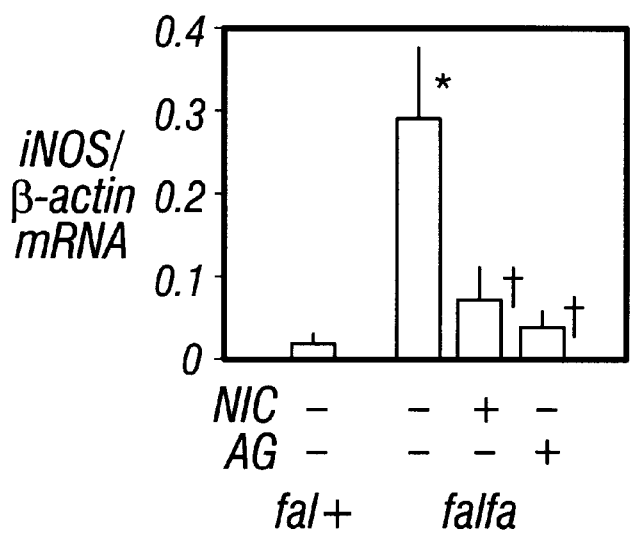
FIG. 8. Effects of a 6-wk course of NIC and AG treatment on iNOS/β-actin in RNA ratio in freshly isolated islets of 12-wk-old obese ZDF (fa/fa) rats that were sham-treated (diabetic), or treated for 6 wk with either NIC (0.5 g/kg$^{-1}$ body wt) or AG (0.4 g/kg$^{-1}$ body wt) administered intraperitoneally. The mean ratio in islets from lean heterozygous ZDF control (fa/+) rats is also shown. All values represent the mean±SEM of three studies. Differences are marked as follows: *P<0.05 vs. untreated lean fa/+ ZDF group and †P<0.05 vs. obese fa/fa ZDF group.

To determine if iNOS expression is increased in β cells of diabetic ZDF rats, iNOS mRNA was semiquantified in islets freshly isolated from 6- and 12-wk-old obese fa/fa ZDF and lean fa/+ ZDF rats (FIG. 8). pancreatic sections also were examined immunocytochemically for the presence of iNOS using an iNOS antibody (anti- iNOS; Transduction Laboratories, Lexington, Ky.). In addition, islets from the NIC- and AG-treated prediabetic rats were examined for iNOS mRNA and immunostainable iNOS. iNOS mRNA could not be detected in islets in any of the 6-wk-old rats; iNOS mRNA was measurable in both homozygous and heterozygous 12-wk-old groups, but was 20 times higher in the homozygous rats, all of which were diabetic. In 12-wk-old "prediabetic" ZDF rats in which the diabetes had been prevented by 6 wk with NIC and AG treatment, iNOS mRNA was reduced almost to normal (FIG. 8). Immunostaining for iNOS was positive only in the diabetic ZDF rats.

EXAMPLE 12

Effect of Islet TG Content on IL-1β-induced Nitrite Production and Cell Viability To determine the influence of islet TG content on IL-1β-induced NO production and cytotoxicity islet nitrite accumulation and cell viability was measured in rats with a wide range of tissue fat. At one extreme 7-wk-old obese male ZDF rats (fa/fa) with fat-laden islets (Lee et al., 1994; Lee et al., 1997) were used; at the other extreme the most stringent method of lipid depletion, induction in normal lean rats of leptin overexpression by AdCMV-leptin infusion (Shimabukuro et al., 1997a and 1997b; Chen et al., 1996) was employed. The phenotype is extreme tissue lipopenia and the disappearance of visible fat. A less profound reduction in islet fat content in vivo was produced by pair-feeding of intact rats to the hyperleptinemic rats (Shimabukuro et al., 1997a and 1997b). The TG content of islets isolated from these groups of rats and from free-feeding control rats infused with AdCMV-β-Gal are indicated in Table 10.

TABLE 10

TG Content of 24-h-cultured Pancreatic Islets Isolated
from AdCMV-β-Gal and AdCMV-leptin Infused Lean
ZDF Rats, Pair-fed Controls and Obese fa/fa ZDF Rats

| | Lean +/+ ZDF | | | Obese fa/fa ZDF |
|---|---|---|---|---|
| | AdCMV-β-Gal | AdCMV-leptin | Pair-fed | Intact |
| TG (ng/islet) | 18.9 ± 1.1 (12) | 2.3 ± 0.4*, (12) | 13.0 ± 1.5 (12) | 70.3 ± 6.3 (4) |

Values are expressed as the mean ± SEM. Numbers of studies are in parentheses.
*P < 0.001 vs. AdCMV-β-Gal, P < 0.001 vs. pair-fed.

Figure 9B:
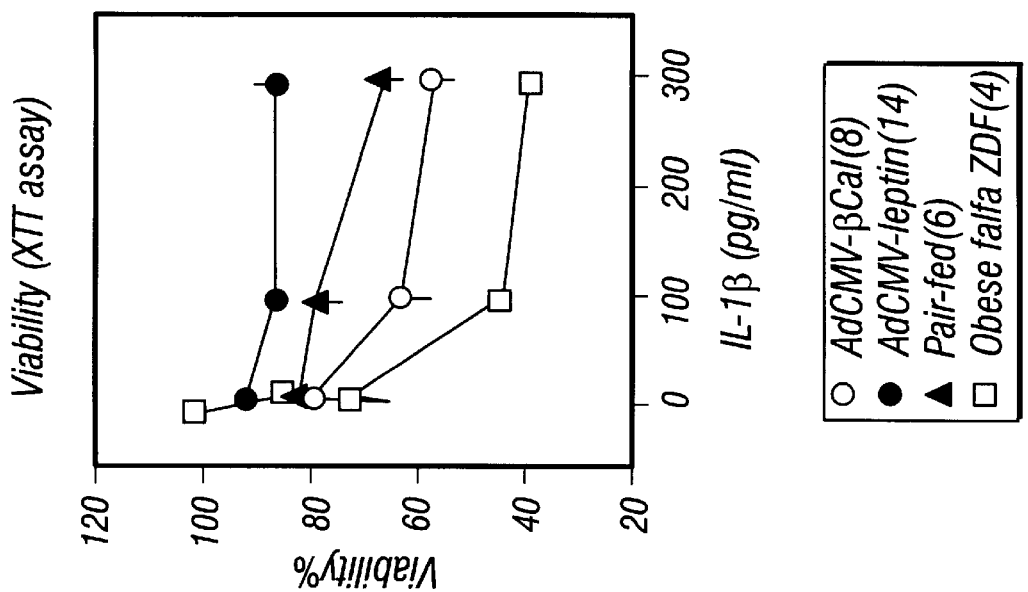
FIG. 9A and FIG. 9B. Effect of TG content on (FIG. 9A) IL-1β-induced nitrite production and (FIG. 9B) cell viability in islets isolated from AdCMV-leptin-induced wild-type (+/+) ZDF rats, the pair-fed controls, free-feeding AdCMV-β-Gal controls, and obese fa/fa ZDF. Islets were isolated 7 d after virus infusion and cultured for 24 h with recombinant human IL-1β at the indicated concentrations. Data are expressed as the mean±SEM. Viability is expressed as the percentage of the values observed in the absence of IL-1β. Numbers of studies are in parentheses.
Figure 9A:
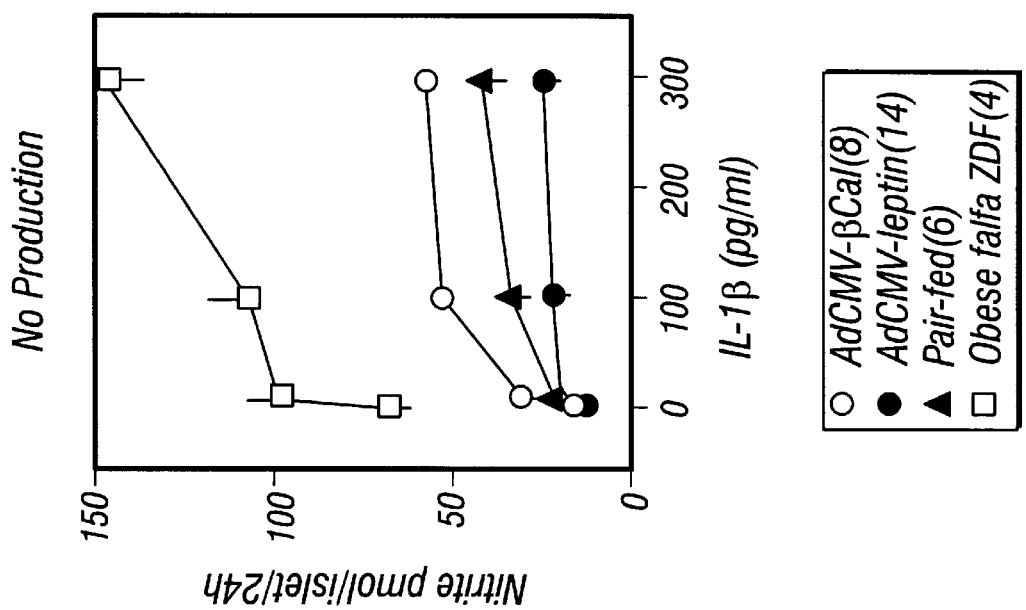

In islets of free-feeding AdCMV-β-Gal-infused controls with normal TG content, nitrite production at 300 pg/ml of IL-1β reached 56 pmol/islet per 24 h (FIG. 9A), and cell viability declined to <60% of the control value (FIG. 9B). In TG-depleted islets of hyperleptinemic rats, by contrast, baseline nitrite accumulation was only ~12 pmol/islet per 24 h and the addition of 300 pg/ml of IL-1β failed to raise it significantly above this level (FIG. 9A); viability remained above 80% of the control value (FIG. 9B). In pair-fed rats with a 50% reduction in islet TG content, nitrite rose significantly in the presence of IL-1β (P<0.001) but remained at ~40 pmol/islet per 24 h, significantly below the nitrite value of 56 pmol/islet per 24 h in free-feeding β-Gal controls (P<0.001) (FIG. 9A); however, viability was not significantly different from the latter (FIG. 9B).

In the fat-laden islets of obese homozygous (fa/fa) ZDF rats, nitrite accumulation, which averaged 68±6.8 pmol/islet per 24 h in the absence of IL-1β β (FIG. 9A), reached a peak level of 147±7.8 pmol/islet per 24 h at the 300 pg/ml concentration of IL-1β, 3.6 times the nitrite level of the lean β-Gal controls (P<0.001) (FIG. 9A); viability was 40%, significantly below that of islets of lean β-Gal controls (P<0.001) (FIG. 9B).

EXAMPLE 13

Effect of FFA on IL-1β-induced Nitrite Production and Cytotoxicity in Islets

Figure 10B:
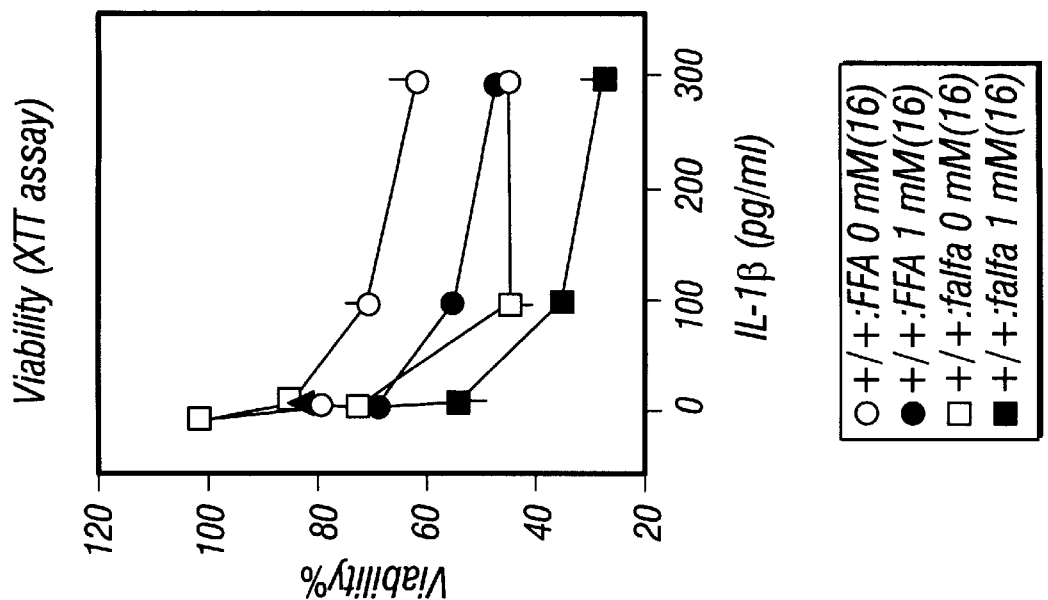
FIG. 10A and FIG. 10B. Effect of 1 mM FFA on (FIG. 10A) nitrite production and (FIG. 10B) cell viability in lean wild-type (+/+) ZDF rats and obese (fa/fa) ZDF rats. Islets isolated from intact rats were cultured with recombinant human IL-1β at the indicated concentrations, either with or without 1 mM FFA mixture (oleate/palmitate, 2:1) for 24 h. Data are expressed as the mean±SEM. Viability is expressed as the percentage of the values observed in the absence of IL-1β. Numbers of studies are in parentheses.
Figure 10A:
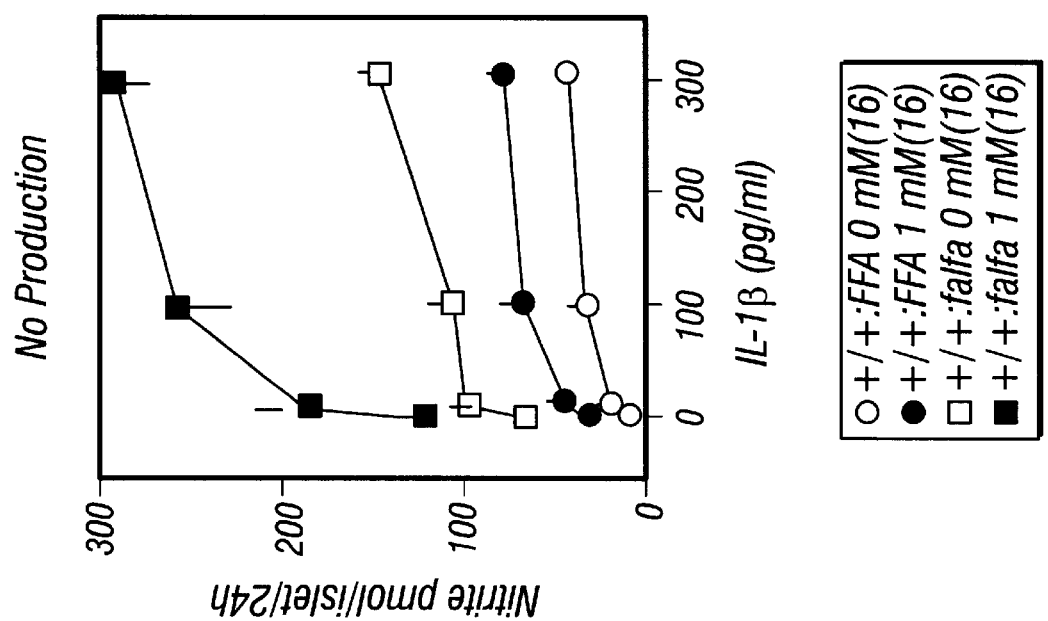

To compare the in vitro effects of FFA on IL-1β-induced nitrite production in islets with varying esterification capacities islets from normal rats and from obese ZDF rats, which have been shown to have a high esterification capacity (Lee et al., 1997) were isolated; these were cultured with or without 1 mM FFA and examined IL-1β-induced nitrite production and cytotoxicity (FIG. 10). In the absence of IL-1β, FFA raised nitrite accumulation in islets from lean rats to 33±5.2 pmol/islet per 24 h, close to the peak values induced by the cytokine in the absence of FFA; FFA plus IL-1β increased nitrite production to ~80 pmol/islet per 24 h (FIG. 10A). In the islets from obese rats cultured in FFA without IL-1β, nitrite accumulation exceeded the peak induced in islets of lean rats by FFA plus 300 pg/ml of IL-1β; in islets of obese rats FFA plus 300 pg/ml of IL-1β increased the cumulative nitrite level to ~300 pmol/islet per 24 h (FIG. 10A). This was significantly above the response of lean controls (291±23.0 vs. 77±4.9 pmol/islet per 24 h, P<0.001). In the presence of 300 pg/ml of IL-1β, 1 mM FFA reduced viability of normal islets to ~45%, about the same as islets from obese rats without the FFA. Viability of islets of obese rats declined below 30% when 1 mM FFA and 300 pg/ml of IL-1β were both present in the culture medium (FIG. 10B).

EXAMPLE 14

Effect of Troglitazone on IL-1β-mediated

Nitrite Production and Cytotoxicity in Islets

Figure 11A:
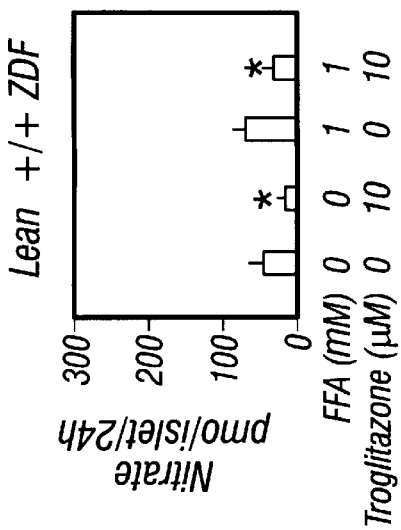
FIG. 11A, FIG. 11B, FIG. 11C, FIG. 11D, FIG. 11E and FIG. 11F. Effect of troglitazone on (FIG. 11A and FIG. 11B) islet TG content, (FIG. 11C and FIG. 11D) nitrite production, and (FIG. 11E and FIG. 11F) islet cell viability. Islets isolated from wild-type (+/+) ZDF rats and obese (fa/fa) ZDF rats were cultured for 24 h with 300 pg/ml IL-1β, with or without FFA and with or without troglitazone. Data are expressed as the mean±SEM of three studies. Viability is expressed as the percentage of the values observed at IL-1β 0 pg/ml. Statistical significance is indicated as *P<0.001 vs. troglitazone 0 pg/ml.
Figure 11B:
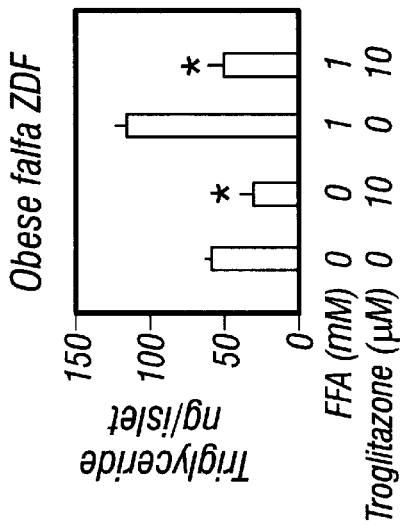
Figure 11C:
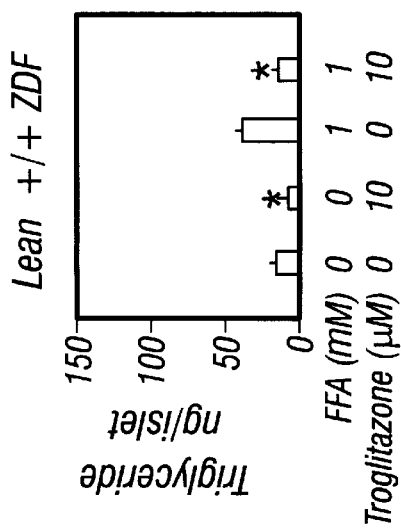
Figure 11D:
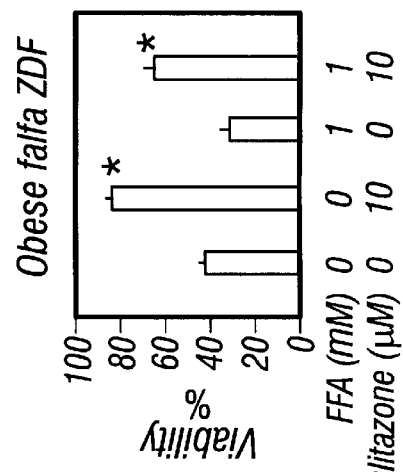
Figure 11E:
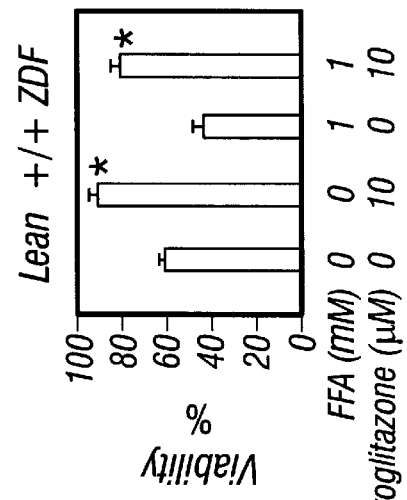
Figure 11F:
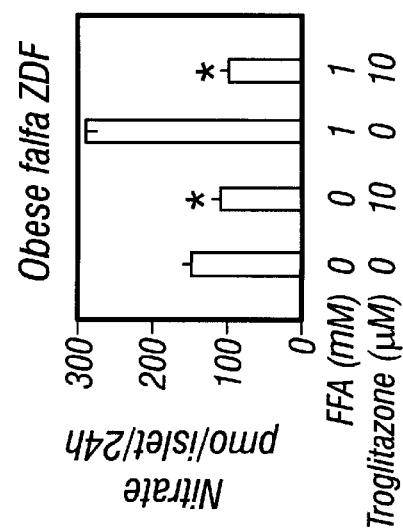

Troglitazone has been shown to reduce tissue TG content of liver (Fulgencio et al., 1996), while leptin depletes TG in islets (Shimabukuro et al., 1997a and 1997b). To determine if this thiazolidinedione also depletes TG in islets, the TG content of islets from normal lean rats cultured for 24 h in the presence of 10 μM troglitazone was measured. TG declined by 42% and, when 1 mM FFA was present, TG accumulation was prevented by troglitazone (FIG. 11A and FIG. 11B). Thus like leptin (Corbett et al., 1993), troglitazone reduces endogenous TG of islets and prevents the formation of new TG from FFA (Shimabukuro et al., 1997a and 1997b). Troglitazone reduced by 47% the rate of nitrite accumulation in response to IL-1β alone and abolished the enhancing effect of FFA on IL-1β-induced nitrite production (FIG. 11C and FIG. 11D). In the absence of FFA, troglitazone improved viability to over 90% despite the presence of 300 pg/ml of IL-1β; in the presence of FFA plus IL-1β viability exceeded 75%, which was still significantly above the controls (P<0.001) (FIG. 11E and FIG. 11F).

Because of their mutated leptin receptor (Phillips et al., 1996; Iida et al., 1996), leptin has no effect on TG content of islets from obese fa/fa ZDF rats (Shimabukuro et al., 1997a and 1997b); however, troglitazone significantly reduced the TG content (FIG. 11A and FIG. 11B). Nitrite production declined (FIG. 11C and FIG. 11D), and viability was significantly improved above the values observed in the absence of troglitazone (P<0.001) (FIG. 11E and FIG. 11F).

Relationship between TG content and IL-1β-mediated nitrite production and cytotoxicity in islets.

Figure 12A:
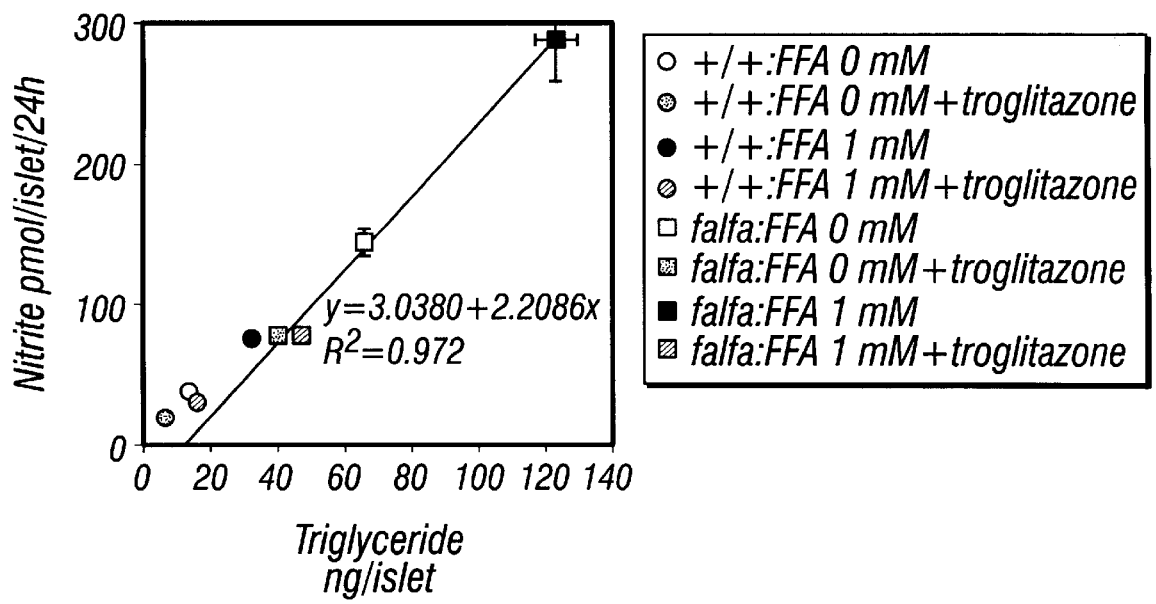
FIG. 12A and FIG. 12B.
Figure 12B:
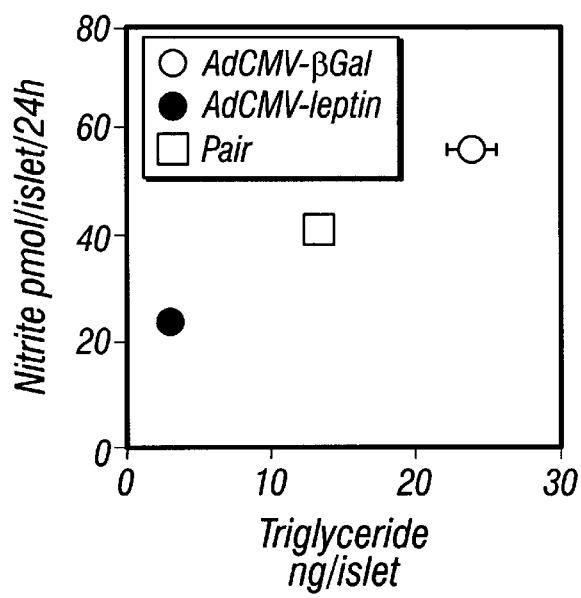

The relationship between tissue TG content and IL-1β action was further scrutinized by combining all available in vivo and in vitro data in the various groups to compare islet fat content with IL-1β-induced nitrite production. A remarkably strong correlation was apparent ($R2=0.972$, $P<0.001$) (FIG. 12A and FIG. 12B).

EXAMPLE 15

Effects of Free Fatty Acids on β-Cell Proliferation

The pathogenesis of type-II diabetes involves an initial period of β-cell hyperplasia to compensate for the insulin resistance. This is likely instigated by the mild hyperplasia which in turn mediates glucose-induced β-cell proliferation. However, after this initial period for expansion of the β-cell population, there is then a marked decline in β-cell mass, so that compensation for the peripheral insulin resistance can longer take place and diabetes ensues. As well as circulating glucose levels increasing during the pathogenesis of type-II diabetes, circulating FFA levels also rise resulting in increased accumulation of intracellular lipid stores (including that of the β-cell). The inventors' discovery of FFA inhibition of glucose-induced β-cell proliferation is likely a key factor in the reduction of the β-cell population during the evolution of type-II diabetes. Thus, prevention of FFA induced inhibition of glucose-induced β-cell proliferation would likely lead to a novel pharmacological therapy for type-II diabetes. The data presented herein were generated using a high through-put 96-well plate assay. This assay is ideally amenable for use in screening for compounds that might prevent FFA induced inhibition of glucose-induced β-cell proliferation.

Figure 13:
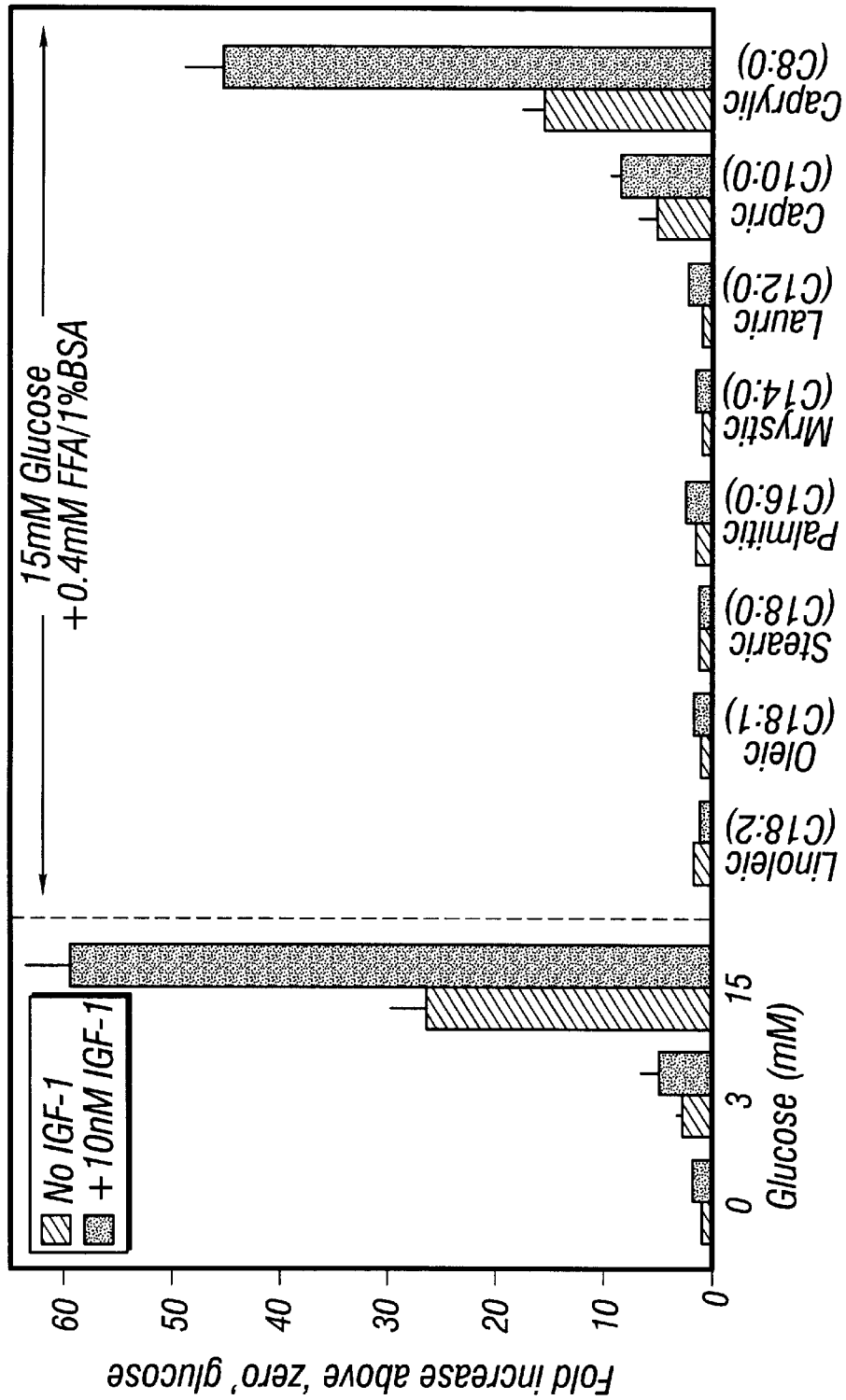
FIG. 13. Free fatty acids (FFA) inhibit glucose-induced mitogenesis in pancreatic β-cells-the effect of FFA chain length. Approximately 10$^5$ quiescent INS-1 cells/well of a 96-well plate were incubated for 24 h in RPMI 1640 medium containing 0.1% BSA, 0.3 mM. or 15 mM glucose+10 nM IGF-1, in the presence of either 1% BSA or 0.4 mM FFA complexed to 1% BSA as indicated. INS-1 cell proliferation rate was then assessed by [$^3$H]thymidine incorporation over a 4 h incubation period (Hugl et al., 1998). All studies were done in triplicate on at least 3 independent occasions. The data are expressed as a fold increase above the control observation in the absence of glucose and IGF-1 (i.e. 500–1200 cpm/10$^5$ cells), and depicted as a mean±SE (n≧3).

In order to investigate the effects of varying fatty acid chain length on the inhibition of glucose-induced β-cell proliferation an assay was set up in which linoleic acid (C18:2), oleic (C18:1), stearic (C18:0), palmitic (C16:0). myristic (C14:0), lauric (C12:0). capric (C10:0) and caprylic (C8:0) were used (FIG. 13). Above a FFA chain length of C10 (capric acid), glucose-, and glucose -dependent IGF-1 induced INS-1 cell mitogenesis was significantly inhibited within 24 h. IGF-1 induced β-cell proliferation is dependent on glucose being present in the physiologically relevant concentration range (Hugl et al., 1998). As such FFAs (>C 10:0) are most likely inhibiting glucose-induced β-cell proliferation that in turn abolishes a glucose-dependent IGF-1 stimulation of β-cell growth.

Figure 14:
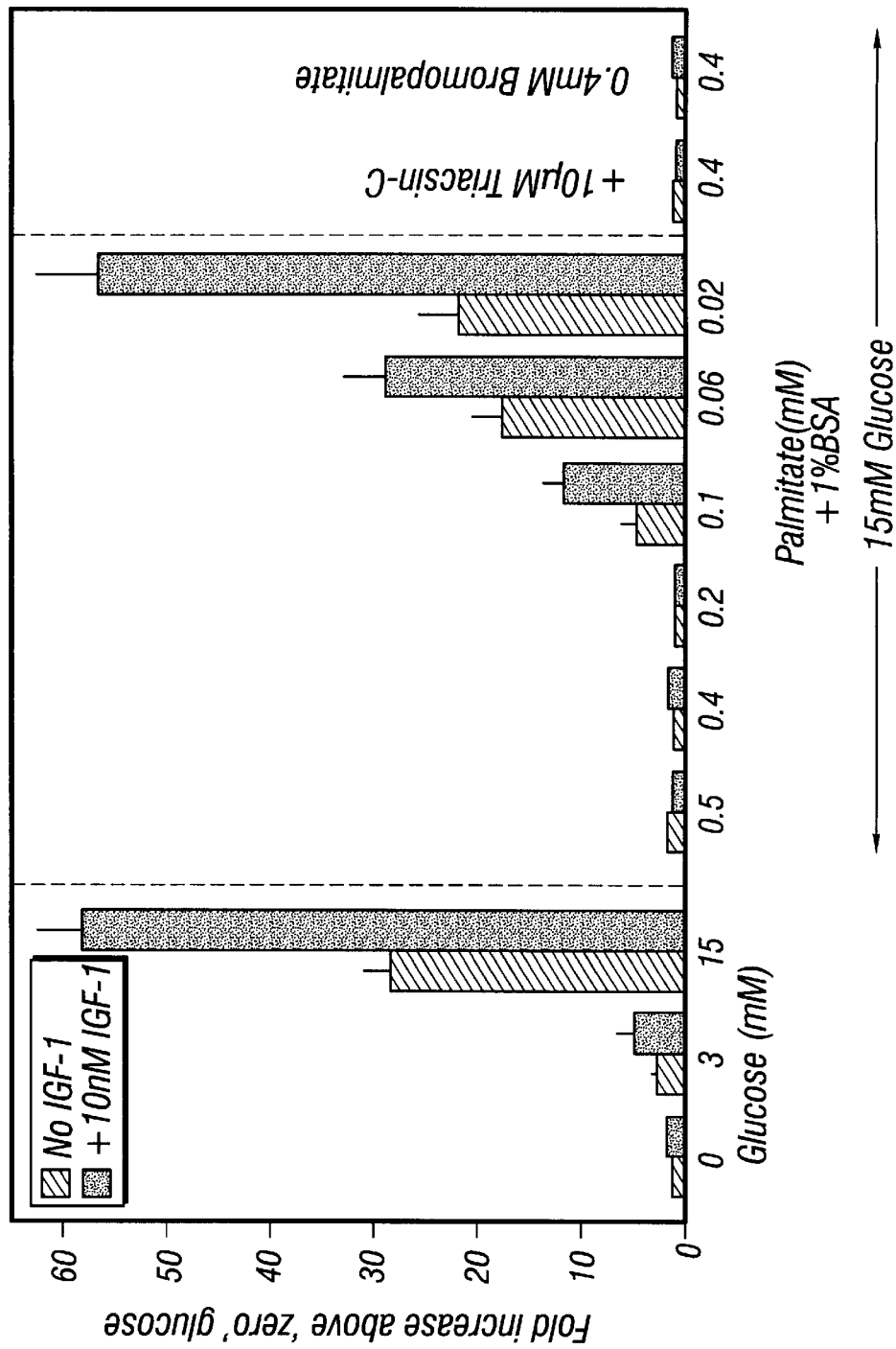
FIG. 14. Free fatty acids inhibit glucose induced mitogenesis in pancreatic b-cells. Dose response of palmitate. Approximately 10$^5$ quiescent INS-1 cells/well of a 96-well plate were incubated for 24 h in RPMI 1640 medium containing 0.1% BSA, 0.3 mM, or 15 mM glucose±10 nM IGF-1, in the presence of either 1% BSA or increasing amounts of palmitate (0.02–0.5 mM) complexed to a constant 1% BSA concentration as indicated. In addition, INS-1 cell were similarly incubated in the presence of 0.4 mM bromopalmitate complexed to 1% BSA, and 0.4 mM palmitate complexed to 1% BSA plus 10 µM triacsin-C (an inhibitor of fatty acyl-CoA synthase). INS-1 cell proliferation rate was then assessed by [$^3$H]thymidine incorporation over a 4 h incubation period (Hugl et al., 1998). All studies were done in triplicate on at least 3 independent occasions. The data are expressed as a fold increase above the control observation in the absence of glucose and IGF-1 (i.e. 500–1200 cpm/10$^5$ cells), and depicted as a mean±SE (n≧3).

One of these fatty acids was chosen to investigate the role of FFA concentration on β-cell mitogenesis. Palmitate significantly inhibited glucose-, and glucose-dependent IGF-1, induced INS-1 cell proliferation >0.05 mM palmitate/1% BSA, reaching a maximum inhibition >0.2 mM palmitate/1% BSA (FIG. 14). The $K_{10.5}$=0.13+0.03 mM palmitate for 15 mM glucose-induced INS-1 cell proliferation, and $K_{10.5}$= 0.11=0.02 mM palmitate for 15 mM glucose+10 nM IGF-1 induced INS-1 cell proliferation. There was no difference in the $K_{10.5}$ for palmitate inhibition of glucose-induced β-cell growth whether IGF-1 was present or not. Triacsin-C had no affect on palmitate inhibition of glucose/IGF-1 induced INS-1 cell proliferation suggesting that a modification of FFA to fatty acyl-CoA was not necessary to produce this inhibitory effect. Moreover, bromopalmitate (which is not metabolized in pancreatic β-cells) also inhibited glucose/IGF-1 induced INS-1 cell proliferation suggesting that FFA oxidation was not required to produce this inhibitory effect and it was likely a direct effect of the FFA. In considering that very low concentrations of FFA (i.e. >0.2 mM palmitate/1% BSA) were required to inhibit glucose/IGF-1 induced INS-1 cell proliferation it was unlikely that this was due to a non-specific detergent-like effect of the FFA. Moreover, it should be noted that the considered physiological relevant concentration required to stimulate insulin release from β-cells is >0.3 mM/1% BSA.

Figure 15:
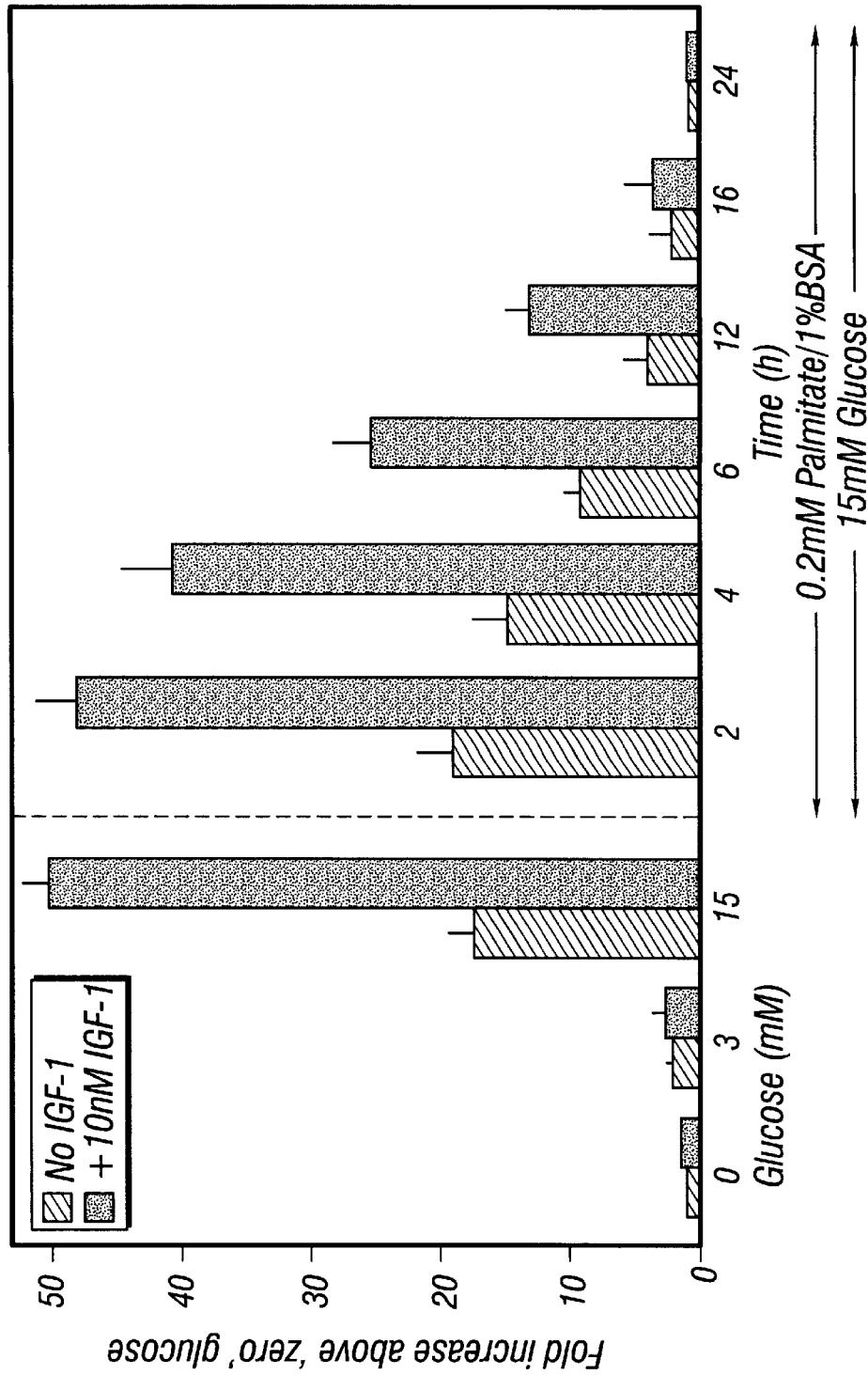
FIG. 15. Free fatty acids inhibit glucose-induced mitogenesis in pancreatic β-cells—time course for 0.2 mm palmitate/1% BSA. Approximately 10$^5$ quiescent INS-1 cells/well of a 96-well plate were incubated for 2–24 h in RPMI 1640 medium containing 0.1% BSA, 0.3 mM, or 15 mM glucose—10 nM IGF-1, in the presence of either 1% BSA or 0.2 mM palmitate complexed to 1% BSA as indicated. INS-1 cell proliferation rate was then assessed by [$^3$H]thymidine incorporation over a 4 h incubation period (Hugl et al., 1998). All studies were done in triplicate on at least 3 independent occasions. The data are expressed as a fold increase above the control observation in the absence of glucose and IGF-1 (i.e. 500–1200 cpm/10$^5$ cells), and depicted as a mean±SE (n≧3).

When a similar assay was set up to measure the time course of the FFA effect, it was found that the 0.2 mM palmitate/1% BSA significantly inhibited glucose-, and glucose-dependent IGF-1, induced INS-1 cell proliferation 6 h, reaching a maximum inhibition by 24 h (FIG. 15). The $t_{0.5}$ for 0.2 mM palmitate/1% BSA inhibition of both 15 mM glucose alone and 15 mM glucose—10 nM IGF-1 induced INS-1 cell proliferation ~7–8 h.

Figure 16:
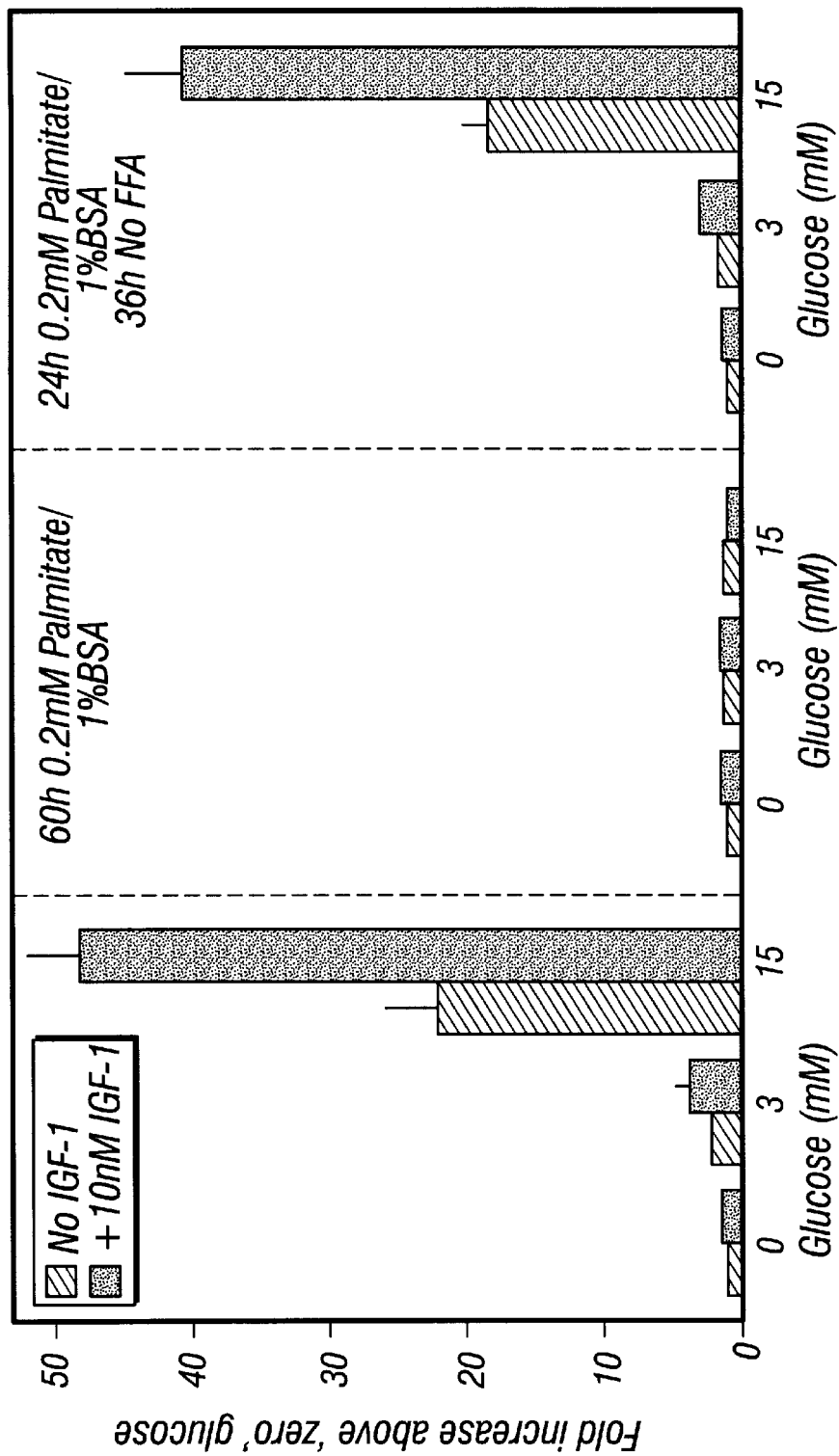
FIG. 16 Free fatty acids inhibit glucose-induced mitogenesis in pancreatic β-cells—the FFA effect is reversible. Approximately 10$^5$ quiescent INS-1 cells/well of a 96-well plate were incubated for either 60 h in RPMI 1640 medium containing 0.2 mM palmitate complexed to 1% BSA or for 24 h in RPMI 1640 medium containing 0.2 mM palmitate complexed to 1% BSA then for a further 36 h in the same media but in the absence of 0.2 mM palmitate/1% BSA (0.1% BSA only was used). The final 24 h incubation period was in RPMI 1640 medium containing either, 0, 3 mM, or 15 mM glucose+10 nM IGF-1, in the presence of either 1% BSA or 0.2 mM palmitate/1% BSA as indicated. INS-1 cell proliferation rate was then assessed by [$^3$H]thymidine incorporation over a 4 h incubation period (Hugl et al., 1998). All studies were done in triplicate on at least 2 independent occasions. The data are expressed as a fold increase above the control observation in the absence of glucose and IGF-1 (i.e. 500–1200 cpm/10$^5$ cells), and depicted as a mean±SE.

Furthermore, the FFA effect is reversible (FIG. 16). 0.2 mM palmitate/1% BSA significantly inhibited glucose-, and glucose-dependent IGF-1, induced INS-1 cell proliferation compared to controls after the 60 h incubation with palmitate. However, in INS-1 cells incubated for 24 h in the presence of 0.2 mM palmitate/1% BSA then incubated for a further 36 h after removal of 0.2 mM palmitate/1% BSA it was found that 15 mM glucose-, and 15 mM glucose—10 nM IGF-1, induced B-cell proliferation could be restored to that of the controls. This argues that the FFA induced inhibition of glucose/IGF-1 induced INS-1 cell proliferation and it was unlikely due to a non-specific detergent-like effect of the FFA.

Figure 17:
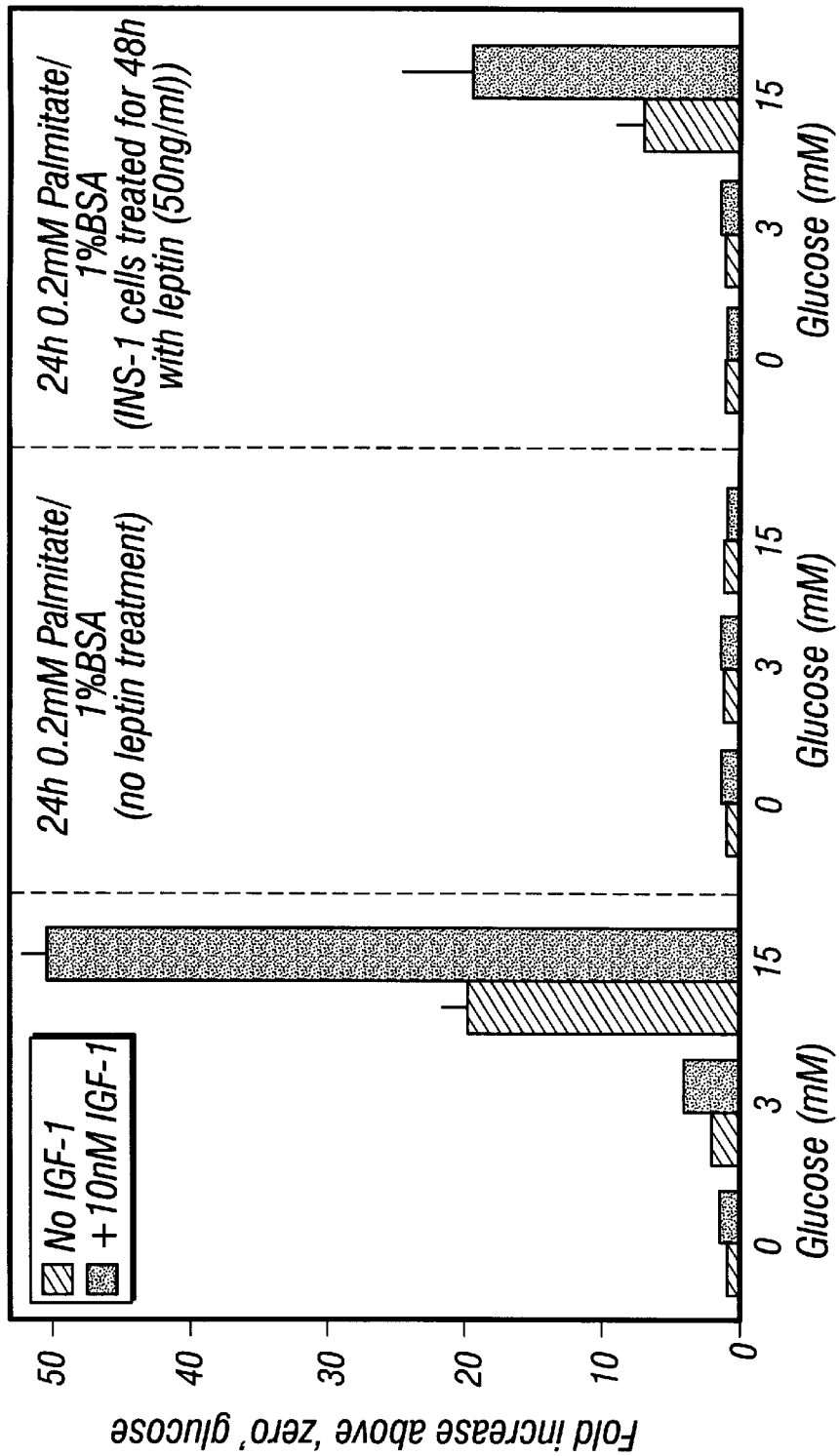
FIG. 17. Free fatty acids inhibit glucose-induced mitogenesis in pancreatic β-cells—the FFA effect is reduced in leptin treated β-cells. INS-1 cells were preincubated for 48 h±50 ng/ml leptin. Then approximately 10$^5$ quiescent INS-1 cells/well of a 96-well plate were incubated for 24 h in RPMI 1640 medium containing 0.1% BSA, 0.3 mM, or 15 mM glucose+10 nM IGF-1, in the presence of either 1% BSA or 0.2 mM palmitate complexed to 1% BSA as indicated. INS-1 cell proliferation rate was then assessed by [$^3$H]thymidine incorporation over a 4 h incubation period (Hugl et al., 1998). All studies were done in triplicate on at least 2 independent occasions. The data are expressed as a fold increase above the control observation in the absence of glucose and IGF-1 (i.e. 500–1200 cpm/$10^5$ cells), and depicted as a mean±SE.

In a further assay, the effects of FFA in leptin treated β-cells was examined (FIG. 17) After 48 h of exposure, leptin did not affect glucose-, or glucose-dependent IGF-1, induced INS-1 cell proliferation compared to controls. However, in leptin-treated INS-1 cells incubated for 24 h in the presence of 0.2 mM palmitate/1% BSA an alleviation of the inhibition of glucose/IGF-1 induced INS-1 cell proliferation was observed compared to INS-1 cells that were not exposed to leptin. It has been previously shown that leptin can deplete intracellular lipid stores in β-cells by driving an increased rate of FFA oxidation. Thus it is likely that the accumulation of intracellular FFA in β-cells is responsible for inhibition of glucose/IGF-1 induced β-cell proliferation.

EXAMPLE 16

Selection of naturally occurring cytokine resistant cells

The present example provides a strategy for selecting naturally occurring cells which gain resistance to IL-1β and γ-IFN induced cell death.

Cells (e.g., INS-1) were seeded in 35×10 mm falcon dishes. When the cells reached about 80% confluence, the culture medium was changed to medium containing IL-1β (0.5 ng/ml)+γ-IFN (5 units/ml). The cells were kept in this media for 72 h. After 48 h, more than 80% of the cells were in suspension. At 72 h, the media containing the suspended cells was transferred to 15 ml Falcon centrifuge tubes, and spun at 1000 rpm for 5 min. The cell pellets were resuspended in fresh media and transferred to a 25 ml tissue culture flask (5 dishes floating cells to one flask in 4 ml of medium). Fresh media was added to the culture dishes which still had a small number of adherent cells. This media comprised 1 volume of normal INS-1 culture media (Hugl et al., 1998) plus 1 volume of conditioned medium (normal media was added to 60–70% confluent INS-1 cells, harvested after 48 h, spun at 1000 rpm for 5 min, supernatants were kept at −20° C. before use), additional 2% fetal bovine serum was added to balance the loss of serum growth factors in the conditioned medium. IL-1β and γ-IFN were added to the media to the desired concentration prior to use.

The cells were allowed to grow and the media in the dishes and flasks was changed every 72 h. After two to three wk, there were cells which were able to grow in adherent culture in the presence of the cytokine containing media (adherent cells as viewed by microscopy). Cells from 5 dishes and 1 flask were trypsinized and transferred to a new 35×10 mm dish. At confluence these cells were subcultured in a ratio of 1 to 4 (1 dish to two 25 ml of flasks). After the cells started to grow, the media was changed to normal media supplemented with IL-1β and γ-IFN of the desired concentration. The cells were subcultured again in order to generate sufficient cell numbers to be frozen. The media for freezing the cell is normal medium with 6–8% DMSO and 20% fetal bovine serum. The procedure includes 4° C. for 30 mins. to 1 h; −20° C. for 1.5 to 3 h, −80° C. for 2 h to overnight.

Once there were sufficient cells that survived the cytokine-containing media, the concentration of IL-1β and γ-IFN was increased to 1 ng/ml and 10 units/ml respectively and the resistant cells were selected and grown as above. These growth steps may be repeated until the concentration of IL-1β and γ-IFN goes to 10 ng/ml and 100 units/ml, for example, the cytokine concentration may be increased in the following increments IL-1β: 0.5; 1; 2.5; 5; 10 ng/ml and the corresponding γ-IFN: 5; 10; 25; 50; 100 units/ml. In this manner it is possible to generate cytokine resistant cells.

Figure 19:
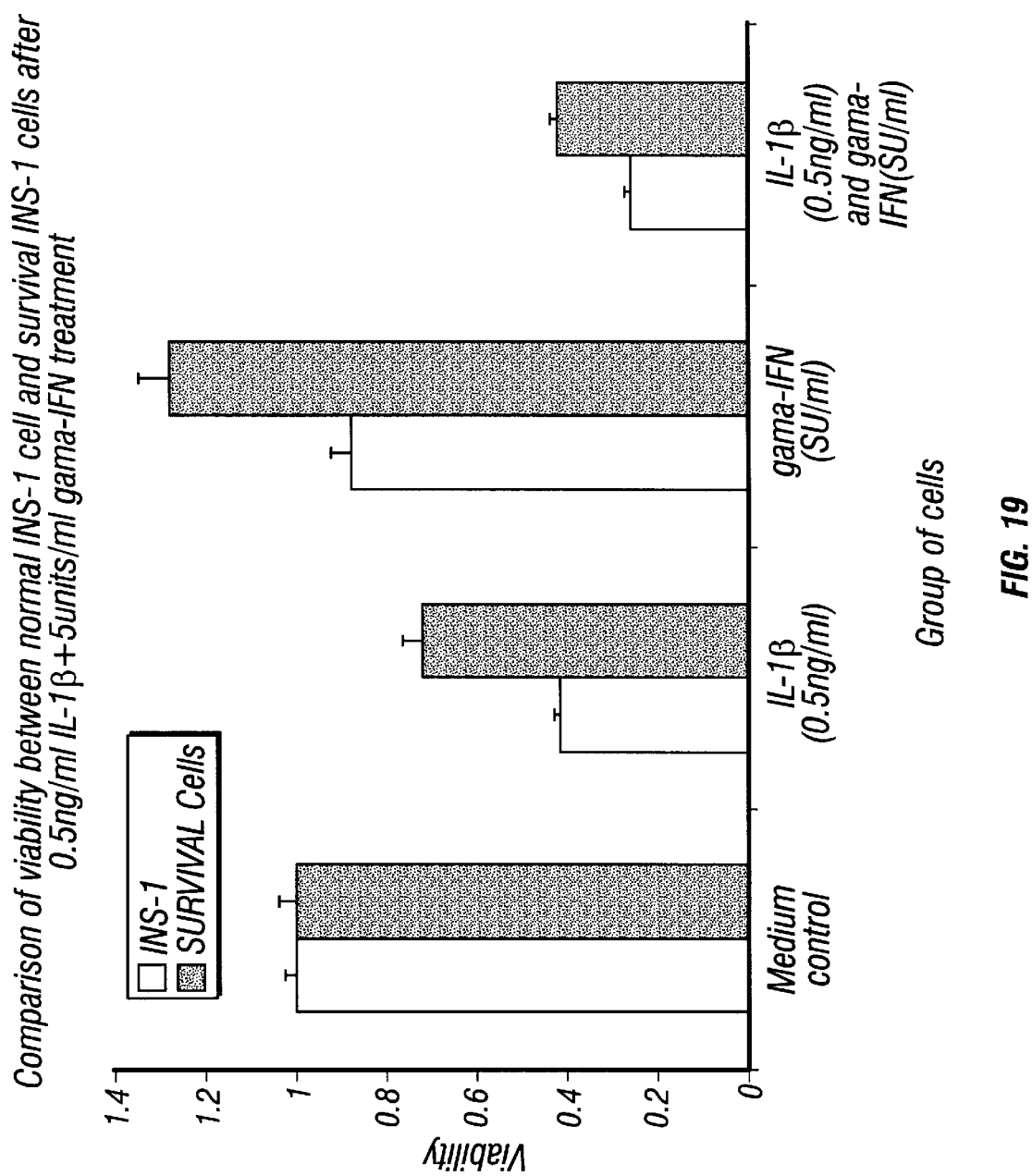
FIG. 19. Comparison of the viability between normal INS-1 cells and survival INS-1 cells after growth in 0.5 ng/ml IL-1β+5 units/ml γ-IFN.

A cytokine resistant cell line was generated using the above protocol. FIG. 19 shows a comparison of the viability between normal INS-1 cells and survival INS-1 cells after growth in 0.5 ng/ml IL-1β+5 units/m γ-IFN.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adams et al., *Bioch. Med. Met. Biol.*, 45:271–291, 1991.
Aguilar-Bryan et al., *Science*, 268:423–426, 1995.
Akabane, A., *Biochem. Biophys. Res. Commun*, 215:524–530, 1995.
Altman et al., *Diabetes* 35:625–633, 1986.
Anderson et al., *J.B.C*, 264:8222–8229, 1989.
Andersson et al., *Eur. J. Immunol.*, 20:1591–1596, 1990.
Arimura et al., The Pituitary Gland, 2nd Edition, Chap.9:217–259. H. Imura, Ed., Raven Press, N.Y., 1994.
Arora et al., *J.B.C,*. 268:18259–18266, 1993.
Arya et al., *Hum Gene Ther.* 9(9): 1371–1380, 1998
Asayama et al., *J. Lab. Clin. Med.*, 107:459–464, 1986.
Asfari et al., *Endocrinology*, 130:167–178, 1992.
Bahnemann et al., *Abs. Pap. ACS*, 180:5. 1980.
Baichwal and Sugden, In: *Gene Transfer*, Kucherlapati R, ed., New York, Plenum Press, pp.117–148,1986.
Baijal et al., *J. E. Arch. Bioch. Biophys.*, 298:271–278, 1992.
Bailey and Davidson, *Anal. Biochem.*, 70:75–85, 1976.
Bailey et al., *Anal. Biochem.*, 70:75–85, 1976.
Bannister et al., *Crit. Rev. Biochem.*, 22:111–180, 1987.
Barbosa and Bach, *Diabetes Metab Rev*, 3(4):981–1004, 1987.
Barr et al., *Science*, 254:1507–1509, 1991.
Bauchwitz and Holloman, *Gene*, 96:285–288, 1990.
Becker et al., *J. Biol. Chem.*, 271:390–394, 1996.
Becker et al., *J. Biol. Chem.*, 269:21234–21238, 1994.
Bell et al., *Eur. J. Biochem.*, 209:951–959, 1992.
Bell et al., *Nature*, 282:525–527, 1979.
Bendtzen et al., *Science*, 232:1545–1547, 1986.
Bendtzen, *Immunol. Lett.*, 19:183–192, 1988.
Benjannet et al., *Biochem. J.*, 294:735–743, 1993.
Benvenisty and Neshif, *Proc. Nat'l Acad. Sci. USA*, 83:9551–9555, 1986.
Berzal-Herranz et al., *Genes and Devel.*, 6:129–134, 1992.
Blomer et al., *J. Virol.* 71(9): 6641–6649, 1997
Boitard et al., *C R Seances Acad Sci III*, 294(20):979–84, 1982.
Bradford, *Anal. Biochem.*, 72:248–254, 1976.
Brewer, In: *Methods in Cell Biology*, 43:233–245, Roth, M., Ed. New York, Academic Press, 1992.
Brunstedt et al., *B.B.R.C.*, 106:1383–1389, 1982.
Burgess et al., *Ann. Rev. Cell Biology*, 3:243–293, 1987.
Burkart and Kolb, *Clin. Exp. Immunol.*, 93:273–278, 1993.
Campbell et al., *Am. J. Physiol.*, 266:E600–E605, 1994.
Capaldi et al., *Biochem. Biophys. Res. Comm.*, 76:425, 1977.
Carter and Flotte, *Curr. Top. Microbiol. Immunol.*, 218:119–144, 1996.

Castano and Eisenbarth, *Ann. Rev. Immunol.,* 8:647–679, 1994.
Cavallo et al., *Immunology,* 75(4): 664–668, 1992
Cech et al., *Cell,* 27:487–496, 1981.
Challita et al., *Proc. Nat'l. Acad. Sci. USA,* 91:2567–2571, 1994.
Chang et al., *Hepatology,* 14:134A, 1991.
Charlton et al., *Diabetes,* 37(7):930–5, 1988.
Chatteijee, et al., *Ann. N.Y. Acad. Sci.,* 770:79–90, 1995.
Chavez et al., *In: Methods in Cell. Biology,* 43:263–288, Roth, M., Ed. New York, Academic Press, 1994.
Chen and Okayama, *Mol. Cell Biol.,* 7:2745–2752, 1987.
Chen et al., *Biotechnology,* 13:1191–1197, 1995.
Chen et al., *Proc. Nat'l Acad. Sci. USA,* 93:14795, 1996.
Clark et al., *Diabetes,* 46:958–967, 1997.
Clark et al., *Endocrinology,* 126:1895–1903, 1990.
Coffin, *In: Virology,* Fields et al. (eds.), New York: Raven Press, pp. 1437–1500, 1990.
Cole-Strauss et al., *Science* 273: 1386–1389, 1996.
Coligunet et al., Greene Publishing and Wiley-Interscience, New York, 1992.
Cone et al., *Proc. Nat'l Acad. Sci U.S.A.,* 81:6349–6353, 1984.
Corbett and McDaniel, *Biochem. J.,* 299:719–724, 1994.
Corbett and McDaniel, *Diabetes,* 41:897–903, 1992.
Corbett and McDaniel, *J. Exp. Med,* 181:559–568, 1995.
Corbett and McDaniel, *Methods Enzymol,* 268:398–408, 1996.
Corbett et al., *J Clin Invest.* 90(6): 2384–2391, 1992.
Corbett et al., *J. Biol. Chem.* 266: 21351–21354, 1991.
Corbett et al., *Proc. Nat'l. Acad. Sci USA.* 90:8992–8995, 1993.
Cordell et al., *Cell,* 18:533–543, 1979.
Couch et al., *Am. Rev. Resp. Dis.,* 88:394–403, 1963.
Coupar et al., *Gene,* 68:1–10, 1988.
Danos et al., *Proc. Nat'l Acad. Sci. U.S.A.* 85:6460–6464, 1988.
Dawson, M., CRC Press, Boca Raton, Fla., 1991.
DeFronzo, R. A., *Diabetes,* 37:667–687, 1988.
Delaney et al., *FEBS Lett.,* 394:300–306, 1996.
Dubensky et al., *Proc. Nat. Acad. Sci. USA,* 81:7529–7533, 1984.
Duke and Sellins *J Immunol.* 141(7): 2191–2194, 1988
Efrat et al., *Diabetes,* 42:901–907, 1993.
Efrat et al., *Proc. Nat'l. Acad. Sci., USA,* 85:9037–9041, 1988.
Efrat et al., *Proc. Nat'l. Acad. Sci., USA,* 92: 3576–3580, 1995.
Efrat, et al., *Proc. Nat'l. Acad. Sci. USA,* 91:2051–2055, 1994.
Eipper et al., *Annu. Rev. Neuroscience,* 15:57–85, 1992a.
Eipper et al., *J. Biol. Chem.,* 267:4008–4015, 1992b.
Eizirik et al., *Diabetologia,* 34:445–448, 1991.
Eizirik et al., *Diabetologia,* 39:875–890, 1996.
Eizirik et al., *Endocrinology,* 127 5 p2290-7, 1990.
Eizirik et al., *J. Clin. Invest.,* 93:1968–1974, 1994b.
Eizirik et al., *Proc. Nat'l. Acad. Sci. USA.,* 91:9253–9256, 1994a.
Eizirik, D. L., *Autoimmunity,* 10 2 p107-13, 1991.
EPO 0273085
Evers et al., *Gastroenterology,* 101(2): 303–311, 1991.
Fechheimer et al., *Proc. Nat'l Acad. Sci. USA,* 84:8463–8467, 1987.
Feldman, M., Fourth Edition eds. Ivan, Roitt, Jonathan Brostoff, and David Male, Times Mirron International Publishers Limited, Barcelona, Spain, 1996.
Ferber et al., *J. Biol. Chem.,* 269:11523–11529, 1994.
Ferber et al., *Mol Endocrinol.* 5 3 p319-26, 1991.
Ferkol et al., *FASEB J.,* 7:1081–1091, 1993.
Ferrari, et al., *J. Virol.,* 70:3227–3234, 1996.
Fisher et al., *J. Virol,* 70:520–532, 1996.
Flotte et al., *Proc. Nat'l. Acad. Sci. USA,* 90:10613–10617, 1993.
Forster and Symons, *Cell,* 49:211–220, 1987.
Fraley et al., *Proc. Nat'l Acad. Sci. USA,* 76:3348–3352, 1979.
Fricker, *Ann. Rev. Physiology,* 50:309–321, 1988.
Friedmann, *Science,* 244:1275–1281, 1989.
Fritschy et al., *Diabetes,* 40:37, 1991.
Frougel et al., *N. Engl. J. Med.,* 328:105–112, 1993.
Fujiwara et al., *Diabetes,* 37:1549–1558, 1998.
Fulgencio et al., *Diabetes,* 45:1556–1562, 1996.
Gazdar et al. *Proc. Nat'l. Acad. Sci. USA,* 77:3519–3523, 1980.
Gelb et al., *Proc. Nat'l. Acad. Sci. USA,* 89:202–206, January, 1992.
Gerlach et al., *Nature,* 328:802–805, 1987.
Ghosh-Choudhury et al., *EMBO J.,* 6:1733–1739, 1987.
Ghosh and Bachhawat, *In: Liver diseases, targeted diagnosis and therapy using specific receptors and ligands,* Wu G. and C. Wu ed., New York: Marcel Dekker, pp. 87–104, 1991.
Giddings et al., *Diabetes,* 31:624–629, 1982.
Gomez-Foix et al., *J. Biol. Chem.,* 267:25129–25134, 1992.
Goodman, et al., *Blood,* 84:1492–1500, 1994.
Gopal, *Mol. Cell Biol.,* 5:1188–1190, 1985.
Gossen et al., *Proc. Nat'l. Acad. Sci. USA,* 89:5547–5551, 1992.
Graham and Prevec, *Biotechnology,* 20:363–390, 1992.
Graham and Prevec, *In: Methods in Molecular Biology: Gene Transfer and Expression Protocol,* E. J. Murray ed., Clifton, N.J.: Humana Press, 7:109–128, 1991.
Graham and van der Eb, *Virology,* 52:456–467, 1973.
Graham et al., *J. Gen. Virol.,* 36:59–72, 1977.
Grampp et al., *Advances in Biochemical Engineering,* 46:35–62, 1992.
Gray et al., *Proc. Nat'l. Acad. Sci. USA,* 86:8497–8501, 1989.
Green et al., *Anal. Biochem.* 126:131–138, 1982.
Gross et al., *Proc. Nat'l. Acad. Sci. USA,* 86:4107–4111, 1989.
Grunhaus and Horwitz, *Seminar in Virology,* 3:237–252, 1992.
Gueli et al., *J. Exp. Clin. Cancer Res.,* 6:281, 1987.
Hakan Borg et al., *Endocrinology,* 130:2851–2857, 1992.
Hakes et al., *Endocrinology,* 129:3053–3063, 1991.
Halban et al., *Biochem. J.,* 212:439–443, 1983.
Halban et al., *Diabetologia,* 29:893–896, 1986.
Halban et al., *J. Biol. Chem.,* 255:6003–6006, 1980.
Halban, *Diabetologia,* 34:767–778, 1991.
Harland and Weintraub, *J. Cell Biol.,* 101:1094–1099, 1985.
Hart et al., *J. Neuroirnmunol.,* 44:49–56, 1993.
Haseloff and Gerlach, *Nature,* 334:585–591, 1988.
Hassan, *Free Radic. Biol. Med.,* 5:377–385, 1988.
Heitmeier et al., *J. Biol. Chem.,* 272:13697–13704, 1997.
Hermonat and Muzycska, *Proc. Nat'Acad. Sci. USA,* 81:6466–6470, 1984.
Hersdorffer et al., *DNA Cell Biol.,* 9:713–723, 1990.
Herz and Gerard, *Proc. Nat'l Acad. Sci. USA* 90:2812–2816, 1993.
Hirose et al., *J. Biol. Chem,* 271:5633–5637, 1996.
Ho and Crapo, *Nuc. Acids Res.,* 15:10070, 1987.
Hohmeier et al., *Diabetes,* 46:968–977, 1997.
Hopcroft et al., *Metab. Res.,* 17:559–561, 1985.

Hoppener et al., *J. Cell. Biochem.,* 55S:39–53, 1994.
Horwich et al., *J. Virol.,* 64:642–650, 1990.
Hosokawa et al., *Diabetes* 44:1328–1333, 1995.
Hughes et al., *J. Biol. Chem.,* 266:4521–4530, 1991.
Hughes et al., *J. Biol. Chem.,* 268:15205–15212, 1993.
Hughes et al., *Proc. Nat'l. Acad Sci. USA,* 89:688–692, 1992.
Hugl et al., *J. Biol. Chem.* 273(28): 17771–17779, 1998
Iida et al., *Biochem. Biophys. Res. Commun.,* 224:597–604, 1996.
Inagaki et al., *Science,* 270:1166–1170, 1995.
Isaksson et al., *Ann. Rev. Physiol.,* 47:483–499, 1985.
Ishibashi et al., *J. Clin. Invest,* 92:883–893, 1993.
Janjic and Asfari, *J. Endocrinol.,* 132:67–76, 1992.
Japanese Patent No. 60-051189/Australian Patent No. 570067
Johnson et al., "Peptide Turn Mimetics" *In: BIOTECHNOLOGY AND PHARMACY,* Pezzuto et al., Eds., Chapman and Hall, New York 1993
Johnson et al., *In: Biotechnology And Pharmacy,* Pezzuto et al., eds., Chapman and Hall, New York, 1993.
Johnson et al., *Science,* 250:546–549, 1990.
Jones and Shenk, *Cell,* 13:181–188, 1978.
Jonsson et al., *Nature,* 371:606–609, 1994.
Joshi et al., *Res. Commun. Mol. Pathol. Pharmacol.* 91:339–346, 1996.
Joyce, *Nature,* 338:217–244, 1989.
Kaneda et al., *Science,* 243:375–378, 1989.
Kaneto et al., *Diabetes,* 44:733–738, 1995.
Kaplitt et al., *Methods,* 10(3): 343–350, 1996
Kaplitt et al., *Nat. Genet.,* 8:148–153, 1994.
Karlsen et al., *Diabetes,* 44:753–758, 1995.
Karlsson et al., *EMBO J.,* 5:2377–2385, 1986.
Karlsson et al., *Mol. Cell. Biol,* 9:823–827, 1989.
Karlsson et al., *Proc. Nat'l. Acad. Sci. USA,* 84:8819–8823, 1987.
Kato et al., *J. Biol. Chem.,* 266:3361–3364, 1991.
Kessler et al., *J. Leukocyte Biol.,* 60:729–736, 1996.
Kim and Cech, *Proc. Nat'l. Acad Sci. USA,* 84:8788–8792, 1987.
Kleemann et al., *FEBS Lett.* 328(1–2): 9–12, 1993
Klein et al., *Nature,* 327:70–73, 1987.
Kmiec et al., *Mol. Cell. Biol.* 14: 7163–7172, 1994.
Koeberl et al., *Proc. Nat'l Acad. Sci USA,* 94:1426–1431, 1997.
Krajewski et al., *Am J Pathol;* 146(6): 1309–1319, 1995
Kruse et al., *Genes and Dev.,* 7:774–786, 1993.
Kwon et al., *Endocrinology,* 136:4790–4795, 1995.
Kyte and Doolittle, *J. Mol. Biol.,* 1571:105–132,1982.
Lacy et al., *Science,* 254:1782–1784, 1991.
Lander, *FASEB J.,* 11:118–124, 1997.
Larsson and Litwin, *Dev. Biol. Standard.,* 66:385–390, 1987.
Le Gal La Salle et al., *Science,* 259:988–990, 1993.
Lee et al., *Diabetes,* 46:408–413, 1997.
Lee et al., *Proc. Nat'l. Acad. Sci USA.,* 91:10878–10882, 1994.
Lenzen et al., *Free Radic. Biol. Med.,* 20: 463–466, 1995.
Leonard et al., *Mol Endocrinol,* 7:1275–1283, 1993.
Levrero et al., *Gene,* 101:195–202, 1991.
Liang et al., *J. Biol. Chem.,* 266:6999–7007, 1991.
Liang et al., *J. Cell. Biochem.* Supplement 21A:379, 1995.
Liang, et al., *J. Biol. Chem.* 265:16863–16866, 1990.
Lim, U.S. Pat. No. 4,352,883, Oct. 5, 1982.
Linden et al., *FEBS Lett.,* 141:189–192, 1982.
Lindsay et al., *Diabetes,* 44:365–368, 1995.
Lipes et al., *Diabetes,* 45(Supp. 2):23A, 1996.
Macejak and Sarnow, *Nature,* 353:90–94, 1991.
Madsen et al., *Proc. Nat'l. Acad. Sci. U.S.A.,* 85:6652–6656, 1988.
Malaisse et al., *Proc. Nat'l. Acad. Sci. U.S.A,.* 79:927–930, 1982.
Mandrup-Poulsen et al., *Diabetes,* 36:641–647, 1987.
Mandrup-Poulsen, *Diabetologia,* 39:1005–1029, 1996.
Mann et al., *Cell,* 33:153–159,1983.
Marie et al., *J. Biol. Chem.,* 268:23881–23890, 1993.
Marklund, *In: CRC Handbook of Methods for Oxygen Radical Research,* Greenwald, editor, CRC Press, Boca Raton, Fla., pp. 243–247, 1985.
Markowitz et al., *J. Virol.,* 62:1120–1124, 1988.
Massie et al., *J. Virol.,* 72:3,2289–2296, 1998.
Masuda et al., *FASEB J.,* 2:3087–3091, 1988.
McCown et al., *Brain Res.,* 713:99–107, 1996.
McDaniel et al., *Proc. Soc. Exp. Biol. Med,* 211:24–32, 1996.
Meglasson and Matschinsky, *Diabetes Metab. Rev.,* 2:163–214, 1986.
Meredith et al., *Diabetes,* 45:1783–1791, 1996.
Michel and Westhof, *J. Mol. Biol.,* 216:585–610, 1990.
Milburn et al., *J Biol. Chem,* 270:1295–1299, 1995.
Miller et al., *EMBO J.,* 13:1145–1156,1994.
Miyazaki et al., *Endocrinology,* 127:126–132, 1990.
Mizrahi, *Process Biochem.,* Aug.: 9–12, 1983.
Mizukami, et al., *Virology,* 217:124–130, 1996.
Moncada et al., *Pharmacol. Rev.,* 43:109–142, 1991.
Monia et al., *J. Biol. Chem.,* 271:14533–14540, 1996.
Moore et al., *Cell,* 35:531–538, 1983.
Moore et al., *J.C.B.,* 101:1773–1781, 1985.
Mosmann, *J. Immunol. Meth.,* 65:55–63, 1983.
Mulligan et al., *Science,* 209:1422–1427, 1980.
Mulligan, *Science,* 260:926–932, 1993.
Myers, EPO 0273085
Newgard and McGarry, *Ann. Rev. Biochem.,* 64:689–719, 1995
Newgard et al., *Biochem. Soc. Trans.,* 18:851–853, 1990.
Newgard et al., *Diabetologia,* 40 Suppl 2: S42–S47, 1997.
Nicol et al., *J. Endocrinol.,* 126(2):255–259, 1990.
Nicolas and Rubinstein, *In: Vectors: A survey of molecular cloning vectors and their uses,* Rodriguez and Denhardt eds., Stoneham: Butterworth, pp. 494–513, 1988.
Nicolau and Sene, *Biochem. Biophys. Acta,* 721:185–190, 1982.
Nicolau et al., *Methods Enzymol.,* 149:157–176, 1987.
Nilsson and Mosbach, *Dev. Biol. Standard.,* 66:183–193, 1987
Noel et al., *J. Biol. Chem.,* 272:18621–18627, 1997.
O'Shea and Sun, *Diabetes* 35:943–946, 1986.
Oberley et al., *Am. J. Patrol.,* 137:199–214, 1990.
Ohlsson et al., *EMBO J.,* 12:4251–4259, 1993.
Ohneda et al., *Diabetologia,* 38:173–179, 1995.
Orci et al., *Proc. Nat'l. Acad Sci.,* 87:9953–9957, 1990.
Otonkoski et al., *J Clin Invest.* 92(3): 1459–1466, 1993;
Papaccio, *Diabetes Res Clin Pract.;* 13(1–2): 95–102, 1991
Parekh et al., *Pancreas,* 9(1):83–90, 1994.
Paskind et al., *Virology,* 67:242–248, 1975.
PCT WO95/15972
PCT, WO 96/22364
Peers et al., *Mol Endocrin,* 8:1798–1806, 1994.
Pelletier and Sonenberg, *Nature,* 334:320–325, 1988.
Perales et al., *Proc. Nat'l. Acad. Sci. USA,* 91:4086–4090, 1994.
Peterson et al., *ILAR News,* 32:16–19, 1990.
Petricciani, *Dev. Biol. Standard.,* 66:3–12, 1985.
Phillips et al., *In: Large Scale Mammalian Cell Culture* Feder, J. and Tolbert, W. R., eds., Academic Press, Orlando, Fla., U.S.A., 1985.

Phillips et al., *Nat. Genet.,* 13:18–19, 1996.
Ping, et al., *Microcirculation,* 3:225–228, 1996.
Ponnazhagan, et al., *Gene,* 190:203–210, 1997c.
Ponnazhagan, et al., *Hum. Gene Ther.,* 8:275–284, 1997a.
Ponnazhagan, et al., *J. Virol.,* 71 :,1997b.
Ponnazhagan, et al., *J. Virol.,* 71:3098–3104, 1997d.
Potter et al., *Proc. Nat'l Acad. Sci. USA,* 81:7161–7165, 1984.
Pozzilli et al., *Diabetes Care,* 19:1357–1363, 1996.
Quaade et al., *FEBS Lett,* 280:47–52, 1991.
Rabinovitch, *Diabetes Rev.,* 1:215–240, 1993.
Racher et al., *Biotechnology Techniques,* 9:169–174, 1995.
Radons et al., *Biochem. Biophys. Res. Commun.,* 199:1270–1277, 1994.
Ragot et al., *Nature,* 361:647–650, 1993.
Reinhold-Hurek and Shub, *Nature,* 357:173–176, 1992.
Renan, *Radiother. Oncol.,* 19:197–218, 1990.
Rich et al., *Hum. Gene Ther.,* 4:461–476, 1993.
Ricordi et al., *Diabetes,* 37:413–420, 1988.
Ridgeway, In: *Vectors: A survey of molecular cloning vectors and their uses,* Rodriguez R L, Denhardt D T, ed. Stoneham: Butterworth, pp. 467–492, 1988.
Rippe et al., *Mol. Cell Biol.,* 10:689–695, 1990.
Rosenfeld et al., *Cell,* 68:143–155, 1992.
Rosenfeld et al., *Science,* 252:431–434, 1991.
Rossini et al., *Autoimmunity,* 8:221–235, 1991.
Roux et al., *Proc. Nat'l. Acad. Sci. USA,* 86:9079–9083, 1989.
Rubin et al., *Mol. Cell. Biol.,* 14: 6287–6296.
Ruddle, *Immunol. Today,* 8:129–130, 1987.
Samulski et al., *J. Virol.,* 6110:3096–3101, 1987.
Santerre et al., *Proc. Nat'l. Acad. Sci.,* 78:4339–4343, 1981.
Sarver, et al., *Science,* 247:1222–1225, 1990.
Sato et al., *Proc. Nat'l Acad. Sci. U.S.A.* 48:1184–1190, 1962.
Sauer, *Methods in Enzymology,* 225:890–900, 1993.
Scanlon et al., *Proc. Nat'l Acad. Sci. USA,* 88:10591–10595, 1991.
Schnedl et al., *Diabetes,* 43:1326–1333, 1994.
Sen and Packer, *FASEB J.,* 10:709–720, 1996
Shimabukuro et al., *J. Clin. Invest.* 100:290–295, 1997a.
Shimabukuro et al., *J. Clin. Invest.,* 100:1750–1754, 1997b.
Sioud et al., *J. Mol. Biol.,* 223:831–835, 1992.
Sizonenko and Halban, *Biochemistry J.,* 278:621–625, 1991.
Smeekens and Steiner, *J. Biol. Chem.,* 265:2997–3000, 1990.
Smith and Wilson, *Arch. Bioch. Biophys.* 287:359–366, 1991.
Southern et al., *FEBS Lett.,* 276:42–44, 1990.
Steiner et al., *J. Biol. Chem.,* 267:23435–23438, 1992.
Stossel, T., Chapter 14, pp. 499–533, W. B. Saunders Co., Philadelphia, Pa., 1987.
Stratford-Perricaudet and Perricaudet, p. 51–61, In: *Human Gene Transfer,* Eds, O. Cohen-Haguenauer and M. Boiron, Editions John Libbey Eurotext, France, 1991.
Stratford-Penicaudet et al., *Hum. Gene Ther.,* 1:241–256, 1990.
Sullivan et al., *Science* 252:718–721, 1991.
Sumoski et al., *Diabetologia,* 32:792–796, 1989.
Svensson et al., *Endocrinology* 135:849–853, 1994.
Temin, In: *Gene Transfer,* Kucherlapati ed., New York: Plenum Press, pp. 149–188, 1986.
Thorens et al., *Cell,* 55:281–290, 1988.
Thorens et al., *J. Clin. Invest,* 90:77–85, 1992a.
Thorens et al., *J. Clin. Invest.,* 90:77–85, 1992b.
Thorens et al., *Proc. Nat'l. Acad. Sci. USA,* 87:6492–6496, 1990.
Thorens, *Proc. Nat'l. Acad. Sci. USA,* 89:8641–8646, 1992.
Top et al., *J. Infect. Dis.,* 124:155–160, 1971.
Touati, *Free Radic. Biol. Med.,* 5:393–402, 1988.
Tsukudaeta et al., *Gene* 85:335–341, 1989
Tur-Kaspa et al., *Mol. Cell Biol.,* 6:716–718, 1986.
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,298,002
U.S. Pat. No. 4,298,002
U.S. Pat. No. 4,366,241
U.S. Pat. No. 4,554,101
U.S. Pat. No. 4,889,935
U.S. Pat. No. 4,892,538
U.S. Pat. No. 4,959,317
U.S. Pat. No. 5,382,574
U.S. Pat. No. 5,002,661
U.S. Pat. No. 5,011,472
U.S. Pat. No. 5,108,930
U.S. Pat. No. 5,246,847
U.S. Pat. No. 5,266,561
U.S. Pat. No. 5,280,014
U.S. Pat. No. 5,281,581
U.S. Pat. No. 5,314,471
U.S. Pat. No. 5,321,008
U.S. Pat. No. 5,354,855
U.S. Pat. No. 5,364,841
U.S. Pat. No. 5,367,052
U.S. Pat. No. 5,376,638
U.S. Pat. No. 5,399,346
U.S. Pat. No. 5,405,831
U.S. Pat. No. 5,427,940
U.S. Pat. No. 5,472,691
U.S. Pat. No. 5,472,691
U.S. Pat. No. 5,508,260
U.S. Pat. No. 5,527,771
U.S. Pat. No. 5,540,911
U.S. Pat. No. 5,545,223
U.S. Pat. No. 5,549,675
U.S. Pat. No. 5,569,462.
U.S. Pat. No. 5,585,402
U.S. Pat. No. 5,589,371
U.S. Pat. No. 5,593,440,
U.S. Pat. No. 5,614,551
U.S. Pat. No. 5,700,820
U.S. Pat. No. 4,959,317
U.S. Pat. No. 5,354,855
U.S. Pat. No. 5,539,132
U.S. Pat. No. 4,402,694
U.S. Pat. No. 5,002,661
U.S. Pat. No. 5,011,472
U.S. Pat. No. 5,314,471
U.S. Pat. No. 5,427,940
U.S. Pat. No. 5,545,223
U.S. Pat. No. 5,549,675
U.S. Pat. No. 5,569,462
U.S. Pat. No. 5,593,440
U.S. Pat. No. 5,626,561
Unger, *Diabetes,* 44:863–870, 1995.
Unger, *Science,* 251:1200–1205, 1991.
Usdin et al., *Endocrinology,* 133:2861–2870, 1993.
van Wezel, *Nature,* 216:64–65, 1967.
Varmus et al., *Cell,* 25:23–36, 1981.
Vollenweider et al., *Diabetes,* 44:1075–1080, 1995.

Waeber et al., *J. Biol. Chem.*, 43:26912–26919, 1994.
Wagner et al., *Science*, 260:1510–1513, 1990.
Wang et al., *Diabetes*, 36 4 535–538,1987.
Wang et al., *In: Animal Cell Technology: Basic & Applied Aspects*, S. Kaminogawa et al., eds, vol. 5, pp463–469, Kluwer Academic Publishers, Netherlands, 1993.
Wang et al., *Proc. Jap. Soc. Anim. Cell Tech.*, 1994.
Welsh and Sandler, *Biochem Biophys Res Commun.*, 182 1 p333–40, 1992.
Welsh et al., *Autoimmunity*, 91:p33–40, 1991.
Welsh et al., *J. Biol. Chem.*, 261:12915–12917, 1986.
White and Wilson, *Arch. Bioch. Biophys.* 277:26–34, 1990.
Whitesell et al., *Biochemistry*, 30:11560–11566, 1991.
WO 89/01967
WO 90/02580
WO 90/15637
WO 91/10425
WO 94/17178
WO 95/15972
WO 96/22364
WO 91/10470
Wong and Goeddel, *Science*, 242:941–944, 1988.
Wong et al., *Cell*, 58:923–931, 1989.
Wong et al., *Gene*, 10:87–94, 1980.
Wu and Wu, *Adv. Drug Delivery Rev.*, 12:159–167, 1993.
Wu and Wu, *Biochemistry*, 27:887–892, 1988.
Wu and Wu, *J. Biol. Chem.*, 262:4429–4432, 1987.
Xiao, et al., *J. Virol.*, 70:8098–8108, 1996.
Yamada et al., *Acta Endocrin.*, 128:379–384, 1993.
Yang et al., *Proc. Nat'l Acad. Sci. USA*, 87:9568–9572, 1990.
Yang et al., *Proc. Nat'l. Acad. Sci. USA*, 91:4407–4411, 1994.
Yang et al., *Proc. Nat'l. Acad. Sci. USA.*, 94: 2557–2562, 1997.
Yao, et al., *J. Immunol.* 155:5483–5486, 1995.
Yoon et al., *Proc. Nat'l. Acad. Sci USA* 93: 2071–1076, 1996.
Zelenin et al., *FEBS Lett.*, 280:94–96, 1991.

What is claimed is:

1. A method of generating a mammalian cell line that is resistant to IL-1β mediated immunotoxicity comprising:
   (a) providing a mammalian cell;
   (b) introducing in vitro an MnSOD (maganese superoxide dismutase) protein encoding gene operatively linked to a first promoter into said mammalian cell;
   (c) selecting a cell from step (b) that exhibits an increased level of MnSOD activity as compared to the mammalian cell of step (a); and
   (d) propagating said selected cell into a cell line,
wherein increased level of MnSOD activity provides said cell line with resistance to IL-1β mediated immunotoxicity by inhibiting iNOS (inducible form of nitric synthase) and blocking NO (nitric oxide) production in said cell line.

2. The method of claim 1, further comprising introducing into said cell a selected gene operatively linked to a second promoter active in said cell.

3. The method of claim 2, wherein said selected gene encodes insulin.

4. The method of claim 3, wherein said first and second promoters are CMV IE (human cytomegandovirus immediate early gene promoter).

* * * * *

UNITED STATES PATENT AND TRADEMARK OFFICE
CERTIFICATE OF CORRECTION

PATENT NO. : 6,171,856 B1
DATED : January 9, 2001
INVENTOR(S) : Thigpen et al.

It is certified that error appears in the above-identified patent and that said Letters Patent is hereby corrected as shown below:

Claim 4, column 44,
Line 10, please delete "cytomegandovirus" and insert -- cytomegalovirus -- therefor.

Signed and Sealed this

Sixteenth Day of October, 2001

Attest:

*Nicholas P. Godici*

NICHOLAS P. GODICI
*Attesting Officer*    *Acting Director of the United States Patent and Trademark Office*

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 976 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GCGGGCGGCG CAGGAGCGGC ACTCGTGGCT GTGGTGGCTT CGGCAGCGGC TTCAGCAGAT      60

CGGCGGCATC AGCGGTAGCA CCAGCACTAG CAGCATGTTG AGCCGGGCAG TGTGCGGCAC     120

CAGCAGGCAG CTGGCTCCGG CTTTGGGGTA TCTGGGCTCC AGGCAGAAGC ACAGCCTCCC     180

CGACCTGCCC TACGACTACG GCGCCCTGGA ACCTCACATC AACGCGCAGA TCATGCAGCT     240

GCACCACAGC AAGCACCACG CGGCCTACGT GAACAACCTG AACGTCACCG AGGAGAAGTA     300

CCAGGAGGCG TTGGCCAAGG GAGATGTTAC AGCCCAGACA GCTCTTCAGC CTGCACTGAA     360

GTTCAATGGT GGTGGTCATA TCAATCATAG CATTTTCTGG ACAAACCTCA GCCCTAACGG     420

TGGTGGAGAA CCCAAAGGGG AGTTGCTGGA AGCCATCAAA CGTGACTTTG GTTCCTTTGA     480

CAAGTTTAAG GAGAAGCTGA CGGCTGCATC TGTTGGTGTC CAAGGCTCAG GTTGGGGTTG     540

GCTTGGTTTC AATAAGGAAC GGGGACACTT ACAAATTGCT GCTTGTCCAA ATCAGGATCC     600

ACTGCAAGGA ACAACAGGCC TTATTCCACT GCTGGGGATT GATGTGTGGG AGCACGCTTA     660

CTACCTTCAG TATAAAAATG TCAGGCCTGA TTATCTAAAA GCTATTTGGA ATGTAATCAA     720

CTGGGAGAAT GTAACTGAAA GATACATGGC TTGCAAAAAG TAAACCACGA TCGTTATGCT     780

GAGTATGTTA AGCTCTTTAT GACTGTTTTT GTAGTGGTAT AGAGTACTGC AGAATACAGT     840

AAGCTGCTCT ATTGTAGCAT TTCTTGATGT TGCTTAGTCA CTTATTTCAT AAACAACTTA     900

ATGTTCTGAA TAATTTCTTA CTAAACATTT TGTTATTGGG CAAGTGATTG AAAATAGTAA     960

ATGCTTTGTG TGATTG                                                    976
```

(2) INFORMATION FOR SEQ ID NO:2:

(i) SEQUENCE CHARACTERISTICS:
        (A) LENGTH: 222 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

```
Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Thr Ala Leu Gln Pro Ala Leu Lys Phe Asn Gly Gly His Ile
                85                  90                  95

Asn His Ser Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220
```

(2) INFORMATION FOR SEQ ID NO:3:

(i) SEQUENCE CHARACTERISTICS:
        (A) LENGTH: 874 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CTGCAGCGTC TGGGGTTTCC GTTGCAGTCC TCGGAACCAG GACCTCGGCG TGGCCTAGCG      60

AGTTATGGCG ACGAAGGCCG TGTGCGTGCT GAAGGGCGAC GGCCCAGTGC AGGGCATCAT     120

CAATTTCGAG CAGAAGGAAA GTAATGGACC AGTGAAGGTG TGGGGAAGCA TTAAAGGACT     180

GACTGAAGGC CTGCATGGAT TCCATGTTCA TGAGTTTGGA GATAATACAG CAGGCTGTAC     240

CAGTGCAGGT CCTCACTTTA ATCCTCTATC CAGAAACAC GGTGGGCCAA AGGATGAAGA     300
```

-continued

```
GAGGCATGTT GGAGACTTGG GCAATGTGAC TGCTGACAAA GATGGTGTGG CCGATGTGTC    360

TATTGAAGAT TCTGTGATCT CACTCTCAGG AGACCATTGC ATCATTGGCC GCACACTGGT    420

GGTCCATGAA AAAGCAGATG ACTTGGGCAA AGGTGGAAAT GAAGAAAGTA CAAAGACAGG    480

AAACGCTGGA AGTCGTTTGG CTTGTGGTGT AATTGGGATC GCCCAATAAA CATTCCCTTG    540

GATGTAGTCT GAGGCCCCTT AACTCATCTG TTATCCTGCT AGCTGTAGAA ATGTATCCTG    600

ATAAACATTA AACACTGTAA TCTTAAAAGT GTAATTGTGT GACTTTTTCA GAGTTGCTTT    660

AAAGTACCTG TAGTGAGAAA CTGATTTATG ATCACTTGGA AGATTTGTAT AGTTTTATAA    720

AACTCAGTTA AAATGTCTGT TTCAATGACC TGTATTTTGC CAGACTTAAA TCACAGATGG    780

GTATTAAACT TGTCAGAATT TCTTTGTCAT TCAAGCCTGT GAATAAAAAC CCTGTATGGC    840

ACTTATTATG AGGCTATTAA AGAATCCAA ATTC                                 874
```

(2) INFORMATION FOR SEQ ID NO:4:

(i) SEQUENCE CHARACTERISTICS:
  (A) LENGTH: 154 amino acids
  (B) TYPE: amino acid
  (C) STRANDEDNESS:
  (D) TOPOLOGY: linear (xi) SEQUENCE DESCRIPTION: SEQ ID NO:4:

```
Met Ala Thr Lys Ala Val Cys Val Leu Lys Gly Asp Gly Pro Val Gln
1               5                   10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```

(2) INFORMATION FOR SEQ ID NO:5:

(i) SEQUENCE CHARACTERISTICS:
  (A) LENGTH: 911 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:5:

```
TGATTGAAGA CACCCCCTCG TCCAAGAATG CAAAGCACAT CCAATAAAAT AGCTGGATTA     60

TAACTCCTCT TCTTTCTCTG GGGGCCGTGG GGTGGGAGCT GGGGCGAGAG GTGCCGTTGG    120

CCCCCGTTGC TTTTCCTCTG GGAAGGATGG CGCACGCTGG GAGAACGGGG TACGACAACC    180
```

```
GGGAGATAGT GATGAAGTAC ATCCATTATA AGCTGTCGCA GAGGGGCTAC GAGTGGGATG      240

CGGGAGATGT GGGCGCCGCG CCCCCGGGGG CCGCCCCCGC ACCGGGCATC TTCTCCTCCC      300

AGCCCGGGCA CACGCCCCAT CCAGCCGCAT CCCGCGACCC GGTCGCCAGG ACCTCGCCGC      360

TGCAGACCCC GGCTGCCCCC GGCGCCGCCG CGGGGCCTGC GCTCAGCCCG GTGCCACCTG      420

TGGTCCACCT GGCCCTCCGC CAAGCCGGCG ACGACTTCTC CCGCCGCTAC CGCGGCGACT      480

TCGCCGAGAT GTCCAGCCAG CTGCACCTGA CGCCCTTCAC CGCGCGGGGA CGCTTTGCCA      540

CGGTGGTGGA GGAGCTCTTC AGGGACGGGG TGAACTGGGG GAGGATTGTG GCCTTCTTTG      600

AGTTCGGTGG GGTCATGTGT GTGGAGAGCG TCAACCGGGA GATGTCGCCC TGGTGGACA       660

ACATCGCCCT GTGGATGACT GAGTACCTGA ACCGGCACCT GCACACCTGG ATCCAGGATA      720

ACGGAGGCTG GGTAGGTGCA TCTGGTGATG TGAGTCTGGG CTGAGGCCAC AGGTCCGAGA      780

TCGGGGGTTG GAGTGCGGGT GGGCTCCTGG GCAATGGGAG GCTGTGGAGC CGGCGAAATA      840

AAATCAGAGT TGTTGCTTCC CGGCGTGTCC CTACCTCCTC CTCTGGACAA AGCGTTCACT      900

CCCAACCTGA C                                                          911

(2) INFORMATION FOR SEQ ID NO:6:

(i) SEQUENCE CHARACTERISTICS:
        (A) LENGTH: 205 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
                20                  25                  30

Gly Asp Val Gly Ala Ala Pro Pro Gly Ala Ala Pro Ala Pro Gly Ile
            35                  40                  45

Phe Ser Ser Gln Pro Gly His Thr Pro His Pro Ala Ala Ser Arg Asp
        50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Ala
                85                  90                  95

Leu Arg Gln Ala Gly Asp Asp Phe Ser Arg Arg Tyr Arg Gly Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190

Gly Gly Trp Val Gly Ala Ser Gly Asp Val Ser Leu Gly
        195                 200                 205
```

(2) INFORMATION FOR SEQ ID NO:7:

(i) SEQUENCE CHARACTERISTICS:
        (A) LENGTH: 1618 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
GAGCGCCGGC GCGGGACCGA GCTGGCGGCG GGCGGCGCGC GCTTCCGAGG CTTCCTGCTG      60
CTTCTGCCCG AGCCCGCGGC CTCACGCGCG CCCTCTCCCG TGCCATGGCC TGCAGGCAGG     120
AGCCGCAGCC GCAGGGCCCG CCGCCCGCTG CTGGCGCCGT GGCCTCCTAT GACTACCTGG     180
TGATCGGGGG CGGCTCGGGC GGGCTGGCCA GCGCGCGCAG GCGGCCGAG CTGGGTGCCA      240
GGGCCGCCGT GGTGGAGAGC CACAAGCTGG GTGGCACTTG CGTGAATGTT GGATGTGTAC     300
CCAAAAAGGT AATGTGGAAC ACAGCTGTCC ACTCTGAATT CATGCATGAT CATGCTGATT     360
ATGGCTTTCC AAGTTGTGAG GGTAAATTCA ATTGGCGTGT TATTAAGGAA AAGCGGGATG     420
CCTATGTGAG CCGCCTGAAT GCCATCTATC AAAACAATCT CACCAAGTCC CATATAGAAA     480
TCATCCGTGG CCATGCAGCC TTCACGAGTG ATCCCAAGCC CACAATAGAG GTCAGTGGGA     540
AAAAGTACAC CGCCCCACAC ATCCTGATCG CCACAGGTGG TATGCCCTCC ACCCCTCATG     600
AGAGCCAGAT CCCCGGTGCC AGCTTAGGAA TAACCAGCGA TGGATTTTTT CAGCTGGAAG     660
AATTGCCCGG CCGCAGCGTC ATTGTTGGTG CAGGTTACAT TGCTGTGGAG ATGGCAGGGA     720
TCCTGTCAGC CCTGGGTTCT AAGACATCAC TGATGATACG GCATGATAAG GTACTTAGAA     780
GTTTTGATTC AATGATCAGC ACCAACTGCA CGGAGGAGCT GGAGAACGCT GGCGTGGAGG     840
TGCTGAAGTT CTCCCAGGTC AAGGAGGTTA AAAAGACTTT GTCGGGCTTG AAGTCAGCA      900
TGGTTACTGC AGTTCCCGGT AGGCTACCAG TCATGACCAT GATTCCAGAT GTTGACTGCC     960
TGCTCTGGGC CATTGGGCGG GTCCCGAATA CCAAGGACCT GAGTTTAAAC AAACTGGGGA    1020
TTCAAACCGA TGACAAGGGT CATATCATCG TAGACGAATT CCAGAATACC AACGTCAAAG    1080
GCATCTATGC AGTTGGGGAT GTATGTGGAA AAGCTCTTCT TACTCCAGTT GCAATAGCTG    1140
CTGGCCGAAA ACTTGCCCAT CGACTTTTTG AATATAAGGA AGATTCCAAA TTAGATTATA    1200
ACAACATCCC AACTGTGGTC TTCAGCCACC CCCTATTGG GACAGTGGGA CTCACGGAAG     1260
ATGAAGCCAT TCATAAATAT GGAATAGAAA ATGTGAAGAC CTATTCAACG AGCTTTACCC    1320
CGATGTATCA CGCAGTTACC AAAAGGAAAA CAAAATGTGT GATGAAAATG GTCTGTGCTA    1380
ACAAGGAAGA AAAGGTGGTT GGGATCCATA TGCAGGGACT TGGGTGTGAT GAAATGCTGC    1440
AGGGTTTTGC TGTTGCAGTG AAGATGGGAG CAACGAAGGC AGACTTTGAC AACACAGTCG    1500
CCATTCACCC TACCTCTTCA GAAGAGCTGG TCACACTTCG TTGAGAACCA GGAGACACGT    1560
GTGGCGGGCA GTGGGACCCA TAGATCTTCT GAAATGAAAC AATAATCAC ATTGACTT      1618
```

(2) INFORMATION FOR SEQ ID NO:8:

(i) SEQUENCE CHARACTERISTICS:
        (A) LENGTH: 479 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Met Ala Cys Arg Gln Glu Pro Gln Pro Gln Gly Pro Pro Ala Ala
1               5                   10                  15

Gly Ala Val Ala Ser Tyr Asp Tyr Leu Val Ile Gly Gly Ser Gly
            20                  25                  30

Gly Leu Ala Ser Ala Arg Arg Ala Ala Glu Leu Gly Ala Arg Ala Ala
        35                  40                  45

Val Val Glu Ser His Lys Leu Gly Thr Cys Val Asn Val Gly Cys
    50                  55                  60

Val Pro Lys Lys Val Met Trp Asn Thr Ala Val His Ser Glu Phe Met
65                  70                  75                  80

His Asp His Ala Asp Tyr Gly Phe Pro Ser Cys Glu Gly Lys Phe Asn
            85                  90                  95

Trp Arg Val Ile Lys Glu Lys Arg Asp Ala Tyr Val Ser Arg Leu Asn
                100                 105                 110

Ala Ile Tyr Gln Asn Asn Leu Thr Lys Ser His Ile Glu Ile Ile Arg
            115                 120                 125

Gly His Ala Ala Phe Thr Ser Asp Pro Lys Pro Thr Ile Glu Val Ser
    130                 135                 140

Gly Lys Lys Tyr Thr Ala Pro His Ile Leu Ile Ala Thr Gly Gly Met
145                 150                 155                 160

Pro Ser Thr Pro His Glu Ser Gln Ile Pro Gly Ala Ser Leu Gly Ile
                165                 170                 175

Thr Ser Asp Gly Phe Phe Gln Leu Glu Glu Leu Pro Gly Arg Ser Val
            180                 185                 190

Ile Val Gly Ala Gly Tyr Ile Ala Val Glu Met Ala Gly Ile Leu Ser
        195                 200                 205

Ala Leu Gly Ser Lys Thr Ser Leu Met Ile Arg His Asp Lys Val Leu
    210                 215                 220

Arg Ser Phe Asp Ser Met Ile Ser Thr Asn Cys Thr Glu Glu Leu Glu
225                 230                 235                 240

Asn Ala Gly Val Glu Val Leu Lys Phe Ser Gln Val Lys Glu Val Lys
                245                 250                 255

Lys Thr Leu Ser Gly Leu Glu Val Ser Met Val Thr Ala Val Pro Gly
            260                 265                 270

Arg Leu Pro Val Met Thr Met Ile Pro Asp Val Asp Cys Leu Leu Trp
    275                 280                 285

Ala Ile Gly Arg Val Pro Asn Thr Lys Asp Leu Ser Leu Asn Lys Leu
    290                 295                 300

Gly Ile Gln Thr Asp Asp Lys Gly His Ile Ile Val Asp Glu Phe Gln
305                 310                 315                 320

Asn Thr Asn Val Lys Gly Ile Tyr Ala Val Gly Asp Val Cys Gly Lys
                325                 330                 335

Ala Leu Leu Thr Pro Val Ala Ile Ala Ala Gly Arg Lys Leu Ala His
            340                 345                 350

Arg Leu Phe Glu Tyr Lys Glu Asp Ser Lys Leu Asp Tyr Asn Asn Ile
        355                 360                 365

Pro Thr Val Val Phe Ser His Pro Pro Ile Gly Thr Val Gly Leu Thr
    370                 375                 380

Glu Asp Glu Ala Ile His Lys Tyr Gly Ile Glu Asn Val Lys Thr Tyr
385                 390                 395                 400

Ser Thr Ser Phe Thr Pro Met Tyr His Ala Val Thr Lys Arg Lys Thr
            405                 410                 415
```

-continued

```
Lys Cys Val Met Lys Met Val Cys Ala Asn Lys Glu Glu Lys Val Val
            420                 425                 430

Gly Ile His Met Gln Gly Leu Gly Cys Asp Glu Met Leu Gln Gly Phe
            435                 440                 445

Ala Val Ala Val Lys Met Gly Ala Thr Lys Ala Asp Phe Asp Asn Thr
        450                 455                 460

Val Ala Ile His Pro Thr Ser Ser Glu Glu Leu Val Thr Leu Arg
465                 470                 475
```

(2) INFORMATION FOR SEQ ID NO:9:

(i) SEQUENCE CHARACTERISTICS:
        (A) LENGTH: 2264 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
TTTGCCTGCT GAGGGTGGAG ACCCACGAGC CGAGGCCTCC TGCAGTGTTC TGCACAGCAA      60

ACCGCACGCT ATGGCTGACA GCCGGGATCC CGCCAGCGAC CAGATGCAGC ACTGGAAGGA     120

GCAGCGGGCC GCGCAGAAAG CTGATGTCCT GACCACTGGA GCTGGTAACC AGTAGGAGA     180

CAAACTTAAT GTTATTACAG TAGGGCCCCG TGGGCCCCTT CTTGTTCAGG ATGTGGTTTT     240

CACTGATGAA ATGGCTCATT TTGACCGAGA GAGAATTCCT GAGAGAGTTG TGCATGCTAA     300

AGGAGCAGGG GCCTTTGGCT ACTTTGAGGT CACACATGAC ATTACCAAAT ACTCCAAGGC     360

AAAGGTATTT GAGCATATTG GAAAGAAGAC TCCCATCGCA GTTCGGTTCT CCACTGTTGC     420

TGGAGAATCG GGTTCAGCTG ACACAGTTCG GGACCCTCGT GGGTTTGCAG TGAAATTTTA     480

CACAGAAGAT GGTAACTGGG ATCTCGTTGG AAATAACACC CCCATTTTCT TCATCAGGGA     540

TCCCATATTG TTTCCATCTT TTATCCACAG CCAAAAGAGA AATCCTCAGA CACATCTGAA     600

GGATCCGGAC ATGGTCTGGG ACTTCTGGAG CCTACGTCCT GAGTCTCTGC ATCAGGTTTC     660

TTTCTTGTTC AGTGATCGGG GGATTCCAGA TGGACATCGC CACATGAATG GATATGGATC     720

ACATACTTTC AAGCTGGTTA ATGCAAATGG GGAGGCAGTT TATTGCAAAT TCCATTATAA     780

GACTGACCAG GGCATCAAAA ACCTTTCTGT TGAAGATGCG GCGAGACTTT CCCAGGAAGA     840

TCCTGACTAT GGCATCCGGG ATCTTTTTAA CGCCATTGCC ACAGGAAAGT ACCCCTCCTG     900

GACTTTTTAC ATCCAGGTCA TGACATTTAA TCAGGCAGAA ACTTTTCCAT TTAATCCATT     960

CGATCTCACC AAGGTTTGGC CTCACAAGGA CTACCCTCTC ATCCCAGTTG GTAAACTGGT    1020

CTTAAACCGG AATCCAGTTA ATTACTTTGC TGAGGTTGAA CAGATAGCCT TCGACCCAAG    1080

CAACATGCCA CCTGGCATTG AGGCCAGTCC TGACAAAATG CTTCAGGGCC GCCTTTTTGC    1140

CTATCCTGAC ACTCACCGCC ATCGCCTGGG ACCCAATTAT CTTCATATAC CTGTGAACTG    1200

TCCCTACCGT GCTCGAGTGG CCAACTACCA GCGTGATGGC CCGATGTGCA TGCAGGACAA    1260

TCAGGGTGGT GCTCCAAATT ACTACCCCAA CAGCTTTGGT GCTCCGGAAC AACAGCCTTC    1320

TGCCCTGGAG CACAGCATCC AATATTCTGG AGAAGTGCGG AGATTCAACA CTGCCAATGA    1380

TGATAACGTT ACTCAGGTGC GGGCATTCTA TGTGAACGTG CTGAATGAGG AACAGAGGAA    1440

ACGTCTGTGT GAGAACATTG CCGGCCACCT GAAGGATGCA CAAATTTTCA TCCAGAAGAA    1500

AGCGGTCAAG AACTTCACTG AGGTCCACCC TGACTACGGG AGCCACATCC AGGCTCTTCT    1560

GGACAAGTAC AATGCTGAGA AGCCTAAGAA TGCGATTCAC ACCTTTGTGC AGTCCGGATC    1620
```

-continued

```
TCACTTGGCG GCAAGGGAGA AGGCAAATCT GTGAGGCCGG GGCCCTGCAC CTGTGCAGCG      1680

AACGTTAGCG TTCATCCGTG TAACCCGCTC ATCACTGGAT GAAGATTCTC CTGTGCTAGA      1740

TGTGCAAATG CAAGCTAGTG GCTTCAAAAT AGAGAATCCC ACTTTCTATA GCAGATTGTG      1800

TAACAATTTT AATGCTATTT CCCCAGGGGA AAATGAAGGT TAGGATTTAA CAGTCATTTA      1860

AAAAAAAAAT TTGTTTTGAC GGATGATTGG ATTATTCATT TAAAATGATT AGAAGGCAAG      1920

TTTCTAGCTT AGAAATATGA TTTTATTTGA CAAAATTTGT TGAAATTATG TATGTTTACA      1980

TATCACCTCA TGGCCTATTA TATTAAAATA TGGCTATAAA TATATAAAAA GAAAAGATAA      2040

AGATGATCTA CTCAGAAATT TTTATTTTTC TAAGGTTCTC ATAGGAAAAG TACATTTAAT      2100

ACAGCAGTGT CATCAGAAGA TAACTTGAGC ACCGTCATGG CTTAATGTTT ATTCCTGATA      2160

ATAATTGATC AAATTCATTT TTTTCACTGG AGTTACATTA ATGTTAATTC AGCACTGATT      2220

TCACAACAGA TCAATTTGTA ATTGCTTACA TTTTTACAAT AAAT                      2264
```

(2) INFORMATION FOR SEQ ID NO:10:

(i) SEQUENCE CHARACTERISTICS:
        (A) LENGTH: 527 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:10:

```
Met Ala Asp Ser Arg Asp Pro Ala Ser Asp Gln Met Gln His Trp Lys
 1               5                  10                  15

Glu Gln Arg Ala Ala Gln Lys Ala Asp Val Leu Thr Thr Gly Ala Gly
            20                  25                  30

Asn Pro Val Gly Asp Lys Leu Asn Val Ile Thr Val Gly Pro Arg Gly
        35                  40                  45

Pro Leu Leu Val Gln Asp Val Val Phe Thr Asp Glu Met Ala His Phe
    50                  55                  60

Asp Arg Glu Arg Ile Pro Glu Arg Val Val His Ala Lys Gly Ala Gly
65                  70                  75                  80

Ala Phe Gly Tyr Phe Glu Val Thr His Asp Ile Thr Lys Tyr Ser Lys
                85                  90                  95

Ala Lys Val Phe Glu His Ile Gly Lys Lys Thr Pro Ile Ala Val Arg
            100                 105                 110

Phe Ser Thr Val Ala Gly Glu Ser Gly Ser Ala Asp Thr Val Arg Asp
        115                 120                 125

Pro Arg Gly Phe Ala Val Lys Phe Tyr Thr Glu Asp Gly Asn Trp Asp
    130                 135                 140

Leu Val Gly Asn Asn Thr Pro Ile Phe Phe Ile Arg Asp Pro Ile Leu
145                 150                 155                 160

Phe Pro Ser Phe Ile His Ser Gln Lys Arg Asn Pro Gln Thr His Leu
                165                 170                 175

Lys Asp Pro Asp Met Val Trp Asp Phe Trp Ser Leu Arg Pro Glu Ser
            180                 185                 190

Leu His Gln Val Ser Phe Leu Phe Ser Asp Arg Gly Ile Pro Asp Gly
        195                 200                 205

His Arg His Met Asn Gly Tyr Gly Ser His Thr Phe Lys Leu Val Asn
    210                 215                 220

Ala Asn Gly Glu Ala Val Tyr Cys Lys Phe His Tyr Lys Thr Asp Gln
225                 230                 235                 240
```

```
Gly Ile Lys Asn Leu Ser Val Glu Asp Ala Ala Arg Leu Ser Gln Glu
                245                 250                 255

Asp Pro Asp Tyr Gly Ile Arg Asp Leu Phe Asn Ala Ile Ala Thr Gly
            260                 265                 270

Lys Tyr Pro Ser Trp Thr Phe Tyr Ile Gln Val Met Thr Phe Asn Gln
                275                 280                 285

Ala Glu Thr Phe Pro Phe Asn Pro Phe Asp Leu Thr Lys Val Trp Pro
        290                 295                 300

His Lys Asp Tyr Pro Leu Ile Pro Val Gly Lys Leu Val Leu Asn Arg
305                 310                 315                 320

Asn Pro Val Asn Tyr Phe Ala Glu Val Glu Gln Ile Ala Phe Asp Pro
                325                 330                 335

Ser Asn Met Pro Pro Gly Ile Glu Ala Ser Pro Asp Lys Met Leu Gln
            340                 345                 350

Gly Arg Leu Phe Ala Tyr Pro Asp Thr His Arg His Arg Leu Gly Pro
            355                 360                 365

Asn Tyr Leu His Ile Pro Val Asn Cys Pro Tyr Arg Ala Arg Val Ala
370                 375                 380

Asn Tyr Gln Arg Asp Gly Pro Met Cys Met Gln Asp Asn Gly Gly
385                 390                 395                 400

Ala Pro Asn Tyr Tyr Pro Asn Ser Phe Gly Ala Pro Glu Gln Gln Pro
                405                 410                 415

Ser Ala Leu Glu His Ser Ile Gln Tyr Ser Gly Glu Val Arg Arg Phe
            420                 425                 430

Asn Thr Ala Asn Asp Asp Asn Val Thr Gln Val Arg Ala Phe Tyr Val
            435                 440                 445

Asn Val Leu Asn Glu Glu Gln Arg Lys Arg Leu Cys Glu Asn Ile Ala
450                 455                 460

Gly His Leu Lys Asp Ala Gln Ile Phe Ile Gln Lys Lys Ala Val Lys
465                 470                 475                 480

Asn Phe Thr Glu Val His Pro Asp Tyr Gly Ser His Ile Gln Ala Leu
                485                 490                 495

Leu Asp Lys Tyr Asn Ala Glu Lys Pro Lys Asn Ala Ile His Thr Phe
            500                 505                 510

Val Gln Ser Gly Ser His Leu Ala Ala Arg Glu Lys Ala Asn Leu
            515                 520                 525

(2) INFORMATION FOR SEQ ID NO:11:

(i) SEQUENCE CHARACTERISTICS:
        (A) LENGTH: 4062 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

TACCCCGGGG AGGCAGTGCA GCCAGCTGCA AGCCCCACAG TGAAGAACAT CTGAGCTCAA      60

ATCCAGATAA GTGACATAAG TGACCTGCTT TGTAAAGCCA TAGAGATGGC CTGTCCTTGG    120

AAATTTCTGT TCAAGACCAA ATTCCACCAG TATGCAATGA ATGGGGAAAA AGACATCAAC    180

AACAATGTGG AGAAAGCCCC CTGTGCCACC TCCAGTCCAG TGACACAGGA TGACCTTCAG    240

TATCACAACC TCAGCAAGCA GCAGAATGAG TCCCCGCAGC CCCTCGTGGA GACGGGAAAG    300

AAGTCTCCAG AATCTCTGGT CAAGCTGGAT GCAACCCCAT TGTCCTCCCC ACGGCATGTG    360
```

-continued

```
AGGATCAAAA ACTGGGGCAG CGGGATGACT TTCCAAGACA CACTTCACCA TAAGGCCAAA    420

GGGATTTTAA CTTGCAGGTC CAAATCTTGC CTGGGGTCCA TTATGACTCC CAAAAGTTTG    480

ACCAGAGGAC CCAGGGACAA GCCTACCCCT CCAGATGAGC TTCTACCTCA AGCTATCGAA    540

TTTGTCAACC AATATTACGG CTCCTTCAAA GAGGCAAAAA TAGAGGAACA TCTGGCCAGG    600

GTGGAAGCGG TAACAAAGGA GATAGAAACA ACAGGAACCT ACCAACTGAC GGGAGATGAG    660

CTCATCTTCG CCACCAAGCA GGCCTGGCGC AATGCCCCAC GCTGCATTGG GAGGATCCAG    720

TGGTCCAACC TGCAGGTCTT CGATGCCCGC AGCTGTTCCA CTGCCCGGGA AATGTTTGAA    780

CACATCTGCA GACACGTGCG TTACTCCACC AACAATGGCA ACATCAGGTC GGCCATCACC    840

GTGTTCCCCC AGCGGAGTGA TGGCAAGCAC GACTTCCGGG TGTGGAATGC TCAGCTCATC    900

CGCTATGCTG GCTACCAGAT GCCAGATGGC AGCATCAGAG GGACCCTGC CAACGTGGAA     960

TTCACTCAGC TGTGCATCGA CCTGGGCTGG AAGCCCAAGT ACGGCCGCTT CGATGTGGTC   1020

CCCCTGGTCC TGCAGGCCAA TGGCCGTGAC CCTGAGCTCT TCGAAATCCC ACCTGACCTT   1080

GTGCTTGAGG TGGCCATGGA ACATCCCAAA TACGAGTGGT TCGGGAACT GGAGCTAAAG    1140

TGGTACGCCC TGCCTGCAGT GGCCAACATG CTGCTTGAGG TGGGCGGCCT GGAGTTCCCA   1200

GGGTGCCCCT TCAATGGCTG GTACATGGGC ACAGAGATCG GAGTCCGGGA CTTCTGTGAC   1260

GTCCAGCGCT ACAACATCCT GGAGGAAGTG GGCAGGAGAA TGGGCCTGGA AACGCACAAG   1320

CTGGCCTCGC TCTGGAAAGA CCAGGCTGTC GTTGAGATCA ACATTGCTGT GCTCCATAGT   1380

TTCCAGAAGC AGAATGTGAC CATCATGGAC CACCACTCGG CTGCAGAATC CTTCATGAAG   1440

TACATGCAGA ATGAATACCG GTCCCGTGGG GGCTGCCCGG CAGACTGGAT TTGGCTGGTC   1500

CCTCCCATGT CTGGGAGCAT CACCCCCGTG TTTCACCAGG AGATGCTGAA CTACGTCCTG   1560

TCCCCTTTCT ACTACTATCA GGTAGAGGCC TGGAAAACCC ATGTCTGGCA GGACGAGAAG   1620

CGGAGACCCA AGAGAAGAGA GATTCCATTG AAAGTCTTGG TCAAAGCTGT GCTCTTTGCC   1680

TGTATGCTGA TGCGCAAGAC AATGGCGTCC CGAGTCAGAG TCACCATCCT CTTTGCGACA   1740

GAGACAGGAA AATCAGAGGC GCTGGCCTGG GACCTGGGGG CCTTATTCAG CTGTGCCTTC   1800

AACCCCAAGG TTGTCTGCAT GGATAAGTAC AGGCTGAGCT GCCTGGAGGA GGAACGGCTG   1860

CTGTTGGTGG TGACCAGTAC GTTTGGCAAT GGAGACTGCC CTGGCAATGG AGAGAAACTG   1920

AAGAAATTGC TCTTCATGCT GAAAGAGCTC AACAACAAAT TCAGGTACGC GTGTTTGGC    1980

CTCGGCTCCA GCATGTACCC TCGGTTCTGC GCCTTTGCTC ATGACATTGA TCAGAAGCTG   2040

TCCCACCTGG GGGCCTCTCA GCTCACCCCG ATGGGAGAAG GGGATGAGCT CAGTGGGCAG   2100

GAGGACGCCT TCCGCAGCTG GGCCGTGCAA ACCTTCAAGG CAGCCTGTGA GACGTTTGAT   2160

GTCCGAGGCA AACAGCACAT TCAGATCCCC AAGCTCTACA CCTCCAATGT GACCTGGGAC   2220

CCGCACCACT ACAGGCTCGT GCAGGACTCA CAGCCTTTGG ACCTCAGCAA AGCCCTCAGC   2280

AGCATGCATG CCAAGAACGT GTTCACCATG AGGCTCAAAT CTCGGCAGAA TCTACAAAGT   2340

CCGACATCCA GCCGTGCCAC CATCCTGGTG GAACTCTCCT GTGAGGATGG CCAAGGCCTG   2400

AACTACCTGC CGGGGGAGCA CCTTGGGGTT TGCCCAGGCA ACCAGCCGGC CCTGGTCCAA   2460

GGCATCCTGG AGCGAGTGGT GGATGGCCCC ACACCCCACC AGACAGTGCG CCTGGAGGCC   2520

CTGGATGAGA GTGGCAGCTA CTGGGTCAGT GACAAGAGGC TGCCCCCCTG CTCACTCAGC   2580

CAGGCCCTCA CCTACTTCCT GGACATCACC ACACCCCCAA CCCAGCTGCT GCTCCAAAAG   2640

CTGGCCCAGG TGGCCACAGA AGAGCCTGAG AGACAGAGGC TGGAGGCCCT GTGCCAGCCC   2700
```

```
TCAGAGTACA GCAAGTGGAA GTTCACCAAC AGCCCCACAT TCCTGGAGGT GCTAGAGGAG    2760

TTCCCGTCCC TGCGGGTGTC TGCTGGCTTC CTGCTTTCCC AGCTCCCCAT TCTGAAGCCC    2820

AGGTTCTACT CCATCAGCTC CTCCCGGGAT CACACGCCCA CAGAGATCCA CCTGACTGTG    2880

GCCGTGGTCA CCTACCACAC CCGAGATGGC CAGGGTCCCC TGCACCACGG CGTCTGCAGC    2940

ACATGGCTCA ACAGCCTGAA GCCCAAGAC CCAGTGCCCT GCTTTGTGCG GAATGCCAGC    3000

GGCTTCCACC TCCCCGAGGA TCCCTCCCAT CCTTGCATCC TCATCGGGCC TGGCACAGGC    3060

ATCGCGCCCT TCCGCAGTTT CTGGCAGCAA CGGCTCCATG ACTCCCAGCA CAAGGGAGTG    3120

CGGGGAGGCC GCATGACCTT GGTGTTTGGG TGCCGCCGCC CAGATGAGGA CCACATCTAC    3180

CAGGAGGAGA TGCTGGAGAT GGCCCAGAAG GGGGTGCTGC ATGCGGTGCA CACAGCCTAT    3240

TCCCGCCTGC CTGGCAAGCC CAAGGTCTAT GTTCAGGACA TCCTGCGGCA GCAGCTGGCC    3300

AGCGAGGTGC TCCGTGTGCT CCACAAGGAG CCAGGCCACC TCTATGTTTG CGGGGATGTG    3360

CGCATGGCCC GGGACGTGGC CCACACCCTG AAGCAGCTGG TGGCTGCCAA GCTGAAATTG    3420

AATGAGGAGC AGGTCGAGGA CTATTTCTTT CAGCTCAAGA GCCAGAAGCG CTATCACGAA    3480

GATATCTTTG GTGCTGTATT TCCTTACGAG GCGAAGAAGG ACAGGGTGGC GGTGCAGCCC    3540

AGCAGCCTGG AGATGTCAGC GCTCTGAGGG CCTACAGGAG GGGTTAAAGC TGCCGGCACA    3600

GAACTTAAGG ATGGAGCCAG CTCTGCATTA TCTGAGGTCA CAGGGCCTGG GGAGATGGAG    3660

GAAAGTGATA TCCCCCAGCC TCAAGTCTTA TTTCCTCAAC GTTGCTCCCC ATCAAGCCCT    3720

TTACTTGACC TCCTAACAAG TAGCACCCTG GATTGATCGG AGCCTCCTCT CTCAAACTGG    3780

GGCCTCCCTG GTCCCTTGGA GACAAAATCT TAAATGCCAG GCCTGGCAAG TGGGTGAAAG    3840

ATGGAACTTG CTGCTGAGTG CACCACTTCA AGTGACCACC AGGAGGTGCT ATCGCACCAC    3900

TGTGTATTTA ACTGCCTTGT GTACAGTTAT TTATGCCTCT GTATTTAAAA AACTAACACC    3960

CAGTCTGTTC CCCATGGCCA CTTGGGTCTT CCCTGTATGA TTCCTTGATG GAGATATTTA    4020

CATGAATTGC ATTTTACTTT AATCACAAAA AAAAAAAAA AA                       4062
```

(2) INFORMATION FOR SEQ ID NO:12:

(i) SEQUENCE CHARACTERISTICS:
        (A) LENGTH: 1146 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
Met Ala Cys Pro Trp Lys Phe Leu Phe Lys Thr Lys Phe His Gln Tyr
 1               5                  10                  15

Ala Met Asn Gly Glu Lys Asp Ile Asn Asn Val Glu Lys Ala Pro
                20                  25                  30

Cys Ala Thr Ser Ser Pro Val Thr Gln Asp Asp Leu Gln Tyr His Asn
            35                  40                  45

Leu Ser Lys Gln Gln Asn Glu Ser Pro Gln Pro Val Glu Thr Gly
        50                  55                  60

Lys Lys Ser Pro Glu Ser Leu Val Lys Leu Asp Ala Thr Pro Leu Ser
65                  70                  75                  80

Ser Pro Arg His Val Arg Ile Lys Asn Trp Gly Ser Gly Met Thr Phe
                85                  90                  95

Gln Asp Thr Leu His His Lys Ala Lys Gly Ile Leu Thr Cys Arg Ser
            100                 105                 110
```

-continued

```
Lys Ser Cys Leu Gly Ser Ile Met Thr Pro Lys Ser Leu Thr Arg Gly
            115                 120                 125
Pro Arg Asp Lys Pro Thr Pro Pro Asp Glu Leu Leu Pro Gln Ala Ile
130                 135                 140
Glu Phe Val Asn Gln Tyr Tyr Gly Ser Phe Lys Glu Ala Lys Ile Glu
145                 150                 155                 160
Glu His Leu Ala Arg Val Ala Val Thr Lys Glu Ile Glu Thr Thr
            165                 170                 175
Gly Thr Tyr Gln Leu Thr Gly Asp Glu Leu Ile Phe Ala Thr Lys Gln
            180                 185                 190
Ala Trp Arg Asn Ala Pro Arg Cys Ile Gly Arg Ile Gln Trp Ser Asn
            195                 200                 205
Leu Gln Val Phe Asp Ala Arg Ser Cys Ser Thr Ala Arg Glu Met Phe
            210                 215                 220
Glu His Ile Cys Arg His Val Arg Tyr Ser Thr Asn Asn Gly Asn Ile
225                 230                 235                 240
Arg Ser Ala Ile Thr Val Phe Pro Gln Arg Ser Asp Gly Lys His Asp
            245                 250                 255
Phe Arg Val Trp Asn Ala Gln Leu Ile Arg Tyr Ala Gly Tyr Gln Met
            260                 265                 270
Pro Asp Gly Ser Ile Arg Gly Asp Pro Ala Asn Val Glu Phe Thr Gln
            275                 280                 285
Leu Cys Ile Asp Leu Gly Trp Lys Pro Lys Tyr Gly Arg Phe Asp Val
            290                 295                 300
Val Pro Leu Val Leu Gln Ala Asn Gly Arg Asp Pro Glu Leu Phe Glu
305                 310                 315                 320
Ile Pro Pro Asp Leu Val Leu Glu Val Ala Met Glu His Pro Lys Tyr
            325                 330                 335
Glu Trp Phe Arg Glu Leu Glu Leu Lys Trp Tyr Ala Leu Pro Ala Val
            340                 345                 350
Ala Asn Met Leu Leu Glu Val Gly Gly Leu Glu Phe Pro Gly Cys Pro
            355                 360                 365
Phe Asn Gly Trp Tyr Met Gly Thr Glu Ile Gly Val Arg Asp Phe Cys
370                 375                 380
Asp Val Gln Arg Tyr Asn Ile Leu Glu Glu Val Gly Arg Arg Met Gly
385                 390                 395                 400
Leu Glu Thr His Lys Leu Ala Ser Leu Trp Lys Asp Gln Ala Val Val
            405                 410                 415
Glu Ile Asn Ile Ala Val Leu His Ser Phe Gln Lys Gln Asn Val Thr
            420                 425                 430
Ile Met Asp His His Ser Ala Ala Glu Ser Phe Met Lys Tyr Met Gln
            435                 440                 445
Asn Glu Tyr Arg Ser Arg Gly Gly Cys Pro Ala Asp Trp Ile Trp Leu
            450                 455                 460
Val Pro Pro Met Ser Gly Ser Ile Thr Pro Val Phe His Gln Glu Met
465                 470                 475                 480
Leu Asn Tyr Val Leu Ser Pro Phe Tyr Tyr Gln Val Glu Ala Trp
            485                 490                 495
Lys Thr His Val Trp Gln Asp Glu Lys Arg Pro Lys Arg Arg Glu
            500                 505                 510
Ile Pro Leu Lys Val Leu Val Lys Ala Val Leu Phe Ala Cys Met Leu
            515                 520                 525
```

```
Met Arg Lys Thr Met Ala Ser Arg Val Arg Val Thr Ile Leu Phe Ala
    530                 535                 540

Thr Glu Thr Gly Lys Ser Glu Ala Leu Ala Trp Asp Leu Gly Ala Leu
545                 550                 555                 560

Phe Ser Cys Ala Phe Asn Pro Lys Val Cys Met Asp Lys Tyr Arg
                565                 570                 575

Leu Ser Cys Leu Glu Glu Arg Leu Leu Leu Val Val Thr Ser Thr
                580                 585                 590

Phe Gly Asn Gly Asp Cys Pro Gly Asn Gly Glu Lys Leu Lys Leu
                595                 600                 605

Leu Phe Met Leu Lys Glu Leu Asn Asn Lys Phe Arg Tyr Ala Val Phe
    610                 615                 620

Gly Leu Gly Ser Ser Met Tyr Pro Arg Phe Cys Ala Phe Ala His Asp
625                 630                 635                 640

Ile Asp Gln Lys Leu Ser His Leu Gly Ala Ser Gln Leu Thr Pro Met
                645                 650                 655

Gly Glu Gly Asp Glu Leu Ser Gly Gln Glu Asp Ala Phe Arg Ser Trp
                660                 665                 670

Ala Val Gln Thr Phe Lys Ala Ala Cys Glu Thr Phe Asp Val Arg Gly
                675                 680                 685

Lys Gln His Ile Gln Ile Pro Lys Leu Tyr Thr Ser Asn Val Thr Trp
    690                 695                 700

Asp Pro His His Tyr Arg Leu Val Gln Asp Ser Gln Pro Leu Asp Leu
705                 710                 715                 720

Ser Lys Ala Leu Ser Ser Met His Ala Lys Asn Val Phe Thr Met Arg
                725                 730                 735

Leu Lys Ser Arg Gln Asn Leu Gln Ser Pro Thr Ser Ser Arg Ala Thr
                740                 745                 750

Ile Leu Val Glu Leu Ser Cys Glu Asp Gly Gln Gly Leu Asn Tyr Leu
                755                 760                 765

Pro Gly Glu His Leu Gly Val Cys Pro Gly Asn Gln Pro Ala Leu Val
    770                 775                 780

Gln Gly Ile Leu Glu Arg Val Val Asp Gly Pro Thr Pro His Gln Thr
785                 790                 795                 800

Val Arg Leu Glu Ala Leu Asp Glu Ser Gly Ser Tyr Trp Val Ser Asp
                805                 810                 815

Lys Arg Leu Pro Pro Cys Ser Leu Ser Gln Ala Leu Thr Tyr Phe Leu
                820                 825                 830

Asp Ile Thr Thr Pro Pro Thr Gln Leu Leu Leu Gln Lys Leu Ala Gln
                835                 840                 845

Val Ala Thr Glu Glu Pro Glu Arg Gln Arg Leu Glu Ala Leu Cys Gln
850                 855                 860

Pro Ser Glu Tyr Ser Lys Trp Lys Phe Thr Asn Ser Pro Thr Phe Leu
865                 870                 875                 880

Glu Val Leu Glu Glu Phe Pro Ser Leu Arg Val Ser Ala Gly Phe Leu
                885                 890                 895

Leu Ser Gln Leu Pro Ile Leu Lys Pro Arg Phe Tyr Ser Ile Ser Ser
                900                 905                 910

Ser Arg Asp His Thr Pro Thr Glu Ile His Leu Thr Val Ala Val Val
                915                 920                 925

Thr Tyr His Thr Arg Asp Gly Gln Gly Pro Leu His His Gly Val Cys
                930                 935                 940

Ser Thr Trp Leu Asn Ser Leu Lys Pro Gln Asp Pro Val Pro Cys Phe
```

```
945                 950                 955                 960
Val Arg Asn Ala Ser Gly Phe His Leu Pro Glu Asp Pro Ser His Pro
                965                 970                 975
Cys Ile Leu Ile Gly Pro Gly Thr Gly Ile Ala Pro Phe Arg Ser Phe
            980                 985                 990
Trp Gln Gln Arg Leu His Asp Ser Gln His Lys Gly Val Arg Gly Gly
        995                 1000                1005
Arg Met Thr Leu Val Phe Gly Cys Arg Arg Pro Asp Glu Asp His Ile
    1010                1015                1020
Tyr Gln Glu Glu Met Leu Glu Met Ala Gln Lys Gly Val Leu His Ala
1025                1030                1035                1040
Val His Thr Ala Tyr Ser Arg Leu Pro Gly Lys Pro Lys Val Tyr Val
                1045                1050                1055
Gln Asp Ile Leu Arg Gln Gln Leu Ala Ser Glu Val Leu Arg Val Leu
            1060                1065                1070
His Lys Glu Pro Gly His Leu Tyr Val Cys Gly Asp Val Arg Met Ala
        1075                1080                1085
Arg Asp Val Ala His Thr Leu Lys Gln Leu Val Ala Ala Lys Leu Lys
    1090                1095                1100
Leu Asn Glu Glu Gln Val Glu Asp Tyr Phe Phe Gln Leu Lys Ser Gln
1105                1110                1115                1120
Lys Arg Tyr His Glu Asp Ile Phe Gly Ala Val Phe Pro Tyr Glu Ala
                1125                1130                1135
Lys Lys Asp Arg Val Ala Val Gln Pro Ser
            1140                1145
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

AAGCTGACCC AGGATCCACG                                              20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

TCTGCTCTTC AGATGACTGG                                              20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

AGAGTTAAAG CTAAGGTTGG                                           20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

ACAGAGAGCA AGGACTTAGG                                           20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CCATCATTGC GTGTGCCTGC                                           20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AGCTTCTTCA AAGTGGTAGC                                           20

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

CGCCTCAGCA ATGTTGTGTC G                                         21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

AGGGCTTCAC TTCTTGCAAA C                                         21